United States Patent
Hadida-Ruah et al.

(10) Patent No.: US 9,725,440 B2
(45) Date of Patent: *Aug. 8, 2017

(54) MODULATORS OF CFTR

(71) Applicant: Vertex Pharmaceuticals Incorporated, Boston, MA (US)

(72) Inventors: Sara Hadida-Ruah, La Jolla, CA (US); Mark Miller, San Diego, CA (US); Brian Bear, Carlsbad, CA (US); Jinglan Zhou, San Diego, CA (US); Jason McCartney, Cardiff by the Sea, CA (US); Peter Grootenhuis, San Diego, CA (US)

(73) Assignee: Vertex Pharmaceuticals Incorporated, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/633,278

(22) Filed: Feb. 27, 2015

(65) Prior Publication Data

US 2015/0166516 A1     Jun. 18, 2015

Related U.S. Application Data

(63) Continuation of application No. 12/117,941, filed on May 9, 2008, now Pat. No. 8,969,386.

(60) Provisional application No. 60/928,334, filed on May 9, 2007.

(51) Int. Cl.
| | | |
|---|---|---|
| C07D 405/14 | (2006.01) | |
| C07D 213/75 | (2006.01) | |
| C07D 401/04 | (2006.01) | |
| A61K 31/444 | (2006.01) | |
| G01N 33/50 | (2006.01) | |

(52) U.S. Cl.
CPC .......... *C07D 405/14* (2013.01); *A61K 31/444* (2013.01); *C07D 213/75* (2013.01); *C07D 401/04* (2013.01); *G01N 33/502* (2013.01); *G01N 2333/705* (2013.01); *G01N 2500/04* (2013.01); *G01N 2500/10* (2013.01)

(58) Field of Classification Search
None
See application file for complete search history.

(56) References Cited

U.S. PATENT DOCUMENTS

| | | |
|---|---|---|
| 3,758,475 A | 9/1973 | Hardtmann et at |
| 4,501,729 A | 2/1985 | Boucher et al. |
| 5,739,345 A | 4/1998 | Fujita et al. |
| 5,876,700 A | 3/1999 | Boucher, Jr. et al. |
| 5,948,814 A | 9/1999 | Hwang et al. |
| 5,981,714 A | 11/1999 | Cheng et al. |
| 6,046,211 A | 4/2000 | Hansen, Jr. et al. |
| 6,426,331 B1 | 7/2002 | McKinney et al. |
| 6,479,483 B2 | 11/2002 | Bös et al. |
| 6,627,646 B2 | 9/2003 | Bakale et al. |
| 6,770,637 B2 | 8/2004 | Godel et al. |
| 7,005,436 B2 | 2/2006 | Lloyd et al. |
| 7,223,778 B2 | 5/2007 | Ping et al. |
| 7,297,700 B2 | 11/2007 | Kelly et al. |
| 7,407,976 B2 | 8/2008 | Miller |
| 7,446,117 B2 | 11/2008 | Beswick et al. |
| 7,476,744 B2 | 1/2009 | Ferro et al. |
| 7,482,469 B2 | 1/2009 | Palin et al. |
| 7,495,103 B2 | 2/2009 | Hadida-Ruah et al. |
| 7,553,855 B2 | 6/2009 | Young et al. |
| 7,585,885 B2 | 9/2009 | Shepherd et al. |
| 7,598,412 B2 | 10/2009 | Hadida Ruah et al. |
| 7,645,789 B2 | 1/2010 | Hadida Ruah et al. |
| 7,659,268 B2 | 2/2010 | Hadida-Ruah et al. |
| 7,671,221 B2 | 3/2010 | Hadida Ruah et al. |
| 7,691,902 B2 | 4/2010 | Hadida Ruah et al. |
| 7,741,321 B2 | 6/2010 | Hadida Ruah et al. |
| 7,754,739 B2 | 7/2010 | Hadida-Ruah et al. |
| 7,776,905 B2 | 8/2010 | Hadida Ruah et al. |
| 7,846,951 B2 | 12/2010 | Miller et al. |
| 7,893,094 B2 | 2/2011 | Pollard et al. |
| 7,956,052 B2 | 6/2011 | Hadida Ruah et al. |
| 7,973,038 B2 | 7/2011 | Hadida Ruah et al. |
| 7,973,169 B2 | 7/2011 | Hadida Ruah et al. |
| 7,977,322 B2 | 7/2011 | Ruah et al. |
| 7,999,113 B2 | 8/2011 | Hadida Ruah et al. |
| 8,012,999 B2 | 9/2011 | Hadida Ruah et al. |

(Continued)

FOREIGN PATENT DOCUMENTS

| | | |
|---|---|---|
| AU | 2006311650 B2 | 2/2012 |
| CA | 2539250 A1 | 4/2005 |
| CA | 2605300 A1 | 10/2006 |
| CN | 1335771 A | 2/2002 |
| CN | 1356988 A | 7/2002 |
| CN | 1938279 A | 3/2007 |
| CN | 101006076 A | 7/2007 |
| CN | 101198333 A | 6/2008 |
| CN | 101287732 A | 10/2008 |
| CN | 101460489 A | 6/2009 |

(Continued)

OTHER PUBLICATIONS

Stankovic et al. Genet. Test Sep. 2008; 12(3):357-62.*
Dahl and Nordestgaard, International Journal of COPD (2009) 4: 157-167.*
Abadi, A. et al. (1999) Synthesis of 4-alkyl (aryl)-6-aryl-3-cyano-2(1H)-pyridinones and their 2-imino isosteres as nonsteroidal cardiotonic agents *II Farmaco*, 54:195-201.
Amaral, M. D. and C.M. Farinha (2013) "Rescuing Mutant CFTR: A Multi-task Approach to a Better Outcome in Treating Cystic Fibrosis" *Curr Pharm Des*, 19:3497-3508.

(Continued)

*Primary Examiner* — James D Anderson
(74) *Attorney, Agent, or Firm* — Finnegan, Henderson, Farabow, Garrett & Dunner, LLP

(57) ABSTRACT

Compounds of the present invention, and pharmaceutically acceptable compositions thereof, are useful as modulators of ATP-Binding Cassette ("ABC") transporters or fragments thereof, including Cystic Fibrosis Transmembrane Conductance Regulator ("CFTR"). The present invention also relates to methods of treating CFTR mediated diseases using compounds of the present invention.

7 Claims, No Drawings

(56) References Cited

U.S. PATENT DOCUMENTS

| | | |
|---|---|---|
| 8,039,491 B2 | 10/2011 | Hadida Ruah et al. |
| 8,076,357 B2 | 12/2011 | Young et al. |
| 8,101,767 B2 | 1/2012 | Ruah et al. |
| 8,124,781 B2 | 2/2012 | Siesel et al. |
| 8,163,772 B2 | 4/2012 | DeMattei et al. |
| 8,188,283 B2 | 5/2012 | Binch et al. |
| 8,227,615 B2 | 7/2012 | Hadida Ruah et al. |
| 8,232,302 B2 | 7/2012 | Miller et al. |
| 8,242,149 B2 | 8/2012 | Ruah et al. |
| 8,299,099 B2 | 10/2012 | Ruah et al. |
| 8,314,239 B2 | 11/2012 | Binch et al. |
| 8,314,256 B2 | 11/2012 | Ruah et al. |
| 8,318,733 B2 | 11/2012 | Hadida Ruah et al. |
| 8,324,207 B2 | 12/2012 | Hadida Ruah et al. |
| 8,324,242 B2 | 12/2012 | Ruah et al. |
| 8,344,147 B2 | 1/2013 | Ambhaikar et al. |
| 8,354,427 B2 | 1/2013 | Van Goor |
| 8,362,253 B2 | 1/2013 | DeMattei et al. |
| 8,367,660 B2 | 2/2013 | Binch et al. |
| 8,389,727 B2 | 3/2013 | Zhang et al. |
| 8,399,479 B2 | 3/2013 | Binch et al. |
| 8,404,849 B2 | 3/2013 | Sun et al. |
| 8,404,865 B2 | 3/2013 | Ambhaikar et al. |
| 8,410,132 B2 | 4/2013 | Binch et al. |
| 8,410,274 B2 | 4/2013 | Hurter et al. |
| 8,415,387 B2 | 4/2013 | Ruah et al. |
| 8,431,605 B2 | 4/2013 | Hadida Ruah et al. |
| 8,436,014 B2 | 5/2013 | Zhang et al. |
| 8,461,156 B2 | 6/2013 | Hadida Ruah et al. |
| 8,461,342 B2 | 6/2013 | Siesel et al. |
| 8,461,352 B2 | 6/2013 | Ambhaikar et al. |
| 8,471,029 B2 | 6/2013 | Arekar et al. |
| 8,476,442 B2 | 7/2013 | DeMattei et al. |
| 8,507,524 B2 | 8/2013 | Ruah et al. |
| 8,507,534 B2 | 8/2013 | Keshavarz-Shokri |
| 8,507,687 B2 | 8/2013 | Keshavarz-Shokri et al. |
| 8,513,282 B2 | 8/2013 | Binch et al. |
| 8,524,767 B2 | 9/2013 | Hadida Ruah et al. |
| 8,524,910 B2 | 9/2013 | Hadida Ruah et al. |
| 8,541,453 B2 | 9/2013 | Hadida Ruah et al. |
| 8,552,006 B2 | 10/2013 | Binch et al. |
| 8,552,034 B2 | 10/2013 | Verwijs et al. |
| 8,563,573 B2 | 10/2013 | Ruah et al. |
| 8,563,593 B2 | 10/2013 | Alargova et al. |
| 8,575,209 B2 | 11/2013 | Ruah et al. |
| 8,586,615 B2 | 11/2013 | Hadida-Ruah et al. |
| 8,592,602 B2 | 11/2013 | Siesel et al. |
| 8,598,181 B2 | 12/2013 | Hadida Ruah et al. |
| 8,598,205 B2 | 12/2013 | Binch et al. |
| 8,604,203 B2 | 12/2013 | Binch et al. |
| 8,609,703 B2 | 12/2013 | Ruah et al. |
| 8,614,325 B2 | 12/2013 | Yang et al. |
| 8,614,327 B2 | 12/2013 | Sheth et al. |
| 8,623,894 B2 | 1/2014 | DeMattei et al. |
| 8,623,905 B2 | 1/2014 | Ruah et al. |
| 8,629,162 B2 | 1/2014 | Hadida-Ruah et al. |
| 8,633,189 B2 | 1/2014 | Binch et al. |
| 8,642,609 B2 | 2/2014 | Makings et al. |
| 8,653,103 B2 | 2/2014 | Keshavarz-Shokri et al. |
| 8,674,108 B2 | 3/2014 | Luisi et al. |
| 8,710,075 B2 | 4/2014 | Binch et al. |
| 8,716,338 B2 | 5/2014 | Young et al. |
| 8,722,704 B2 | 5/2014 | Hadida Ruah et al. |
| 8,741,922 B2 | 6/2014 | Zhang et al. |
| 8,741,925 B2 | 6/2014 | Hadida Ruah et al. |
| 8,741,933 B2 | 6/2014 | Hadida Ruah et al. |
| 8,741,939 B2 | 6/2014 | Hadida Ruah et al. |
| 8,742,122 B2 | 6/2014 | Keshavarz-Shokri et al. |
| 8,748,612 B2 | 6/2014 | Binch et al. |
| 8,754,222 B2 | 6/2014 | Ambhaikar et al. |
| 8,754,224 B2 | 6/2014 | Hurter et al. |
| 8,759,335 B2 | 6/2014 | Hadida Ruah et al. |
| 8,765,957 B2 | 7/2014 | DeMattei et al. |
| 8,785,476 B2 | 7/2014 | Arekar et al. |
| 8,785,640 B2 | 7/2014 | Binch et al. |
| 8,796,308 B2 | 8/2014 | Yang et al. |
| 8,796,312 B2 | 8/2014 | Hadida Ruah et al. |
| 8,802,700 B2 | 8/2014 | Sheth et al. |
| 8,802,844 B2 | 8/2014 | Gallardo-Godoy et al. |
| 8,802,868 B2 | 8/2014 | Keshavarz-Shokri et al. |
| 8,816,093 B2 | 8/2014 | Siesel et al. |
| 8,822,451 B2 | 9/2014 | Ruah et al. |
| 8,829,204 B2 | 9/2014 | Hadida-Ruah et al. |
| 8,835,639 B2 | 9/2014 | DeMattei et al. |
| 8,846,718 B2 | 9/2014 | Keshavarz-Shokri et al. |
| 8,846,753 B2 | 9/2014 | Hadida Ruah et al. |
| 8,853,254 B2 | 10/2014 | Hadida Ruah et al. |
| 8,853,415 B2 | 10/2014 | Hadida Ruah et al. |
| 8,883,206 B2 | 11/2014 | Dokou et al. |
| 8,884,018 B2 | 11/2014 | Ambhaikar et al. |
| 8,889,875 B2 | 11/2014 | Ruah et al. |
| 8,912,199 B2 | 12/2014 | Hadida Ruah et al. |
| 8,952,049 B2 | 2/2015 | Ruah et al. |
| 8,952,050 B2 | 2/2015 | Ruah et al. |
| 8,962,856 B2 | 2/2015 | Hadida-Ruah et al. |
| 8,969,382 B2 | 3/2015 | Binch et al. |
| 8,969,386 B2 * | 3/2015 | Hadida-Ruah ....... C07D 213/75 514/333 |
| 8,969,574 B2 | 3/2015 | Keshavarz-Shokri et al. |
| 8,993,600 B2 | 3/2015 | Hadida Ruah et al. |
| 8,999,976 B2 | 4/2015 | Binch et al. |
| 9,012,473 B2 | 4/2015 | Hadida Ruah et al. |
| 9,012,496 B2 | 4/2015 | Alargova et al. |
| 9,012,652 B2 | 4/2015 | Siesel |
| 9,035,072 B2 | 5/2015 | Belmont et al. |
| 9,045,425 B2 | 6/2015 | Luisi et al. |
| 9,051,303 B2 | 6/2015 | Keshavarz-Shokri et al. |
| 9,051,324 B2 | 6/2015 | Binch et al. |
| 9,079,916 B2 | 7/2015 | Hadida Ruah et al. |
| 9,090,619 B2 | 7/2015 | Hadida-Ruah et al. |
| 9,102,672 B2 | 8/2015 | Hadida-Ruah et al. |
| 9,139,530 B2 | 9/2015 | Hurter et al. |
| 9,150,552 B2 | 10/2015 | Keshavarz-Shokri et al. |
| 9,192,606 B2 | 11/2015 | Young |
| 9,216,969 B2 | 12/2015 | Ruah et al. |
| 9,241,934 B2 | 1/2016 | Verwijs et al. |
| 9,249,131 B2 | 2/2016 | Hadida Ruah et al. |
| 9,254,291 B2 | 2/2016 | Looker et al. |
| 9,314,455 B2 | 4/2016 | Keshavarz-Shokri et al. |
| 9,321,725 B2 | 4/2016 | Miller et al. |
| 9,351,962 B2 | 5/2016 | Hadida Ruah et al. |
| 9,371,287 B2 | 6/2016 | DeMattei et al. |
| 9,399,648 B2 | 7/2016 | Gallardo-Godoy |
| 9,434,717 B2 | 9/2016 | Keshavarz-Shokri et al. |
| 9,504,683 B2 | 11/2016 | Hadida Ruah et al. |
| 9,522,145 B2 | 12/2016 | Hadida Ruah et al. |
| 9,550,761 B2 | 1/2017 | Hadida-Ruah et al. |
| 2002/0115619 A1 | 8/2002 | Rubenstein et al. |
| 2003/0125315 A1 | 7/2003 | Mjalli et al. |
| 2005/0070718 A1 | 3/2005 | Lubisch et al. |
| 2005/0113379 A1 | 5/2005 | Ge et al. |
| 2005/0113423 A1 | 5/2005 | VanGoor et al. |
| 2005/0130970 A1 | 6/2005 | Miller et al. |
| 2005/0148648 A1 | 7/2005 | Hadida Ruah et al. |
| 2006/0003005 A1 | 1/2006 | Cao et al. |
| 2006/0069110 A1 | 3/2006 | Andersen et al. |
| 2006/0074075 A1 | 4/2006 | Hadida-Ruah et al. |
| 2006/0173050 A1 | 8/2006 | Liu et al. |
| 2006/0217448 A1 | 9/2006 | Kelly et al. |
| 2007/0142411 A1 | 6/2007 | Hagan et al. |
| 2008/0090864 A1 | 4/2008 | Young et al. |
| 2008/0138803 A1 | 6/2008 | Galvan-Goldman (nee Galvan) et al. |
| 2008/0260820 A1 | 10/2008 | Borrelly et al. |
| 2008/0306062 A1 | 12/2008 | Hadida Ruah et al. |
| 2009/0105272 A1 | 4/2009 | Grootenhuis |
| 2009/0176839 A1 | 7/2009 | Keshavarz-Shokri et al. |
| 2009/0246820 A1 | 10/2009 | Singh et al. |
| 2010/0036130 A1 | 2/2010 | Siesel et al. |
| 2010/0074949 A1 | 3/2010 | Rowe et al. |
| 2010/0087435 A1 | 4/2010 | Hadida Ruah et al. |
| 2010/0105739 A1 | 4/2010 | Hadida Ruah et al. |
| 2010/0125090 A1 | 5/2010 | Hadida Ruah et al. |
| 2010/0144798 A1 | 6/2010 | Van Goor et al. |

(56) References Cited

U.S. PATENT DOCUMENTS

| | | |
|---|---|---|
| 2010/0168094 A1 | 7/2010 | Binch et al. |
| 2010/0168158 A1 | 7/2010 | Binch et al. |
| 2010/0210638 A1 | 8/2010 | Ruah et al. |
| 2010/0249180 A1 | 9/2010 | Gallardo-Godoy |
| 2010/0256184 A1 | 10/2010 | Rowe et al. |
| 2010/0261750 A1 | 10/2010 | Binch et al. |
| 2011/0008259 A1 | 1/2011 | Binch et al. |
| 2011/0064811 A1 | 3/2011 | Hurter et al. |
| 2011/0098311 A1 | 4/2011 | Van Goor et al. |
| 2011/0123449 A1 | 5/2011 | Zhang et al. |
| 2011/0177999 A1 | 7/2011 | Singh et al. |
| 2011/0251253 A1 | 10/2011 | Keshavarz-Shokri et al. |
| 2011/0257223 A1 | 10/2011 | Goor et al. |
| 2011/0288122 A1 | 11/2011 | Van Goor et al. |
| 2012/0035179 A1 | 2/2012 | Hadida Ruah et al. |
| 2012/0046330 A1 | 2/2012 | Alargova et al. |
| 2012/0061869 A1 | 3/2012 | Boeckx et al. |
| 2012/0064157 A1 | 3/2012 | Dokou et al. |
| 2012/0122921 A1 | 5/2012 | DeMattei et al. |
| 2012/0122922 A1 | 5/2012 | Young et al. |
| 2012/0184583 A1 | 7/2012 | Van Goor et al. |
| 2012/0220625 A1 | 8/2012 | Rowe et al. |
| 2012/0232059 A1 | 9/2012 | Hadida Ruah et al. |
| 2012/0258983 A1 | 10/2012 | Rowe et al. |
| 2013/0011923 A1 | 1/2013 | Ruah et al. |
| 2013/0012536 A1 | 1/2013 | Hadida Ruah et al. |
| 2013/0018071 A1 | 1/2013 | Arekar et al. |
| 2013/0085158 A1 | 4/2013 | Keshavarz-Shokri et al. |
| 2013/0090354 A1 | 4/2013 | Van Goor et al. |
| 2013/0095181 A1 | 4/2013 | Verwijs et al. |
| 2013/0116238 A1 | 5/2013 | Looker et al. |
| 2013/0131107 A1 | 5/2013 | Van Goor et al. |
| 2013/0143919 A1 | 6/2013 | Van Goor et al. |
| 2013/0158071 A1 | 6/2013 | Van Goor et al. |
| 2013/0184276 A1 | 7/2013 | Hadida Ruah et al. |
| 2013/0186801 A1 | 7/2013 | Verwijs et al. |
| 2013/0224293 A1 | 8/2013 | Dokou et al. |
| 2013/0231368 A1 | 9/2013 | Zhang et al. |
| 2013/0237569 A1 | 9/2013 | Hadida Ruah et al. |
| 2013/0245010 A1 | 9/2013 | Hadida Ruah et al. |
| 2013/0245011 A1 | 9/2013 | Hadida Ruah et al. |
| 2013/0303484 A1 | 11/2013 | Grootenhuis et al. |
| 2013/0324743 A1 | 12/2013 | Belmont |
| 2013/0331567 A1 | 12/2013 | Hadida Ruah et al. |
| 2014/0011846 A1 | 1/2014 | Keshavarz-Shokri et al. |
| 2014/0012003 A1 | 1/2014 | DeMattei et al. |
| 2014/0023706 A1 | 1/2014 | Verwijs et al. |
| 2014/0024672 A1 | 1/2014 | Hadida Ruah et al. |
| 2014/0051724 A1 | 2/2014 | Hadida-Ruah et al. |
| 2014/0057906 A1 | 2/2014 | Hadida Ruah et al. |
| 2014/0072995 A1 | 3/2014 | Hadida Ruah et al. |
| 2014/0073653 A1 | 3/2014 | Binch et al. |
| 2014/0080825 A1 | 3/2014 | Hadida-Ruah et al. |
| 2014/0080826 A1 | 3/2014 | Ruah et al. |
| 2014/0088141 A1 | 3/2014 | Binch et al. |
| 2014/0088160 A1 | 3/2014 | Alargova et al. |
| 2014/0094499 A1 | 4/2014 | Alargova et al. |
| 2014/0112988 A1 | 4/2014 | Rowe et al. |
| 2014/0121208 A1 | 5/2014 | Van Goor et al. |
| 2014/0121379 A1 | 5/2014 | Siesel et al. |
| 2014/0121381 A1 | 5/2014 | Hadida-Ruah et al. |
| 2014/0142138 A1 | 5/2014 | Van Goor et al. |
| 2014/0142312 A1 | 5/2014 | Luisi et al. |
| 2014/0155431 A1 | 6/2014 | Hadida-Ruah et al. |
| 2014/0155626 A1 | 6/2014 | Hadida Ruah et al. |
| 2014/0163011 A1 | 6/2014 | Van Goor et al. |
| 2014/0163068 A1 | 6/2014 | Verwijs et al. |
| 2014/0187787 A1 | 7/2014 | Ambhaikar et al. |
| 2014/0206689 A1 | 7/2014 | Hadida Ruah et al. |
| 2014/0206720 A1 | 7/2014 | Young et al. |
| 2014/0221424 A1 | 8/2014 | Zha et al. |
| 2014/0221430 A1 | 8/2014 | Keshavarz-Shokri et al. |
| 2014/0235625 A1 | 8/2014 | Binch et al. |
| 2014/0235668 A1 | 8/2014 | Binch et al. |
| 2014/0242172 A1 | 8/2014 | Hurter et al. |
| 2014/0243289 A1 | 8/2014 | Grootenhuis |
| 2014/0255483 A1 | 9/2014 | Dokou et al. |
| 2014/0256770 A1 | 9/2014 | DeMattei et al. |
| 2014/0303204 A1 | 10/2014 | Binch et al. |
| 2014/0303205 A1 | 10/2014 | Yang et al. |
| 2014/0315948 A1 | 10/2014 | Rowe et al. |
| 2014/0323521 A1 | 10/2014 | Van Goor et al. |
| 2014/0329855 A1 | 11/2014 | Arekar et al. |
| 2014/0330023 A1 | 11/2014 | Siesel et al. |
| 2014/0336393 A1 | 11/2014 | Ambhaikar et al. |
| 2014/0343098 A1 | 11/2014 | Sheth et al. |
| 2014/0343315 A1 | 11/2014 | Hadida Ruah et al. |
| 2014/0350281 A1 | 11/2014 | DeMattei et al. |
| 2014/0371230 A1 | 12/2014 | Hadida Ruah et al. |
| 2014/0371275 A1 | 12/2014 | Keshavarz-Shokri et al. |
| 2015/0005344 A1 | 1/2015 | Keshavarz-Shokri et al. |
| 2015/0010628 A1 | 1/2015 | Dokou et al. |
| 2015/0024047 A1 | 1/2015 | Dokou et al. |
| 2015/0025076 A1 | 1/2015 | Hadida Ruah et al. |
| 2015/0031720 A1 | 1/2015 | Gallardo-Godoy |
| 2015/0031722 A1 | 1/2015 | Hadida-Ruah et al. |
| 2015/0065487 A1 | 3/2015 | Hadida-Ruah et al. |
| 2015/0065497 A1 | 3/2015 | Hadida-Ruah et al. |
| 2015/0065500 A1 | 3/2015 | Hadida-Ruah et al. |
| 2015/0080431 A1 | 3/2015 | Van Goor et al. |
| 2015/0094304 A1 | 4/2015 | Ruah et al. |
| 2015/0119441 A1 | 4/2015 | Hadida Ruah et al. |
| 2015/0164881 A1 | 6/2015 | Van Goor et al. |
| 2015/0166516 A1 | 6/2015 | Hadida-Ruah et al. |
| 2015/0174098 A1 | 6/2015 | Ruah et al. |
| 2015/0182517 A1 | 7/2015 | Alargova et al. |
| 2015/0203478 A1 | 7/2015 | Keshavarz-Shokri et al. |
| 2015/0218122 A1 | 8/2015 | Tanoury et al. |
| 2015/0231142 A1 | 8/2015 | Van Goor et al. |
| 2015/0246031 A1 | 9/2015 | Dokou et al. |
| 2015/0293078 A1 | 10/2015 | Singh et al. |
| 2015/0320736 A1 | 11/2015 | Phenix et al. |
| 2015/0336898 A1 | 11/2015 | Grootenhuis et al. |
| 2015/0336956 A1 | 11/2015 | Hadida-Ruah et al. |
| 2016/0022664 A2 | 1/2016 | Van Goor et al. |
| 2016/0022665 A2 | 1/2016 | Van Goor et al. |
| 2016/0039800 A1 | 2/2016 | Young |
| 2016/0067239 A9 | 3/2016 | Van Goor et al. |
| 2016/0095858 A1 | 4/2016 | Miller et al. |
| 2016/0096807 A1 | 4/2016 | Strohmeier et al. |
| 2016/0143898 A1 | 5/2016 | Hadida Ruah et al. |
| 2016/0166540 A1 | 6/2016 | Looker et al. |
| 2016/0200712 A1 | 7/2016 | Siesel |
| 2016/0213648 A1 | 7/2016 | Duncton et al. |
| 2016/0221952 A1 | 8/2016 | Yang et al. |
| 2016/0221995 A1 | 8/2016 | Keshavarz-Shokri et al. |
| 2016/0228414 A1 | 8/2016 | Hadida Ruah et al. |
| 2016/0229806 A1 | 8/2016 | Hurter et al. |
| 2016/0237079 A1 | 8/2016 | Hadida Ruah et al. |
| 2016/0271105 A1 | 9/2016 | Hadida Ruah et al. |
| 2016/0303096 A1 | 10/2016 | Verwijs et al. |
| 2016/0318931 A1 | 11/2016 | Hadida Ruah et al. |
| 2016/0324788 A1 | 11/2016 | Verwijs et al. |
| 2016/0324846 A1 | 11/2016 | Verwijs et al. |
| 2016/0332997 A1 | 11/2016 | Hadida Ruah et al. |

FOREIGN PATENT DOCUMENTS

| | | |
|---|---|---|
| CN | 102164587 A | 8/2011 |
| EP | 0081756 A1 | 6/1983 |
| EP | 0574174 A2 | 12/1993 |
| EP | 0591830 A1 | 4/1994 |
| EP | 1026149 A1 | 8/2000 |
| EP | 2231606 B1 | 2/2013 |
| EP | 2615085 A1 | 7/2013 |
| JP | 58-121274 A | 7/1983 |
| JP | 5-78356 A | 3/1993 |
| JP | 8-301870 A | 11/1996 |
| JP | 2002-114777 A | 4/2002 |
| JP | 2003-501420 A | 1/2003 |
| JP | 2003-155285 A | 5/2003 |
| JP | 2003-519698 A | 6/2003 |
| JP | 2003-221386 A | 8/2003 |
| JP | 2004-520394 A | 7/2004 |

(56) References Cited

FOREIGN PATENT DOCUMENTS

| | | |
|---|---|---|
| JP | 2005-053902 A | 3/2005 |
| JP | 2005-508904 A | 4/2005 |
| JP | 2005-525389 A | 8/2005 |
| JP | 2005-529114 A | 9/2005 |
| JP | 2006-507247 A | 3/2006 |
| JP | 2006-508016 A | 3/2006 |
| JP | 2006-512338 A | 4/2006 |
| JP | 2007-511572 A | 5/2007 |
| JP | 2007-519740 A | 7/2007 |
| JP | 2007-533740 A | 11/2007 |
| JP | 2008-504097 A | 2/2008 |
| JP | 2011-529101 A | 12/2011 |
| JP | 5165586 B2 | 3/2013 |
| JP | 5317184 B2 | 10/2013 |
| JP | 5497633 B2 | 5/2014 |
| JP | 5666525 B2 | 2/2015 |
| RU | 96121599 A | 2/1999 |
| RU | 2154064 C2 | 8/2000 |
| WO | WO 95/06046 A1 | 3/1995 |
| WO | WO 96/10027 A1 | 4/1996 |
| WO | WO 96/19444 A1 | 6/1996 |
| WO | WO 97/36876 A1 | 10/1997 |
| WO | WO 98/07420 A1 | 2/1998 |
| WO | WO 98/28980 A1 | 7/1998 |
| WO | WO 98/47868 A1 | 10/1998 |
| WO | WO 99/41405 A1 | 8/1999 |
| WO | WO 99/64394 A1 | 12/1999 |
| WO | WO 00/16798 A1 | 3/2000 |
| WO | WO 00/35452 A1 | 6/2000 |
| WO | WO 00/50398 A2 | 8/2000 |
| WO | WO 00/50401 A1 | 8/2000 |
| WO | WO 00/75120 A1 | 12/2000 |
| WO | WO 01/46165 A2 | 6/2001 |
| WO | WO 01/51919 A2 | 7/2001 |
| WO | WO 01/54690 A1 | 8/2001 |
| WO | WO 01/56989 A2 | 8/2001 |
| WO | WO 01/81317 A1 | 11/2001 |
| WO | WO 01/83517 A1 | 11/2001 |
| WO | WO 01/92235 A1 | 12/2001 |
| WO | WO 02/16324 A1 | 2/2002 |
| WO | WO 02/22601 A1 | 3/2002 |
| WO | WO 02/30875 A1 | 4/2002 |
| WO | WO 02/34739 A1 | 5/2002 |
| WO | WO 02/38107 A2 | 5/2002 |
| WO | WO 02/44183 A2 | 6/2002 |
| WO | WO 02/062804 A1 | 8/2002 |
| WO | WO 02/079134 A1 | 10/2002 |
| WO | WO 02/085458 A2 | 10/2002 |
| WO | WO 02/096421 A1 | 12/2002 |
| WO | WO 03/006016 A2 | 1/2003 |
| WO | WO 03/007888 A2 | 1/2003 |
| WO | WO 03/007945 A1 | 1/2003 |
| WO | WO 03/022852 A2 | 3/2003 |
| WO | WO 03/042191 A2 | 5/2003 |
| WO | WO 03/055482 A1 | 7/2003 |
| WO | WO 03/063797 A2 | 8/2003 |
| WO | WO 03/082186 A2 | 10/2003 |
| WO | WO 03/084997 A1 | 10/2003 |
| WO | WO 03/088908 A2 | 10/2003 |
| WO | WO 03/105788 A2 | 12/2003 |
| WO | WO 2004/024691 A1 | 3/2004 |
| WO | WO 2004/035571 A1 | 4/2004 |
| WO | WO 2004/041163 A2 | 5/2004 |
| WO | WO 2004/054505 A2 | 7/2004 |
| WO | WO 2004/063179 A1 | 7/2004 |
| WO | WO 2004/072038 A1 | 8/2004 |
| WO | WO 2004/099168 A2 | 11/2004 |
| WO | WO 2005/000300 A1 | 1/2005 |
| WO | WO 2005/023806 A2 | 3/2005 |
| WO | WO 2005/026137 A2 | 3/2005 |
| WO | WO 2005/030702 A1 | 4/2005 |
| WO | WO 2005/030755 A1 | 4/2005 |
| WO | WO 2005/039589 A2 | 5/2005 |
| WO | WO 2005/044797 A1 | 5/2005 |
| WO | WO 2005/049018 A1 | 6/2005 |
| WO | WO 2005/049034 A2 | 6/2005 |
| WO | WO 2005/075435 A1 | 8/2005 |
| WO | WO 2005/080348 A1 | 9/2005 |
| WO | WO 2005/100353 A1 | 10/2005 |
| WO | WO 2005/108391 A1 | 11/2005 |
| WO | WO 2005/115399 A2 | 12/2005 |
| WO | WO 2006/002421 A2 | 1/2006 |
| WO | WO 2006/003504 A1 | 1/2006 |
| WO | WO 2006/014012 A2 | 2/2006 |
| WO | WO 2006/040520 A1 | 4/2006 |
| WO | WO 2006/051394 A1 | 5/2006 |
| WO | WO 2006/063999 A1 | 6/2006 |
| WO | WO 2006/067931 A1 | 6/2006 |
| WO | WO 2006/080884 A1 | 8/2006 |
| WO | WO 2006/082952 A1 | 8/2006 |
| WO | WO 2006/108695 A2 | 10/2006 |
| WO | WO 2006/113704 A2 | 10/2006 |
| WO | WO 2006/113919 A2 | 10/2006 |
| WO | WO 2006/129199 A1 | 12/2006 |
| WO | WO 2006/130403 A1 | 12/2006 |
| WO | WO 2006/136829 A2 | 12/2006 |
| WO | WO 2007/021982 A2 | 2/2007 |
| WO | WO 2007/028654 A2 | 3/2007 |
| WO | WO 2007/039420 A1 | 4/2007 |
| WO | WO 2007/045462 A2 | 4/2007 |
| WO | WO 2007/054480 A1 | 5/2007 |
| WO | WO 2007/056341 A1 | 5/2007 |
| WO | WO 2007/067506 A2 | 6/2007 |
| WO | WO 2007/075946 A1 | 7/2007 |
| WO | WO 2007/079139 A2 | 7/2007 |
| WO | WO 2007/087066 A2 | 8/2007 |
| WO | WO 2007/117715 A2 | 10/2007 |
| WO | WO 2007/134279 A2 | 11/2007 |
| WO | WO 2008/065068 A2 | 6/2008 |
| WO | WO 2008/127399 A2 | 10/2008 |
| WO | WO 2008/141119 A2 | 11/2008 |
| WO | WO 2008/147952 A1 | 12/2008 |
| WO | WO 2009/006315 A1 | 1/2009 |
| WO | WO 2009/023509 A2 | 2/2009 |
| WO | WO 2009/033561 A1 | 3/2009 |
| WO | WO 2009/036412 A1 | 3/2009 |
| WO | WO 2009/038683 A2 | 3/2009 |
| WO | WO 2009/038913 A2 | 3/2009 |
| WO | WO 2009/073757 A1 | 6/2009 |
| WO | WO 2009/074749 A2 | 6/2009 |
| WO | WO 2009/076141 A2 | 6/2009 |
| WO | WO 2009/076142 A2 | 6/2009 |
| WO | WO 2009/076593 A1 | 6/2009 |
| WO | WO 2009/123896 A1 | 10/2009 |
| WO | WO 2010/013035 A1 | 2/2010 |
| WO | WO 2010/019239 A2 | 2/2010 |
| WO | WO 2010/037066 A2 | 4/2010 |
| WO | WO 2010/048526 A2 | 4/2010 |
| WO | WO 2010/048564 A1 | 4/2010 |
| WO | WO 2010/053471 A1 | 5/2010 |
| WO | WO 2010/054138 A2 | 5/2010 |
| WO | WO 2010/138484 A2 | 12/2010 |
| WO | WO 2011/127241 A2 | 10/2011 |
| WO | WO 2011/133951 A1 | 10/2011 |
| WO | WO 2011/133953 A1 | 10/2011 |
| WO | WO 2011/133956 A1 | 10/2011 |
| WO | WO 2013/112804 A1 | 8/2013 |
| WO | WO 2013/185112 A1 | 12/2013 |
| WO | WO 2014/014841 A1 | 1/2014 |
| WO | WO 2016/086103 A1 | 6/2016 |
| WO | WO 2016/086136 A1 | 6/2016 |
| WO | WO 2016/087665 A2 | 6/2016 |
| WO | WO 2016/185423 A1 | 11/2016 |

OTHER PUBLICATIONS

AVENTiS Pharmaceuticals, Inc. (May 12, 2003) Prescribing Information for Allegra® (10 pages).

Batt, G.D. and G.C. Houghton (May 1995) "Polyfunctional pyridines from nitroacetamidine and β-diketones. A useful synthesis of substituted imidazo [4,5-b] pyridines and related compounds" *J Heterocyci Chem*, 32(3):963-969.

(56) References Cited

OTHER PUBLICATIONS

Bavin, M. (Aug. 1989) "Polymorphism in Process Development" *Chemistry & Industry*, 16:527-529.
Bazant. V. et al. (Jan. 1968) "Properties of sodium-bis-(2-methoxyethoxy)aluminumhydride. I. Reduction of some organic functional groups" *Tetrahedron Letters*, 9(29):3303-3306.
Bell, T.W. et al. (Oct. 16, 1995) "Highly Effective Hydrogen-Bonding Receptors for Guanine Derivatives" *Angewandte Chemie—International Edition*, 34(19):2163-2165.
Bernstein, J. (2002) *Polymorphism in Molecular Crystals*. Oxford: Oxford Science Publications; pp. 9-10.
Bhalerao, U.T. et al. (Jul. 1995) "A mild and efficient method for the dehydrogenation of dihydropyrido-pyrimidinones and related compounds by using active $MnO_2$," *Indian J Chem*, 34B:587-590.
Bhattacharya, S. et al. (2009) "Thermoanalytical and Crystallographic Methods" in *Polymorphism in Pharmaceutical Solids*. 2nd edition. Harry G. Brittain (ed.) New York, NY: Informa Healthcare USA, Inc.; pp. 318-335.
Bombieri, C. et al. (1998) "Complete mutational screening of the CFTR gene in 120 patients with pulmonary disease" *Hum Genet*. 103:718-722.
Boyle, M.P. et al. (Oct. 1, 2011) "VX-809, an Investigational CFTR Corrector, in Combination With VX-770, an Investigational CFTR Potentiator, in Subjects With CF and Homozygous for the F508del-CFTR Mutation" *Pediatric Pulmonology*, 46:287, Abstract 212.
Braga, D. et al. (2009) "Crystal Polymorphism and Multiple Crystal Forms" *Struct Bond*, 132:25-50.
Brittain (Ed.) (1999) *Polymorphism on Pharmaceutical Science*. NY:Marcel Dekker, Inc.; pp. 1-2, 183-226, 235-238.
Bryn, S. et al. (1995) "Pharmaceutical Solids: A Strategic Approach to Regulatory Considerations" *Pharmaceutical Research*, 12(7):945-954.
Cabeza, J. A. et al. (2004) "Triruthenium, Hexaruthenium, and Triosmium Carbonyl Derivatives of 2-Amino-6-phenylpyridine" *Organometallics*, 23(5):1107-1115.
Caira. M.R. (1998) "Crystalline Polymorphism of Organic Compounds" in *Topics in Current Chemistry*, vol. 198, pp. 163-208.
CAPLUS Database Accession No. 1960:17025; Document No. 54:17025. Ridi, M. (1959) *Annali di Chimica*, 49:944-957 (2 pages).
CAPLUS Database Accession No. 1970:435253; Document No. 73:352253. Van Allan, J.A. et al. (1970) *J Heterocycl Chem*, 7(3):495-507 (1 page).
CAPLUS Database Accession No. 1979:420373; Document No. 91:20373. Nantka-Namirski, P. et al. (1978) *Polish Journal of Pharmacology and Pharmacy*, 30(4):569-572 (2 pages).
CAPLUS Database Accession No. 1988:186521; Document No. 108:186521. Mertens, H. et al. (1987) *Archiv der Pharmazie*, 320(11):1143-1149 (2 pages).
CAPLUS Database Accession No. 1991:6375: Document No. 114:6375, Jure, M. et al. (1990) *Latvijas PSR Zinatnu Akadernijas Vestis, Kimijas Serija*. 4:439-444 (3 pages).
CAPLUS Database Accession No. 1994:244582; Document No. 120:244582. Troscheutz, R. et al. (1994) *Archiv der Pharmazie*, 327(2):85-89 (1 page).
CAPLUS Database Accession No. 2005:406839; Document No. 143:248209; RN 134643-28-0. Spitzner (2005) *Science of Synthesis*, 15:11-284 (1 page).
Carnegie Mellon, Dept. of Physics (2002) "CMU Seed Fund Project on Detection and Control of Pharmaceutical Polymorphism" [online]. Retrieved from the Internet: http://andrew.cmu.edu/user/suter/polymorph.html; on Apr. 3, 2008, 3 pages.
Cerny, M. et al. (Mar. 1969) "Properties of sodium bis(2-methoxyethoxy)aluminurn hydride. III. Reduction of carboxylic acids and their derivatives" *Collection of Czechoslovak Chemical Communications, Institute of Organic Chemistry & Biochemistry*, 34(3):1025-1032.
Clancy, J.P. et al. (Jan. 2012) "Results of a phase IIa study of VX-809, an investigational CFTR corrector compound, in subjects with cystic fibrosis homozygous for the F508del-CFTR mutation" *Thorax*, 67(1):12-18 NIH Public Access Author Manuscript; available in PMC Aug. 19, 2013 (16 pages).
*Concise Encyclopedia Chemistry*, NY: Walter de Gruyter, 1993, pp. 872-873.
Corning Inc. (2013) "Corning® Gentest™ ATPase Assay Kit. Colorimetric Reagent Kit for ABC Transporter Membrane ATPase Assays" Product information, 2 pages.
Costa, M. et al. (Jun. 2005) "Diabetes: a major co-morbidity of cystic fibrosis" *Diabetes Metab*, 31(3 Pt 1):221-232 (French; English summary on p. 221).
Cowart, M. et al. (Jan. 2001) "Structure-activity studies of 5-substituted pyridopyrimidines as adenosine kinase inhibitors" *Bioorg Med Chem Lett*, 11(1):83-86.
Cystic Fibrosis Foundation (2006) *Annual Report*. (58 pages).
Dahl, M. et al. (Oct. 9, 2005) "Asthma and COPD in cystic fibrosis intron-8 5T carriers. A population-based study" *Respiratory Research*, 6:113, doi:10.1186/1465-9921-6-113, 9 pages.
Damasio, A.R. (1996) "Alzheimer's Disease and Related Dementias" in *Cecil Textbook of Medicine*. 20th edition. J. Claude Bennett and F. Plum (Eds.). Philadelphia: W.B. Saunders Co.; vol. 2, pp. 1992-1996.
Danswan. G. et al. (1989) "Synthesis of (imidazo[1,2-C]pyrimidin-2-yl)phenylmethanones and 6-benzoylpyrrolo[2,3-D]pyrimidinones" *J Heterocyclic Chem*, 26(2):293-299.
Davidovich et al. (2004) "Detection of Polymorphism by Powder X-Ray Diffraction: Interference by Preferred Orientation" *American Pharmaceutical Review*, 7(1):10, 12, 14, 16 and 100.
Dhenge, R.M. et al. (2010) "Twin screw wet granulation: Granule properties" *Chemical Engineering Journal*, 164:322-329.
Doelker, E. (2002) "Modifications Cyrisallines et Transformations Polymorphes au Cours des Operations Galeniques (Crystalline Modifications and Polymorphous Changes During Drug Manufacture" English translation of *Ann. Pharm. Fr.*, 60:161-176 (40 pages).
Doelker, E (1999) "Physicochemical Behaviors of Active Substances Their Consequences for the Feasibility and the Stability of Pharmaceutical Forms" *S.T.P. Pharma Pratiques*, 9(5):399-409. French with English translation.
Dornow, A. and P. Karlson (1940) "Über eine neue Synthese von 2-Amino-pyridin-Derivaten" *Berichte der Deutschen Chemischen Gesellschaft A/B*, 73(5):542-546.
Dornow, A. and E. Neuse (1951) "Über die Reaktion von Amidinen mit β-Dicarbonyl-Verbindungen" *Chemische Berichte*, 84:296-304 (German).
Dörwald, F.Z. (2005) *Side Reactions in Organic Synthesis*. Weinheim, Germany: Wiley-VCH; Preface, pp. 1-15 and Chapter 8, pp. 279-308.
Elkady, M. et al. (1980) "Some reactions of β-aroylacrylic acids" *Revue Roumanie de Chimie*, 25:1361-1366.
Evens, G. and P. Caluwe (1975) "Pyrido[2,3-d]-pyrimidines. Latent 2-Aminonicotinaldehydes" *J Org Chem*, 40(10):1438-1439.
Farhanullah et al. (2003) "Synthesis of Aminonicotinonitriles and Diaminopyridines through Base-Catalyzed Ring Transformation of 2H-Pyran-2-ones" *J Org Chem*, 68(7):2983-2985.
Ferec, C. et al. (2012) "Assessing the Disease-Liability of Mutations in CFTR" *Cold Spring Harbor Perspect Med*, 2:a009480 (13 pages).
Florence, A.T. (2011) *Physicochemical Principles of Pharmacy*. Chapter 1, pp. 7-42.
Flume, P.A. (2012) "Ivacaftor in Subjects With Cystic Fibrosis Who Are Homozygous for the *F508del-CFTR* Mutation" *Chest*, 142(3): 718-724.
Galietta,L.J.V. and O. Moran (2004) "Identification of CFTR activators and inhibitors: chance or design?" *Curr Opin Pharmacol*, 4:497-503.
Genomembrane Co. Ltd. (2015) "ABC Transporter and Assay" [online]. Retrieved from: http://www.genomembrane.com/E_ABC_Transporter_and_Assay.html; on Aug. 4, 2015 (3 pages).

(56) References Cited

OTHER PUBLICATIONS

Giardina, G.A.M. et al. (1999) "Replacement of the quinoline system in 2-phenyl-4-quinolinecarboxamide NK-3 receptor antagonists" *Il Farmaco*, 54:364-374.
Giron, D. (2001) "Investigations of polymorphism and pseudo-polymorphism in pharmaceuticals by combined thermoanalytical techniques" *J Thermal Analysis Calorimetry*, 64:37-60.
google.com (2016) "'New assay' cystic fibrosis transmembrane conductance regulator" Partial results of Internet search [online]. Retrieved from https://www.google.com, on Feb. 2, 2016 (2 pages).
Goshayev, M. et al. (1973) "Amination of 2-phenylpyridine under different conditions" *Izvestiya Akademii Nauk Turkmenskoi SSR, Seriya Giziko-Tekhnicheskikh, Khimicheskikh I Geologicheskikh Nauk*, 1973:108-109 (English abstract on p. 109).
Haleblian et al. (1969) "Pharmaceutical applications of polymorphism" *J Pharm Sci*, 58(8):911-929.
Hancock, B.C. and M. Parks (Apr. 2000) "What is the true solubility advantage for amorphous pharmaceuticals?" *Pharm Res*, 17(4):397-404.
HCAPLUS Database Accession No. 2005:823671 (2011) "Preparation of mainly N-thiazolyl carboxamides as modulators of ATP-binding cassette transporters" (3 pages).
Hirayama (Jul. 25, 2008) Yuuki kagoubutsu no kettshou sakusei handobuttku—genri to nouhou—(Handbook of preparation of crystal of organic compound—principle and know-how). Maruzen Co., Ltd, pp. 59-60 (Japanese).
Hisano, T. et al. (1982) "Raction of Aromatic N-Oxides with Dipolarophiles. V. 1,3-Cycloaddition of 2-Substituted Pyridine N-Oxides with Phenyl Isocyanates" *Chem Pharm Bull*, 30(10):3776-3781.
International Patent Application No. PCT/US2006/043289, filed Nov. 8, 2006, by Vertex Pharmaceuticals Inc.: International Search Report and Written Opinion, mailed Mar. 9, 2007.
International Patent Application No. PCT/US2006/049412, filed Dec. 28, 2006, by Vertex Pharmaceuticals Inc.: International Search Report and Written Opinion, mailed Sep. 4, 2007.
International Patent Application No. PCT/US2008/063144, filed May 9, 2008, by Vertex Pharmaceuticals Inc.: International Search Report and Written Opinion, mailed Mar. 24, 2009.
International Patent Application No. PCT/US2008/083517, filed Nov. 14, 2008, by Vertex Pharmaceuticals Inc.: International Search Report and Written Opinion mailed Feb. 19, 2009.
International Patent Application No. PCT/US2008/085456, filed Dec. 4, 2008, by Vertex Pharmaceuticals Inc.: International Search Report and Written Opinion, mailed Feb. 26, 2009.
International Patent Application No. PCT/US2008/085458, filed Dec. 4, 2008, by Vertex Pharmaceuticals Inc.: International Search Report and Written Opinion, mailed Aug. 7, 2009.
International Patent Application No. PCT/US2009/035064, filed Feb. 25, 2009, by Vertex Pharmaceuticals Inc.: International Search Report and Written Opinion, mailed Oct. 12, 2009.
International Patent Application No. PCT/US2009/038203, filed Mar. 25, 2009, by Vertex Pharmaceuticals Inc.: International Search Report and Written Opinion, mailed Jul. 9, 2009.
International Patent Application No. PCT/US2009/058677, filed Sep. 29, 2009, by Vertex Pharmaceuticals Inc.: International Search Report and Written Opinion, mailed Mar. 23, 2010.
International Patent Application No. PCT/US2011/031519, filed Apr. 7, 2011, by Vertex Pharmaceuticals Inc.: International Search Report and Written Opinion, mailed Dec. 16, 2011.
International Patent Application No. PCT/US2011/031588, filed Apr. 7, 2011, by Vertex Pharmaceuticals Inc.: International Search Report and Written Opinion, mailed Dec. 16, 2011.
International Patent Application No. PCT/US2011/033687, filed Apr. 22, 2011, by Vertex Pharmaceuticals Inc.: International Search Report and Written Opinion mailed Aug. 30, 2011.
International Patent Application No. PCT/US2011/033689, filed Apr. 22, 2011, by Vertex Pharmaceuticals Inc.: International Search Report and Written Opinion mailed Aug. 30, 2011.
International Patent Application No. PCT/US2013/023100, filed Jan. 25, 2013, by Vertex Pharmaceuticals Inc.: International Search Report and Written Opinion, mailed May 7, 2013.
International Patent Application No. PCT/US2013/067952, filed Nov. 1, 2013, by Vertex Pharmaceuticals Inc.: International Search Report arid Written Opinion, mailed Feb. 5, 2014.
International Patent Application No. PCT/US2014/063506, filed Oct. 31, 2014, by Vertex Pharmaceuticals Inc.: International Search Report and Written Opinion, mailed Jan. 21, 2015.
Ito, K. et al. (1959) "A New Route to 2-Amino- or 2-Hydroxy-3-pyridinecalboxylic Acid Derivatives" *J Heterocyclic Chem*, 26:773-778.
Itoh, T. and T. Mase (May 16, 2005) "Direct synthesis of heterobiaryl compounds containing an unprotected $NH_2$ group via Suzuki-Miyaura reaction" *Tetrahedron Lett*, 46(20):3573-3577.
Ivanisevic, I. et al. (Aug./Sep. 2011) "Uses of X-Ray Powder Diffraction in the Pharmaceutical Industry" *Pharmaceutical Formulation & Quality*, pp. 30-33.
Jalgaonkar, S.V. et al. (2010) "ABC Membrane Transporters: Target for Drugs and Diseases" *Global J Pharmc*, 4(2):75-82.
Jain, N.K. and M.N. Mohammed (1986) "Polymorphism in Pharmacy" *Indian Drugs*, 23(6):315-329.
Jonat, S. (2004) "Investigation of Compacted Hydrophilic and Hydrophobic Colloidal Silicon Dioxides as Glidants for Pharmaceutical Excipients" *Powder Technology*, 141:31-43.
Jones, P.M. and A.M. George (2004) "The ABC transporter structure and mechanism: perspectives on recent research" *Cell Mol Life Sci*, 61(6):682-699.
Jones, A.M. and J.M. Helm (2009) "Emerging Treatments in Cystic Fibrosis" *Drugs*, 69(14):1903-1910.
Jure, M. et al. (1990) "Synthesis of 3-Alkyl-5-Phenyl-7-Trifluoromethylimidzao[4,5-b]pyridin-2-ones" *Latvijas PSR Zinatnu Akademijas Vestis, Kimijas Serija*, 1990(4):439-444 (English summary on p. 444).
Kaczmarek, L. et al. (Aug. 1, 1992) "An Excellent Method for the Mild and Safe Oxidation of N-Heteroaromatic Compounds and Tertiary Amines" *Chem Ber*, 125(8):1965-1966.
Kaminski, W. et al. (2006) "ABC A-subfamily transporters: Structure, function and disease" *Biochim Biophys Acta*, 1762(5):510-524.
Kanth, S. et al (2005) "Multistep Synthesis of Pyrido[3',2':4,5]pyrrolo[3,2-d][1,3]oxazin-4(5H)-one from 2-Aminonicotinonitriles" *Heterocycles*, 65(6):1415-1423.
Katoh, A. et al. (1984) "Ring Transformation Reactions of 1-Substituted 2(1H)-Pyrimidinones and Related compounds with Active Methylene Compounds" *Chem Pharm Bull*, 32(8):2942-2946.
*Kirk-Othmer Encyclopedia of Chemical Technology*. vol. 8. John Wiley & Sons, Inc , 2002; pp. 95-147.
Koitz, G. et al. (1981) "Synthese und Fluoreszenzeigenschaften von cyansubstituierten 2-Aminopyridinen" *Monatshefte für Chemie*, 112:973-985, (German; English abstract on p. 973).
Lachman, L. et al. (1990) *The Theory and Practice of Industrial Pharmacy*. 3rd Edition. Bombay, India: Varghese Publication House; pp. 221-222.
Layzer, R.B. (1996) "Section Five—Degenerative Diseases of the Nervous System" in *Cecil Textbook of Medicine*. 20th edition. J. Claude Bennett and F. Plum (Eds.). Philadelphia: W.B. Saunders Co.; vol. 2, pp. 2050-2057.
Levin, M.H. et al. (2005 Apr) "CFTR-Regulated Chloride Transport at the Ocular Surface in Living Mice Measured by Potential Differences" *Invest Ophthalmol Vis Sci*, 46(4):1428-1434.
Lin, S. et al. (Dec. 2010) "Identification of Synergistic Combinations of F508del Cystic Fibrosis Transmembrane Conductance Regulator (CFTR) Modulators" *ASSAY Drug Dev Tech*, 8(6):669-684.
Liu, Y. et al. (2005) "Expression Profiling of ABC Transporters in a Drug-Resistant Breast Cancer Cell Line Using AmpArray" *Mol Pharmacol*, 68(2):430-438.
Mathe, S. and A. Rassat (Jan. 29, 1998) "Synthesis of 1,1,1-Ethanetriacetonitrile, Precursor of 6-Substituted-4-methyl-2-aminopyridines" *Tetrahedron Lett*, 39:383-384.
Mertens, H. et al. (1986) "Synthese von 2-Amino-3-nitropyridinen und -1,4-dihydropyridinen" *Liebigs Ann Chem*, 1986:380-383 (German; English abstract on p. 380).

(56) References Cited

OTHER PUBLICATIONS

Mertens, H. and R. Troschütz (1987) "Synthese von N²-substituierten 2-Amino-3-nitropyridinen ats Vorstufen von Pyrido[2,3-b]pyrazinen (3-Desazapteridinen)" *Arch Pharm (Weinheim)*, 320:1143-1149 (German; English abstract on p. 1143).
Muzaffar, N.A. and M.A. Sheikh (1979) "Polymorphism and Drug Availability. A Reveiw" *J Pharmacy (Lahore)*, 1(1):59-66.
Narsaiah, B. et al. (1994) "A novel synthetic route to 2-amino-3-cyano-4-trifluoromethyl-6-substituted pyridines" *J Fluorine Chem*, 67:87-90.
Ngiam, N.S.P. et al. (2006) "Cystic fibrosis transmembrane conductance regulator (*CFTR*) gene mutations in Asians with chronic pulmonary disease: A pilot study" *J Cystic Fibrosis*, 5:159-164.
Nitta, M. et al. (1991) "On the Reaction of (Vinylimino)phosphoranes. Part 17. Preparation of N Vinylcarbodiimides and Their [4+2] Cycloaddition with Several Dienophiles to Give Pyridine Ring System" *Bull Chem Soc Japan*, 64(4):1325-1331.
Noone, P.G. et al. (2001) "'CFTR-opathies': disease phenotypes associated with cystic fibrosis transmembrane regulator gene mutations" *Respiratory Research*, 2(6):1-5.
Notice of Allowance and Fee(s) Due for U.S. Appl. No. 13/290,491, mailed Oct. 25, 2012.
Notice of Allowance and Fee(s) Due for U.S. Appl. No. 13/871,349, mailed Aug. 12, 2014.
Notice of Allowance and Fee(s) Due for U.S. Appl. No. 13/871,349, mailed Apr. 17, 2015.
Notice of Allowance and Fee(s) Due for U.S. Appl. No. 13/871,349, mailed Oct. 13, 2015.
Notice of Allowance and Fee(s) Due for U.S. Appl. No. 13/887,839, mailed Jul. 7, 2014.
Notice of Allowance and Fee(s) Due for U.S. Appl. No. 13/887,839, mailed Oct. 16, 2014.
Notice of Allowance and Fee(s) Due for U.S. Appl. No. 13/887,839, mailed Feb. 2, 2015.
Notice of Allowance and Fee(s) Due for U.S. Appl. No. 13/887,839, mailed Sep. 30, 2015.
Notice of Allowance and Fee(s) Due for U.S. Appl. No. 14/031,360, mailed Aug. 14, 2014.
Notice of Allowance and Fee(s) Due for U.S. Appl. No. 14/298,245, mailed Jul. 21, 2015.
Notice of Allowance and Fee(s) Due for U.S. Appl. No. 14/298,245, mailed Nov. 12, 2015.
Notice of Allowance and Fee(s) Due for U.S. Appl. No. 14/326,930, mailed Aug. 14, 2015.
Notice of Allowance and Fee(s) Due for U.S. Appl. No. 14/326,930, mailed Dec. 8, 2015.
Notice of Allowance and Fee(s) Due for U.S. Appl. No. 14/334,902, mailed Oct. 19, 2015.
Notice of Allowance and Fee(s) Due for U.S. Appl. No. 14/334,902, mailed Feb. 18, 2016.
Notice of Allowance and Fee(s) Due for U.S. Appl. No. 14/532,791, mailed Jul. 24, 2015.
Notice of Allowance and Fee(s) Due for U.S. Appl. No. 14/532,791, mailed Nov. 6, 2015.
Notice of Allowance and Fee(s) Due for U.S. Appl. No. 14/532,791, mailed Mar. 1, 2016.
Notice of Allowance and Fee(s) Due for U.S. Appl. No. 14/567,475, mailed Sep. 21, 2015.
Notice of Allowance and Fee(s) Due for U.S. Appl. No. 14/567,475, mailed Jan. 5, 2016.
Notice of Allowance and Fee(s) Due for U.S. Appl. No. 14/579,098, mailed Feb. 1, 2016.
Notice of Allowability for U.S. Appl. No. 14/579,098, mailed Apr. 18, 2016.
Notice of Allowance and Fee(s) Due for U.S. Appl. No. 14/579,098, mailed May 12, 2016.
Notice of Allowance and Fee(s) Due for U.S. Appl. No. 14/656,043, mailed Aug. 4, 2016.
Notice of Allowance and Fee(s) Due for U.S. Appl. No. 14/687,286, mailed Feb. 10, 2016.
Notice of Allowance and Fee(s) Due for U.S. Appl. No. 14/687,286, mailed May 19, 2016.
Notice of Allowance and Fee(s) Due for U.S. Appl. No. 14/687,286, mailed Sep. 28, 2016.
Notice of Allowance and Fee(s) Due for U.S. Appl. No. 14/877,914, mailed Jul. 27, 2016.
Notice of Allowance and Fee(s) Due for U.S. Appl. No. 14/877,914, mailed Nov. 14, 2016.
Notice of Allowance and Fee(s) Due for U.S. Appl. No. 14/925,804, mailed May 17, 2016.
Notice of Allowance and Fee(s) Due for U.S. Appl. No. 15/001,036, mailed Feb. 10, 2017.
Notice of Allowance and Fee(s) Due for U.S. Appl. No. 15/073,591, mailed Sep. 28, 2016.
Ochiai, Michiko et al., United States Court of Appeals for the Federal Circuit 71 F.3d 1565; 1995, U.S. Patent and Trademark Office Board of Patent Appeals and Interferences. (U.S. Appl. No. 07/462,492).
Okiyoneda, T. and G.L. Lukacs (Oct. 15, 2012) "Fixing cystic fibrosis by correcting CFTR domain assembly" *J Cell Biol*, 199(2):199-204.
Otuska, M. et al. (1999) "Effect of Polymorphic Forms of Bulk Powders on Pharmaceutical Properties of Carbamazepine Granules"*Chem Pharm Bull*, 47(6) 852-656.
Paranjape, S.M. et al. (2008) "Atypical Cystic fibrosis and CFTR-Related Diseases" *Clinic Rev Allerg Immunol*, 35(3):116-123.
Patani, G. et al (1996) "Bioisosterism: A Rational Approach in Drug Design" *Chem Rev*, 96(8):3147-3176.
Qiao, J. X. et al. (Nov. 2, 2004) "5-Amidinobenzo[b]thiophenes as dual inhibitors of factors IXa and Xa" *Bioorg Med Chem Lett*, 15(1):29-35.
Registry Database RN 477866-05-0 (Dec. 31, 2002) "3-Pyridinecarboxylic acid, 5-cyano-2-phenyl-6-[(phenylmethyl)amino]-" Retrieved from STN [online]; retrieved on Nov. 28, 2016 (1 page).
Registry Database RN 478068-14-3 (Jan. 3, 2003) "3,4,5-Pyridinetricarbonitrile, 2-amino-6-(4-bromophenyl)-" Retrieved from STN [online]; retrieved on Nov. 28, 2016 (1 page).
Registry Database RN 478068-16-5 (Jan. 3, 2003) "3,4,5-Pyridinetricarbonitrile, 2-amino-6-[4-(trifluoromethyl)phenyl]-" Retrieved from STN [online]; retrieved on Nov. 28, 2016 (1 page).
Registry Database RN 478081-23-1 (Jan. 3, 2003) "3,4,5-Pyridinetricarbonitrile, 2-amino-6-(4-methylphenyl)-" Retrieved from STN [online]; retrieved on Nov. 28, 2016 (1 page).
Registry Database RN 881299-60-1 (Apr. 20, 2006) "3-Pyridinecarbonitrile, 6-(4-methoxyphenyl)-2-[(1-phenylethyl)amino]-" Retrieved from STN [online]; retrieved on Nov. 28, 2016 (1 page).
Registry Database RN 881300-29-4 (Apr. 20, 2006) "3-Pyridinecarbonitrile, 6-(4-methoxyphenyl)-2-(phenylamino)-" Retrieved from STN [online]; retrieved on Nov. 28, 2016 (1 page).
Registry Database RN 912772-80-6 (Nov. 9, 2006) "2,5 Pyridinediamine, 6-phenyl-" Retrieved from STN [online]; retrieved on Nov. 28, 2016 (1 page).
Registry Database RN 912772-97-5 (Nov. 9, 2006) "2-Pyridinamine, 5-nitro-6-phenyl-" Retrieved from STN [online]; retrieved on Nov. 28, 2016 (1 page).
Registry Database RN 925921-90-0 (Mar. 9, 2007) "2-Pyridinamine, 4-chloro-6-(2-methoxyphenyl)-" Retrieved from STN [online]; retrieved on Nov. 28, 2016 (1 page).
Registry Database RN 929400-78-2 (Apr. 8, 2007) "3-Pyridinecarbonitrile, 2-(cyclohexyllamino)-6-(4-methoxyphenyl)-" Retrieved from STN [online]; retrieved on Nov. 28, 2016 (1 page).
Registry Database RN 929443-65-2 (Apr. 9, 2007) "3-Pyridinecarbonitrile, 2-(cycloheptylamino)-6-(4-methoxyphenyl)-'" Retrieved from STN [online]; retrieved on Nov. 28, 2016 (1 page).

(56) References Cited

OTHER PUBLICATIONS

Registry Database RN 929443-63-0 (Apr. 9, 2007) "3-Pyridinecartronitrile, 6-(4-methoxyphenyl)-2-(4-piperidinylamino)-" Retrieved from STN [online]; retrieved on Nov. 28, 2016 (1 page).
Ridi, M. (1959) "Richerch sopra derivati della piridina. Nota II. Richerche sopra sistemi 3 H-1,2,6,7,9-pentaazafenalenci. pirido(3,4-d)piridazinici a pirido(2,3-d)pirimidinici" *Annali di Chimica*, 49:944-957 (Italian).
Robins. R.K. and G.H. Hitchings (1958) "Studies on Condensed Pyrimidine Systems. XIX. A New Synthesis of Pyrido [2,3-d] pyrimidines. The Condensation of 1,3-Diketones and 3-Ketoaldehydes with 4-Aminopyrimidines" *J Am Chem*, 80(13):3449-3457.
Rodon, J. et al. (2010) "Combining Targeted Therapies: Practical Issues to Consider at the Bench and Bedside" *The Oncologist*, 15:37-50.
Rodríguez-Spong, B. et al. (2004) "General principles of a pharmaceutical solid polymorphism: a supramolecular perspective" *Adv Drug Delivery Reviews*, 56:241-274.
Rouhi, A.M. (2003) "The Right Stuff. From research and development to the clinic, getting drug crystals right is full of pitfalls" *Chem Eng News*, 81(8):32-35.
Rows, S.M. et al. (2005) "Cystic Fibrosis" *N Engl J Med*, 352(19):1992-2001.
Rowland, M. and T.N. Tozer (1995) *Clinical Pharmacokinetics. Concepts and Applications*. p. 123.
Saito, T. et al. (1993) "Lewis Acid-Induced Hetero Diels-Alder Reaction of Conjugated Carbodiimides" *Chem Lett*, pp. 1127-1130.
Saito, T. et al. (1998) "Thermal or Lewis acid-promoted electrocyclisation and hetero Diels-Alder cycloaddition of α,β-unsaturated (conjugated) carbodiimides: a facile synthesis of nitrogen-containing heterocycles" *J Chem Soc. Perkin Trans*, 1:3065-3080.
Schmidt, H-W. et al. (1980) "Synthesen mit Nitrilen; 59[1]. Ein einfacher Weg zu 2-Amino-3,4,5-tricyanopyridinen" *Synthesis*, 1980(6):471-472. (German).
Schultheiss, N. et al. (2009) "Pharmaceutical Cocrystals and Their Physiochemical Properties" *Crystal Growth & Design*, 9(6):2950-2967.
Shah, U. and L. Augsburger (2002) "Multiple Sources of Sodium Starch Glycolate, NF: Evaluation of Functional Equivalence and Development of Standard Performance Tests" *Pharmaceutical Development and Technology*, 7(3):345-359.
Silverman, R B (1993) *The Organic Chemistry of Drug Design and Drug Action*. Academic Press Inc.; pp. 72-76.
Silverman, R.B (2004) *The Organic Chemistry of Drug Design and Drug Action*. 2nd Ed. Elsevier Academic Press; pp. 26 and 29-32.
Singhal, D. and W. Curatolo (2004) "Drug Polymorphism and dosage form design: a practical perspective" *Advanced Drug Delivery Reviews*, 56:335-347.
Suloeva, E. et al. (2001) "Synthesis of 5-Phenyl-7-trifluoromethyl-2,3-dihydroimidazo[1,2-a]pyridines" *Chem Heterocyclic Compounds*, 37:329-337.
Taday, P.F. et al. (2003) "Using Terahertz Pulse Spectroscopy to Study the Crystalline Structure of a Drug: A Case Study of the Polymorphs of Ranitidine Hydrochloride" *J Pharm Sci*, 92(4):831-838.
Takata, N. (2009) "Cocrystal" *Pharm Tech Japan*, 25(12):155-166 (Japanese with English abstract).
The Associated Press (Sep. 24, 2003) "FDA mulls drug to slow late-stage Alzheimer's" CNN.com/HEALTH [online]. Retrieved from: http://www.cnn.com/2003/HEALTH/conditions/09/24/alzheimers.drug.ap/index.html, on Sep. 24, 2003 (2 pages).
Troschütz, R. (1979) "6-Substituierte 2-Aminonicotinsäure-ethylester" *Archiv der Pharmazie*, 312:455-457 (German).
Troschütz, R. and A. Lückel (1992) "Synthese von substituierten 2-Amino-3-nitropyridinen aus 1,3-Biselektrophilen und 2-Nitroethen-1,1-diamin" *Archiv der Pharmazie*, 325(12):785-789 (German; English abstract on p. 785).
Troschütz, R. and T. Dennstedt (1994) "Synthese von substituierten 2-Aminonicotinonitrile" *Archiv der Pharmazie*, 327:33-40 (German; English abstract on p. 33).
Troschütz, R. and T. Dennstedt (1994) "Substituierte 2-Aminonicotinonitrile" *Archiv der Pharmazie*, 327:85-89 (German; English abstract on p. 85).
Tzetis, M. et al. (2001) "CFTR gene mutations—including three novel nucleotide substitutions—and haplotype background in patients with asthma, disseminated bronchiectasis and chronic obstructive pulmonary disease" *Hum. Genet.*, 108:216-221.
U.S. Department of Health and Human Services, Food and Drug Administration (FDA) (May 1999) *Guideline for industry. Container Closure Systems for Packaging Human Drugs and Biologics*. (56 pages).
U.S. Appl. No. 13/091,411, filed Apr. 21, 2011.
U.S. Appl. No. 13/632,835, filed Oct. 1, 2012.
U.S. Appl. No. 14/077,885, filed Nov. 12, 2013.
U.S. Appl. No. 14/179,762, filed Feb. 13, 2014.
U.S. Appl. No. 14/444,451, filed Jul. 28, 2014.
U.S. Appl. No. 14/870,592, filed Sep. 30, 2015.
U.S. Appl. No. 14/877,860, filed Oct. 7, 2015.
U.S. Appl. No. 14/920,836, filed Oct. 22, 2015.
U.S. Appl. No. 14/935,777, filed Nov. 9, 2015.
U.S. Appl. No. 14/951,142, filed Nov. 24, 2015.
U.S. Appl. No. 14/982,973, filed Dec. 29, 2015.
U.S. Appl. No. 14/994,487, filed Jan. 13, 2016, by Hadida Ruah et al.
U.S. Appl. No. 14/996,781, filed Jan. 15, 2016.
U.S. Appl. No. 15/035,969, filed May 11, 2016, by Swinney et al.
U.S. Appl. No. 15/043,049, filed Feb. 12, 2016.
U.S. Appl. No. 15/056,436, filed Feb. 29, 2016.
U.S. Appl. No. 15/064,122, filed Mar. 8, 2016, by Bhalchandra Arnbhaikar at al.
U.S. Appl. No. 15/160,100, filed May 20, 2016, by Demattei et al.
U.S. Appl. No. 15/170,263, filed Jun. 1, 2016, by Hadida-Ruah at al.
U.S. Appl. No. 15/173,325, filed Jun. 3, 2016, by Hadida-Ruah et al.
U.S. Appl. No. 15/181,114, filed Jun. 13, 2016, by Dokou et al.
U.S. Appl. No. 15/234,877, filed Aug. 11, 2016, by Hadida-Ruah et al.
U.S. Appl. No. 15/253,636, filed Aug. 31, 2016, by Rowe at al.
U.S. Appl. No. 15/297,983, filed Oct. 19, 2016, by Hadida Ruah et al.
U.S. Appl. No. 15/342,999, filed Nov. 3, 2016, by Alargova et al.
*U.S Pharrnacopie #23, National Forumulary #18*, (1995), pp. 1843-1844.
Ulicky, L and T.J. Kemp (Eds.) (1992) *Comprehensive Dictionary of Physical Chemistry*. Czecho-Slovakia: ALFA/Ellis Horwood Ltd.; p. 21.
Van Goor, F. et al. (2006) "Rescue of ΔF580-CFTR trafficking and gating in human cystic fibrosis airway primary cultures by small molecules" *Am J Physiol Lung Cell Mol Physiol*, 290(6):L1117-L1130.
Vanallan, J.A. et al. (Jun. 1970) "Reactions of Some 4-Methylene-4H-pyran Derivatives with Primary and Secondary Amines" *J Heterocyclic Chem*, 7:495-507.
Vertex Pharmaceuticals, Inc. (May 17, 2005) "Vertex Phamiaceuticals Initiates Phase I Development for VX-770 in Cystic Fibrosis. FDA Grants Fast Track Designation to VX-770" Press Release [online]. Retrieved from: http://investors.vrtx.com/releasedetail.cfm?ReleaseID=233045; on Jan. 19, 2015 (2 pages).
Vertex Pharmaceuticals, Inc. (Mar. 2011) "Study of VX-809 Alone and in Combination With VX-770 in Cystic Fibrosis (CF) Patients Homozygous for the F508del-CFTR Mutation" ClinicalTrials.gov [online]. Retrieved from: https://clinicaltrials.gov/archive/NCT01225211/2011_03_01; Identifier: NCT01225211.
Vertex Pharmaceuticals, Inc. (Jun. 25, 2015) Summary Review of Regulatory Action for Lumacaftor/ivacaftor Tablets. U.S. FDA, Center for Drug Evaluation and Research, Division of Pulmonary, Allergy, and Rheumatology, Products, CDER; Director Badrul A. Chowdhury, MD, PhD.; Application No. 206038Orig1s000 (18 pages).

(56) References Cited

OTHER PUBLICATIONS

Wang, Y. et al. (2006) "Specific Rescue of Cystic Fibrosis Transmembrane Conductance Regulator Processing Mutants Using Pharmacological Chaperones" *Mol Pharmacol*, 70(1):297-302.

Wikipedia (Jul. 13, 2008) "ATP-binding cassette transporter" [online]. [Retrieved on Sep. 24, 2008]; Retrieved from the Internet: http://en.wikipedia.org/wiki/ATP-binding_cassette_transporter (6 pages).

Wikipedia (2009) "ATP-binding cassette transporter" [online]. [Retrieved on Jul. 10, 2009]; retrieved from the Internet: http://en.wikipedia.org/wiki/ATP-binding_cassette_transporter (20 pages).

Wikipedia (2011) "Solid solution" [online]. Retrieved from: http://www.wikipedia.com; Retrieved on Sep. 20, 2011, 3 pages.

Yin, J. et al. (Jun. 2007) "A general and efficient 2-amination of pyridines and quinolines" *J Org Chem*, 72(12):4554-4557.

Yogi, S. et al. (1986) "Synthesis of Stable 1,2-Diazocines, 4,7-Disubstituted 3,8-Diaryl-1,2-diazacycloocta-2,4,6,8-tetraenes, and Their Termolysis" *Bull Chem Sec Jpn*, 59:1087-1094.

Yurugi, S. et al. (1972) "Studies on the Synthesis of N-Heterocyclic Compounds. XII. Syntheses of Pyrido[3,4-d]pyridazine and Pyrido[2,3-d]pyridazine Derivatives" *Yakugaku Zasshi* (*Journal of the Pharmaceutical Society of Japan*), 92(11):1333-1338. Japanese with English abstract on p. 1333.

Zhang, W. et al. (Mar. 2012) "Recent advances and new perspectives in targeting CFTR for therapy of cystic fibrosis and enterotoxin-induced secretory diarrheas" *Future Med Chem*, 4(3):329-345. NIH Author Manuscript; available in PMC Jan. 1, 2013 (28 pages).

Zhu, J. et al. (2006) "Solid-phase synthesis of 4-biaryl-piperidine-4-caroxamides" *Tetrahedron Lett*, 47:7267-7270.

\* cited by examiner

MODULATORS OF CFTR

CROSS REFERENCE TO RELATED APPLICATIONS

This application is a continuation of U.S. patent application Ser. No. 12/117,941, filed May 9, 2008, which claims the benefit under 35 U.S.C. §119 to U.S. provisional patent application Ser. No. 60/928,334, filed May 9, 2007, the entire contents of both applications are incorporated herein by reference.

TECHNICAL FIELD OF THE INVENTION

The present invention relates to modulators of Cystic Fibrosis Transmembrane Conductance Regulator ("CFTR"), compositions thereof, and methods therewith. The present invention also relates to methods of treating CFTR mediated diseases using such modulators.

BACKGROUND OF THE INVENTION

ABC transporters are a family of membrane transporter proteins that regulate the transport of a wide variety of pharmacological agents, potentially toxic drugs, and xenobiotics, as well as anions. ABC transporters are homologous membrane proteins that bind and use cellular adenosine triphosphate (ATP) for their specific activities. Some of these transporters were discovered as multi-drug resistance proteins (like the MDR1-P glycoprotein, or the multi-drug resistance protein, MRP1), defending malignant cancer cells against chemotherapeutic agents. To date, 48 ABC Transporters have been identified and grouped into 7 families based on their sequence identity and function.

ABC transporters regulate a variety of important physiological roles within the body and provide defense against harmful environmental compounds. Because of this, they represent important potential drug targets for the treatment of diseases associated with defects in the transporter, prevention of drug transport out of the target cell, and intervention in other diseases in which modulation of ABC transporter activity may be beneficial.

One member of the ABC transporter family commonly associated with disease is the cAMP/ATP-mediated anion channel, CFTR. CFTR is expressed in a variety of cells types, including absorptive and secretory epithelia cells, where it regulates anion flux across the membrane, as well as the activity of other ion channels and proteins. In epithelia cells, normal functioning of CFTR is critical for the maintenance of electrolyte transport throughout the body, including respiratory and digestive tissue. CFTR is composed of approximately 1480 amino acids that encode a protein made up of a tandem repeat of transmembrane domains, each containing six transmembrane helices and a nucleotide binding domain. The two transmembrane domains are linked by a large, polar, regulatory (R)-domain with multiple phosphorylation sites that regulate channel activity and cellular trafficking.

The gene encoding CFTR has been identified and sequenced (See Gregory, R. J. et al. (1990) Nature 347:382-386; Rich, D. P. et al. (1990) Nature 347:358-362), (Riordan, J. R. et al. (1989) Science 245:1066-1073). A defect in this gene causes mutations in CFTR resulting in Cystic Fibrosis ("CF"), the most common fatal genetic disease in humans. Cystic Fibrosis affects approximately one in every 2,500 infants in the United States. Within the general United States population, up to 10 million people carry a single copy of the defective gene without apparent ill effects. In contrast, individuals with two copies of the CF associated gene suffer from the debilitating and fatal effects of CF, including chronic lung disease.

In patients with cystic fibrosis, mutations in CFTR endogenously expressed in respiratory epithelia leads to reduced apical anion secretion causing an imbalance in ion and fluid transport. The resulting decrease in anion transport contributes to enhanced mucus accumulation in the lung and the accompanying microbial infections that ultimately cause death in CF patients. In addition to respiratory disease, CF patients typically suffer from gastrointestinal problems and pancreatic insufficiency that, if left untreated, results in death. In addition, the majority of males with cystic fibrosis are infertile and fertility is decreased among females with cystic fibrosis. In contrast to the severe effects of two copies of the CF associated gene, individuals with a single copy of the CF associated gene exhibit increased resistance to cholera and to dehydration resulting from diarrhea—perhaps explaining the relatively high frequency of the CF gene within the population.

Sequence analysis of the CFTR gene of CF chromosomes has revealed a variety of disease causing mutations (Cutting, G. R. et al. (1990) Nature 346:366-369; Dean, M. et al. (1990) Cell 61:863:870; and Kerem, B-S. et al. (1989) Science 245:1073-1080; Kerem, B-S et al. (1990) Proc. Natl. Acad. Sci. USA 87:8447-8451). To date, >1000 disease causing mutations in the CF gene have been identified (http://www.genet.sickkids.on.ca/cftr/). The most prevalent mutation is a deletion of phenylalanine at position 508 of the CFTR amino acid sequence, and is commonly referred to as ΔF508-CFTR. This mutation occurs in approximately 70% of the cases of cystic fibrosis and is associated with a severe disease.

The deletion of residue 508 in ΔF508-CFTR prevents the nascent protein from folding correctly. This results in the inability of the mutant protein to exit the ER, and traffic to the plasma membrane. As a result, the number of channels present in the membrane is far less than observed in cells expressing wild-type CFTR. In addition to impaired trafficking, the mutation results in defective channel gating. Together, the reduced number of channels in the membrane and the defective gating lead to reduced anion transport across epithelia leading to defective ion and fluid transport. (Quinton, P. M. (1990), FASEB J. 4: 2709-2727). Studies have shown, however, that the reduced numbers of ΔF508-CFTR in the membrane are functional, albeit less than wild-type CFTR. (Dalemans et al. (1991), Nature Lond. 354: 526-528; Denning et al., supra; Pasyk and Foskett (1995), J. Cell. Biochem. 270: 12347-50). In addition to ΔF508-CFTR, other disease causing mutations in CFTR that result in defective trafficking, synthesis, and/or channel gating could be up- or down-regulated to alter anion secretion and modify disease progression and/or severity.

Although CFTR transports a variety of molecules in addition to anions, it is clear that this role (the transport of anions) represents one element in an important mechanism of transporting ions and water across the epithelium. The other elements include the epithelial $Na^+$ channel, ENaC, $Na^+/2Cl^-/K^+$ co-transporter, $Na^+$—$K^+$-ATPase pump and the basolateral membrane $K^+$ channels, that are responsible for the uptake of chloride into the cell.

These elements work together to achieve directional transport across the epithelium via their selective expression and localization within the cell. Chloride absorption takes place by the coordinated activity of ENaC and CFTR present on the apical membrane and the $Na^+$—$K^+$-ATPase pump and Cl− channels expressed on the basolateral surface of the cell. Secondary active transport of chloride from the luminal side leads to the accumulation of intracellular chloride, which can then passively leave the cell via Cl− channels, resulting in a vectorial transport. Arrangement of $Na^+/2Cl^-/K^+$ co-transporter, $Na^+$—$K^+$-ATPase pump and the basolateral membrane $K^+$ channels on the basolateral surface and CFTR on the luminal side coordinate the secretion of chloride via CFTR on the luminal side. Because water is probably never actively transported itself, its flow across epithelia depends on tiny transepithelial osmotic gradients generated by the bulk flow of sodium and chloride.

In addition to Cystic Fibrosis, modulation of CFTR activity may be beneficial for other diseases not directly caused by mutations in CFTR, such as secretory diseases and other protein folding diseases mediated by CFTR. These include, but are not limited to, chronic obstructive pulmonary disease (COPD), dry eye disease, and Sjögren's Syndrome.

COPD is characterized by airflow limitation that is progressive and not fully reversible. The airflow limitation is due to mucus hypersecretion, emphysema, and bronchiolitis. Activators of mutant or wild-type CFTR offer a potential treatment of mucus hypersecretion and impaired mucociliary clearance that is common in COPD. Specifically, increasing anion secretion across CFTR may facilitate fluid transport into the airway surface liquid to hydrate the mucus and optimized periciliary fluid viscosity. This would lead to enhanced mucociliary clearance and a reduction in the symptoms associated with COPD. Dry eye disease is characterized by a decrease in tear aqueous production and abnormal tear film lipid, protein and mucin profiles. There are many causes of dry eye, some of which include age, Lasik eye surgery, arthritis, medications, chemical/thermal burns, allergies, and diseases, such as Cystic Fibrosis and Sjögrens's syndrome. Increasing anion secretion via CFTR would enhance fluid transport from the corneal endothelial cells and secretory glands surrounding the eye to increase corneal hydration. This would help to alleviate the symptoms associated with dry eye disease. Sjögrens's syndrome is an autoimmune disease in which the immune system attacks moisture-producing glands throughout the body, including the eye, mouth, skin, respiratory tissue, liver, vagina, and gut. Symptoms, include, dry eye, mouth, and vagina, as well as lung disease. The disease is also associated with rheumatoid arthritis, systemic lupus, systemic sclerosis, and polymypositis/dermatomyositis. Defective protein trafficking is believed to cause the disease, for which treatment options are limited. Modulators of CFTR activity may hydrate the various organs afflicted by the disease and help to elevate the associated symptoms.

As discussed above, it is believed that the deletion of residue 508 in ΔF508-CFTR prevents the nascent protein from folding correctly, resulting in the inability of this mutant protein to exit the ER, and traffic to the plasma membrane. As a result, insufficient amounts of the mature protein are present at the plasma membrane and chloride transport within epithelial tissues is significantly reduced. In fact, this cellular phenomenon of defective ER processing of ABC transporters by the ER machinery has been shown to be the underlying basis not only for CF disease, but for a wide range of other isolated and inherited diseases. The two ways that the ER machinery can malfunction is either by loss of coupling to ER export of the proteins leading to degradation, or by the ER accumulation of these defective/misfolded proteins [Aridor M, et al., Nature Med., 5(7), pp 745-751 (1999); Shastry, B. S., et al., Neurochem. International, 43, pp 1-7 (2003); Rutishauser, J., et al., Swiss Med Wkly, 132, pp 211-222 (2002); Morello, J P et al., TIPS, 21, pp. 466-469 (2000); Bross P., et al., Human Mut., 14, pp. 186-198 (1999)]. The diseases associated with the first class of ER malfunction are Cystic fibrosis (due to misfolded ΔF508-CFTR as discussed above), Hereditary emphysema (due to al-antitrypsin; non Piz variants), Hereditary hemochromatosis, Coagulation-Fibrinolysis deficiencies, such as Protein C deficiency, Type 1 hereditary angioedema, Lipid processing deficiencies, such as Familial hypercholesterolemia, Type 1 chylomicronemia, Abetalipoproteinemia, Lysosomal storage diseases, such as I-cell disease/Pseudo-Hurler, Mucopolysaccharidoses (due to Lysosomal processing enzymes), Sandhof/Tay-Sachs (due to β-Hexosaminidase), Crigler-Najjar type II (due to UDP-glucuronyl-sialyc-transferase), Polyendocrinopathy/Hyperinsulemia, Diabetes mellitus (due to Insulin receptor), Laron dwarfism (due to Growth hormone receptor), Myleoperoxidase deficiency, Primary hypoparathyroidism (due to Pre-proparathyroid hormone), Melanoma (due to Tyrosinase). The diseases associated with the latter class of ER malfunction are Glycanosis CDG type 1, Hereditary emphysema (due to α1-Antitrypsin (PiZ variant), Congenital hyperthyroidism, Osteogenesis imperfecta (due to Type I, II, IV procollagen), Hereditary hypofibrinogenemia (due to Fibrinogen), ACT deficiency (due to α1-Antichymotrypsin), Diabetes insipidus (DI), Neurophyseal DI (due to Vasopvessin hormone/V2-receptor), Neprogenic DI (due to Aquaporin II), Charcot-Marie Tooth syndrome (due to Peripheral myelin protein 22), Perlizaeus-Merzbacher disease, neurodegenerative diseases such as Alzheimer's disease (due to βAPP and presenilins), Parkinson's disease, Amyotrophic lateral sclerosis, Progressive supranuclear plasy, Pick's disease, several polyglutamine neurological disorders such as Huntington, Spinocerebullar ataxia type I, Spinal and bulbar muscular atrophy, Dentatorubal pallidoluysian, and Myotonic dystrophy, as well as Spongiform encephalopathies, such as Hereditary Creutzfeldt-Jakob disease (due to Prion protein processing defect), Fabry disease (due to lysosomal α-galactosidase A) and Straussler-Scheinker syndrome (due to Prp processing defect).

In addition to up-regulation of CFTR activity, reducing anion secretion by CFTR modulators may be beneficial for the treatment of secretory diarrheas, in which epithelial water transport is dramatically increased as a result of secretagogue activated chloride transport. The mechanism involves elevation of cAMP and stimulation of CFTR.

Although there are numerous causes of diarrhea, the major consequences of diarrheal diseases, resulting from excessive chloride transport are common to all, and include dehydration, acidosis, impaired growth and death.

Acute and chronic diarrheas represent a major medical problem in many areas of the world. Diarrhea is both a significant factor in malnutrition and the leading cause of death (5,000,000 deaths/year) in children less than five years old.

Secretory diarrheas are also a dangerous condition in patients of acquired immunodeficiency syndrome (AIDS) and chronic inflammatory bowel disease (IBD). 16 million travelers to developing countries from industrialized nations every year develop diarrhea, with the severity and number of cases of diarrhea varying depending on the country and area of travel.

Diarrhea in barn animals and pets such as cows, pigs, and horses, sheep, goats, cats and dogs, also known as scours, is a major cause of death in these animals. Diarrhea can result from any major transition, such as weaning or physical movement, as well as in response to a variety of bacterial or viral infections and generally occurs within the first few hours of the animal's life.

The most common diarrhea causing bacteria is enterotoxogenic *E-coli* (ETEC) having the K99 pilus antigen. Common viral causes of diarrhea include rotavirus and coronavirus. Other infectious agents include cryptosporidium, giardia lamblia, and salmonella, among others.

Symptoms of rotaviral infection include excretion of watery feces, dehydration and weakness. Coronavirus causes a more severe illness in the newborn animals, and has a higher mortality rate than rotaviral infection. Often, however, a young animal may be infected with more than one virus or with a combination of viral and bacterial microorganisms at one time. This dramatically increases the severity of the disease.

There is a need for modulators of CFTR activity that can be used to modulate the activity of CFTR in the cell membrane of a mammal.

There is a need for methods of treating CFTR-mediated diseases using such modulators of CFTR activity.

There is a need for methods of modulating CFTR activity in an ex vivo cell membrane of a mammal.

SUMMARY OF THE INVENTION

It has now been found that compounds of this invention, and pharmaceutically acceptable compositions thereof, are useful as modulators of CFTR. These compounds have the general formula (I):

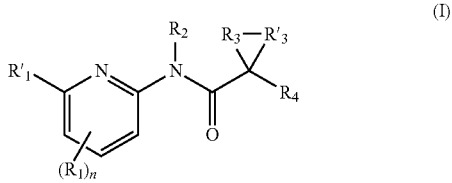

or a pharmaceutically acceptable salt thereof, wherein $R_1$, $R'_1$, $R_2$, $R_3$, $R'_3$, $R_4$, and n are described herein.

These compounds and pharmaceutically acceptable compositions are useful for treating or lessening the severity of a variety of diseases, disorders, or conditions, including, but not limited to, cystic fibrosis, hereditary emphysema, hereditary hemochromatosis, coagulation-fibrinolysis deficiencies, such as protein C deficiency, Type 1 hereditary angioedema, lipid processing deficiencies, such as familial hypercholesterolemia, Type 1 chylomicronemia, abetalipoproteinemia, lysosomal storage diseases, such as I-cell disease/pseudo-Hurler, mucopolysaccharidoses, Sandhof/Tay-Sachs, Crigler-Najjar type II, polyendocrinopathy/hyperinsulemia, Diabetes Mellitus, Laron dwarfism, myleoperoxidase deficiency, primary hypoparathyroidism, melanoma, glycanosis CDG type 1, hereditary emphysema, congenital hyperthyroidism, osteogenesis imperfecta, hereditary hypofibrinogenemia, ACT deficiency, Diabetes Insipidus (DI), neurophyseal DI, neprogenic DI, Charcot-Marie Tooth syndrome, Perlizaeus-Merzbacher disease, neurodegenerative diseases such as Alzheimer's disease, Parkinson's disease, amyotrophic lateral sclerosis, progressive supranuclear plasy, Pick's disease, several polyglutamine neurological disorders asuch as Huntington, spinocerebullar ataxia type I, spinal and bulbar muscular atrophy, dentatorubal pallidoluysian, and myotonic dystrophy, as well as spongiform encephalopathies, such as hereditary Creutzfeldt-Jakob disease, Fabry disease, Straussler-Scheinker syndrome, COPD, dry-eye disease, and Sjogren's disease.

DETAILED DESCRIPTION OF THE INVENTION

Definitions

As used herein, the following definitions shall apply unless otherwise indicated.

The term "ABC-transporter" as used herein means an ABC-transporter protein or a fragment thereof comprising at least one binding domain, wherein said protein or fragment thereof is present in vivo or in vitro. The term "binding domain" as used herein means a domain on the ABC-transporter that can bind to a modulator. See, e.g., Hwang, T. C. et al., J. Gen. Physiol. (1998): 111(3), 477-90.

The term "CFTR" as used herein means cystic fibrosis transmembrane conductance regulator or a mutation thereof capable of regulator activity, including, but not limited to, ΔF508 CFTR and G551D CFTR (see, e.g., http://www.genet.sickkids.on.ca/cftr/, for CFTR mutations).

The term "modulating" as used herein means increasing or decreasing, e.g. activity, by a measurable amount. Compounds that modulate ABC Transporter activity, such as CFTR activity, by increasing the activity of the ABC Transporter, e.g., a CFTR anion channel, are called agonists. Compounds that modulate ABC Transporter activity, such as CFTR activity, by decreasing the activity of the ABC Transporter, e.g., CFTR anion channel, are called antagonists. An agonist interacts with an ABC Transporter, such as CFTR anion channel, to increase the ability of the receptor to transduce an intracellular signal in response to endogenous ligand binding. An antagonist interacts with an ABC Transporter, such as CFTR, and competes with the endogenous ligand(s) or substrate(s) for binding site(s) on the receptor to decrease the ability of the receptor to transduce an intracellular signal in response to endogenous ligand binding.

The phrase "treating or reducing the severity of an ABC Transporter mediated disease" refers both to treatments for diseases that are directly caused by ABC Transporter and/or CFTR activities and alleviation of symptoms of diseases not directly caused by ABC Transporter and/or CFTR anion channel activities. Examples of diseases whose symptoms may be affected by ABC Transporter and/or CFTR activity include, but are not limited to, Cystic fibrosis, Hereditary emphysema, Hereditary hemochromatosis, Coagulation-Fibrinolysis deficiencies, such as Protein C deficiency, Type 1 hereditary angioedema, Lipid processing deficiencies, such as Familial hypercholesterolemia, Type 1 chylomicronemia, Abetalipoproteinemia, Lysosomal storage diseases, such as I-cell disease/Pseudo-Hurler, Mucopolysaccharidoses, Sandhof/Tay-Sachs, Crigler-Najjar type II, Polyendocrinopathy/Hyperinsulemia, Diabetes mellitus, Laron dwarfism, Myleoperoxidase deficiency, Primary hypoparathyroidism, Melanoma, Glycanosis CDG type 1, Hereditary emphysema, Congenital hyperthyroidism, Osteogenesis imperfecta, Hereditary hypofibrinogenemia, ACT deficiency, Diabetes insipidus (DI), Neurophyseal DI, Neprogenic DI, Charcot-Marie Tooth syndrome, Perlizaeus-Merzbacher disease, neurodegenerative diseases such as Alzheimer's disease, Parkinson's disease, Amyotrophic lateral sclerosis, Progressive supranuclear plasy, Pick's disease, several polyglutamine neurological disorders asuch as Huntington, Spinocerebullar ataxia type I, Spinal and bulbar muscular atrophy, Dentatorubal pallidoluysian, and Myotonic dystrophy, as well as Spongiform encephalopathies, such as Hereditary Creutzfeldt-Jakob disease, Fabry disease, Straussler-Scheinker syndrome, COPD, dry-eye disease, and Sjogren's disease.

For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausolito: 1999, and "March's Advanced Organic Chemistry", 5th Ed., Ed.: Smith, M. B. and March, J., John Wiley & Sons, New York: 2001, the entire contents of which are hereby incorporated by reference.

For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001.

As used herein the term "aliphatic" encompasses the terms alkyl, alkenyl, alkynyl, each of which being optionally substituted as set forth below.

As used herein, an "alkyl" group refers to a saturated aliphatic hydrocarbon group containing 1-8 (e.g., 1-6 or 1-4) carbon atoms. An alkyl group can be straight or branched. Examples of alkyl groups include, but are not limited to, methyl, ethyl, propyl, isopropyl, butyl, isobutyl, sec-butyl, tert-butyl, n-pentyl, n-heptyl, or 2-ethylhexyl. An alkyl group can be substituted (i.e., optionally substituted) with one or more substituents such as halo, cycloaliphatic [e.g., cycloalkyl or cycloalkenyl], heterocycloaliphatic [e.g., heterocycloalkyl or heterocycloalkenyl], aryl, heteroaryl, alkoxy, aroyl, heteroaroyl, acyl [e.g., (aliphatic)carbonyl, (cycloaliphatic)carbonyl, or (heterocycloaliphatic)carbonyl], nitro, cyano, amido [e.g., (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, heteroaralkylcarbonylamino], amino [e.g., aliphaticamino, cycloaliphaticamino, or heterocycloaliphaticamino], sulfonyl [e.g., aliphaticsulfonyl], sulfinyl, sulfanyl, sulfoxy, urea, thiourea, sulfamoyl, sulfamide, oxo, carboxy, carbamoyl, cycloaliphaticoxy, heterocycloaliphaticoxy, aryloxy, heteroaryloxy, aralkyloxy, heteroarylalkoxy, alkoxycarbonyl, alkylcarbonyloxy, or hydroxy. Without limitation, some examples of substituted alkyls include carboxyalkyl (such as HOOC-alkyl, alkoxycarbonylalkyl, and alkylcarbonyloxyalkyl), cyanoalkyl, hydroxyalkyl, alkoxyalkyl, acylalkyl, hydroxyalkyl, aralkyl, (alkoxyaryl)alkyl, (sulfonylamino) alkyl (such as (alkylsulfonylamino)alkyl), aminoalkyl, amidoalkyl, (cycloaliphatic)alkyl, cyanoalkyl, or haloalkyl.

As used herein, an "alkenyl" group refers to an aliphatic carbon group that contains 2-8 (e.g., 2-6 or 2-4) carbon atoms and at least one double bond. Like an alkyl group, an alkenyl group can be straight or branched. Examples of an alkenyl group include, but are not limited to, allyl, isoprenyl, 2-butenyl, and 2-hexenyl. An alkenyl group can be optionally substituted with one or more substituents such as halo, cycloaliphatic, heterocycloaliphatic, aryl, heteroaryl, alkoxy, aroyl, heteroaroyl, acyl [e.g., (cycloaliphatic)carbonyl, or (heterocycloaliphatic)carbonyl], nitro, cyano, acyl [e.g., aliphaticcarbonyl, cycloaliphaticcarbonyl, arylcarbonyl, heterocycloaliphaticcarbonyl or heteroarylcarbonyl], amido [e.g., (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, heteroaralkylcarbonylamino alkylaminocarbonyl, cycloalkylaminocarbonyl, heterocycloalkylaminocarbonyl, arylaminocarbonyl, or heteroarylaminocarbonyl], amino [e.g., aliphaticamino, or aliphaticsulfonylamino], sulfonyl [e.g., alkylsulfonyl, cycloaliphaticsulfonyl, or arylsulfonyl], sulfinyl, sulfanyl, sulfoxy, urea, thiourea, sulfamoyl, sulfamide, oxo, carboxy, carbamoyl, cycloaliphaticoxy, heterocycloaliphaticoxy, aryloxy, heteroaryloxy, aralkyloxy, heteroarylalkoxy, alkoxycarbonyl, alkylcarbonyloxy, or hydroxy.

As used herein, an "alkynyl" group refers to an aliphatic carbon group that contains 2-8 (e.g., 2-6 or 2-4) carbon atoms and has at least one triple bond. An alkynyl group can be straight or branched. Examples of an alkynyl group include, but are not limited to, propargyl and butynyl. An alkynyl group can be optionally substituted with one or more substituents such as aroyl, heteroaroyl, alkoxy, cycloalkyloxy, heterocycloalkyloxy, aryloxy, heteroaryloxy, aralkyloxy, nitro, carboxy, cyano, halo, hydroxy, sulfo, mercapto, sulfanyl [e.g., aliphaticsulfanyl or cycloaliphaticsulfanyl], sulfinyl [e.g., aliphaticsulfinyl or cycloaliphaticsulfinyl], sulfonyl [e.g., aliphaticsulfonyl, aliphaticaminosulfonyl, or cycloaliphaticsulfonyl], amido [e.g., aminocarbonyl, alkylaminocarbonyl, alkylcarbonylamino, cycloalkylaminocarbonyl, heterocycloalkylaminocarbonyl, cycloalkylcarbonylamino, arylaminocarbonyl, arylcarbonylamino, aralkylcarbonylamino, (heterocycloalkyl)carbonylamino, (cycloalkylalkyl)carbonylamino, heteroaralkylcarbonylamino, heteroarylcarbonylamino or heteroarylaminocarbonyl], urea, thiourea, sulfamoyl, sulfamide, alkoxycarbonyl, alkylcarbonyloxy, cycloaliphatic, heterocycloaliphatic, aryl, heteroaryl, acyl [e.g., (cycloaliphatic)carbonyl or (heterocycloaliphatic)carbonyl], amino [e.g., aliphaticamino], sulfoxy, oxo, carboxy, carbamoyl, (cycloaliphatic)oxy, (heterocycloaliphatic)oxy, or (heteroaryl)alkoxy.

As used herein, an "amido" encompasses both "aminocarbonyl" and "carbonylamino". These terms when used alone or in connection with another group refers to an amido group such as N(R$^X$R$^Y$)—C(O)— or R$^Y$C(O)—N(R$^X$)— when used terminally and —C(O)—N(R$^X$)— or —N(R$^X$)—C(O)— when used internally, wherein R$^X$ and R$^Y$ are defined below. Examples of amido groups include alkylamido (such as alkylcarbonylamino or alkylcarbonylamino), (heterocycloaliphatic)amido, (heteroaralkyl)amido, (heteroaryl)amido, (heterocycloalkyl)alkylamido, arylamido, aralkylamido, (cycloalkyl)alkylamido, or cycloalkylamido.

As used herein, an "amino" group refers to —NR$^X$R$^Y$ wherein each of R$^X$ and R$^Y$ is independently hydrogen, alkyl, cycloaliphatic, (cycloaliphatic)aliphatic, aryl, araliphatic, heterocycloaliphatic, (heterocycloaliphatic)aliphatic, heteroaryl, carboxy, sulfanyl, sulfinyl, sulfonyl, (aliphatic)carbonyl, (cycloaliphatic)carbonyl, ((cycloaliphatic)aliphatic)carbonyl, arylcarbonyl, (araliphatic)carbonyl, (heterocycloaliphatic)carbonyl, ((heterocycloaliphatic)aliphatic)carbonyl, (heteroaryl)carbonyl, or (heteroaraliphatic)carbonyl, each of which being defined herein and being optionally substituted. Examples of amino groups include alkylamino, dialkylamino, or arylamino. When the term "amino" is not the terminal group (e.g., alkylcarbonylamino), it is represented by —NR$^X$—. R$^X$ has the same meaning as defined above.

As used herein, an "aryl" group used alone or as part of a larger moiety as in "aralkyl", "aralkoxy", or "aryloxyalkyl" refers to monocyclic (e.g., phenyl); bicyclic (e.g., indenyl, naphthalenyl, tetrahydronaphthyl, tetrahydroindenyl); and tricyclic (e.g., fluorenyl tetrahydrofluorenyl, or tetrahydroanthracenyl, anthracenyl) ring systems in which the monocyclic ring system is aromatic or at least one of the rings in a bicyclic or tricyclic ring system is aromatic. The bicyclic and tricyclic ring systems include benzofused 2-3 membered carbocyclic rings. For example, a benzofused group includes phenyl fused with two or more $C_{4-8}$ carbocyclic moieties. An aryl is optionally substituted with one or more substituents including aliphatic [e.g., alkyl, alkenyl, or alkynyl]; cycloaliphatic; (cycloaliphatic)aliphatic; heterocycloaliphatic; (heterocycloaliphatic)aliphatic; aryl; heteroaryl; alkoxy; (cycloaliphatic)oxy; (heterocycloaliphatic)oxy; aryloxy; heteroaryloxy; (araliphatic)oxy; (heteroaraliphatic)oxy; aroyl; heteroaroyl; amino; oxo (on a non-aromatic carbocyclic ring of a benzofused bicyclic or tricyclic aryl); nitro; carboxy; amido; acyl [e.g., aliphaticcarbonyl; (cycloaliphatic)carbonyl; ((cycloaliphatic)aliphatic)carbonyl; (araliphatic)carbonyl; (heterocycloaliphatic) carbonyl; ((heterocycloaliphatic)aliphatic)carbonyl; or (heteroaraliphatic)carbonyl]; sulfonyl [e.g., aliphaticsulfonyl or aminosulfonyl]; sulfinyl [e.g., aliphaticsulfinyl or cycloaliphaticsulfinyl]; sulfanyl [e.g., aliphaticsulfanyl]; cyano; halo; hydroxy; mercapto; sulfoxy; urea; thiourea; sulfamoyl; sulfamide; or carbamoyl. Alternatively, an aryl can be unsubstituted.

Non-limiting examples of substituted aryls include haloaryl [e.g., mono-, di (such as p,m-dihaloaryl), and (trihalo)aryl]; (carboxy)aryl [e.g., (alkoxycarbonyl)aryl, ((aralkyl)carbonyloxy)aryl, and (alkoxycarbonyl)aryl]; (amido)aryl [e.g., (aminocarbonyl)aryl, (((alkylamino)alkyl)aminocarbonyl)aryl, (alkylcarbonyl)aminoaryl, (arylaminocarbonyl)aryl, and (((heteroaryl)amino)carbonyl)aryl]; aminoaryl [e.g., ((alkylsulfonyl)amino)aryl or ((dialkyl)amino)aryl]; (cyanoalkyl)aryl; (alkoxy)aryl; (sulfamoyl)aryl [e.g., (aminosulfonyl)aryl]; (alkylsulfonyl)aryl; (cyano)aryl; (hydroxyalkyl)aryl; ((alkoxy)alkyl)aryl; (hydroxy)aryl, ((carboxy)alkyl)aryl; (((dialkyl)amino)alkyl)aryl; (nitroalkyl)aryl; (((alkylsulfonyl)amino)alkyl)aryl; ((heterocloaliphatic)carbonyl)aryl; ((alkylsulfonyl)alkyl)aryl; (cyanoalkyl)aryl; (hydroxyalkyl)aryl; (alkylcarbonyl)aryl; alkylaryl; (trihaloalkyl)aryl; p-amino-m-alkoxycarbonylaryl; p-amino-m-cyanoaryl; p-halo-m-aminoaryl; or (m-(heterocycloaliphatic)-o-(alkyl))aryl.

As used herein, an "araliphatic" such as an "aralkyl" group refers to an aliphatic group (e.g., a $C_{1-4}$ alkyl group) that is substituted with an aryl group. "Aliphatic," "alkyl," and "aryl" are defined herein. An example of an araliphatic such as an aralkyl group is benzyl.

As used herein, an "aralkyl" group refers to an alkyl group (e.g., a $C_{1-4}$ alkyl group) that is substituted with an aryl group. Both "alkyl" and "aryl" have been defined above. An example of an aralkyl group is benzyl. An aralkyl is optionally substituted with one or more substituents such as aliphatic [e.g., alkyl, alkenyl, or alkynyl, including carboxyalkyl, hydroxyalkyl, or haloalkyl such as trifluoromethyl], cycloaliphatic [e.g., cycloalkyl or cycloalkenyl], (cycloalkyl)alkyl, heterocycloalkyl, (heterocycloalkyl)alkyl, aryl, heteroaryl, alkoxy, cycloalkyloxy, heterocycloalkyloxy, aryloxy, heteroaryloxy, aralkyloxy, heteroaralkyloxy, aroyl, heteroaroyl, nitro, carboxy, alkoxycarbonyl, alkylcarbonyloxy, amido [e.g., aminocarbonyl, alkylcarbonylamino, cycloalkylcarbonylamino, (cycloalkylalkyl)carbonylamino, arylcarbonylamino, aralkylcarbonylamino, (heterocloalkyl)carbonylamino, (heterocycloalkylalkyl)carbonylamino, heteroarylcarbonylamino, or heteroaralkylcarbonylamino], cyano, halo, hydroxy, acyl, mercapto, alkylsulfanyl, sulfoxy, urea, thiourea, sulfamoyl, sulfamide, oxo, or carbamoyl.

As used herein, a "bicyclic ring system" includes 8-12 (e.g., 9, 10, or 11) membered structures that form two rings, wherein the two rings have at least one atom in common (e.g., 2 atoms in common). Bicyclic ring systems include bicycloaliphatics (e.g., bicycloalkyl or bicycloalkenyl), bicycloheteroaliphatics, bicyclic aryls, and bicyclic heteroaryls.

As used herein, a "cycloaliphatic" group encompasses a "cycloalkyl" group and a "cycloalkenyl" group, each of which being optionally substituted as set forth below.

As used herein, a "cycloalkyl" group refers to a saturated carbocyclic mono- or bicyclic (fused or bridged) ring of 3-10 (e.g., 5-10) carbon atoms. Examples of cycloalkyl groups include cyclopropyl, cyclobutyl, cyclopentyl, cyclohexyl, cycloheptyl, adamantyl, norbornyl, cubyl, octahydroindenyl, decahydro-naphthyl, bicyclo[3.2.1]octyl, bicyclo[2.2.2]octyl, bicyclo[3.3.1]nonyl, bicyclo[3.3.2.]decyl, bicyclo[2.2.2]octyl, adamantyl, azacycloalkyl, or ((aminocarbonyl)cycloalkyl)cycloalkyl. A "cycloalkenyl" group, as used herein, refers to a non-aromatic carbocyclic ring of 3-10 (e.g., 4-8) carbon atoms having one or more double bonds. Examples of cycloalkenyl groups include cyclopentenyl, 1,4-cyclohexa-di-enyl, cycloheptenyl, cyclooctenyl, hexahydro-indenyl, octahydro-naphthyl, cyclohexenyl, cyclopentenyl, bicyclo[2.2.2]octenyl, or bicyclo[3.3.1]nonenyl. A cycloalkyl or cycloalkenyl group can be optionally substituted with one or more substituents such as aliphatic [e.g., alkyl, alkenyl, or alkynyl], cycloaliphatic, (cycloaliphatic) aliphatic, heterocycloaliphatic, (heterocycloaliphatic) aliphatic, aryl, heteroaryl, alkoxy, (cycloaliphatic)oxy, (heterocycloaliphatic)oxy, aryloxy, heteroaryloxy, (araliphatic)oxy, (heteroaraliphatic)oxy, aroyl, heteroaroyl, amino, amido [e.g., (aliphatic)carbonylamino, (cycloaliphatic)carbonylamino, ((cycloaliphatic)aliphatic)carbonylamino, (aryl)carbonylamino, (araliphatic)carbonylamino, (heterocycloaliphatic)carbonylamino, ((heterocycloaliphatic)aliphatic)carbonylamino, (heteroaryl)carbonylamino, or (heteroaraliphatic)carbonylamino], nitro, carboxy [e.g., HOOC—, alkoxycarbonyl, or alkylcarbonyloxy], acyl [e.g., (cycloaliphatic)carbonyl, ((cycloaliphatic) aliphatic)carbonyl, (araliphatic)carbonyl, (heterocycloaliphatic)carbonyl, ((heterocycloaliphatic)aliphatic)carbonyl, or (heteroaraliphatic)carbonyl], cyano, halo, hydroxy, mercapto, sulfonyl [e.g., alkylsulfonyl and arylsulfonyl], sulfinyl [e.g., alkylsulfinyl], sulfanyl [e.g., alkylsulfanyl], sulfoxy, urea, thiourea, sulfamoyl, sulfamide, oxo, or carbamoyl.

As used herein, "cyclic moiety" includes cycloaliphatic, heterocycloaliphatic, aryl, or heteroaryl, each of which has been defined previously.

As used herein, the term "heterocycloaliphatic" encompasses a heterocycloalkyl group and a heterocycloalkenyl group, each of which being optionally substituted as set forth below.

As used herein, a "heterocycloalkyl" group refers to a 3-10 membered mono- or bicylic (fused or bridged) (e.g., 5- to 10-membered mono- or bicyclic) saturated ring structure, in which one or more of the ring atoms is a heteroatom (e.g., N, O, S, or combinations thereof). Examples of a heterocycloalkyl group include piperidyl, piperazyl, tetrahydropyranyl, tetrahydrofuryl, 1,4-dioxolanyl, 1,4-dithianyl, 1,3-dioxolanyl, oxazolidyl, isoxazolidyl, morpholinyl, thiomorpholyl, octahydrobenzofuryl, octahydrochromenyl, octahydrothiochromenyl, octahydroindolyl, octahydropyrindinyl, decahydroquinolinyl, octahydrobenzo[b]thiopheneyl, 2-oxa-bicyclo[2.2.2]octyl, 1-aza-bicyclo[2.2.2]octyl, 3-aza-bicyclo[3.2.1]octyl, and 2,6-dioxa-tricyclo [3.3.1.0$^{3,7}$]nonyl. A monocyclic heterocycloalkyl group can be fused with a phenyl moiety such as tetrahydroisoquinoline. A "heterocycloalkenyl" group, as used herein, refers to a mono- or bicylic (e.g., 5- to 10-membered mono- or bicyclic) non-aromatic ring structure having one or more double bonds, and wherein one or more of the ring atoms is a heteroatom (e.g., N, O, or S). Monocyclic and bicycloheteroaliphatics are numbered according to standard chemical nomenclature.

A heterocycloalkyl or heterocycloalkenyl group can be optionally substituted with one or more substituents such as aliphatic [e.g., alkyl, alkenyl, or alkynyl], cycloaliphatic, (cycloaliphatic)aliphatic, heterocycloaliphatic, (heterocycloaliphatic)aliphatic, aryl, heteroaryl, alkoxy, (cycloaliphatic)oxy, (heterocycloaliphatic)oxy, aryloxy, heteroaryloxy, (araliphatic)oxy, (heteroaraliphatic)oxy, aroyl, heteroaroyl, amino, amido [e.g., (aliphatic)carbonylamino, (cycloaliphatic)carbonylamino, ((cycloaliphatic) aliphatic)carbonylamino, (aryl)carbonylamino, (araliphatic)carbonylamino, (heterocycloaliphatic)carbonylamino, ((heterocycloaliphatic) aliphatic)carbonylamino, (heteroaryl)carbonylamino, or (heteroaraliphatic)carbonylamino], nitro, carboxy [e.g., HOOC—, alkoxycarbonyl, or alkylcarbonyloxy], acyl [e.g., (cycloaliphatic)carbonyl, ((cycloaliphatic) aliphatic)carbonyl, (araliphatic)carbonyl, (heterocycloaliphatic)carbonyl, ((heterocycloaliphatic)aliphatic)carbonyl, or (heteroaraliphatic)carbonyl], nitro, cyano, halo, hydroxy, mercapto, sulfonyl [e.g., alkylsulfonyl or arylsulfonyl], sulfinyl [e.g., alkylsulfinyl], sulfanyl [e.g., alkylsulfanyl], sulfoxy, urea, thiourea, sulfamoyl, sulfamide, oxo, or carbamoyl.

A "heteroaryl" group, as used herein, refers to a monocyclic, bicyclic, or tricyclic ring system having 4 to 15 ring atoms wherein one or more of the ring atoms is a heteroatom (e.g., N, O, S, or combinations thereof) and in which the monocyclic ring system is aromatic or at least one of the rings in the bicyclic or tricyclic ring systems is aromatic. A heteroaryl group includes a benzofused ring system having 2 to 3 rings. For example, a benzofused group includes benzo fused with one or two 4 to 8 membered heterocycloaliphatic moieties (e.g., indolizyl, indolyl, isoindolyl, 3H-indolyl, indolinyl, benzo[b]furyl, benzo[b]thiophenyl, quinolinyl, or isoquinolinyl). Some examples of heteroaryl are azetidinyl, pyridyl, 1H-indazolyl, furyl, pyrrolyl, thienyl, thiazolyl, oxazolyl, imidazolyl, tetrazolyl, benzofuryl, isoquinolinyl, benzthiazolyl, xanthene, thioxanthene, phenothiazine, dihydroindole, benzo[1,3]dioxole, benzo[b]furyl, benzo[b]thiophenyl, indazolyl, benzimidazolyl, benzthiazolyl, puryl, cinnolyl, quinolyl, quinazolyl, phthalazyl, quinazolyl, quinoxalyl, isoquinolyl, 4H-quinolizyl, benzo-1,2,5-thiadiazolyl, or 1,8-naphthyridyl.

Without limitation, monocyclic heteroaryls include furyl, thiophenyl, 2H-pyrrolyl, pyrrolyl, oxazolyl, thiazolyl, imidazolyl, pyrazolyl, isoxazolyl, isothiazolyl, 1,3,4-thiadiazolyl, 2H-pyranyl, 4-H-pyranyl, pyridyl, pyridazyl, pyrimidyl, pyrazolyl, pyrazyl, or 1,3,5-triazyl. Monocyclic heteroaryls are numbered according to standard chemical nomenclature.

Without limitation, bicyclic heteroaryls include indolizyl, indolyl, isoindolyl, 3H-indolyl, indolinyl, benzo[b]furyl, benzo[b]thiophenyl, quinolinyl, isoquinolinyl, indolizyl, isoindolyl, indolyl, benzo[b]furyl, bexo[b]thiophenyl, indazolyl, benzimidazyl, benzthiazolyl, purinyl, 4H-quinolizyl, quinolyl, isoquinolyl, cinnolyl, phthalazyl, quinazolyl, quinoxalyl, 1,8-naphthyridyl, or pteridyl. Bicyclic heteroaryls are numbered according to standard chemical nomenclature.

A heteroaryl is optionally substituted with one or more substituents such as aliphatic [e.g., alkyl, alkenyl, or alkynyl]; cycloaliphatic; (cycloaliphatic)aliphatic; heterocycloaliphatic; (heterocycloaliphatic)aliphatic; aryl; heteroaryl; alkoxy; (cycloaliphatic)oxy; (heterocycloaliphatic)oxy; aryloxy; heteroaryloxy; (araliphatic)oxy; (heteroaraliphatic) oxy; aroyl; heteroaroyl; amino; oxo (on a non-aromatic carbocyclic or heterocyclic ring of a bicyclic or tricyclic heteroaryl); carboxy; amido; acyl [e.g., aliphaticcarbonyl; (cycloaliphatic)carbonyl; ((cycloaliphatic)aliphatic)carbonyl; (araliphatic)carbonyl; (heterocycloaliphatic)carbonyl; ((heterocycloaliphatic)aliphatic)carbonyl; or (heteroaraliphatic)carbonyl]; sulfonyl [e.g., aliphaticsulfonyl or aminosulfonyl]; sulfinyl [e.g., aliphaticsulfinyl]; sulfanyl [e.g., aliphaticsulfanyl]; nitro; cyano; halo; hydroxy; mercapto; sulfoxy; urea; thiourea; sulfamoyl; sulfamide; or carbamoyl. Alternatively, a heteroaryl can be unsubstituted.

Non-limiting examples of substituted heteroaryls include (halo)heteroaryl [e.g., mono- and di-(halo)heteroaryl]; (carboxy)heteroaryl [e.g., (alkoxycarbonyl)heteroaryl]; cyanoheteroaryl; aminoheteroaryl [e.g., ((alkylsulfonyl)amino) heteroaryl and ((dialkyl)amino)heteroaryl]; (amido) heteroaryl [e.g., aminocarbonylheteroaryl, ((alkylcarbonyl) amino)heteroaryl, ((((alkyl)amino)alkyl)aminocarbonyl) heteroaryl, (((heteroaryl)amino)carbonyl)heteroaryl, ((heterocycloaliphatic)carbonyl)heteroaryl, and ((alkylcarbonyl)amino)heteroaryl]; (cyanoalkyl)heteroaryl; (alkoxy) heteroaryl; (sulfamoyl)heteroaryl [e.g., (aminosulfonyl)heteroaryl]; (sulfonyl)heteroaryl [e.g., (alkylsulfonyl) heteroaryl]; (hydroxyalkyl)heteroaryl; (alkoxyalkyl) heteroaryl; (hydroxy)heteroaryl; ((carboxy)alkyl)heteroaryl; [((dialkyl)amino)alkyl]heteroaryl; (heterocycloaliphatic) heteroaryl; (cycloaliphatic)heteroaryl; (nitroalkyl)heteroaryl; (((alkylsulfonyl)amino)alkyl)heteroaryl; ((alkylsulfonyl)alkyl)heteroaryl; (cyanoalkyl)heteroaryl; (acyl) heteroaryl [e.g., (alkylcarbonyl)heteroaryl]; (alkyl) heteroaryl, and (haloalkyl)heteroaryl [e.g., trihaloalkylheteroaryl].

A "heteroaraliphatic" (such as a heteroaralkyl group) as used herein, refers to an aliphatic group (e.g., a $C_{1-4}$ alkyl group) that is substituted with a heteroaryl group. "Aliphatic," "alkyl," and "heteroaryl" have been defined above.

A "heteroaralkyl" group, as used herein, refers to an alkyl group (e.g., a $C_{1-4}$ alkyl group) that is substituted with a heteroaryl group. Both "alkyl" and "heteroaryl" have been defined above. A heteroaralkyl is optionally substituted with one or more substituents such as alkyl (including carboxyalkyl, hydroxyalkyl, and haloalkyl such as trifluoromethyl), alkenyl, alkynyl, cycloalkyl, (cycloalkyl)alkyl, heterocycloalkyl, (heterocycloalkyl)alkyl, aryl, heteroaryl, alkoxy, cycloalkyloxy, heterocycloalkyloxy, aryloxy, heteroaryloxy, aralkyloxy, heteroaralkyloxy, aroyl, heteroaroyl, nitro, carboxy, alkoxycarbonyl, alkylcarbonyloxy, aminocarbonyl, alkylcarbonylamino, cycloalkylcarbonylamino, (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, heteroaralkylcarbonylamino, cyano, halo, hydroxy, acyl, mercapto, alkylsulfanyl, sulfoxy, urea, thiourea, sulfamoyl, sulfamide, oxo, or carbamoyl.

As used herein, "cyclic moiety" includes cycloalkyl, heterocycloalkyl, cycloalkenyl, heterocycloalkenyl, aryl, or heteroaryl, each of which has been defined previously.

As used herein, an "acyl" group refers to a formyl group or $R^X$—C(O)— (such as -alkyl-C(O)—, also referred to as "alkylcarbonyl") where $R^X$ and "alkyl" have been defined previously. Acetyl and pivaloyl are examples of acyl groups.

As used herein, an "aroyl" or "heteroaroyl" refers to an aryl-C(O)— or a heteroaryl-C(O)—. The aryl and heteroaryl portion of the aroyl or heteroaroyl is optionally substituted as previously defined.

As used herein, an "alkoxy" group refers to an alkyl-O— group where "alkyl" has been defined previously.

As used herein, a "carbamoyl" group refers to a group having the structure —O—CO—$NR^XR^Y$ or —$NR^X$—CO—O—$R^Z$ wherein $R^X$ and $R^Y$ have been defined above and $R^Z$ can be aliphatic, aryl, araliphatic, heterocycloaliphatic, heteroaryl, or heteroaraliphatic.

As used herein, a "carboxy" group refers to —COOH, —$COOR^X$, —OC(O)H, —OC(O)$R^X$ when used as a terminal group; or —OC(O)— or —C(O)O— when used as an internal group.

As used herein, a "haloaliphatic" group refers to an aliphatic group substituted with 1, 2, or 3 halogen. For instance, the term haloalkyl includes the group —$CF_3$.

As used herein, a "mercapto" group refers to —SH.

As used herein, a "sulfo" group refers to —$SO_3H$ or —$SO_3R^X$ when used terminally or —$S(O)_3$— when used internally.

As used herein, a "sulfamide" group refers to the structure —$NR^X$—$S(O)_2$—$NR^YR^Z$ when used terminally and —$NR^X$—$S(O)_2$—$NR^Y$— when used internally, wherein $R^X$, $R^Y$, and $R^Z$ have been defined above.

As used herein, a "sulfamoyl" group refers to the structure —$S(O)_2$—$NR^XR^Y$ or —$NR^X$—$S(O)_2$—$R^Z$ when used terminally; or —$S(O)_2$—$NR^X$— or —$NR^X$—$S(O)_2$— when used internally, wherein $R^X$, $R^Y$, and $R^Z$ are defined above.

As used herein a "sulfanyl" group refers to —S—$R^X$ when used terminally and —S— when used internally, wherein $R^X$ has been defined above. Examples of sulfanyls include alkylsulfanyl.

As used herein a "sulfinyl" group refers to —S(O)—$R^X$ when used terminally and —S(O)— when used internally, wherein $R^X$ has been defined above.

As used herein, a "sulfonyl" group refers to —$S(O)_2$—$R^X$ when used terminally and —$S(O)_2$— when used internally, wherein $R^X$ has been defined above.

As used herein, a "sulfoxy" group refers to —O—SO—$R^X$ or —SO—O—$R^X$, when used terminally and —O—S(O)— or —S(O)—O— when used internally, where $R^X$ has been defined above.

As used herein, a "halogen" or "halo" group refers to fluorine, chlorine, bromine or iodine.

As used herein, an "alkoxycarbonyl," which is encompassed by the term carboxy, used alone or in connection with another group refers to a group such as alkyl-O—C(O)—.

As used herein, an "alkoxyalkyl" refers to an alkyl group such as alkyl-O-alkyl-, wherein alkyl has been defined above.

As used herein, a "carbonyl" refer to —C(O)—.

As used herein, an "oxo" refers to =O.

As used herein, an "aminoalkyl" refers to the structure ($R^XR^Y$)N-alkyl-.

As used herein, a "cyanoalkyl" refers to the structure (NC)-alkyl-.

As used herein, a "urea" group refers to the structure —$NR^X$—CO—$NR^YR^Z$ and a "thiourea" group refers to the structure —$NR^X$—CS—$NR^YR^Z$ when used terminally and —$NR^X$—CO—$NR^Y$— or —$NR^X$—CS—$NR^Y$— when used internally, wherein $R^X$, $R^Y$, and $R^Z$ have been defined above.

As used herein, a "guanidino" group refers to the structure —N=C(N($R^XR^Y$))N($R^XR^Y$) wherein $R^X$ and $R^Y$ have been defined above.

As used herein, the term "amidino" group refers to the structure —C=($NR^X$)N($R^XR^Y$) wherein $R^X$ and $R^Y$ have been defined above.

In general, the term "vicinal" refers to the placement of substituents on a group that includes two or more carbon atoms, wherein the substituents are attached to adjacent carbon atoms.

In general, the term "geminal" refers to the placement of substituents on a group that includes two or more carbon atoms, wherein the substituents are attached to the same carbon atom.

The terms "terminally" and "internally" refer to the location of a group within a substituent. A group is terminal when the group is present at the end of the substituent not further bonded to the rest of the chemical structure. Carboxyalkyl, i.e., $R^XO(O)C$-alkyl is an example of a carboxy group used terminally. A group is internal when the group is present in the middle of a substituent to at the end of the substituent bound to the rest of the chemical structure. Alkylcarboxy (e.g., alkyl-C(O)O— or alkyl-OC(O)—) and alkylcarboxyaryl (e.g., alkyl-C(O)O-aryl- or alkyl-O(CO)-aryl-) are examples of carboxy groups used internally.

As used herein, the term "amidino" group refers to the structure —C=($NR^X$)N($R^XR^Y$) wherein $R^X$ and $R^Y$ have been defined above.

As used herein, "cyclic group" includes mono-, bi-, and tri-cyclic ring systems including cycloaliphatic, heterocycloaliphatic, aryl, or heteroaryl, each of which has been previously defined.

As used herein, a "bridged bicyclic ring system" refers to a bicyclic heterocyclicalipahtic ring system or bicyclic cycloaliphatic ring system in which the rings are bridged. Examples of bridged bicyclic ring systems include, but are not limited to, adamantanyl, norbornanyl, bicyclo[3.2.1]octyl, bicyclo[2.2.2]octyl, bicyclo[3.3.1]nonyl, bicyclo[3.2.3]nonyl, 2-oxa-bicyclo[2.2.2]octyl, 1-aza-bicyclo[2.2.2]octyl, 3-aza-bicyclo[3.2.1]octyl, and 2,6-dioxa-tricyclo[3.3.1.03.7]nonyl. A bridged bicyclic ring system can be optionally substituted with one or more substituents such as alkyl (including carboxyalkyl, hydroxyalkyl, and haloalkyl such as trifluoromethyl), alkenyl, alkynyl, cycloalkyl, (cycloalkyl)alkyl, heterocycloalkyl, (heterocycloalkyl)alkyl, aryl, heteroaryl, alkoxy, cycloalkyloxy, heterocycloalkyloxy, aryloxy, heteroaryloxy, aralkyloxy, heteroaralkyloxy, aroyl, heteroaroyl, nitro, carboxy, alkoxycarbonyl, alkylcarbonyloxy, aminocarbonyl, alkylcarbonylamino, cycloalkylcarbonylamino, (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, heteroaralkylcarbonylamino, cyano, halo, hydroxy, acyl, mercapto, alkylsulfanyl, sulfoxy, urea, thiourea, sulfamoyl, sulfamide, oxo, or carbamoyl.

As used herein, an "aliphatic chain" refers to a branched or straight aliphatic group (e.g., alkyl groups, alkenyl groups, or alkynyl groups). A straight aliphatic chain has the structure —$[CH_2]_v$—, where v is 1-6. A branched aliphatic chain is a straight aliphatic chain that is substituted with one or more aliphatic groups. A branched aliphatic chain has the structure —$[CHQ]_v$— where Q is hydrogen or an aliphatic group; however, Q shall be an aliphatic group in at least one instance. The term aliphatic chain includes alkyl chains, alkenyl chains, and alkynyl chains, where alkyl, alkenyl, and alkynyl are defined above.

The phrase "optionally substituted" is used interchangeably with the phrase "substituted or unsubstituted." As described herein, compounds of the invention can optionally be substituted with one or more substituents, such as are illustrated generally above, or as exemplified by particular classes, subclasses, and species of the invention. As described herein, the variables $R_1$, $R_2$, $R_3$, and $R_4$, and other variables contained therein formulae I encompass specific groups, such as alkyl and aryl. Unless otherwise noted, each of the specific groups for the variables $R_1$, $R_2$, $R_3$, and $R_4$, and other variables contained therein can be optionally substituted with one or more substituents described herein. Each substituent of a specific group is further optionally substituted with one to three of halo, cyano, oxoalkoxy, hydroxy, amino, nitro, aryl, haloalkyl, and alkyl. For instance, an alkyl group can be substituted with alkylsulfanyl and the alkylsulfanyl can be optionally substituted with one to three of halo, cyano, oxoalkoxy, hydroxy, amino, nitro, aryl, haloalkyl, and alkyl. As an additional example, the cycloalkyl portion of a (cycloalkyl)carbonylamino can be optionally substituted with one to three of halo, cyano, alkoxy, hydroxy, nitro, haloalkyl, and alkyl. When two alkoxy groups are bound to the same atom or adjacent atoms, the two alkoxy groups can form a ring together with the atom(s) to which they are bound.

In general, the term "substituted," whether preceded by the term "optionally" or not, refers to the replacement of hydrogen radicals in a given structure with the radical of a specified substituent. Specific substituents are described above in the definitions and below in the description of compounds and examples thereof. Unless otherwise indicated, an optionally substituted group can have a substituent at each substitutable position of the group, and when more than one position in any given structure can be substituted with more than one substituent selected from a specified group, the substituent can be either the same or different at every position. A ring substituent, such as a heterocycloalkyl, can be bound to another ring, such as a cycloalkyl, to form a spiro-bicyclic ring system, e.g., both rings share one common atom. As one of ordinary skill in the art will recognize, combinations of substituents envisioned by this invention are those combinations that result in the formation of stable or chemically feasible compounds.

The phrase "up to", as used herein, refers to zero or any integer number that is equal or less than the number following the phrase. For example, "up to 3" means any one of 0, 1, 2, and 3.

The phrase "stable or chemically feasible," as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

As used herein, an effective amount is defined as the amount required to confer a therapeutic effect on the treated patient, and is typically determined based on age, surface area, weight, and condition of the patient. The interrelationship of dosages for animals and humans (based on milligrams per meter squared of body surface) is described by Freireich et al., *Cancer Chemother. Rep.*, 50: 219 (1966). Body surface area may be approximately determined from height and weight of the patient. See, e.g., Scientific Tables, Geigy Pharmaceuticals, Ardsley, N.Y., 537 (1970). As used herein, "patient" refers to a mammal, including a human.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C- or $^{14}$C-enriched carbon are within the scope of this invention. Such compounds are useful, for example, as analytical tools or probes in biological assays.

Compounds

Compounds of the present invention are useful modulators of ABC transporters and are useful in the treatment of ABC transport mediated diseases.

Compounds

The present invention includes a compound of formula I,

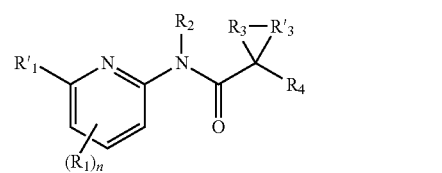

or a pharmaceutically acceptable salt thereof, wherein:
each $R'_1$ is:

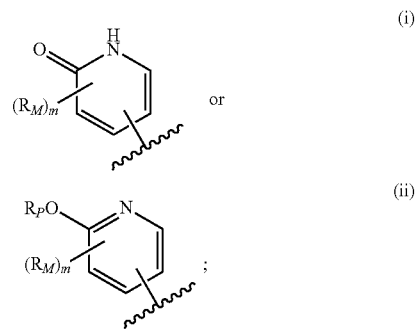

wherein:
m is 0-4;
$R_P$ is optionally substituted C1-C6 aliphatic, wherein up to two carbon units therein are optionally and independently replaced by —CO—, —CONR$^N$—, —CO$_2$—, —OCO—, —NR$^N$CO$_2$—, —O—, —OCONR$^N$—, —NR$^N$CO—, —S—, —SO—, —SO$_2$—, —NR$^N$—;

each $R_M$ is independently —Z$^M$R$_{11}$, wherein each Z$^M$ is independently a bond or an optionally substituted branched or straight C$_{1-6}$ aliphatic chain wherein up to two carbon units of Z$^M$ are optionally and independently replaced by —CO—, —CONR$^N$—, —CO$_2$—, —OCO—, —CHR$^N$—,

—NR$^N$CO$_2$—, —O—, —OCONR$^N$—, —NR$^N$CO—, —S—, —SO—, —SO$_2$—, —NR$^N$—;

each R$_{11}$ is independently R$^N$, halo, —OH, —NH$_2$, —CN, —CF$_3$, or —OCF$_3$;

each R$^N$ is independently hydrogen, an optionally substituted C$_{1-8}$ aliphatic group, an optionally substituted cycloaliphatic, an optionally substituted heterocycloaliphatic, an optionally substituted aryl, or an optionally substituted heteroaryl;

each R$_1$ is an optionally substituted C$_{1-6}$ aliphatic, an optionally substituted C$_{1-6}$ alkoxy, an optionally substituted C$_{3-10}$ cycloaliphatic, —CN, halo, or hydroxy;

each R$_2$ is hydrogen or an optionally substituted C$_{1-6}$ aliphatic;

each R$_3$ and R'$_3$ together with the carbon atom to which they are attached form an optionally substituted C$_{3-7}$ cycloaliphatic or an optionally substituted heterocycloaliphatic;

each R$_4$ is an optionally substituted aryl; and n is 0-3.

Embodiments

Substituent R'$_1$

In one embodiment, R'$_1$ is selected from:

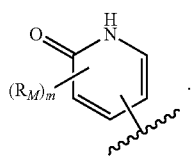

(i)

In one embodiment, R'$_1$ is selected from:

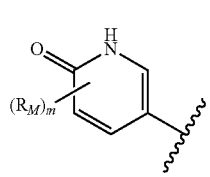

(i-a)

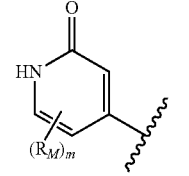

(i-b)

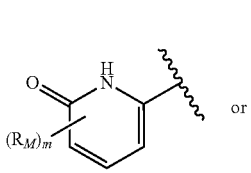

(i-c)

or

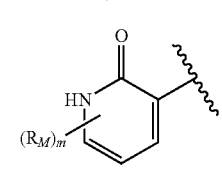

(i-d)

In one embodiment, R'$_1$ is:

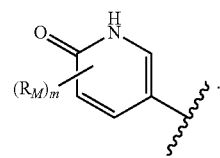

(i-a)

In another embodiment, R'$_1$ is:

(i-b)

In another embodiment, R'$_1$ is:

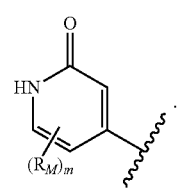

(i-c)

In another embodiment, R'$_1$ is:

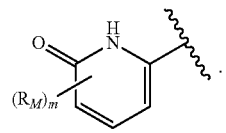

(i-d)

In another embodiment, R'$_1$ is selected from:

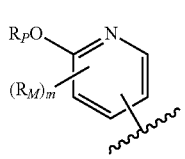

(ii)

In another embodiment, R'$_1$ is selected from:

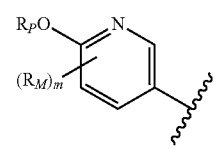

(ii-a)

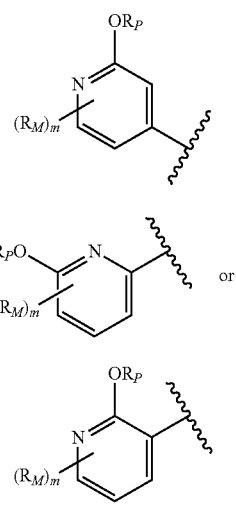

In one embodiment, R'$_1$ is:

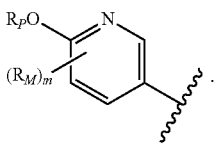

In another embodiment, R'$_1$ is:

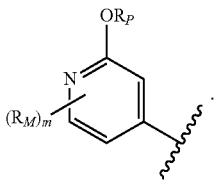

In another embodiment, R'$_1$ is:

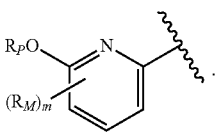

In another embodiment, R'$_1$ is:

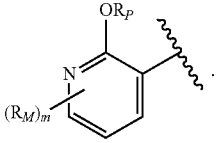

Substituent R$_1$

Each R$_1$ is independently an optionally substituted C$_{1-6}$ aliphatic, an optionally substituted C$_{1-6}$ alkoxy, an optionally substituted C$_{3-10}$ membered cycloaliphatic, —CN, halo, or hydroxy.

In some embodiments, one R$_1$ is an optionally substituted C$_{1-6}$ aliphatic. In several examples, one R$_1$ is an optionally substituted C$_{1-6}$ alkyl, an optionally substituted C$_{2-6}$ alkenyl, or an optionally substituted C$_{2-6}$ alkynyl. In several examples, one R$_1$ is C$_{1-6}$ alkyl, C$_{2-6}$ alkenyl, or C$_{2-6}$ alkynyl.

In several embodiments, R$_1$ is halo.

In several embodiments, R$_1$ is —CN.

In some embodiments, R$_1$ is methyl, ethyl, i-propyl, t-butyl, cyclopropyl, cyclobutyl, cyclopentyl, cyclohexyl, allyl, F, Cl, methoxy, ethoxy, i-propoxy, t-butoxy, or CF$_3$. In several examples, R$_1$ is methyl, or methoxy. Or, R$_1$ can be methyl.

Substituent R$_2$

R$_2$ can be hydrogen. Or, R$_2$ can be an optionally substituted C$_{1-6}$ aliphatic.

In several embodiments, R$_2$ is hydrogen.

Substituents R$_3$ and R'$_3$

Each R$_3$ and R'$_3$ together with the carbon atom to which they are attached form a C$_{3-7}$ cycloaliphatic or a heterocycloaliphatic, each of which is optionally substituted with 1, 2, or 3 substituents.

In several embodiments, R$_3$ and R'$_3$ together with the carbon atom to which they are attached form a C$_{3-7}$ cycloaliphatic or a C$_{3-7}$ heterocycloaliphatic, each of which is optionally substituted with 1, 2, or 3 of —Z$^B$R$_2$, wherein each Z$^B$ is independently a bond, or an optionally substituted branched or straight C$_{1-4}$ aliphatic chain wherein up to two carbon units of Z$^B$ are optionally and independently replaced by —CO—, —CONR$^B$—, —CO$_2$—, —OCO—, —NR$^B$CO$_2$—, —O—, —OCONR$^B$—, —NR$^B$CO—, —S—, —SO—, —SO$_2$—, or —NR$^B$—; each R$_7$ is independently R$^B$, halo, —OH, —NH$_2$, —NO$_2$, —CN, —CF$_3$, or —OCF$_3$; and each R$^B$ is independently hydrogen, an optionally substituted C$_{1-8}$ aliphatic group, an optionally substituted cycloaliphatic, an optionally substituted heterocycloaliphatic, an optionally substituted aryl, or an optionally substituted heteroaryl.

In several embodiments, R$_3$ and R'$_3$ together with the carbon atom to which they are attached form a 3, 4, 5, or 6 membered cycloaliphatic that is optionally substituted with 1, 2, or 3 substituents. In several examples, R$_3$, R'$_3$, and the carbon atom to which they are attached form an optionally substituted cyclopropyl group. In several alternative examples, R$_3$, R'$_3$, and the carbon atom to which they are attached form an optionally substituted cyclobutyl group. In several other examples, R$_3$, R'$_3$, and the carbon atom to which they are attached form an optionally substituted cyclopentyl group. In other examples, R$_3$, R'$_3$, and the carbon atom to which they are attached form an optionally substituted cyclohexyl group. In more examples, R$_3$ and R'$_3$ together with the carbon atom to which they are attached form an unsubstituted cyclopropyl.

In some embodiments, R$_3$ and R'$_3$ together with the carbon atom to which they are attached form an unsubstituted C$_{3-7}$ cycloaliphatic. In several examples, R$_3$ and R'$_3$ together with the carbon atom to which they are attached form an unsubstituted cyclopropyl, an unsubstituted cyclopentyl, or an unsubstituted cyclohexyl. In some embodiments, R$_3$ and R'$_3$ together with the carbon atom to which they are attached form an unsubstituted cyclopropyl.

Substituent R$_4$

In several embodiments, R$_4$ is an aryl having 6 to 10 atoms (e.g., 7 to 10 atoms) optionally substituted with 1, 2, or 3 substituents. Examples of R$_4$ include optionally substituted benzene, naphthalene, or indene. Or, examples of R$_4$ can be optionally substituted phenyl, optionally substituted naphthyl, or optionally substituted indenyl.

In some embodiments, $R_4$ is an aryl, optionally substituted with 1, 2, or 3 of $-Z^C R_8$. In some embodiments, $R_4$ is phenyl optionally substituted with 1, 2, or 3 of $-Z^C R_8$. Each $Z^C$ is independently a bond or an optionally substituted branched or straight $C_{1-6}$ aliphatic chain wherein up to two carbon units of $Z^C$ are optionally and independently replaced by $-CO-$, $-CS-$, $-CONR^C-$, $-CONR^C NR^C-$, $-CO_2-$, $-OCO-$, $-NR^C CO_2-$, $-O-$, $-NR^C CO-NR^C-$, $-OCONR^C-$, $-NR^C NR^C-$, $-NR^C CO-$, $-S-$, $-SO-$, $-SO_2-$, $-NR^C-$, $-SO_2 NR^C-$, $-NR^C SO_2-$, or $-NR^C SO_2 NR^C-$. Each $R_8$ is independently $R^C$, halo, $-OH$, $-NH_2$, $-NO_2$, $-CN$, $-CF_3$, or $-OCF_3$. Each $R^C$ is independently hydrogen, an optionally substituted $C_{1-8}$ aliphatic group, an optionally substituted cycloaliphatic, an optionally substituted heterocycloaliphatic, an optionally substituted aryl, or an optionally substituted heteroaryl.

In some embodiments, two occurrences of $-Z^C R_8$, taken together with carbons to which they are attached, form a 4-8 membered saturated, partially saturated, or aromatic ring with up to 3 ring atoms independently selected from the group consisting of O, NH, $NR^C$, and S; wherein $R^C$ is defined herein.

In several embodiments, $R_4$ is selected from:

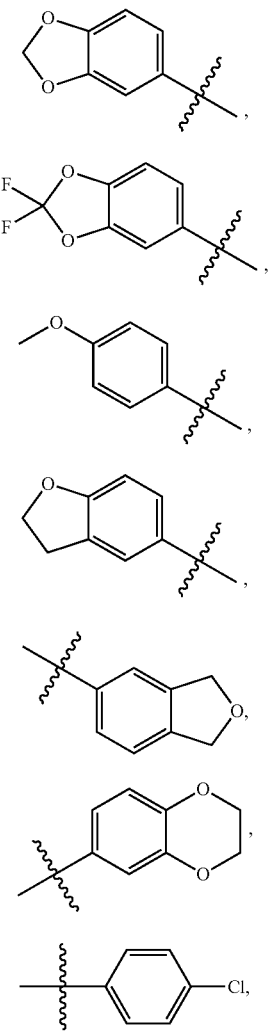

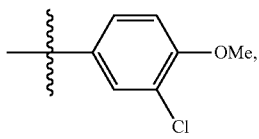

(h)

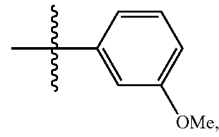

(i)

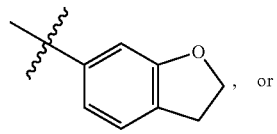

, or (j)

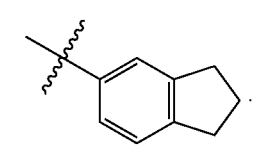

(k)

In one embodiment, $R_4$ is (a). Or, $R_4$ is (b). In some embodiments, $R_4$ is (c). In other embodiments, $R_4$ is (d). In some embodiments, $R_4$ is (e). In some embodiments, $R_4$ is (f). In some embodiments, $R_4$ is (g). In some embodiments, $R_4$ is (h). In some embodiments, $R_4$ is (i). In some embodiments, $R_4$ is (i). In some embodiments, $R_4$ is (k).

In some embodiments, the present invention relates to compounds of formula I and the attendant definitions, wherein m is 0-2. In some embodiments, m is 1. In some embodiments, m is 0.

In some embodiments, the present invention relates to compounds of formula I and the attendant definitions, wherein $R_M$ is independently $-Z^M R_{11}$, wherein each $Z^M$ is independently a bond or $C_{1-4}$ alkyl chain wherein up to two carbon units of $Z^M$ are optionally and independently replaced by $-CO-$, $-CONR^N-$, $-CHR^N-$, $-CO_2-$, $-OCO-$, $-NR^N CO_2-$, $-O-$, $-OCONR^N-$, $-NR^N CO-$, $-S-$, $-SO-$, $-SO_2-$, or $-NR^N-$. In other embodiments, $R_M$ is independently $-Z^M R_{11}$, wherein each $Z^M$ is independently a bond or $C_{1-4}$ alkyl chain wherein up to two carbon units of $Z^M$ are optionally and independently replaced by $-CONR^N-$, $-CO_2-$, $-O-$, $-CHR^N-$, or $-NR^N-$.

In some embodiments, the present invention relates to compounds of formula I and the attendant definitions, wherein $R_{11}$ is independently $R^N$, halo, $-OH$, $-NH_2$, or $-CN$. In some embodiments, $R^N$ is independently hydrogen, C1-C6 aliphatic, or C3-C6 cycloaliphatic.

In some embodiments, the present invention relates to compounds of formula I and the attendant definitions, wherein $R^M$ is absent or is selected from $-CH_2OH$, NHC(O)Me, Et, Me, $-CH_2C(O)OH$, $-CH_2C(O)OMe$, $-CH_2CH_2OH$, $-C(O)OH$, halo, OH, C(O)NHMe, C(O)NH_2, $-CH_2CH(OH)CH_2OH$, $NH_2$, OMe, $CH_2CN$, $CH_2CH_2SO_2CH_3$, $CH_2CONHCN$, $CONMe_2$, or CN.

In some embodiments, the present invention relates to compounds of formula I and the attendant definitions, wherein $R^P$ is C1-C6 aliphatic, wherein up to two carbon units therein are optionally and independently replaced by $-CO-$, $-CS-$, $-CONR^N-$, $-CO_2-$, $-NR^N CO_2-$, $-O-$, $-S-$, $-SO-$, $-SO_2-$, or $-NR^N-$.

In some embodiments, the present invention relates to compounds of formula I and the attendant definitions, wherein n is 1-2. In some embodiments, n is 1.

Exemplary Compound Families

In another aspect, the present invention includes compounds of formula I and the attendant definitions, wherein the compounds have formula II:

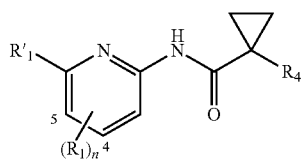

II or a pharmaceutically acceptable salt thereof,
wherein:
$R'_1$ is selected from:

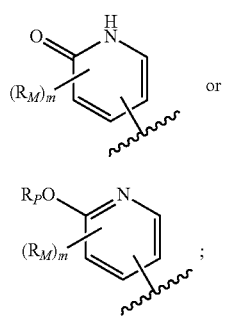

(i)

or (ii)

n is 0-2;
m is 0-4;
$R_1$ is C1-6 aliphatic, halo, or —CN; and
$R_4$ is selected from:

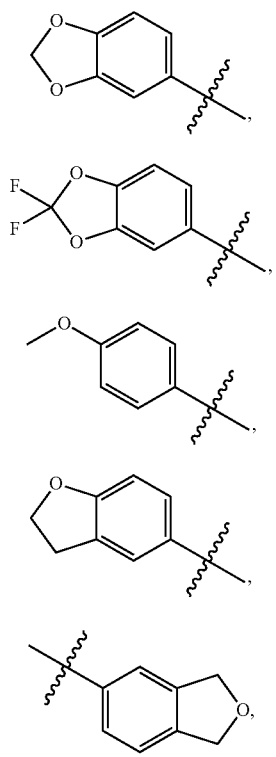

(a)

(b)

(c)

(d)

(e)

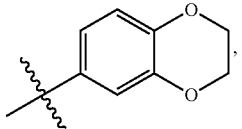

(f)

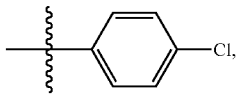

(g)

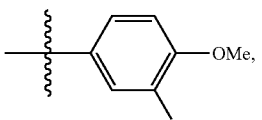

(h)

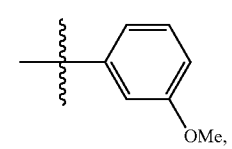

(i)

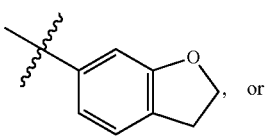

(j)

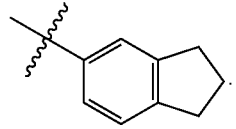

(k)

In some embodiments of formula II, n is 1. Or, n is 2.

In some embodiments, $R_1$ is selected from the group consisting of methyl, ethyl, i-propyl, t-butyl, F, Cl, or —CN. Or, $R_1$ is methyl. In one embodiment, n is 1 and $R_1$ is 5-methyl. In one embodiment, n is 1 and $R_1$ is 4-methyl. In one embodiment, n is 2 and one $R_1$ is 4-methyl and the other $R_1$ is 5-methyl.

In another aspect, the present invention includes compounds of formula II and the attendant definitions, wherein the compounds have formula IIA:

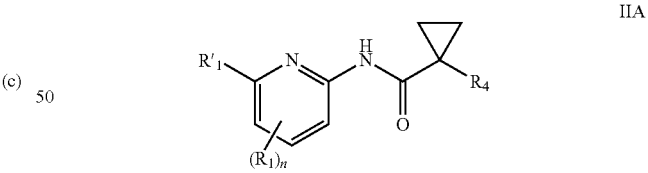

IIA or a pharmaceutically acceptable salt thereof,
wherein:
$R'_1$ is:

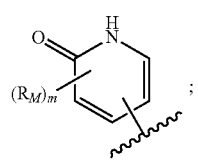

(i)

n is 0-2;
m is 0-4;
$R_1$ is $C_{1-6}$ aliphatic, halo, or —CN; and $R_4$ is selected from:

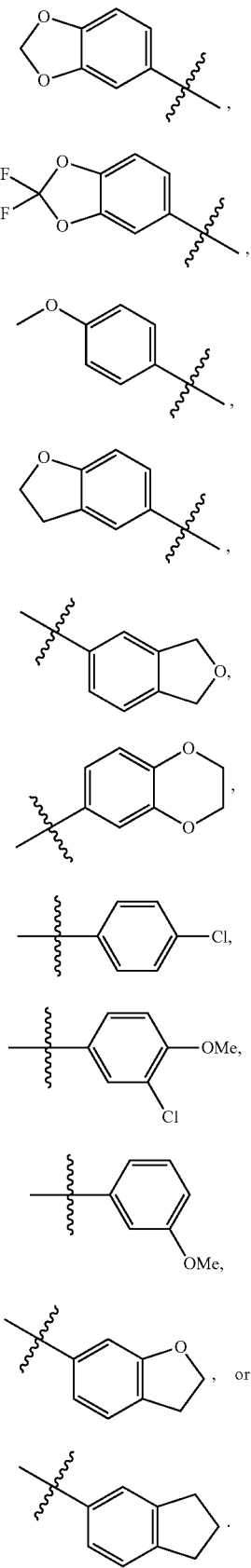

(a), (b), (c), (d), (e), (f), (g), (h), (i), (j), or (k)

In one embodiment of formula IIA, $R'_1$ is selected from:

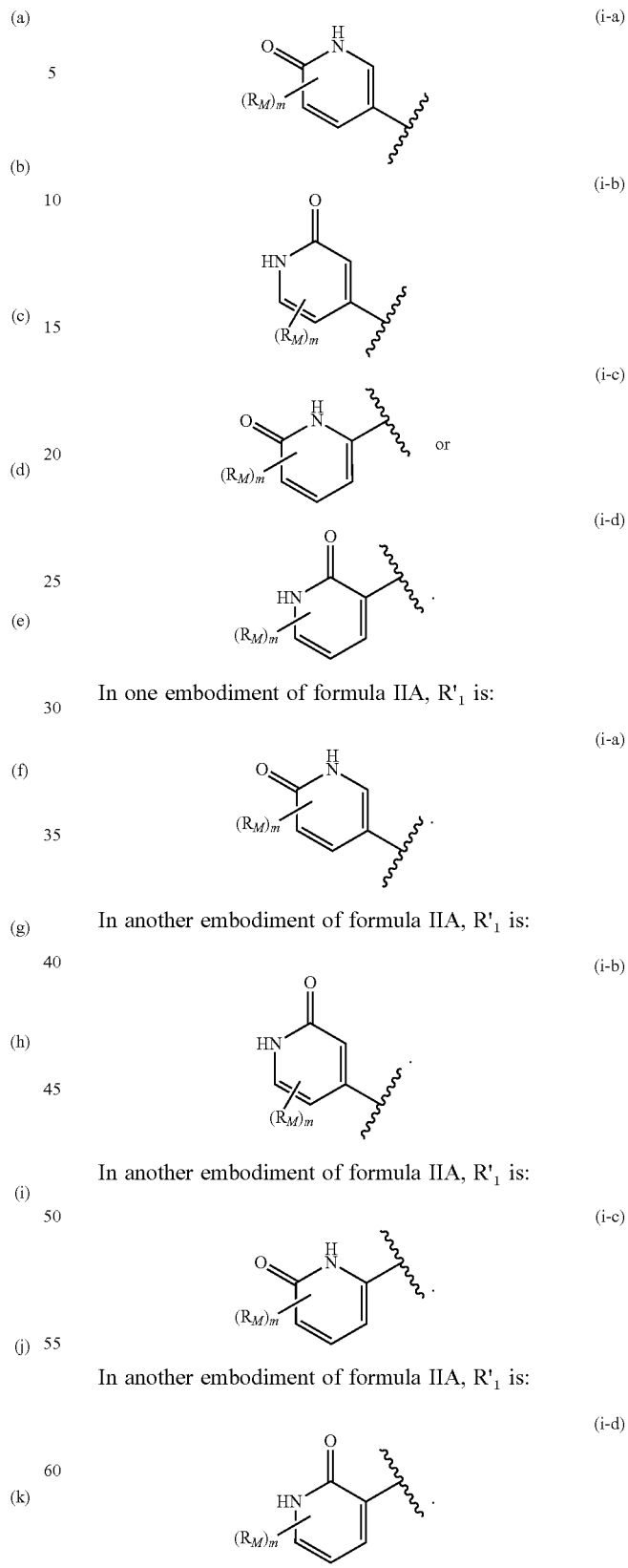

(i-a), (i-b), (i-c), or (i-d)

In one embodiment of formula IIA, $R'_1$ is:

(i-a)

In another embodiment of formula IIA, $R'_1$ is:

(i-b)

In another embodiment of formula IIA, $R'_1$ is:

(i-c)

In another embodiment of formula IIA, $R'_1$ is:

(i-d)

In some embodiments, the present invention includes compounds of formula II and the attendant definitions, wherein the compounds have formula IIB:

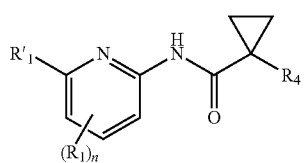
or a pharmaceutically acceptable salt thereof, wherein:
R'₁ is:
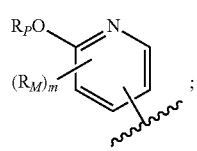
m is 0-4;
n is 0-2;
R₁ is C1-6 aliphatic, halo, or —CN; and
R₄ is selected from:
(a)
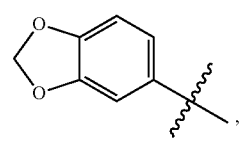
(b)
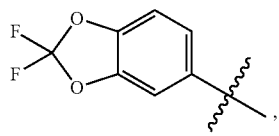
(c)
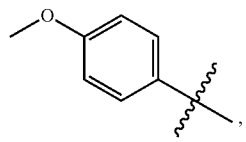
(d)
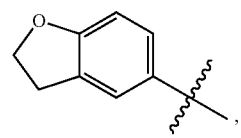
(e)
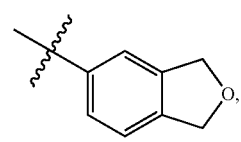
(f)
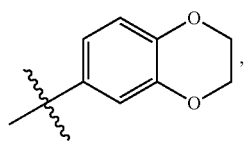
(g)
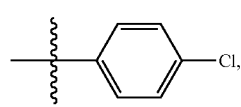
(h)
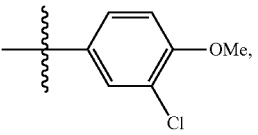
(i)
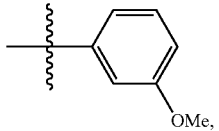
(j)
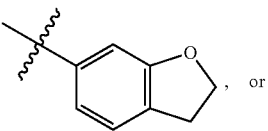, or
(k)
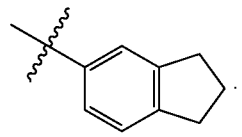.
In another embodiment of formula IIB, R'₁ is selected from:
(ii-a)
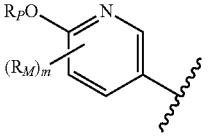
(ii-b)
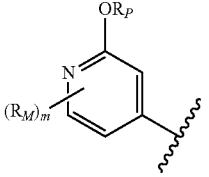
(ii-c)
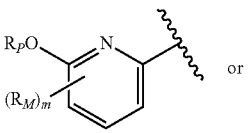 or
(ii-d)
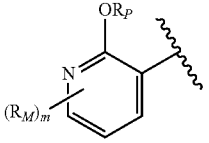
In one embodiment of formula IIB, R'₁ is:
(ii-a)
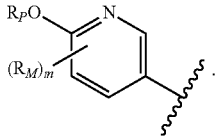.

In another embodiment of formula IIB, R'₁ is:

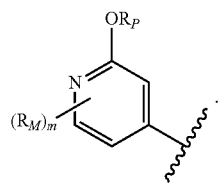
(ii-b)

In another embodiment of formula IIB, R'₁ is:

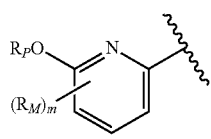
(ii-c)

In another embodiment of formula IIB, R'₁ is:

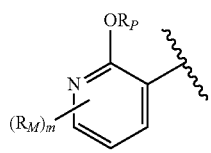
(ii-d)

In some embodiments, the present invention includes compounds of formula I and the attendant definitions, wherein the compounds have formula III:

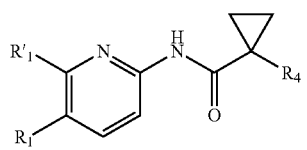
III or a pharmaceutically acceptable salt thereof,
wherein:
R'₁ is selected from:

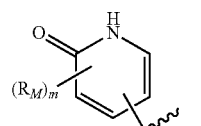
(i)

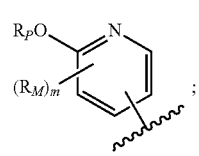
(ii)

m is 0-4;
R₁ is C1-6 aliphatic, halo, or —CN; and

R₄ is selected from:

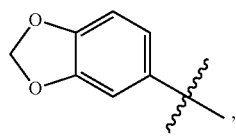
(a)

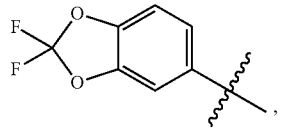
(b)

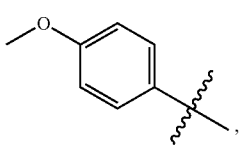
(c)

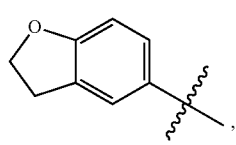
(d)

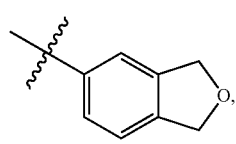
(e)

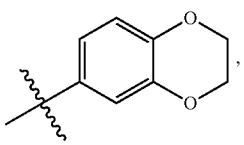
(f)

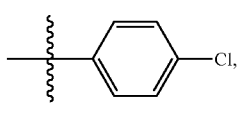
(g)

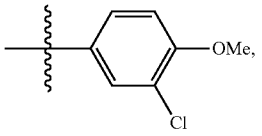
(h)

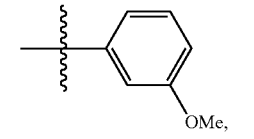
(i)

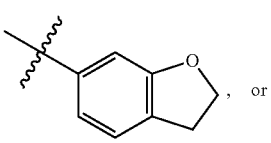
(j)

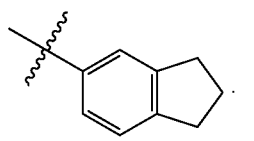
(k)

In one embodiment of compounds of formula III, $R_1$ is methyl. In one embodiment of compounds of formula III, $R_1$ is Cl. In one embodiment of compounds of formula III, $R_1$ is —CN.

In some embodiments, the present invention includes compounds of formula III and the attendant definitions, wherein the compounds have formula IIIA:

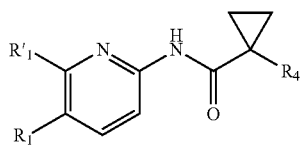

IIIA or a pharmaceutically acceptable salt thereof,
wherein:
$R'_1$ is:

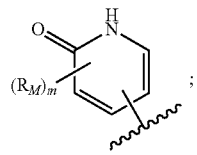

(i)

m is 0-4;
$R_1$ is C1-6 aliphatic, halo, or —CN; and
$R_4$ is selected from:

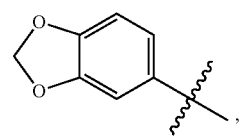

(a)

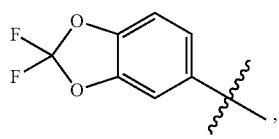

(b)

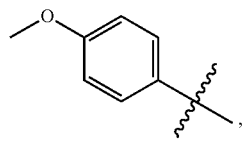

(c)

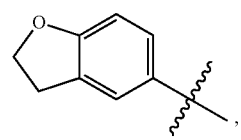

(d)

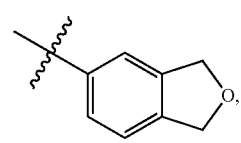

(e)

-continued

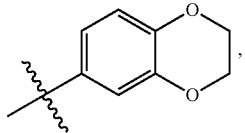

(f)

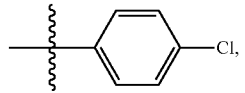

(g)

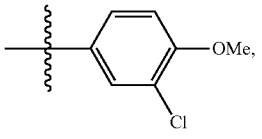

(h)

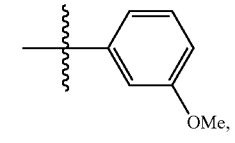

(i)

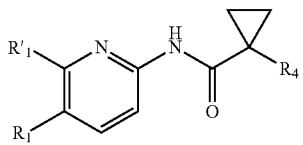

(j)

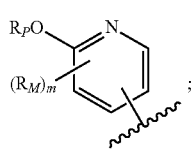

(k)

In one embodiment of compounds of formula IIIA, $R_1$ is methyl. In one embodiment of compounds of formula IIIA, $R_1$ is Cl. In one embodiment of compounds of formula IIIA, $R_1$ is —CN.

In some embodiments, the present invention includes compounds of formula III and the attendant definitions, wherein the compounds have formula IIIB:

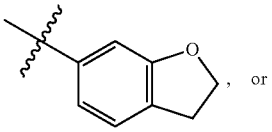

IIIB or a pharmaceutically acceptable salt thereof,
wherein:
$R'_1$ is:

(ii)

m is 0-4;
$R_1$ is C1-6 aliphatic, halo, or —CN; and

R₄ is selected from:

(a) 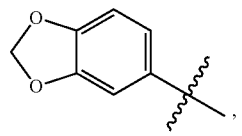, (b) 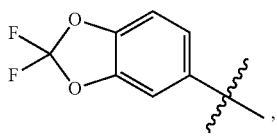, (c) 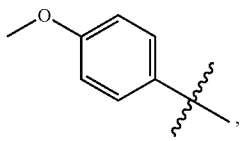, (d) 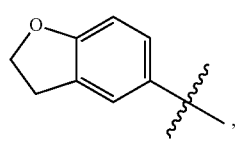, (e) 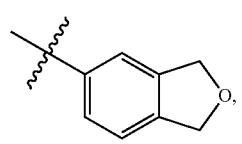, (f) 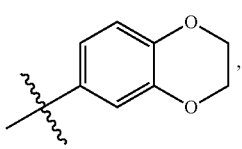, (g) 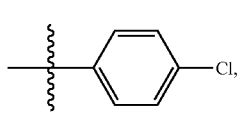, (h) 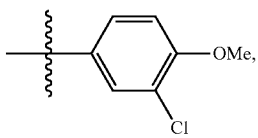, (i) 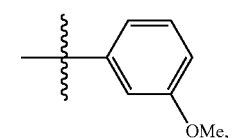, (j) 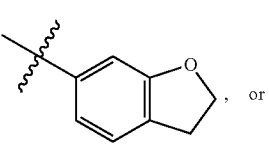, or (k) 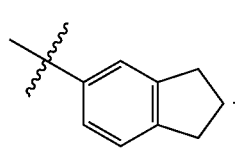.

In one embodiment of compounds of formula IIIB, $R_1$ is methyl. In one embodiment of compounds of formula IIIB, $R_1$ is Cl. In one embodiment of compounds of formula IIIB, $R_1$ is —CN.

In some embodiments, the present invention includes compounds of formula I and the attendant definitions, wherein the compounds have formula IV:

IV

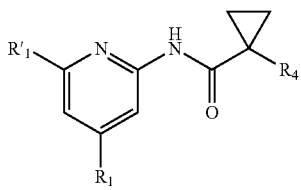

or a pharmaceutically acceptable salt thereof,
wherein:
$R'_1$ is selected from:

(i)

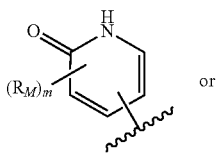 or (ii)

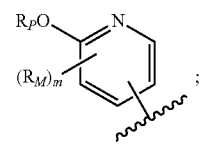;

m is 0-4;
$R_1$ is C1-6 aliphatic, halo, or —CN; and
$R_4$ is selected from:

(a)

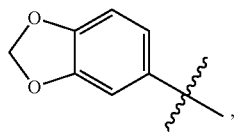, (b)

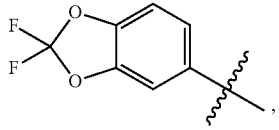, (c)

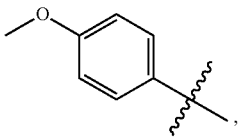, (d)

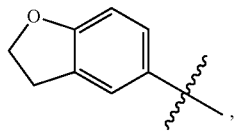, (e)

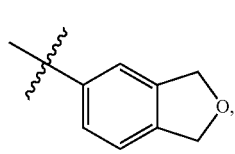,

-continued

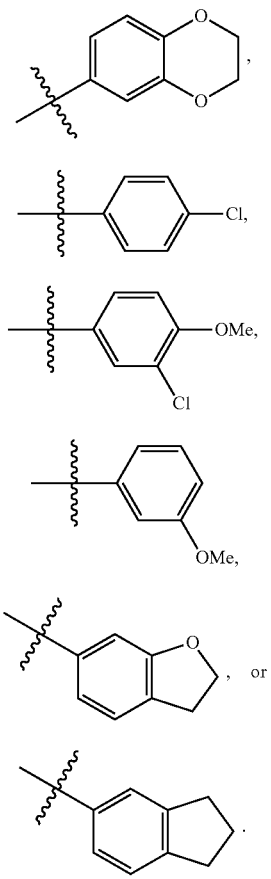

In one embodiment of compounds of formula IV, $R_1$ is methyl. In one embodiment of compounds of formula IV, $R_1$ is Cl. In one embodiment of compounds of formula IV, $R_1$ is —CN.

In some embodiments, the present invention includes compounds of formula IV and the attendant definitions, wherein the compounds have formula IVA:

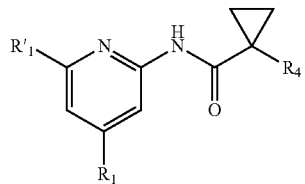

IVA or a pharmaceutically acceptable salt thereof,
wherein:
$R'_1$ is:

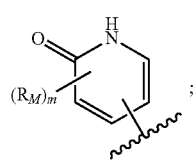

m is 0-4;
$R_1$ is C1-6 aliphatic, halo, or —CN; and $R_4$ is selected from:

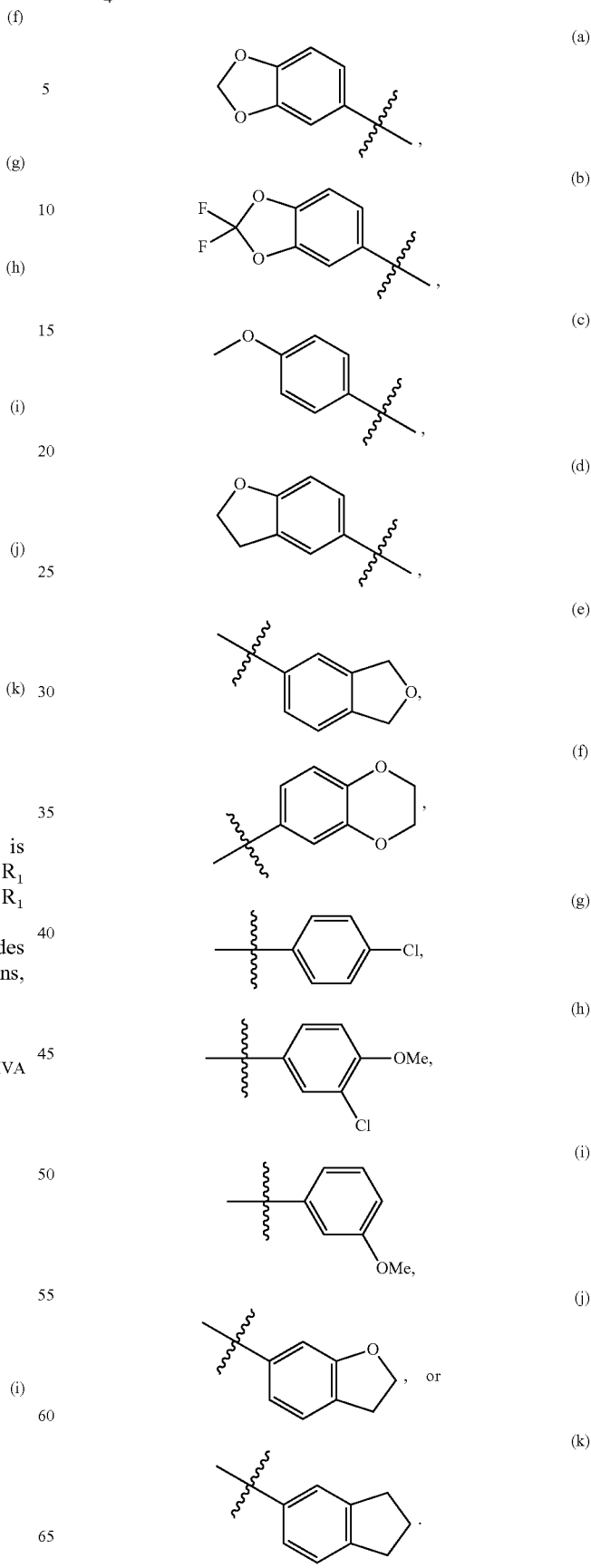

In one embodiment of compounds of formula IVA, $R_1$ is methyl. In one embodiment of compounds of formula IVA, $R_1$ is Cl. In one embodiment of compounds of formula IVA, $R_1$ is —CN.

In some embodiments, the present invention includes compounds of formula IV and the attendant definitions, wherein the compounds have formula IVB:

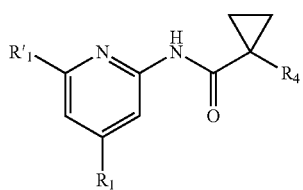
IVB or a pharmaceutically acceptable salt thereof,
wherein:
$R'_1$ is:

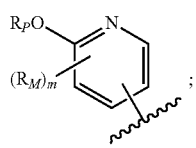
(ii)

m is 0-4;
$R_1$ is C1-6 aliphatic, halo, or —CN; and
$R_4$ is selected from:

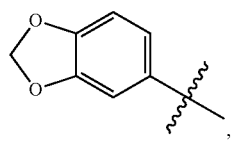
(a)

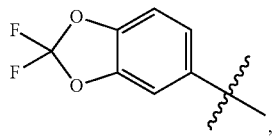
(b)

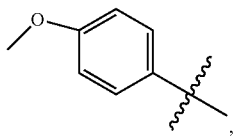
(c)

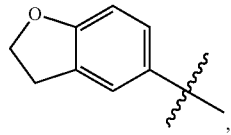
(d)

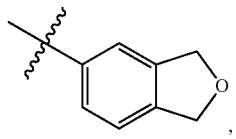
(e)

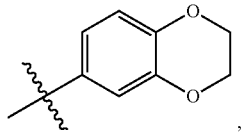
(f)

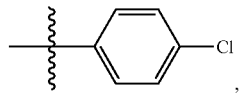
(g)

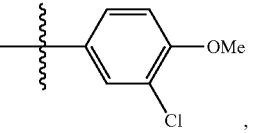
(h)

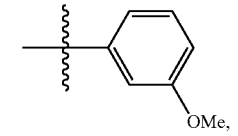
(i)

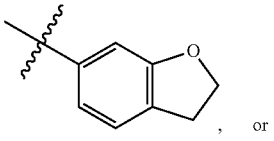
, or (j)

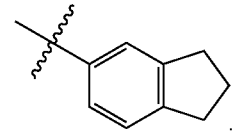
(k)

In one embodiment of compounds of formula IVB, $R_1$ is methyl. In one embodiment of compounds of formula IVB, $R_1$ is Cl. In one embodiment of compounds of formula IVB, $R_1$ is —CN.

In some embodiments, the present invention includes compounds of formula I and the attendant definitions, wherein the compounds have formula V:

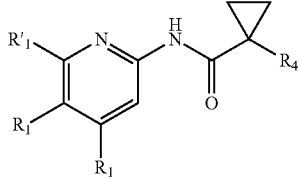
V or a pharmaceutically acceptable salt thereof,
wherein:
$R'_1$ is selected from:

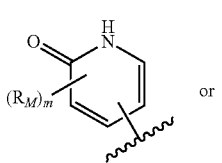
(i)
or

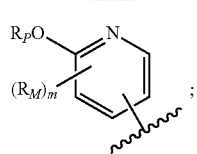

(ii)

m is 0-4;
R₁ is C1-6 aliphatic, halo, or —CN; and
R₄ is selected from:

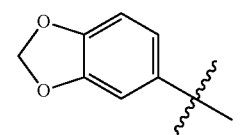
(a)

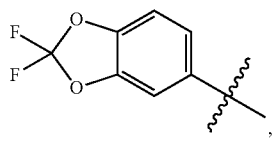
(b)

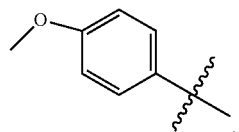
(c)

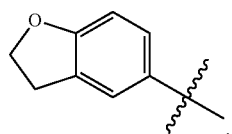
(d)

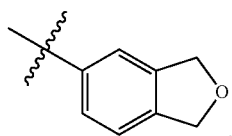
(e)

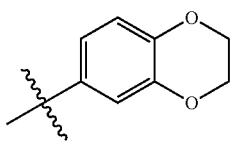
(f)

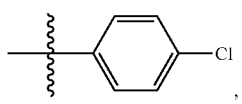
(g)

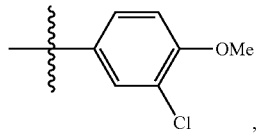
(h)

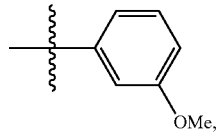
(i)

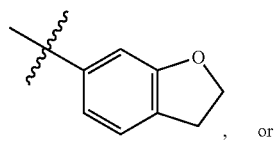
(j)

, or

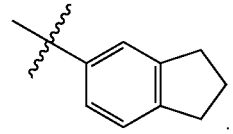
(k)

In one embodiment of compounds of formula V, R₁ is methyl. In one embodiment of compounds of formula V, R₁ is Cl. In one embodiment of compounds of formula V, R₁ is —CN.

In some embodiments, the present invention includes compounds of formula V and the attendant definitions, wherein the compounds have formula VA:

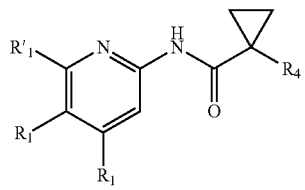

VA or a pharmaceutically acceptable salt thereof,
wherein:
R'₁ is:

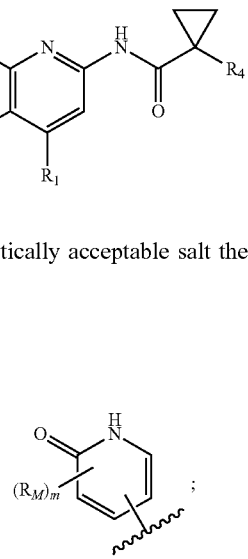
(i)

m is 0-4;
R₁ is C1-6 aliphatic, halo, or —CN; and
R₄ is selected from:

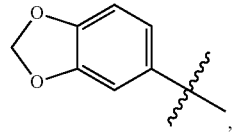
(a)

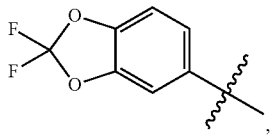
(b)

-continued (c)
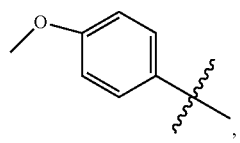

(d)
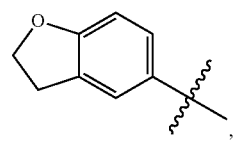

(e)
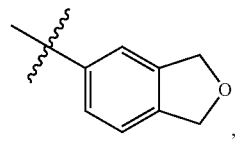

(f)
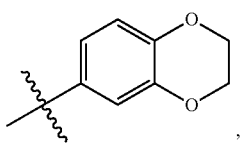

(g)
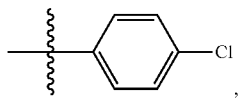

(h)
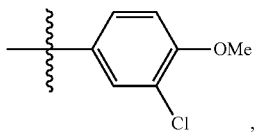

(i)
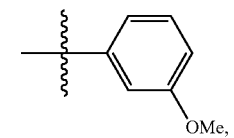

(j)
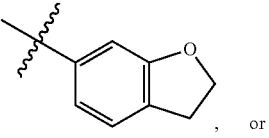, or (k)
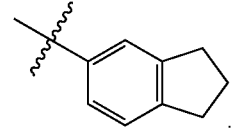

In one embodiment of compounds of formula VA, $R_1$ is methyl. In one embodiment of compounds of formula VA, $R_1$ is Cl. In one embodiment of compounds of formula VA, $R_1$ is —CN.

In some embodiments, the present invention includes compounds of formula V and the attendant definitions, wherein the compounds have formula VB:

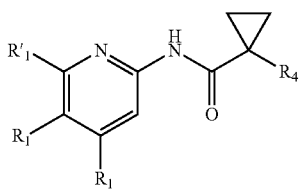

VB or a pharmaceutically acceptable salt thereof,
wherein:
$R'_1$ is:

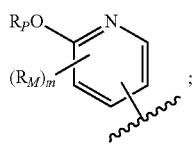

(ii)

m is 0-4;
$R_1$ is C1-6 aliphatic, halo, or —CN; and
$R_4$ is selected from:

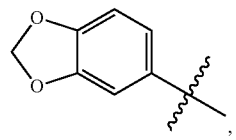

(a)

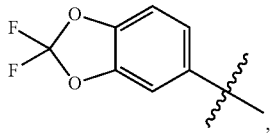

(b)

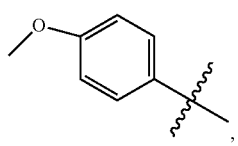

(c)

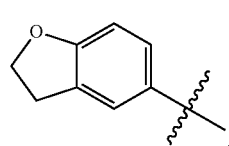

(d)

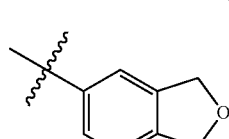

(e)

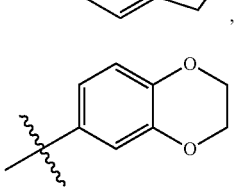

(f)

-continued

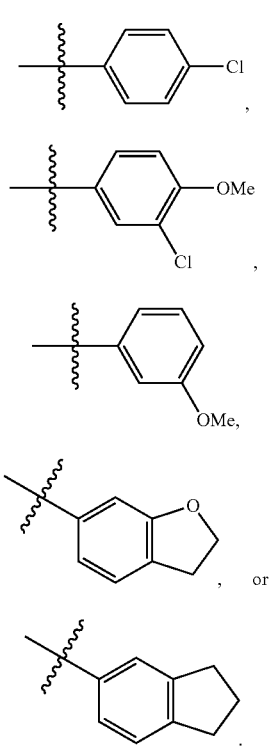

In one embodiment of compounds of formula VB, $R_1$ is methyl. In one embodiment of compounds of formula VB, $R_1$ is Cl. In one embodiment of compounds of formula VB, $R_1$ is —CN.

In another aspect, the present invention includes compounds of formula VI:

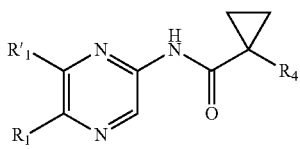

VI or a pharmaceutically acceptable salt thereof, wherein:
$R'_1$ is:

(i)

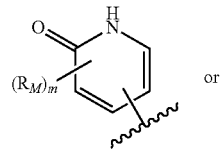

or (ii)

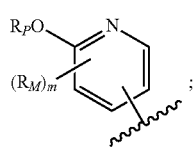

;

m is 0-4;
$R_P$ is optionally substituted C1-C6 aliphatic, wherein up to two carbon units therein are optionally and independently replaced by —CO—, —CONR$^N$—, —CO$_2$—, —OCO—, —NR$^N$CO$_2$—, —O—, —OCONR$^N$—, —NR$^N$CO—, —S—, —SO—, —SO$_2$—, —NR$^N$—;

$R_M$ is independently —Z$^M$R$_{11}$, wherein each Z$^M$ is independently a bond or an optionally substituted branched or straight C$_{1-6}$ aliphatic chain wherein up to two carbon units of Z$^M$ are optionally and independently replaced by —CO—, —CONR$^N$—, —CO$_2$—, —OCO—, —CHR$^N$—, —NR$^N$CO$_2$—, —O—, —OCONR$^N$—, —NR$^N$CO—, —S—, —SO—, —SO$_2$—, —NR$^N$—;

$R_{11}$ is independently R$^N$, halo, —OH, —NH$_2$, —CN, —CF$_3$, or —OCF$_3$;

$R^N$ is independently hydrogen, an optionally substituted C$_{1-8}$ aliphatic group, an optionally substituted cycloaliphatic, an optionally substituted heterocycloaliphatic, an optionally substituted aryl, or an optionally substituted heteroaryl;

$R_1$ is an optionally substituted C$_{1-6}$ aliphatic, an optionally substituted C$_{1-6}$ alkoxy, an optionally substituted C$_{3-10}$ cycloaliphatic, —CN, halo, or hydroxy;

$R_2$ is hydrogen or an optionally substituted C$_{1-6}$ aliphatic;

$R_3$ and R'$_3$ together with the carbon atom to which they are attached form an optionally substituted C$_{3-7}$ cycloaliphatic or an optionally substituted heterocycloaliphatic;

$R_4$ is an optionally substituted aryl; and
n is 0-3.

In one embodiment of compounds of formula VI, $R_4$ is selected from:

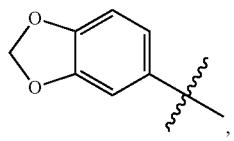
(a)

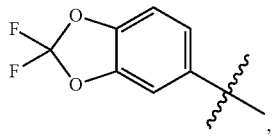
(b)

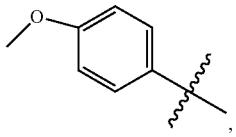
(c)

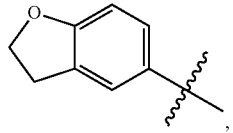
(d)

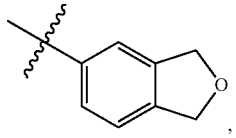
(e)

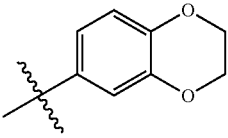
(f)

-continued

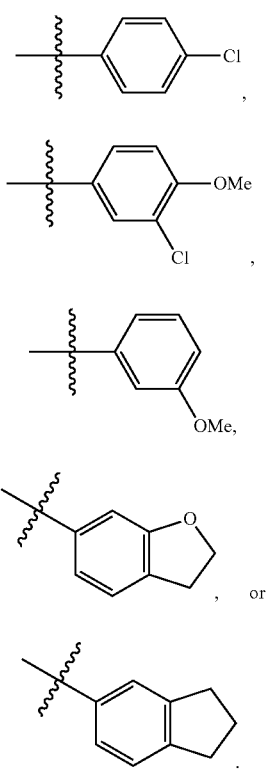

(g)

(h)

(i)

(j), or (k)

In one embodiment of compounds of formula VI, $R_4$ is (b).

In one embodiment of compounds of formula VI, $R_1$ is methyl.

In some embodiments, the present invention includes compounds of formula VI and the attendant definitions, wherein the compounds have formula VIA:

VIA

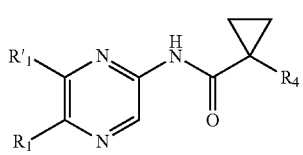

or a pharmaceutically acceptable salt thereof, wherein:

$R'_1$ is selected from:

(i)

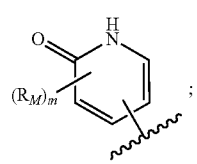

m is 0-4;
$R_1$ is C1-6 aliphatic, halo, or —CN; and $R_4$ is selected from:

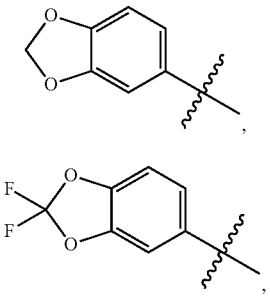

(a)

(b)

(c)

(d)

(e)

(f)

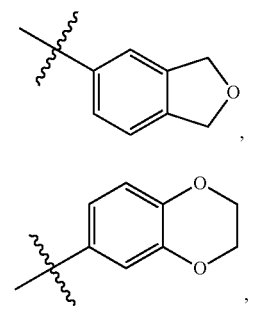

(g)

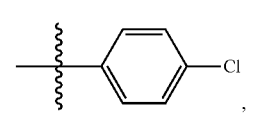

(h)

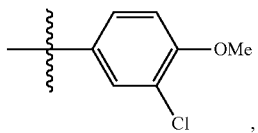

(i)

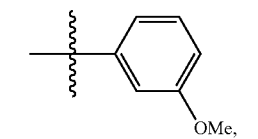

(j)

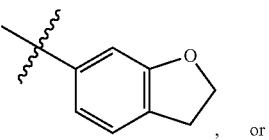

, or

-continued (k)
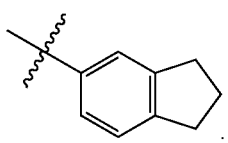

In one embodiment of compounds of formula VIA, R$_1$ is methyl.

In one embodiment of compounds of formula VIA, R'$_1$ is:

(i-a)
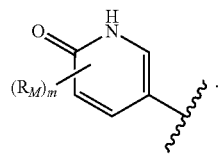

In one embodiment of compounds of formula VIA, R'$_1$ is:

(i-c)
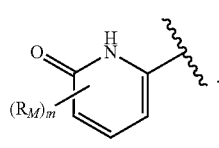

In some embodiments, the present invention includes compounds of formula VI and the attendant definitions, wherein the compounds have formula VIB:

VIB
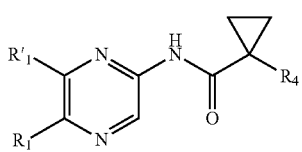

or a pharmaceutically acceptable salt thereof, wherein:

R'$_1$ is selected from:

(ii)
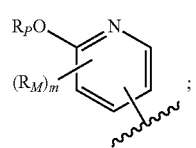

m is 0-4;
R$_1$ is C1-6 aliphatic, halo, or —CN; and
R$_4$ is selected from:

(a)
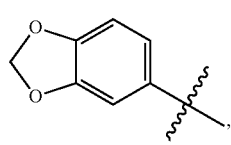

-continued (b)
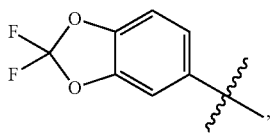

(c)
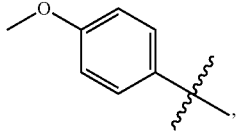

(d)
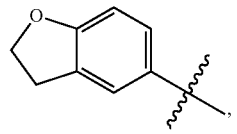

(e)
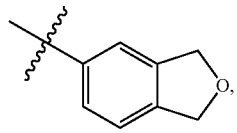

(f)
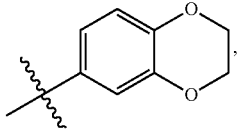

(g)
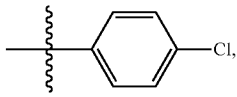

(h)
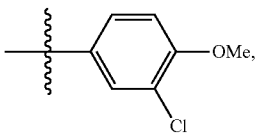

(i)
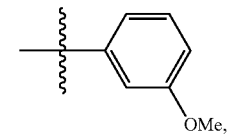

(j)
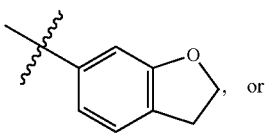

(k)
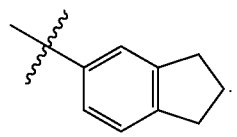

In one embodiment of compounds of formula VIB, R$_1$ is methyl.

Exemplary compounds of the present invention include, but are not limited to, those illustrated in Table 1 below.

TABLE 1
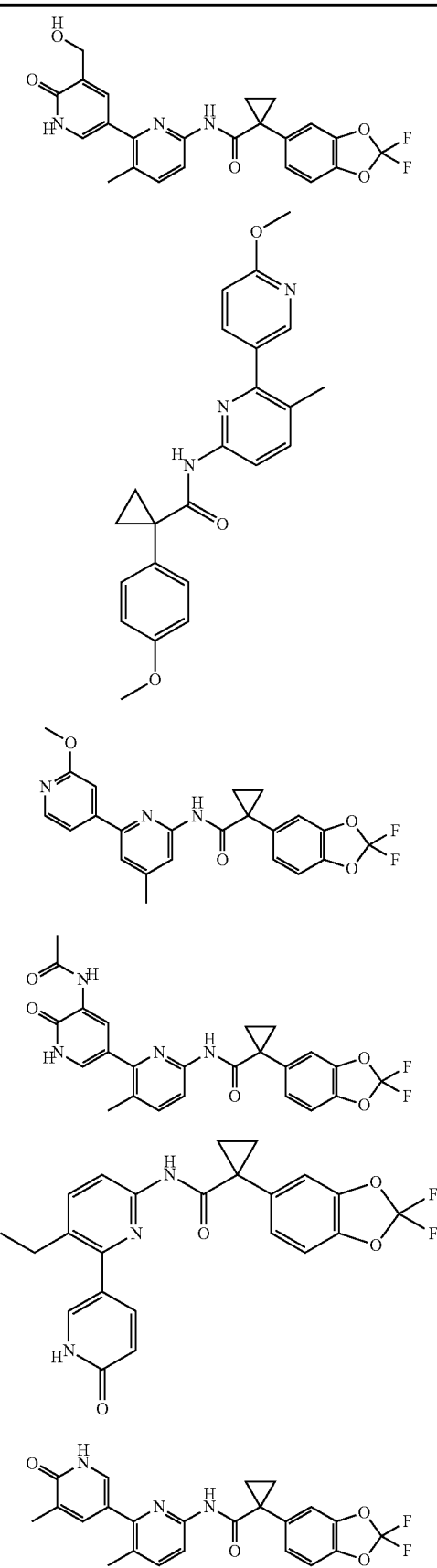
TABLE 1-continued
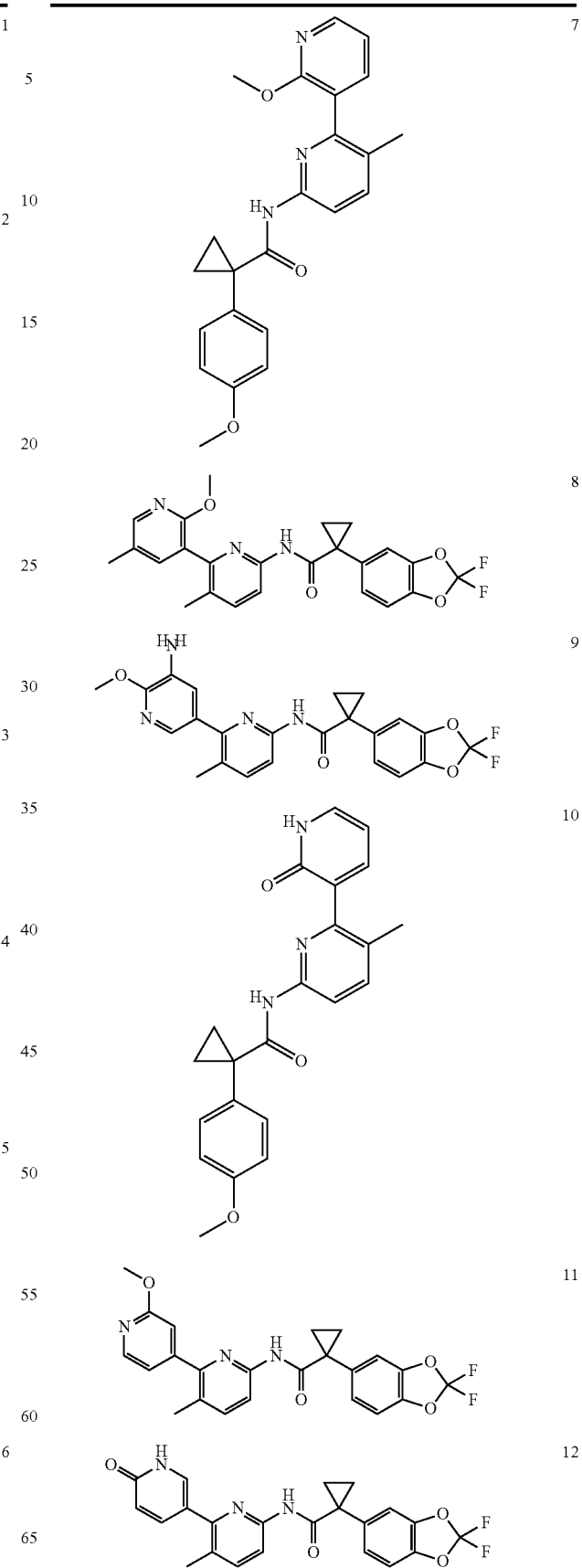

TABLE 1-continued
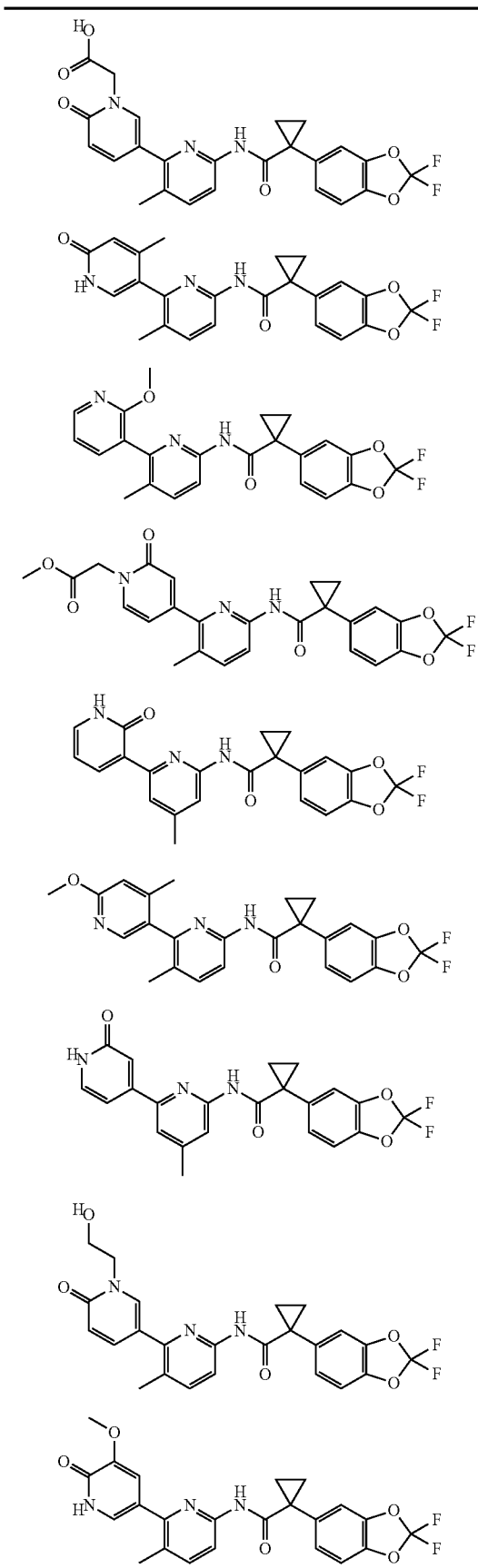
TABLE 1-continued
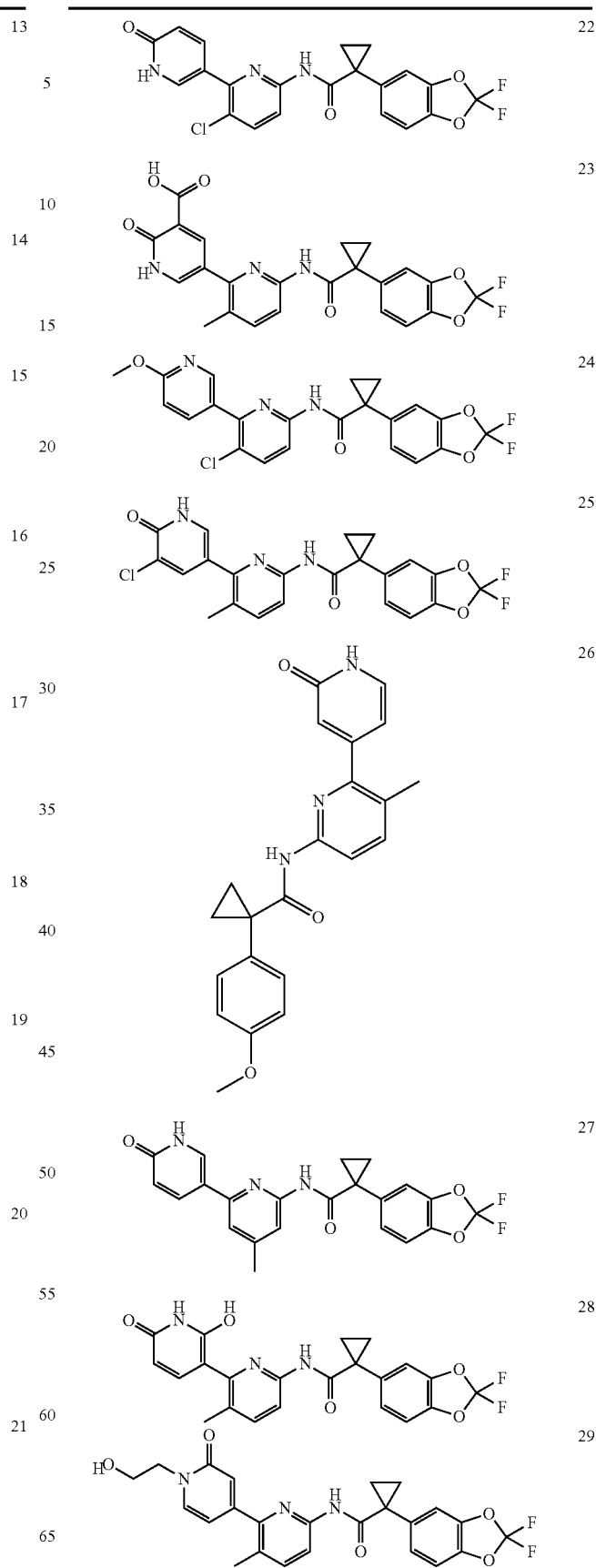

TABLE 1-continued
| | |
|---|---|
| 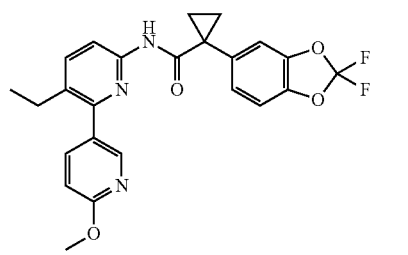 [SMILES: CCc1ccc(NC(=O)C2(c3ccc4c(c3)OC(F)(F)O4)CC2)nc1-c1ccc(OC)nc1] | 30 |
| 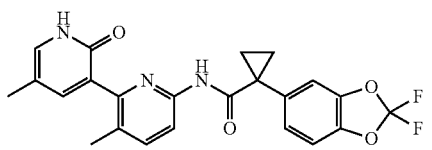 [SMILES: Cc1c[nH]c(=O)c(-c2nc(NC(=O)C3(c4ccc5c(c4)OC(F)(F)O5)CC3)ccc2C)c1] | 31 |
| 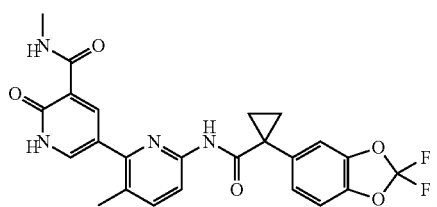 | 32 |
| 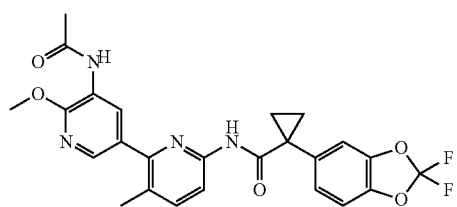 | 33 |
| 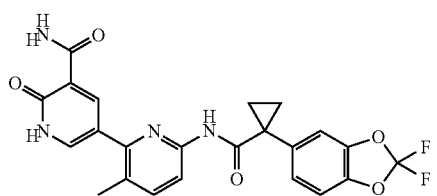 | 34 |
| 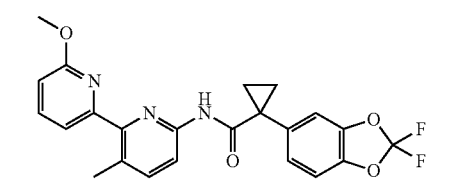 [SMILES: COc1cccc(-c2nc(NC(=O)C3(c4ccc5c(c4)OC(F)(F)O5)CC3)ccc2C)n1] | 35 |
| 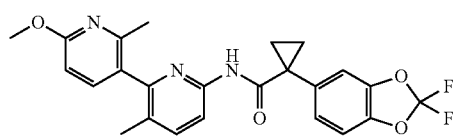 [SMILES: COc1ccc(-c2nc(NC(=O)C3(c4ccc5c(c4)OC(F)(F)O5)CC3)ccc2C)c(C)n1] | 36 |
| 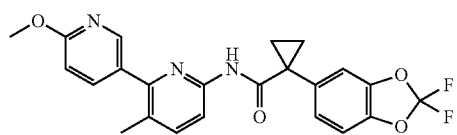 [SMILES: COc1ccc(-c2nc(NC(=O)C3(c4ccc5c(c4)OC(F)(F)O5)CC3)ccc2C)cn1] | 37 |
TABLE 1-continued
| | |
|---|---|
| 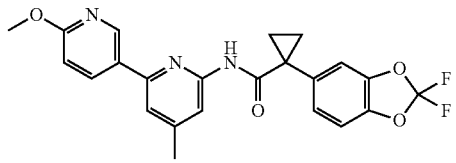 [SMILES: COc1ccc(-c2cc(C)cc(NC(=O)C3(c4ccc5c(c4)OC(F)(F)O5)CC3)n2)cn1] | 38 |
| 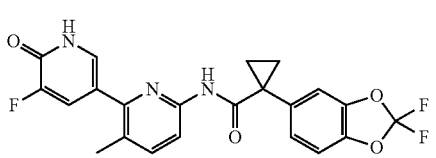 | 39 |
| 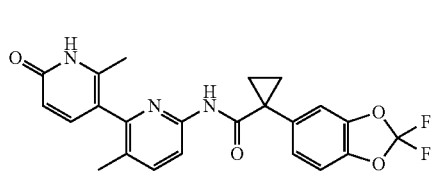 [SMILES: Cc1ccc(NC(=O)C2(c3ccc4c(c3)OC(F)(F)O4)CC2)nc1-c1ccc(=O)[nH]c1C] | 40 |
| 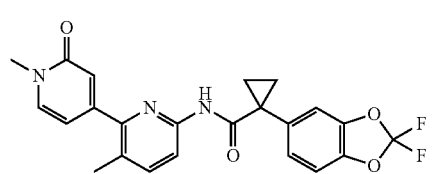 [SMILES: Cc1ccc(NC(=O)C2(c3ccc4c(c3)OC(F)(F)O4)CC2)nc1-c1ccn(C)c(=O)c1] | 41 |
| 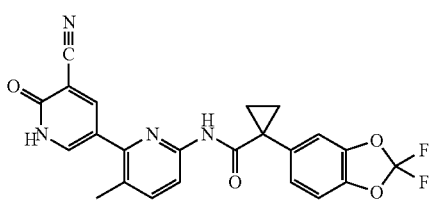 | 42 |
| 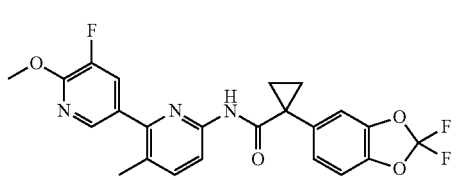 | 43 |
| 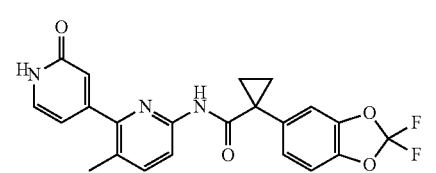 | 44 |

TABLE 1-continued
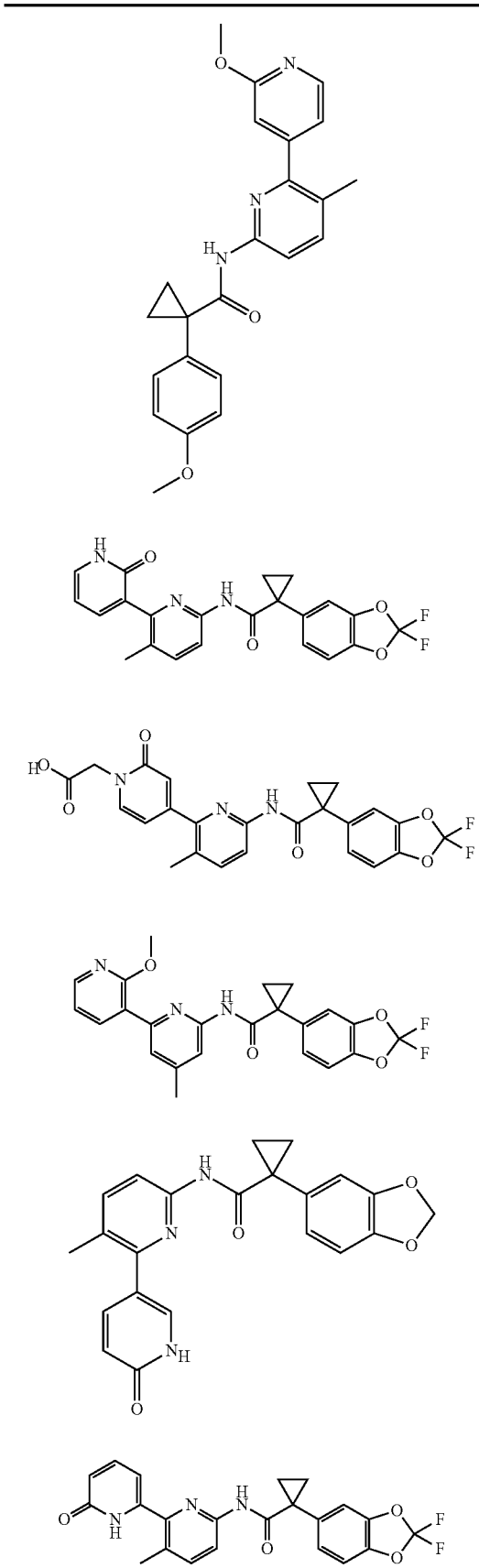
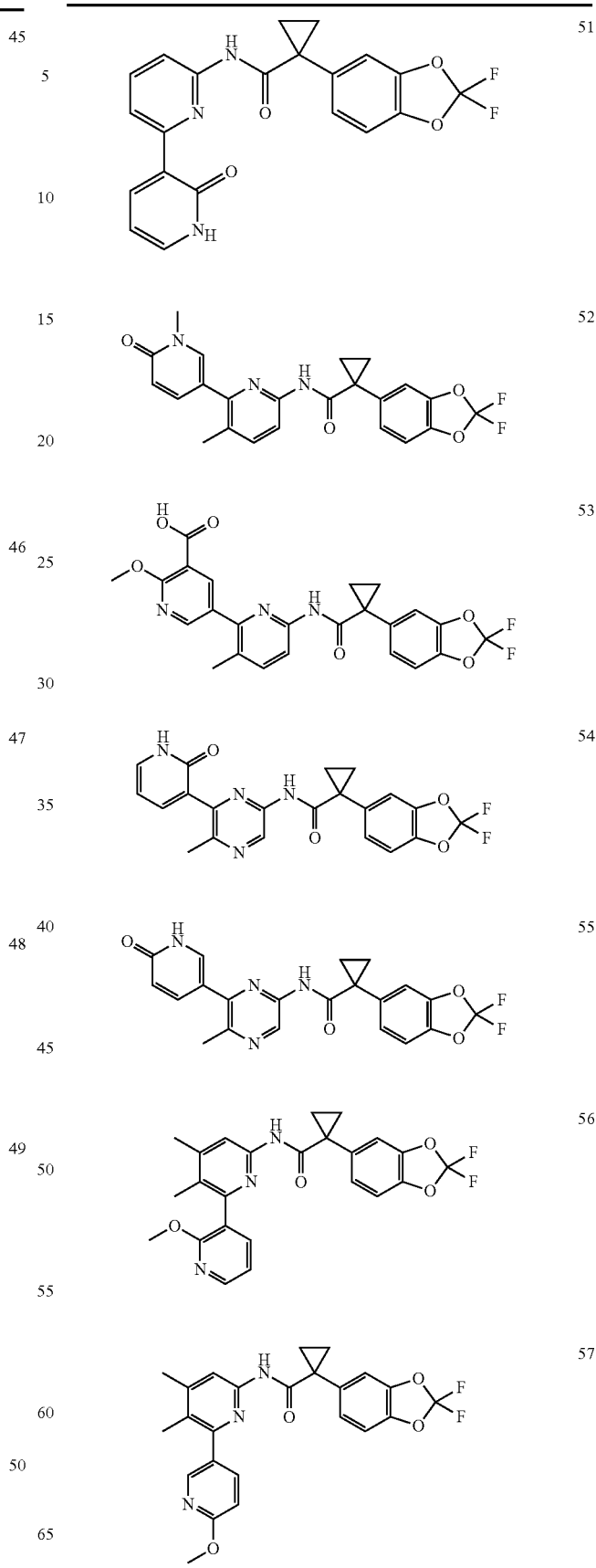

TABLE 1-continued

TABLE 1-continued
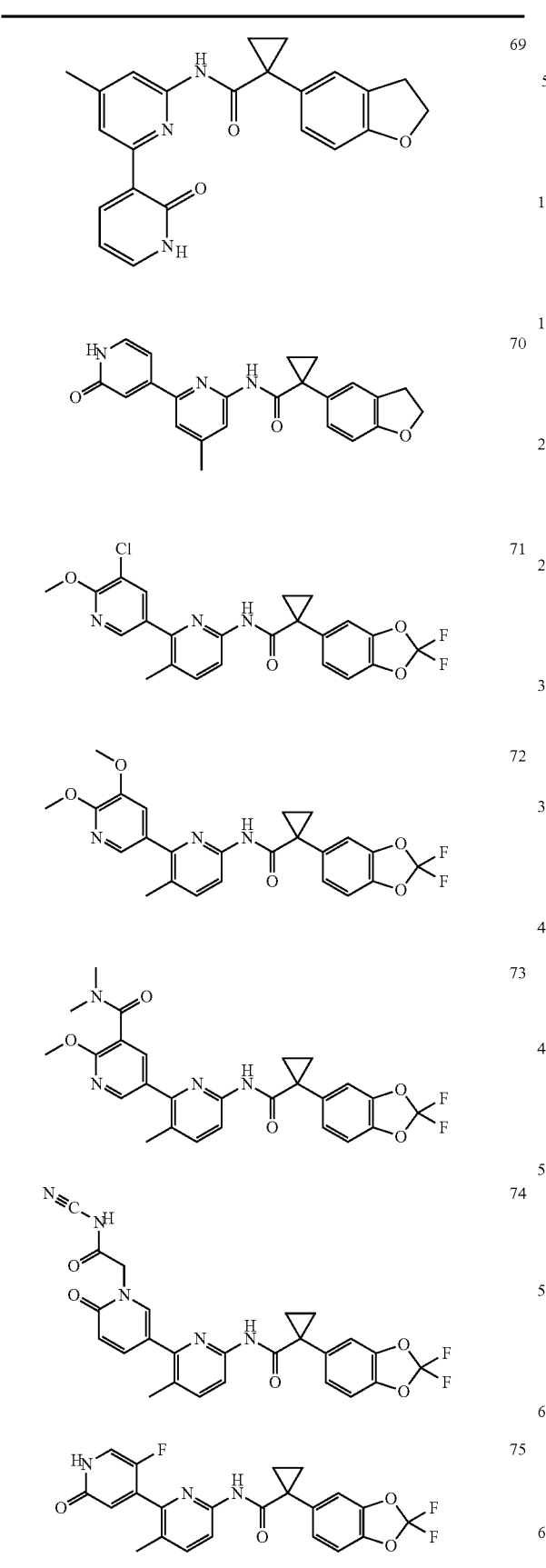
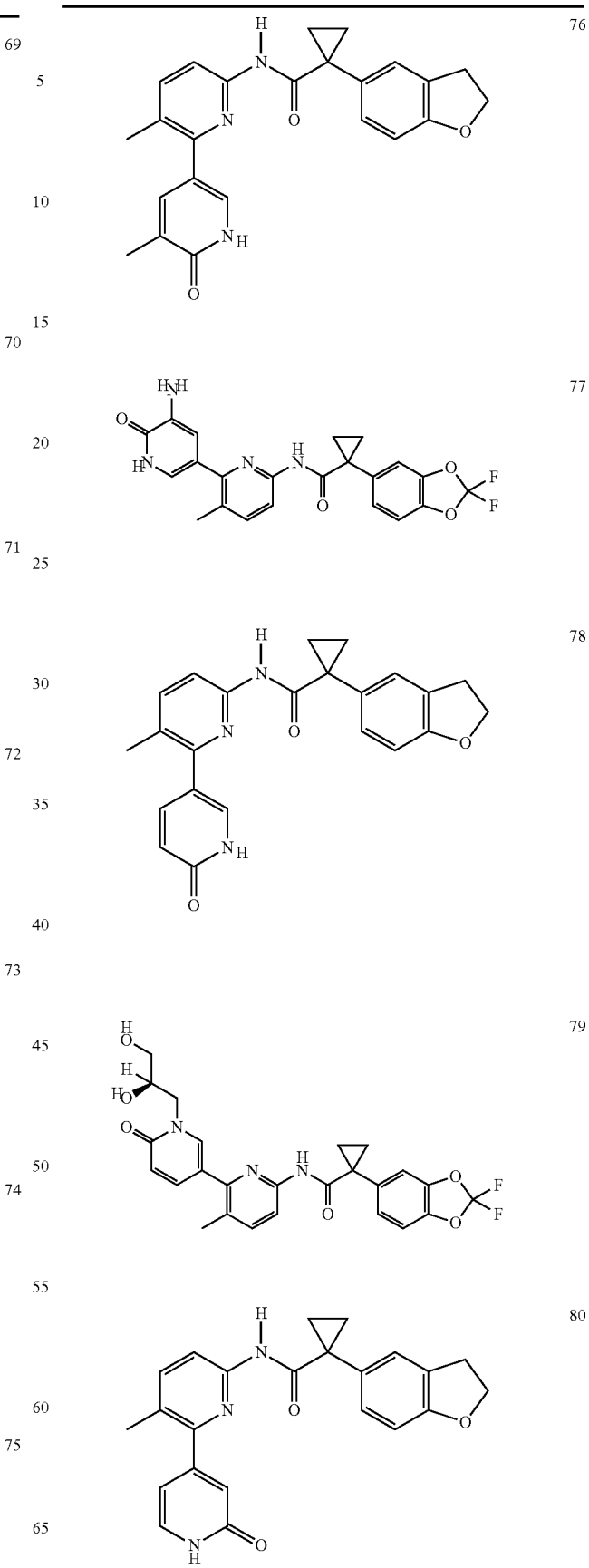

TABLE 1-continued
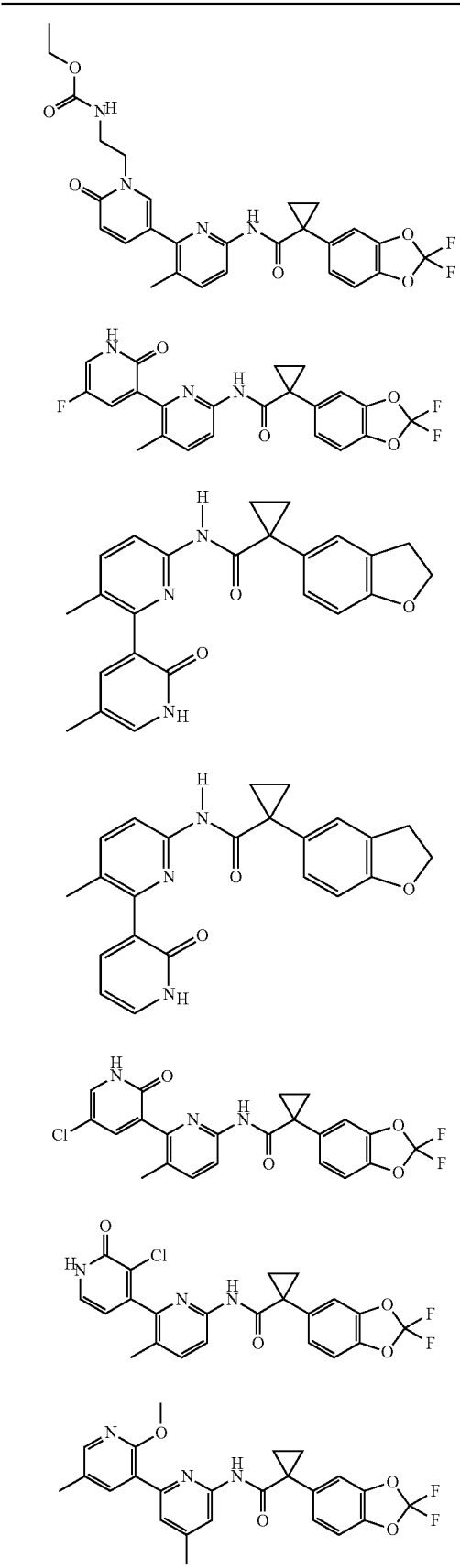
TABLE 1-continued
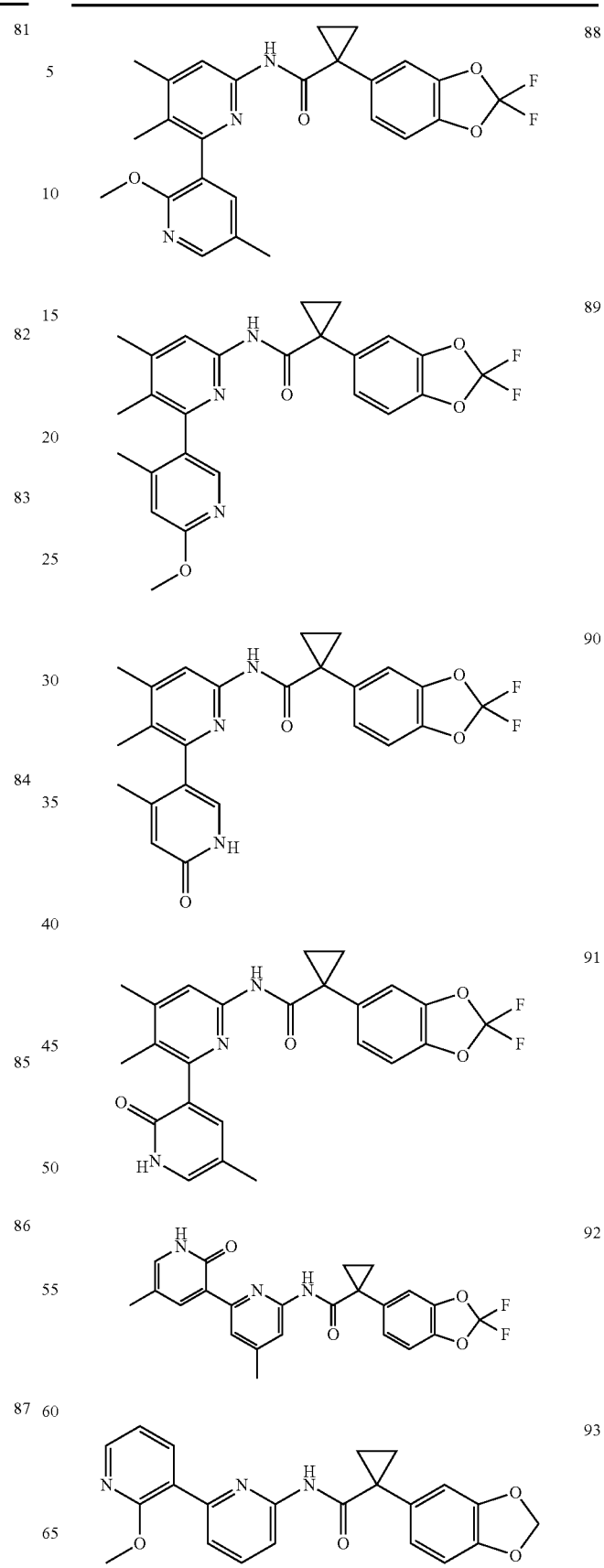

TABLE 1-continued
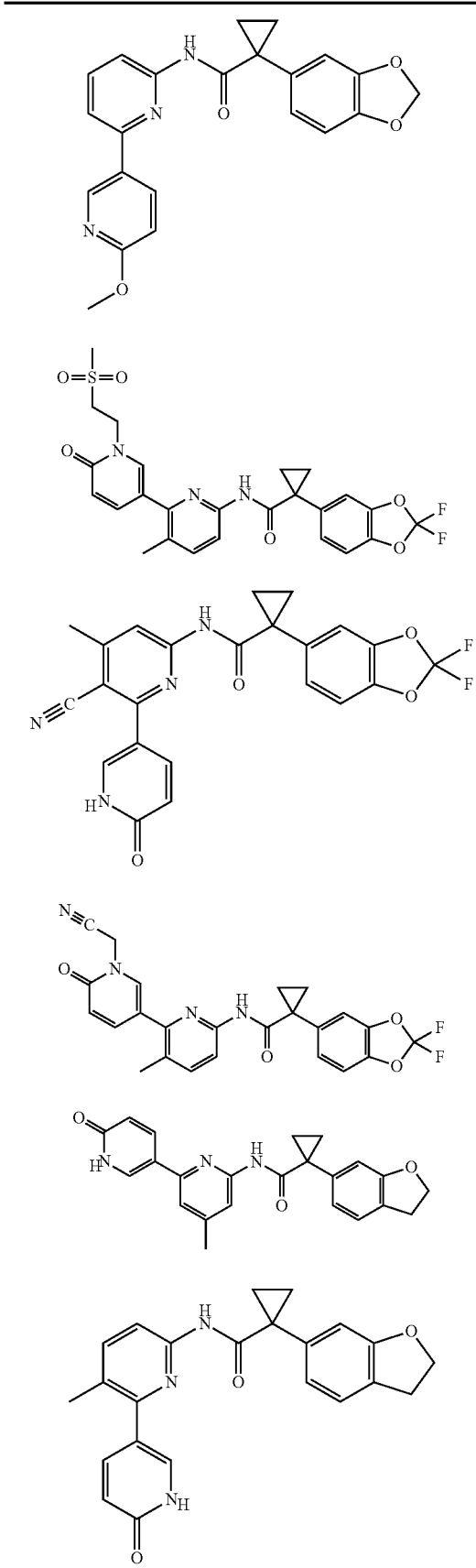
TABLE 1-continued
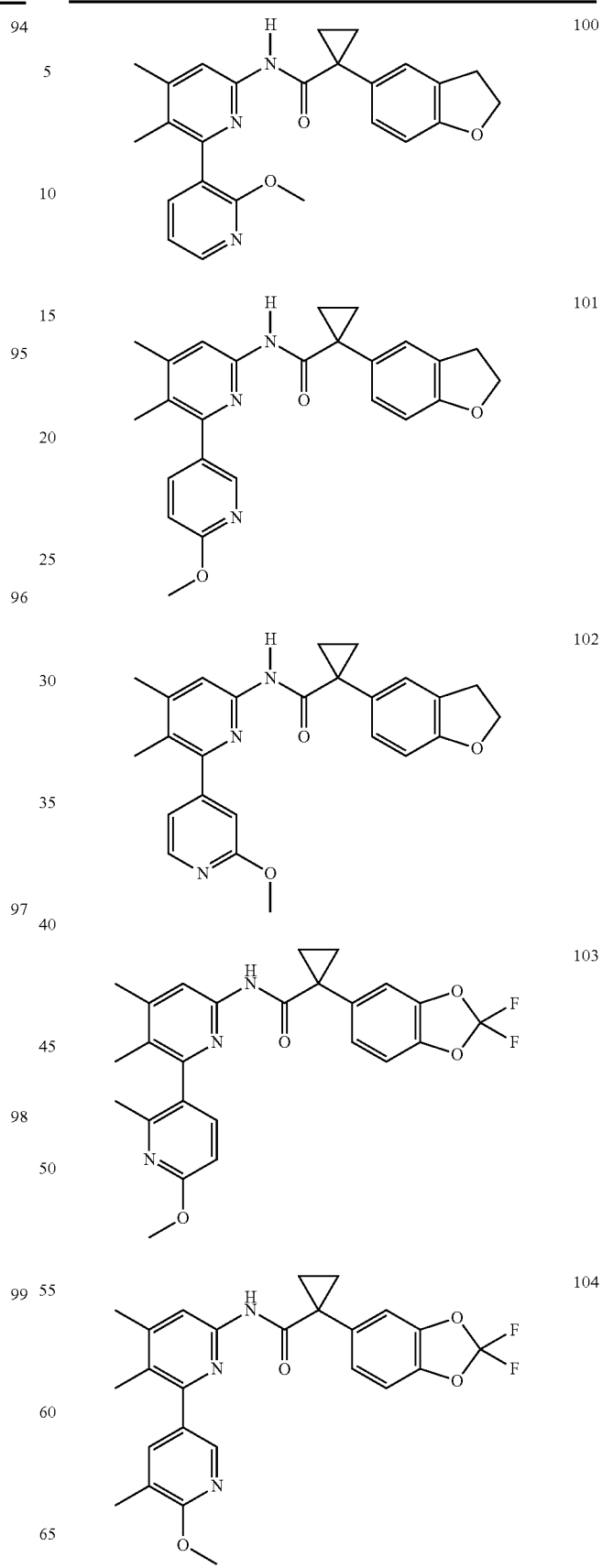

TABLE 1-continued
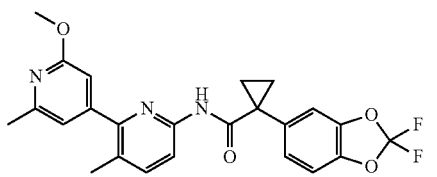 [SMILES: COc1cc(-c2nc(NC(=O)C3(c4ccc5c(c4)OC(F)(F)O5)CC3)ccc2C)cc(C)n1] 105
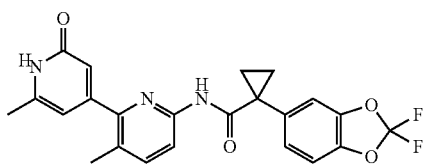 106
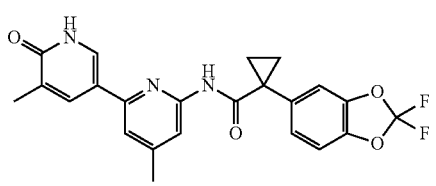 [SMILES: Cc1cc(NC(=O)C2(c3ccc4c(c3)OC(F)(F)O4)CC2)nc(-c2c[nH]c(=O)c(C)c2)c1] 107
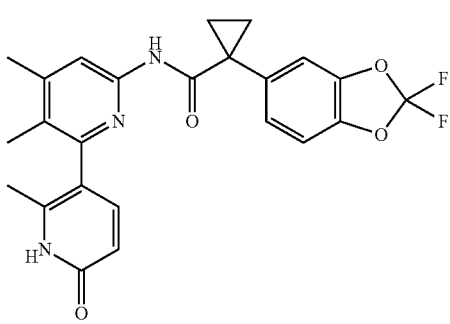 108
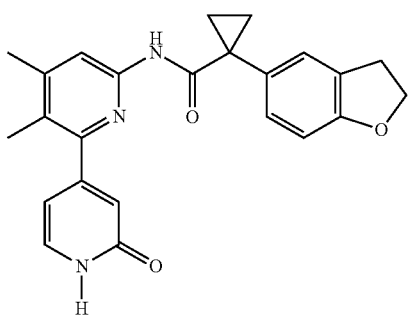 [SMILES: Cc1cc(NC(=O)C2(c3ccc4c(c3)CCO4)CC2)nc(-c2cc[nH]c(=O)c2)c1C] 109
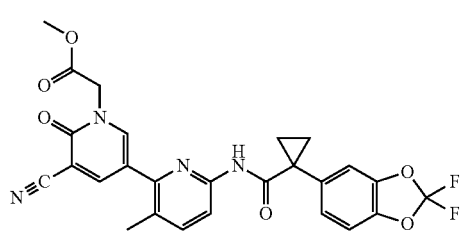 [SMILES: COC(=O)Cn1cc(-c2nc(NC(=O)C3(c4ccc5c(c4)OC(F)(F)O5)CC3)ccc2C)cc(C#N)c1=O] 110
TABLE 1-continued
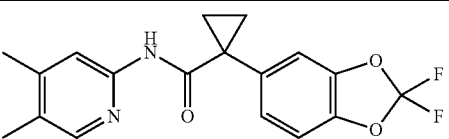 111
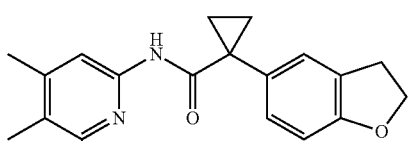 112
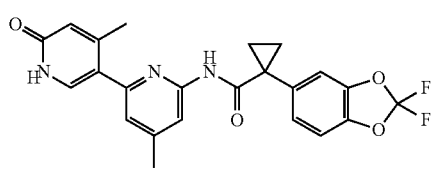 113
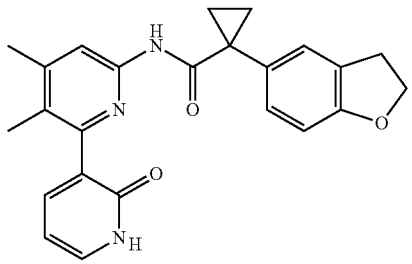 114
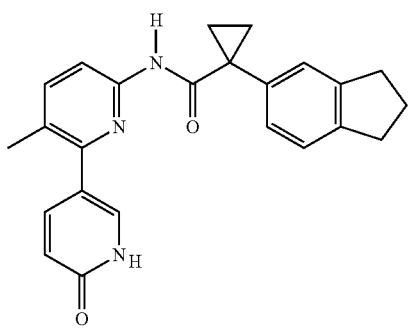 115
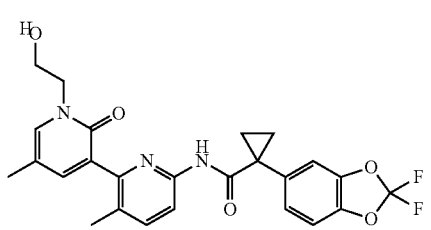 116

TABLE 1-continued

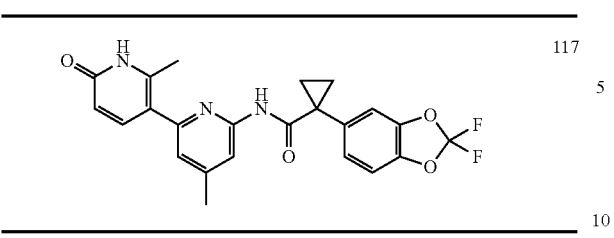

117

SYNTHETIC SCHEMES

Compounds of the invention may be prepared by known methods or as illustrated in the schemes below.

Scheme 1

Preparation of Phenylacetonitriles

Method 1:

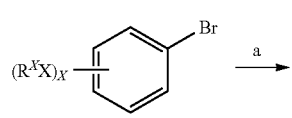

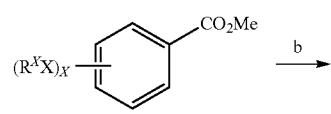

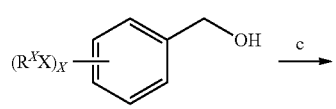

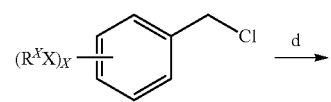

a) Pd(PPh$_3$)$_4$, CO, MeOH; b) LiAlH$_4$, THF; c) SOCl$_2$; d) NaCN.

Method 2:

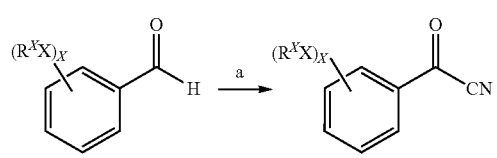

a) p-CH$_3$PhSO$_2$CH$_2$CN, tBuOK.

Scheme 2

Preparation of Cycloaliphatic Carboxylic Acids, e.g., Cyclopropyl Carboxylic Acids Method 1:

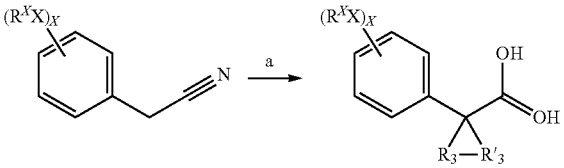

a) Y—R$_3$—R'$_3$—Z; (Y, Z=Cl or Br), NaOH, BTEAC; NaOH, Δ.

Method 2:

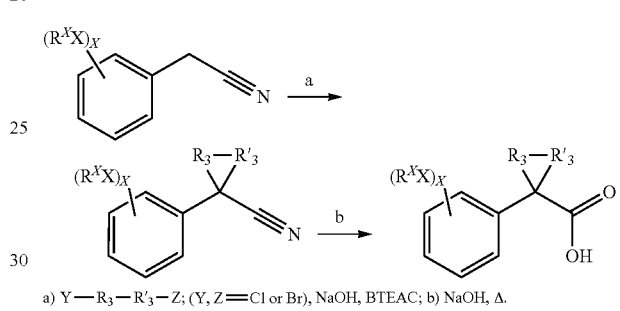

a) Y—R$_3$—R'$_3$—Z; (Y, Z=Cl or Br), NaOH, BTEAC; b) NaOH, Δ.

Scheme 3

Preparation of Acid Chlorides

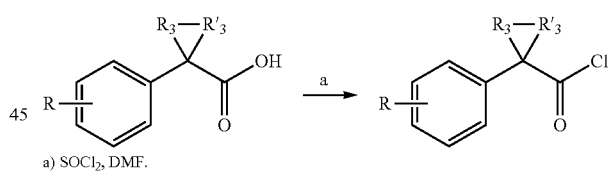

a) SOCl$_2$, DMF.

Scheme 4

Preparation of 2-amino-6-chloropyridines

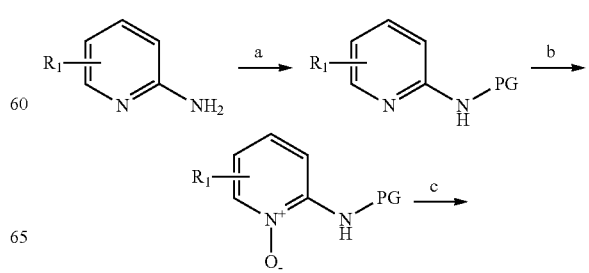

-continued

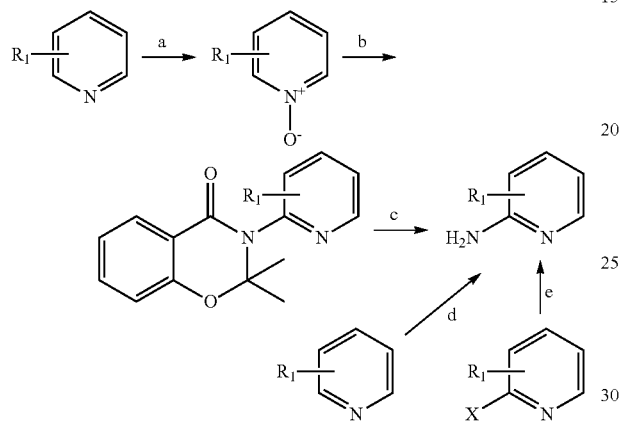

PG = protecting group
a) PG = COR; RCOCl, Et$_3$N; b) H$_2$O$_2$/AcOH, CH$_3$ReO$_3$/H$_2$O$_2$, or mCPBA; d) POCl$_3$, Et$_3$N; e) acid or basic de-protection conditions such as 6N HCl or 1N NaOH.

Preparation of 2-aminopyridines

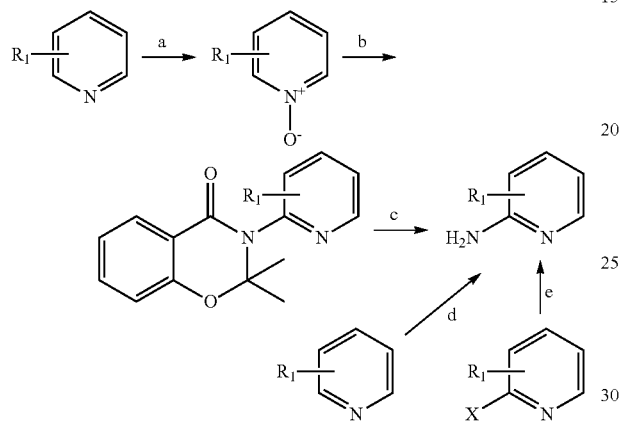

a) oxidating agent like mCPBA, H$_2$O$_2$ in acetic acid, etc ... ;
b) [structure]
c) HCl; d) NaNH$_2$; e) NH$_3$, NH$_4$Cl or other amination reagents.

Scheme 5

Preparation of 2-amino alkylpyridines

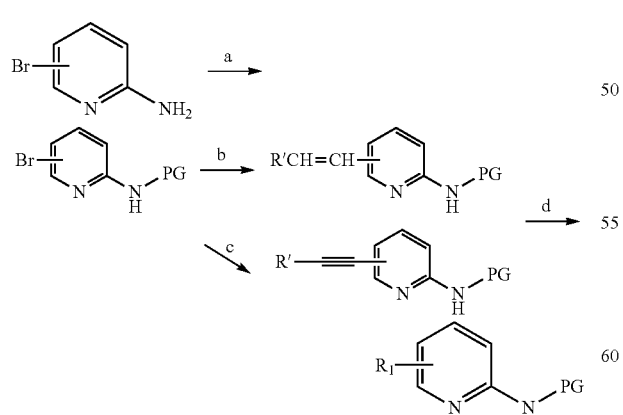

PG = protecting group; R$_1$ = alkyl
a) i.e. PG = COR; RCOCl, Et$_3$N; b) R'CH=CH—M (examples of M are: SnR$_3$, B(OR)$_2$, ZnCl), Pd catalyst, base; c) R'C≡C—M, Pd catalyst, base d) H$_2$, Pd/C.

Scheme 6

Preparation of 2-amino-6-bromo-5-chloro pyridines

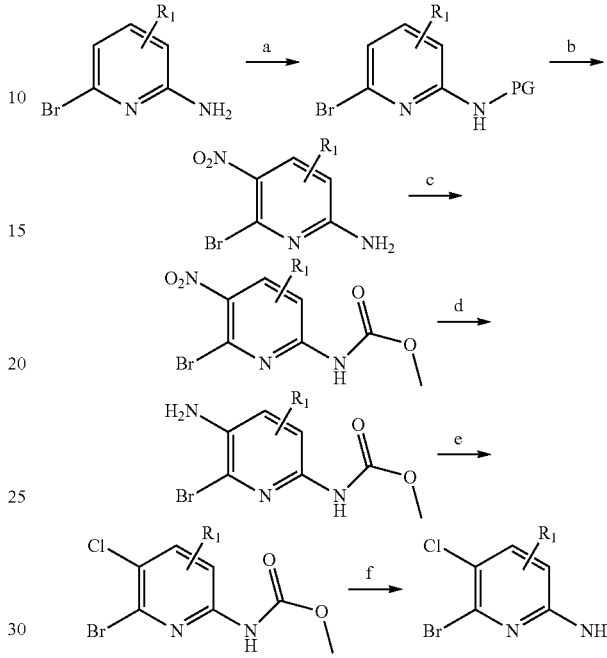

PG = protecting group; a) if PG = COR, RCOCl, Et$_3$N; b) HNO$_3$, H$_2$SO$_4$; c) ClCO$_2$Me, Et$_3$N; d) NiCl$_2$, NaBH$_4$, MeOH; e) CuCl, NaNO$_2$, HCl; f) KOH, MeOH.

Scheme 7

Preparation of 2-Alkoxypyridine Derivatives from Halopyridines

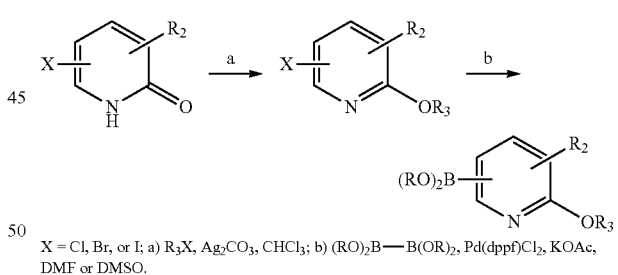

X = Cl, Br, or I; a) R$_3$X, Ag$_2$CO$_3$, CHCl$_3$; b) (RO)$_2$B—B(OR)$_2$, Pd(dppf)Cl$_2$, KOAc, DMF or DMSO.

Scheme 8

Preparation of 1-Substituted Pyridones Derivatives from Halopyridones

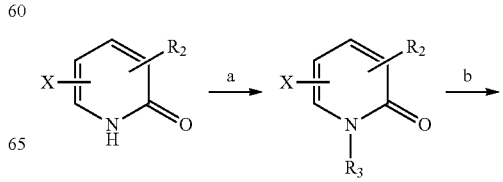

-continued

X = Cl, Br, or I; a) R₃X, K₂CO₃, THF; b) (RO)₂B—B(OR)₂, Pd(dppf)Cl₂, KOAc, DMF or DMSO.

Scheme 9

Preparation of Final Compounds

Method 1:

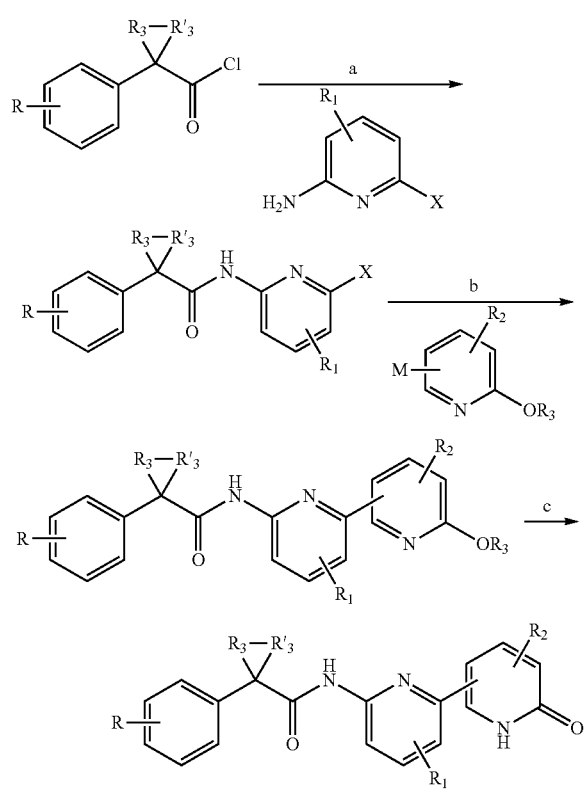

X = Cl, Br, or I; Examples of M are SnR₃, B(OH)₂, B(OR)₂, ZnCl, MgCl
a) Et₃N, CH₂Cl₂; b) Pd catalyst, base; c) dealkylation conditions such as HCl in dioxane, TMSI, or BBr₃.

Method 2:

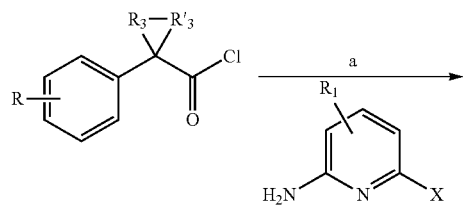

-continued

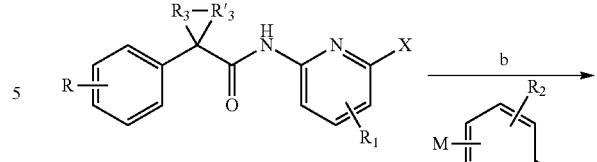

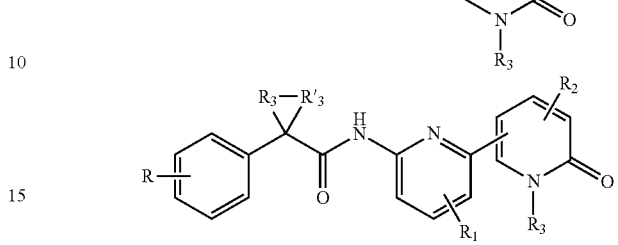

X = Cl, Br, or I; Examples of M are SnR₃, B(OH)₂, B(OR)₂, ZnCl, MgCl
a) Et₃N, CH₂Cl₂; b) Pd catalyst, base.

Method 3:

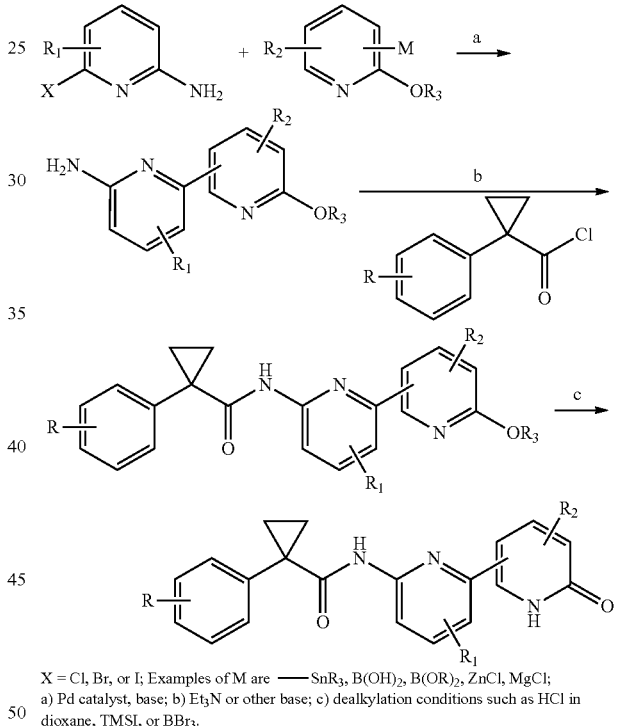

X = Cl, Br, or I; Examples of M are ——SnR₃, B(OH)₂, B(OR)₂, ZnCl, MgCl;
a) Pd catalyst, base; b) Et₃N or other base; c) dealkylation conditions such as HCl in dioxane, TMSI, or BBr₃.

Formulations, Administrations, and Uses
Pharmaceutically Acceptable Compositions Accordingly, in another aspect of the present invention, pharmaceutically acceptable compositions are provided, wherein these compositions comprise any of the compounds as described herein, and optionally comprise a pharmaceutically acceptable carrier, adjuvant or vehicle. In certain embodiments, these compositions optionally further comprise one or more additional therapeutic agents.

It will also be appreciated that certain of the compounds of present invention can exist in free form for treatment, or where appropriate, as a pharmaceutically acceptable derivative or a prodrug thereof. According to the present invention, a pharmaceutically acceptable derivative or a prodrug includes, but is not limited to, pharmaceutically acceptable salts, esters, salts of such esters, or any other adduct or derivative which upon administration to a patient in need is capable of providing, directly or indirectly, a compound as otherwise described herein, or a metabolite or residue thereof.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. A "pharmaceutically acceptable salt" means any non-toxic salt or salt of an ester of a compound of this invention that, upon administration to a recipient, is capable of providing, either directly or indirectly, a compound of this invention or an inhibitorily active metabolite or residue thereof.

Pharmaceutically acceptable salts are well known in the art. For example, S. M. Berge, et al. describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. This invention also envisions the quaternization of any basic nitrogen-containing groups of the compounds disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington: *The Science and Practice of Pharmacy,* 21st edition, 2005, ed. D. B. Troy, Lippincott Williams & Wilkins, Philadelphia, and *Encyclopedia of Pharmaceutical Technology*, eds. J. Swarbrick and J. C. Boylan, 1988-1999, Marcel Dekker, New York, the contents of each of which is incorporated by reference herein, disclose various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

In another aspect, the present invention relates to a pharmaceutical composition comprising (i) a compound of the present invention; and (ii) a pharmaceutically acceptable carrier. In another embodiment, the composition further comprises an additional agent selected from a mucolytic agent, bronchodialator, an anti-biotic, an anti-infective agent, an anti-inflammatory agent, CFTR corrector, or a nutritional agent. In another embodiment, the composition further comprises an additional agent selected from compounds disclosed in U.S. patent application Ser. No. 11/165,818, published as U.S. Published Patent Application No. 2006/0074075, filed Jun. 24, 2005, and hereby incorporated by reference in its entirety. In another embodiment, the composition further comprises N-(5-hydroxy-2,4-ditert-butyl-phenyl)-4-oxo-1H-quinoline-3-carboxamide. These compositions are useful for treating the diseases described below including cystic fibrosis. These compositions are also useful in the kits described below.

Uses of Compounds and Pharmaceutically Acceptable Compositions

In yet another aspect, the present invention provides a method of treating a condition, disease, or disorder implicated by CFTR activity. In certain embodiments, the present invention provides a method of treating a condition, disease, or disorder implicated by a deficiency of CFTR activity, the method comprising administering a composition comprising a compound of the present invention to a subject, preferably a mammal, in need thereof.

In certain preferred embodiments, the present invention provides a method of treating Cystic fibrosis, Hereditary emphysema, Hereditary hemochromatosis, Coagulation-Fibrinolysis deficiencies, such as Protein C deficiency, Type 1 hereditary angioedema, Lipid processing deficiencies, such as Familial hypercholesterolemia, Type 1 chylomicronemia, Abetalipoproteinemia, Lysosomal storage diseases, such as I-cell disease/Pseudo-Hurler, Mucopolysaccharidoses, Sandhof/Tay-Sachs, Crigler-Najjar type II, Polyendocrinopathy/Hyperinsulemia, Diabetes mellitus, Laron dwarfism, Myleoperoxidase deficiency, Primary hypoparathyroidism, Melanoma, Glycanosis CDG type 1, Hereditary emphysema, Congenital hyperthyroidism, Osteogenesis imperfecta, Hereditary hypofibrinogenemia, ACT deficiency, Diabetes insipidus (DI), Neurophyseal DI, Neprogenic DI, Charcot-Marie Tooth syndrome, Perlizaeus-Merzbacher disease, neurodegenerative diseases such as Alzheimer's disease, Parkinson's disease, Amyotrophic lateral sclerosis, Progressive supranuclear plasy, Pick's disease, several polyglutamine neurological disorders such as Huntington, Spinocerebullar ataxia type I, Spinal and bulbar muscular atrophy, Dentatorubal pallidoluysian, and Myotonic dystrophy, as well as Spongiform encephalopathies, such as Hereditary Creutzfeldt-Jakob disease (due to Prion protein processing defect), Fabry disease, Straussler-Scheinker disease, secretory diarrhea, polycystic kidney disease, chronic obstructive pulmonary disease (COPD), dry eye disease, and Sjögren's Syndrome, comprising the step of administering to said mammal an effective amount of a composition comprising a compound of the present invention or a preferred embodiment thereof as set forth above.

According to an alternative preferred embodiment, the present invention provides a method of treating cystic fibrosis comprising the step of administering to said mammal a composition comprising the step of administering to said mammal an effective amount of a composition comprising a compound of the present invention or a preferred embodiment thereof as set forth above.

According to the invention an "effective amount" of the compound or pharmaceutically acceptable composition is that amount effective for treating or lessening the severity of one or more of Cystic fibrosis, Hereditary emphysema, Hereditary hemochromatosis, Coagulation-Fibrinolysis deficiencies, such as Protein C deficiency, Type 1 hereditary angioedema, Lipid processing deficiencies, such as Familial hypercholesterolemia, Type 1 chylomicronemia, Abetalipoproteinemia, Lysosomal storage diseases, such as I-cell disease/Pseudo-Hurler, Mucopolysaccharidoses, Sandhof/Tay-Sachs, Crigler-Najjar type II, Polyendocrinopathy/Hyperinsulemia, Diabetes mellitus, Laron dwarfism, Myleoperoxidase deficiency, Primary hypoparathyroidism, Melanoma, Glycanosis CDG type 1, Hereditary emphysema, Congenital hyperthyroidism, Osteogenesis imperfecta, Hereditary hypofibrinogenemia, ACT deficiency, Diabetes insipidus (DI), Neurophyseal DI, Neprogenic DI, Charcot-Marie Tooth syndrome, Perlizaeus-Merzbacher disease, neurodegenerative diseases such as Alzheimer's disease, Parkinson's disease, Amyotrophic lateral sclerosis, Progressive supranuclear plasy, Pick's disease, several polyglutamine neurological disorders asuch as Huntington, Spinocerebullar ataxia type I, Spinal and bulbar muscular atrophy, Dentatorubal pallidoluysian, and Myotonic dystrophy, as well as Spongiform encephalopathies, such as Hereditary Creutzfeldt-Jakob disease, Fabry disease, Straussler-Scheinker disease, secretory diarrhea, polycystic kidney disease, chronic obstructive pulmonary disease (COPD), dry eye disease, and Sjögren's Syndrome.

The compounds and compositions, according to the method of the present invention, may be administered using any amount and any route of administration effective for treating or lessening the severity of one or more of Cystic fibrosis, Hereditary emphysema, Hereditary hemochromatosis, Coagulation-Fibrinolysis deficiencies, such as Protein C deficiency, Type 1 hereditary angioedema, Lipid processing deficiencies, such as Familial hypercholesterolemia, Type 1 chylomicronemia, Abetalipoproteinemia, Lysosomal storage diseases, such as I-cell disease/Pseudo-Hurler, Mucopolysaccharidoses, Sandhof/Tay-Sachs, Crigler-Najjar type II, Polyendocrinopathy/Hyperinsulemia, Diabetes mellitus, Laron dwarfism, Myleoperoxidase deficiency, Primary hypoparathyroidism, Melanoma, Glycanosis CDG type 1, Hereditary emphysema, Congenital hyperthyroidism, Osteogenesis imperfecta, Hereditary hypofibrinogenemia, ACT deficiency, Diabetes insipidus (DI), Neurophyseal DI, Neprogenic DI, Charcot-Marie Tooth syndrome, Perlizaeus-Merzbacher disease, neurodegenerative diseases such as Alzheimer's disease, Parkinson's disease, Amyotrophic lateral sclerosis, Progressive supranuclear plasy, Pick's disease, several polyglutamine neurological disorders asuch as Huntington, Spinocerebullar ataxia type I, Spinal and bulbar muscular atrophy, Dentatorubal pallidoluysian, and Myotonic dystrophy, as well as Spongiform encephalopathies, such as Hereditary Creutzfeldt-Jakob disease, Fabry disease, Straussler-Scheinker disease, secretory diarrhea, polycystic kidney disease, chronic obstructive pulmonary disease (COPD), dry eye disease, and Sjögren's Syndrome.

The exact amount required will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms are prepared by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

As described generally above, the compounds of the invention are useful as modulators of CFTR. Thus, without wishing to be bound by any particular theory, the compounds and compositions are particularly useful for treating or lessening the severity of a disease, condition, or disorder where hyperactivity or inactivity of CFTR is implicated in the disease, condition, or disorder. When hyperactivity or inactivity of an CFTR is implicated in a particular disease, condition, or disorder, the disease, condition, or disorder may also be referred to as an "CFTR-mediated disease, condition or disorder". Accordingly, in another aspect, the present invention provides a method for treating or lessening the severity of a disease, condition, or disorder where hyperactivity or inactivity of CFTR is implicated in the disease state.

The activity of a compound utilized in this invention as a modulator of CFTR may be assayed according to methods described generally in the art and in the Examples herein.

It will also be appreciated that the compounds and pharmaceutically acceptable compositions of the present invention can be employed in combination therapies, that is, the compounds and pharmaceutically acceptable compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another agent used to treat the same disorder), or they may achieve different effects (e.g., control of any adverse effects). As used herein, additional therapeutic agents that are normally administered to treat or prevent a particular disease, or condition, are known as "appropriate for the disease, or condition, being treated".

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention or pharmaceutically acceptable compositions thereof may also be incorporated into compositions for coating an implantable medical device, such as prostheses, artificial valves, vascular grafts, stents and catheters. Accordingly, the present invention, in another aspect, includes a composition for coating an implantable device comprising a compound of the present invention as described generally above, and in classes and subclasses herein, and a carrier suitable for coating said implantable device. In still another aspect, the present invention includes an implantable device coated with a composition comprising a compound of the present invention as described generally above, and in classes and subclasses herein, and a carrier suitable for coating said implantable device. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccarides, polyethylene glycol, phospholipids or combinations thereof to impart controlled release characteristics in the composition.

Another aspect of the invention relates to modulating CFTR activity in a biological sample or a patient (e.g., in vitro or in vivo), which method comprises administering to the patient, or contacting said biological sample with a compound of formula I or a composition comprising said compound. The term "biological sample", as used herein, includes, without limitation, cell cultures or extracts thereof; biopsied material obtained from a mammal or extracts thereof and blood, saliva, urine, feces, semen, tears, or other body fluids or extracts thereof.

Modulation of CFTR activity in a biological sample is useful for a variety of purposes that are known to one of skill in the art. Examples of such purposes include, but are not limited to, the study of CFTR activity in biological and pathological phenomena and the comparative evaluation of new modulators of CFTR activity.

In yet another embodiment, a method of modulating activity of an anion channel in vitro or in vivo, is provided comprising the step of contacting said channel with a compound of the present invention. In preferred embodiments, the anion channel is a chloride channel or a bicarbonate channel. In other preferred embodiments, the anion channel is a chloride channel.

According to an alternative embodiment, the present invention provides a method of increasing the number of functional CFTR in a membrane of a cell, comprising the step of contacting said cell with a compound of the present invention. The term "functional CFTR" as used herein means an CFTR activity that is capable of transport activity.

According to another preferred embodiment, the activity of the CFTR activity is measured by measuring the transmembrane voltage potential. Means for measuring the voltage potential across a membrane in the biological sample may employ any of the known methods in the art, such as optical membrane potential assay or other electrophysiological methods.

The optical membrane potential assay utilizes voltage-sensitive FRET sensors described by Gonzalez and Tsien (See Gonzalez, J. E. and R. Y. Tsien (1995) "Voltage sensing by fluorescence resonance energy transfer in single cells" *Biophys J* 69(4): 1272-80, and Gonzalez, J. E. and R. Y. Tsien (1997) "Improved indicators of cell membrane potential that use fluorescence resonance energy transfer" *Chem Biol* 4(4): 269-77) in combination with instrumentation for measuring fluorescence changes such as the Voltage/Ion Probe Reader (VIPR) (See Gonzalez, J. E., K. Oades, et al. (1999) "Cell-based assays and instrumentation for screening ion-channel targets" *Drug Discov Today* 4(9): 431-439).

These voltage sensitive assays are based on the change in fluorescence resonant energy transfer (FRET) between the membrane-soluble, voltage-sensitive dye, DiSBAC$_2$(3), and a fluorescent phospholipid, CC2-DMPE, which is attached to the outer leaflet of the plasma membrane and acts as a FRET donor. Changes in membrane potential ($V_m$) cause the negatively charged DiSBAC$_2$(3) to redistribute across the plasma membrane and the amount of energy transfer from CC2-DMPE changes accordingly. The changes in fluorescence emission can be monitored using VIPR™ II, which is an integrated liquid handler and fluorescent detector designed to conduct cell-based screens in 96- or 384-well microtiter plates.

In another aspect the present invention provides a kit for use in measuring the activity of a CFTR activity or a fragment thereof in a biological sample in vitro or in vivo comprising (i) a composition comprising a compound of the present invention; and (ii) instructions for a.) contacting the composition with the biological sample and b.) measuring activity of said CFTR activity or a fragment thereof. In one embodiment, the kit further comprises instructions for a.) contacting an additional composition with the biological sample; b.) measuring the activity of said CFTR activity or a fragment thereof in the presence of said additional compound, and c.) comparing the activity of the CFTR activity in the presence of the additional compound with the density of the CFTR activity in the presence of a compound of the present invention.

PREPARATIONS AND EXAMPLES

A. 1-(2,2-Difluoro-benzo[1,3]dioxol-5-yl)-cyclopropanecarboxylic acid

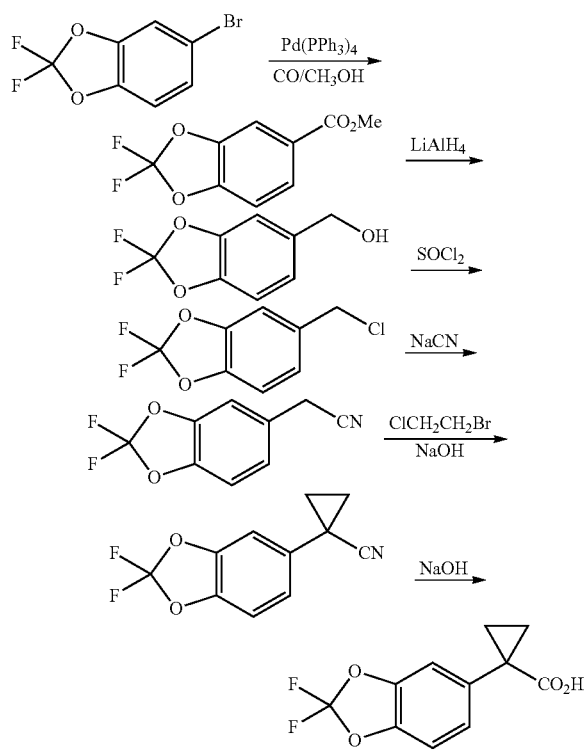

Step a: 2,2-Difluoro-benzo[1,3]dioxole-5-carboxylic acid methyl ester

A solution of 5-bromo-2,2-difluoro-benzo[1,3]dioxole (11.8 g, 50.0 mmol) and tetrakis(triphenylphosphine)palladium (0) [Pd(PPh$_3$)$_4$, 5.78 g, 5.00 mmol] in methanol (20 mL) containing acetonitrile (30 mL) and triethylamine (10 mL) was stirred under a carbon monoxide atmosphere (55 PSI) at 75° C. (oil bath temperature) for 15 hours. The cooled reaction mixture was filtered and the filtrate was evaporated to dryness. The residue was purified by silica gel column chromatography to give crude 2,2-difluoro-benzo[1,3]dioxole-5-carboxylic acid methyl ester (11.5 g), which was used directly in the next step.

Step b: (2,2-Difluoro-benzo[1,3]dioxol-5-yl)-methanol

Crude 2,2-difluoro-benzo[1,3]dioxole-5-carboxylic acid methyl ester (11.5 g) dissolved in 20 mL of anhydrous tetrahydrofuran (THF) was slowly added to a suspension of lithium aluminium hydride (4.10 g, 106 mmol) in anhydrous THF (100 mL) at 0° C. The mixture was then warmed to room temperature. After being stirred at room temperature for 1 hour, the reaction mixture was cooled to 0° C. and treated with water (4.1 mL), followed by sodium hydroxide (10% aqueous solution, 4.1 mL). The resulting slurry was filtered and washed with THF. The combined filtrate was evaporated to dryness and the residue was purified by silica gel column chromatography to give (2,2-difluoro-benzo[1,3]dioxol-5-yl)-methanol (7.2 g, 76% over two steps) as a colourless oil.

Step c: 5-Chloromethyl-2,2-difluoro-benzo[1,3]dioxole

Thionyl chloride (45 g, 38 mmol) was slowly added to a solution of (2,2-difluoro-benzo[1,3]dioxol-5-yl)-methanol (7.2 g, 38 mmol) in dichloromethane (200 mL) at 0° C. The resulting mixture was stirred overnight at room temperature and then evaporated to dryness. The residue was partitioned between an aqueous solution of saturated sodium bicarbonate (100 mL) and dichloromethane (100 mL). The separated aqueous layer was extracted with dichloromethane (150 mL) and the organic layer was dried over sodium sulfate, filtered, and evaporated to dryness to give crude 5-chloromethyl-2,2-difluoro-benzo[1,3]dioxole (4.4 g) which was used directly in the next step.

Step d: (2,2-Difluoro-benzo[1,3]-dioxol-5-yl)-acetonitrile

A mixture of crude 5-chloromethyl-2,2-difluoro-benzo[1,3]dioxole (4.4 g) and sodium cyanide (1.36 g, 27.8 mmol) in dimethylsulfoxide (50 mL) was stirred at room temperature overnight. The reaction mixture was poured into ice and extracted with ethyl acetate (300 mL). The organic layer was dried over sodium sulfate and evaporated to dryness to give crude (2,2-difluoro-benzo[1,3]dioxol-5-yl)-acetonitrile (3.3 g) which was used directly in the next step.

Step e: 1-(2,2-Difluoro-benzo[1,3]dioxol-5-yl)-cyclopropanecarbonitrile

Sodium hydroxide (50% aqueous solution, 10 mL) was slowly added to a mixture of crude (2,2-difluoro-benzo[1,3]dioxol-5-yl)-acetonitrile, benzyltriethylammonium chloride (3.00 g, 15.3 mmol), and 1-bromo-2-chloroethane (4.9 g, 38 mmol) at 70° C. The mixture was stirred overnight at 70° C. before the reaction mixture was diluted with water (30 mL) and extracted with ethyl acetate. The combined organic layers were dried over sodium sulfate and evaporated to dryness to give crude 1-(2,2-difluoro-benzo[1,3]dioxol-5-yl)-cyclopropanecarbonitrile, which was used directly in the next step.

Step f: 1-(2,2-Difluoro-benzo[1,3]dioxol-5-yl)-cyclopropanecarboxylic acid 1-(2,2-Difluoro-benzo[1,3]dioxol-5-yl)-cyclopropanecarbonitrile (crude from the last step) was refluxed in 10% aqueous sodium hydroxide (50 mL) for 2.5 hours. The cooled reaction mixture was washed with ether (100 mL) and the aqueous phase was acidified to pH 2 with 2M hydrochloric acid. The precipitated solid was filtered to give 1-(2,2-difluoro-benzo[1,3]dioxol-5-yl)-cyclopropanecarboxylic acid as a white solid (0.15 g, 1.6% over four steps). ESI-MS m/z calc. 242.2. found 243.3 (M+1)+; $^1$H NMR (CDCl$_3$) δ 7.14-7.04 (m, 2H), 6.98-6.96 (m, 1H), 1.74-1.64 (m, 2H), 1.26-1.08 (m, 2H).

B. 1-Benzo[1,3]dioxol-5-yl-cyclopropanecarboxylic acid

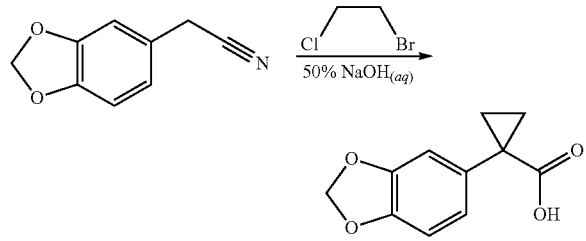

A mixture of benzo[1,3]dioxole-5-acetonitrile (5.10 g, 31.7 mmol), 1-bromo-2-chloro-ethane (9.0 mL, 109 mmol), and benzyltriethylammonium chloride (0.181 g, 0.795 mmol) was heated at 70° C. and then 50% (wt./wt.) aqueous sodium hydroxide (26 mL) was slowly added to the mixture. The reaction was stirred at 70° C. for 18 hours and then heated at 130° C. for 24 hours. The dark brown reaction mixture was diluted with water (400 mL) and extracted once with an equal volume of ethyl acetate and once with an equal volume of dichloromethane. The basic aqueous solution was acidified with concentrated hydrochloric acid to pH less than one and the precipitate filtered and washed with 1 M hydrochloric acid. The solid material was dissolved in dichloromethane (400 mL) and extracted twice with equal volumes of 1 M hydrochloric acid and once with a saturated aqueous solution of sodium chloride. The organic solution was dried over sodium sulfate and evaporated to dryness to give a white to slightly off-white solid (5.23 g, 80%) ESI-MS m/z calc. 206.1. found 207.1 (M+1)+. Retention time of 2.37 minutes. $^1$H NMR (400 MHz, DMSO-d$_6$) δ 1.07-1.11 (m, 2H), 1.38-1.42 (m, 2H), 5.98 (s, 2H), 6.79 (m, 2H), 6.88 (m, 1H), 12.26 (s, 1H).

C. 1-(2,3-Dihydrobenzofuran-5-yl)cyclopropanecarboxylic acid

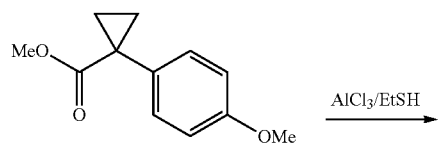

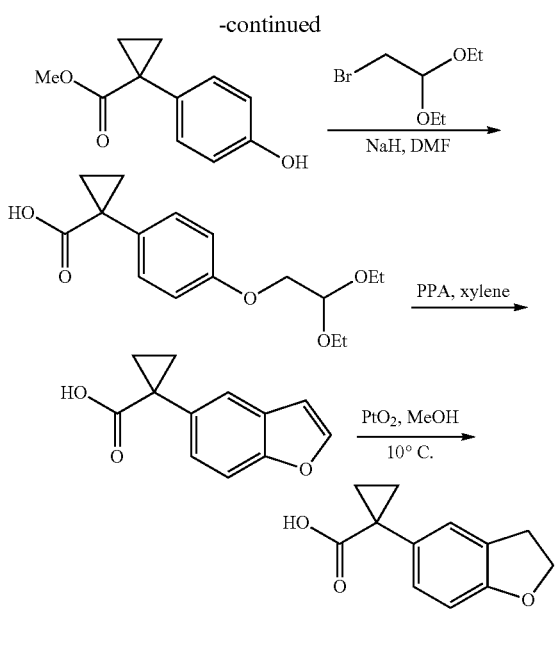

Step a: 1-(4-Hydroxy-phenyl)-cyclopropanecarboxylic acid methyl ester

To a solution of methyl 1-(4-methoxyphenyl)cyclopropanecarboxylate (10.0 g, 48.5 mmol) in dichloromethane (80 mL) was added EtSH (16 mL) under ice-water bath. The mixture was stirred at 0° C. for 20 min before AlCl$_3$ (19.5 g, 0.150 mmol) was added slowly at 0° C. The mixture was stirred at 0° C. for 30 min. The reaction mixture was poured into ice-water, the organic layer was separated, and the aqueous phase was extracted with dichloromethane (50 mL×3). The combined organic layers were washed with H$_2$O, brine, dried over Na$_2$SO$_4$ and evaporated under vacuum to give 1-(4-hydroxy-phenyl)-cyclopropanecarboxylic acid methyl ester (8.9 g, 95%). $^1$H NMR (400 MHz, CDCl$_3$) δ 7.20-7.17 (m, 2H), 6.75-6.72 (m, 2H), 5.56 (s, 1H), 3.63 (s, 3H), 1.60-1.57 (m, 2H), 1.17-1.15 (m, 2H).

Step b: 1-[4-(2,2-Diethoxy-ethoxy)-phenyl]-cyclopropanecarboxylic acid

To a stirred solution of 1-(4-hydroxy-phenyl)-cyclopropanecarboxylic acid methyl ester (15.0 g, 84.3 mmol) in DMF (50 mL) was added sodium hydride (6.7 g, 170 mmol, 60% in mineral oil) at 0° C. After hydrogen evolution ceased, 2-bromo-1,1-diethoxy-ethane (16.5 g, 84.3 mmol) was added drop-wise to the reaction mixture. The reaction was stirred at 160° C. for 15 hours. The reaction mixture was poured onto ice (100 g) and extracted with dichloromethane. The combined organics were dried over Na$_2$SO$_4$. The solvent was evaporated under vacuum to give crude 1-[4-(2,2-diethoxy-ethoxy)-phenyl]-cyclopropanecarboxylic acid (10 g), which was used directly in the next step without purification.

Step c: 1-Benzofuran-5-yl-cyclopropanecarboxylic acid

To a suspension of crude 1-[4-(2,2-diethoxy-ethoxy)-phenyl]-cyclopropanecarboxylic acid (20 g, ~65 mmol) in xylene (100 mL) was added PPA (22.2 g, 64.9 mmol) at room temperature. The mixture was heated at reflux (140° C.) for 1 hour before it was cooled to room temperature and decanted from the PPA. The solvent was evaporated under vacuum to obtain the crude product, which was purified by preparative HPLC to provide 1-(benzofuran-5-yl)cyclopropanecarboxylic acid (1.5 g, 5%). $^1$H NMR (400 MHz, DMSO-$d_6$) δ 12.25 (br s, 1H), 7.95 (d, J=2.8 Hz, 1H), 7.56 (d, J=2.0 Hz, 1H), 7.47 (d, J=11.6 Hz, 1H), 7.25 (dd, J=2.4, 11.2 Hz, 1H), 6.89 (d, J=1.6 Hz, 1H), 1.47-1.44 (m, 2H), 1.17-1.14 (m, 2H).

Step d: 1-(2,3-Dihydrobenzofuran-5-yl)cyclopropanecarboxylic acid

To a solution of 1-(benzofuran-5-yl)cyclopropanecarboxylic acid (700 mg, 3.47 mmol) in MeOH (10 mL) was added PtO$_2$ (140 mg, 20%) at room temperature. The stirred reaction mixture was hydrogenated under hydrogen (1 atm) at 10° C. for 3 days. The reaction mixture was filtered. The solvent was evaporated under vacuum to afford the crude product, which was purified by preparative HPLC to give 1-(2,3-dihydrobenzofuran-5-yl)cyclopropanecarboxylic acid (330 mg, 47%). $^1$H NMR (400 MHz, CDCl$_3$) δ 7.20 (s, 1H), 7.10 (d, J=10.8 Hz, 1H), 6.73 (d, J=11.2 Hz, 1H), 4.57 (t, J=11.6 Hz, 2H), 3.20 (t, J=11.6 Hz, 2H), 1.67-1.63 (m, 2H), 1.25-1.21 (m, 2H).

D. 1-(2,3-Dihydro-1H-inden-5-yl)cyclopropanecarboxylic acid

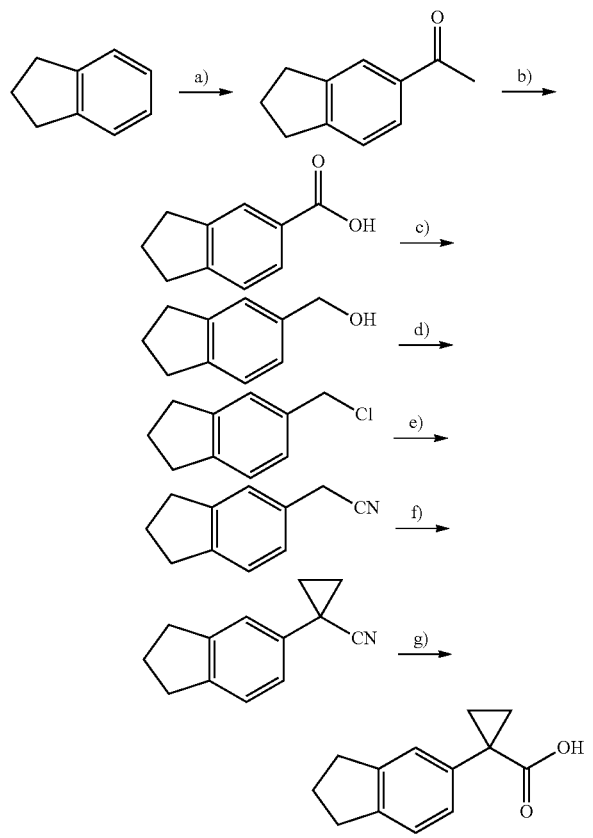

a) Ac$_2$O, AlCl$_3$, CH$_2$Cl$_2$; b) NaClO; c) LiAlH$_4$, THF, -78° C.; d) SOCl$_2$, CHCl$_3$; e) NaCN, DMSO; f) BrCH$_2$CH$_2$Cl, NaOH, Bu$_4$NBr, toluene; g) NaOH.

Step a: 1-(2,3-Dihydro-1H-inden-6-yl)ethanone

A mixture of 2,3-dihydro-1H-indene (100.0 g, 0.85 mol) and acetic anhydride (104.2 g, 1.35 mol) was added dropwise to a slurry of AlCl$_3$ (272.0 g, 2.04 mol) in CH$_2$Cl$_2$ (1000 ml) at 0° C. over a period of 3 h. The reaction mixture was stirred at room temperature under a nitrogen atmosphere for 15 h. Then the reaction mixture was poured into ice water (500 mL) and extracted with ethyl acetate (500 mL×3). The combined organic layers were washed with brine (500 mL), dried over Na$_2$SO$_4$ and evaporated in vacuo. The residue that was purified by column chromatography (petroleum ether:ethyl acetate=20:1) to give the product (120.0 g, 88%). $^1$H NMR (400 MHz, CDCl$_3$) δ 2.08-2.15 (m, 2H), 2.58 (s, 3H), 2.95 (t, J=7.2, 4H), 7.28 (d, J=8.0, 1H), 7.75 (d, J=8.0, 1H) 7.82 (s, 1H).

Step b: 2,3-dihydro-1H-indene-5-carboxylic acid

To a stirred aqueous sodium hypochlorite solution (2230 ml, 1.80 mmol, 6%) at 55° C. was added 1-(2,3-dihydro-1H-inden-6-yl)ethanone (120.0 g, 0.75 mol) and the mixture was stirred at 55° C. for 2 h. After cooling to room temperature, saturated NaHCO$_3$ solution was added until the solution became clear. The produced precipitate was filtered, washed several times with water and dried to afford the desired product (120.0 g, 99%). $^1$H NMR (CDCl$_3$, 300 MHz) δ 2.07-2.17 (m, 2H), 2.96 (t, J=7.5 Hz, 4H), 7.30 (d, J=7.8, 1H), 7.91 (d, J=7.8, 1H), 7.96 (s, 1H).

Step c: (2,3-dihydro-1H-inden-5-yl)methanol

To a stirred solution of lithium aluminium hydride (72.8 g, 1.92 mol) in THF (2.5 L) at 0° C. was slowly added 2,3-dihydro-1H-indene-5-carboxylic acid (100.0 g, 0.62 mol). The reaction mixture was stirred at 0° C. for 1 h. Then the reaction was quenched with H$_2$O (72 ml) and NaOH (68 ml, 20%). The mixture was filtered and the organic layer was dried over Na$_2$SO$_4$, evaporated in vacuo and the residue was purified by column chromatography (petroleum ether:ethyl acetate=10:1) to give the desired product (82.0 g, 90%). $^1$H NMR (CDCl$_3$, 300 MHz); δ 2.03-2.13 (m, 2H), 2.91 (t, J=7.5 Hz, 4H), 4.64 (s, 2H), 7.13 (d, J=7.5, 1H), 7.18-7.24 (m, 2H).

Step d: 5-(chloromethyl)-2,3-dihydro-1H-indene

Thionyl chloride (120 ml, 1.65 mol) was added drop-wise to a rapidly stirred mixture of (2,3-dihydro-1H-inden-5-yl)methanol (81.4 g, 0.55 mol) in chloroform (500 ml) at 0° C. After the addition was complete, the resulting mixture was allowed to warm to room temperature and the stirring was continued for an additional 12 h. The chloroform was evaporated under reduced pressure to give a residue, that was purified by column chromatography (petroleum ether:ethyl acetate=15:1) to afford 5-(chloromethyl)-2,3-dihydro-1H-indene (90.5 g, 99%). $^1$H NMR (300 MHz, CDCl$_3$) δ 2.06-2.19 (m, 4H), 2.93 (t, J=7.5, 4H), 4.54 (s, 2H), 7.15-7.31 (m, 3H).

Step e: 2-(2,3-dihydro-1H-inden-5-yl)acetonitrile

To a stirred solution of 5-(chloromethyl)-2,3-dihydro-1H-indene (90.0 g, 0.54 mol) in DMSO (500 ml) was added sodium cyanide (54.0 g, 1.08 mol) at 0° C. portion wise. The reaction mixture was then stirred at room temperature for 3 hours. The reaction was quenched with water (1000 ml), extracted with ethyl acetate (3×250 mL). The combined organic layers were washed with brine, dried over Na$_2$SO$_4$ and evaporated in vacuo to afford 2-(2,3-dihydro-1H-inden-5-yl)acetonitrile (82.2 g, 97%), that was used in the next step without further purification.

Step f: 1-(2,3-dihydro-1H-inden-6-yl)cyclopropanecarbonitrile

To a stirred solution of 2-(2,3-dihydro-1H-inden-5-yl) acetonitrile (50.0 g, 0.32 mol) in toluene (150 mL) was added sodium hydroxide (300 mL, 50 percent in water W/W), 1-bromo-2-chloroethane (92.6 ml, 1.12 mol) and (n-Bu)$_4$NBr (5 g, 15.51 mmol). The mixture was heated at 60° C. overnight. After cooling to room temperature, the reaction mixture was diluted with water (400 mL) and extracted with EtOAc (3×200 mL). The combined organic extracts were washed with brine, dried over Na$_2$SO$_4$, filtered and concentrated under vacuum and purified by column chromatography (petroleum ether:ethyl acetate=10:1) to yield 1-(2,3-dihydro-1H-inden-6-yl)cyclopropanecarbonitrile (9.3 g, 16%). $^1$H NMR (CDCl$_3$, 300 MHz) δ 1.35-1.38 (m, 2H), 1.66-1.69 (m, 2H), 2.05-2.13 (m, 2H), 2.87-294 (m, 4H), 7.07-7.22 (m, 3H).

Step g: 1-(2,3-dihydro-1H-inden-6-yl)cyclopropanecarboxylic acid

To a stirred 1-(2,3-dihydro-1H-inden-6-yl)cyclopropanecarbonitrile (9.3 g, 50.8 mmol) in methanol (40 mL) was added a solution of 150 mL of sodium hydroxide (25% NaOH w/w in water). The mixture was heated at 100° C. for 8 hours. After cooling to room temperature, the reaction mixture was poured over ice-water (0° C.), the pH was adjusted to pH=4 with hydrogen chloride (1 N) and the mixture was extracted with dichloromethane (3×100 mL). The combined organic layers were dried over Na$_2$SO$_4$ and evaporated under vacuum. The residue that was purified by column chromatography (petroleum ether:ethyl acetate=5:1) to give 1-(2,3-dihydro-1H-inden-6-yl)cyclopropanecarboxylic acid (4.8 g, 47%). $^1$H NMR (CDCl$_3$, 400 MHz) δ 1.23-1.26 (m, 2H), 1.62-1.65 (m, 2H), 2.03-210 (m, 2H), 2.81-2.91 (m, 4H), 7.11-7.21 (m, 3H).

E. 2-(3-Chloro-4-methoxyphenyl)acetonitrile

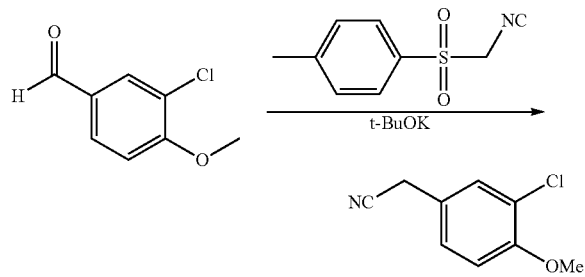

To a suspension of t-BuOK (4.8 g, 40 mmol) in THF (30 mL) was added a solution of TosMIC (3.9 g, 20 mmol) in THF (10 mL) at −78° C. and the mixture was stirred for 10 minutes. A solution of 3-chloro-4-methoxy-benzaldehyde (1.7 g, 10 mmol) in THF (10 mL) was added dropwise, and the reaction was stirred at −78° C. for 1.5 hours. To the cooled reaction mixture was added methanol (10 mL) and the mixture was heated at reflux for 30 minutes. The solvent were evaporated to give a crude residue that was dissolved in water (20 mL). The aqueous phase was extracted with ethyl acetate (20 mL×3). The combined organic layers were dried and evaporated under reduced pressure to give a crude product that was purified by column chromatography (petroleum ether/ethyl acetate 10:1) to yield 2-(3-chloro-4-methoxyphenyl)acetonitrile (1.5 g, 83%). $^1$H NMR (400 MHz, CDCl$_3$) δ 7.33 (d, J=2.4 Hz, 1H), 7.20 (dd, J=2.4, 8.4 Hz, 1H), 6.92 (d, J=8.4 Hz, 1H), 3.91 (s, 3H), 3.68 (s, 2H). $^{13}$C NMR (100 MHz, CDCl$_3$) δ 154.8, 129.8, 127.3, 123.0, 122.7, 117.60, 112.4, 56.2, 22.4.

F. 2-(2,3-Dihydrobenzo[b][1,4]dioxin-6-yl)acetonitrile

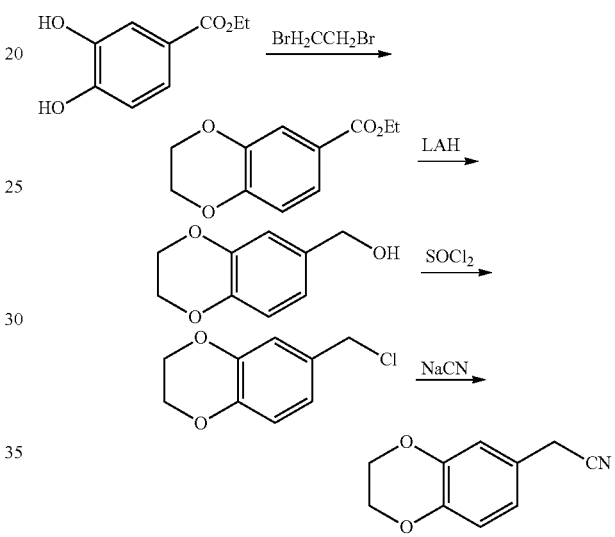

Step a: 2,3-Dihydro-benzo[1,4]dioxine-6-carboxylic acid ethyl ester

To a suspension of Cs$_2$CO$_3$ (270 g, 1.49 mol) in DMF (1000 mL) were added 3,4-dihydroxybenzoic acid ethyl ester (54.6 g, 0.3 mol) and 1,2-dibromoethane (54.3 g, 0.29 mol) at room temperature. The resulting mixture was stirred at 80° C. overnight and then poured into ice-water. The mixture was extracted with ethyl acetate (200 mL×3). The combined organic layers were washed with water (200 mL×3) and brine (100 mL), dried over Na$_2$SO$_4$ and concentrated to dryness. The residue was purified by column chromatography (petroleum ether/ethyl acetate 50:1) on silica gel to obtain 2,3-dihydro-benzo[1,4]dioxine-6-carboxylic acid ethyl ester (18 g, 29%). $^1$H NMR (300 MHz, CDCl$_3$) δ 7.53 (dd, J=1.8, 7.2 Hz, 2H), 6.84-6.87 (m, 1H), 4.22-4.34 (m, 6H), 1.35 (t, J=7.2 Hz, 3H).

Step b: (2,3-Dihydro-benzo[1,4]dioxin-6-yl)-methanol

To a suspension of LiAlH$_4$ (2.8 g, 74 mmol) in THF (20 mL) was added dropwise a solution of 2,3-dihydro-benzo [1,4]dioxine-6-carboxylic acid ethyl ester (15 g, 72 mmol) in THF (10 mL) at 0° C. under N$_2$ atmosphere. The mixture was stirred at room temperature for 1 h and then quenched carefully by addition of water (2.8 mL) and NaOH (10%, 28 mL) with cooling. The precipitated solid was filtered off and the filtrate was evaporated to dryness to yield (2,3-dihydro-benzo[1,4]dioxin-6-yl)-methanol (10.6 g) that was taken into the next step without further purification. $^1$H NMR (300 MHz, DMSO-d$_6$) δ 6.73-6.78 (m, 3H), 5.02 (t, J=5.7 Hz, 1H), 4.34 (d, J=6.0 Hz, 2H), 4.17-4.20 (m, 4H).

Step c:
6-Chloromethyl-2,3-dihydro-benzo[1,4]dioxine

A mixture of (2,3-dihydro-benzo[1,4]dioxin-6-yl)methanol (10.6 g) in SOCl$_2$ (10 mL) was stirred at room temperature for 10 min and then poured into ice-water. The organic layer was separated and the aqueous phase was extracted with dichloromethane (50 mL×3). The combined organic layers were washed with saturated solution of NaHCO$_3$, water and brine, dried over Na$_2$SO$_4$ and concentrated to dryness to obtain 6-chloromethyl-2,3-dihydro-benzo[1,4]dioxine (12 g, 88% over two steps), which was used directly in next step without further purification.

Step d: 2-(2,3-Dihydrobenzo[b][1,4]dioxin-6-yl)acetonitrile

A mixture of 6-chloromethyl-2,3-dihydro-benzo[1,4]dioxine (12.5 g, 67.7 mmol) and NaCN (4.30 g, 87.8 mmol) in DMSO (50 mL) was stirred at 25° C. for 1 h. The mixture was poured into water (150 mL) and then extracted with dichloromethane (50 mL×4). The combined organic layers were washed with water (50 mL×2), brine (50 mL), dried over Na$_2$SO$_4$ and concentrated to dryness. The residue was purified by silica gel column chromatography (petroleum ether/ethyl acetate 50:1) to yield 2-(2,3-dihydrobenzo[b][1,4]dioxin-6-yl)acetonitrile as a yellow oil (10.2 g, 86%). $^1$H-NMR (300 MHz, CDCl$_3$) δ 6.78-6.86 (m, 3H), 4.25 (s, 4H), 3.63 (s, 2H).

G. 2-(2,3-Dihydrobenzofuran-6-yl)acetonitrile

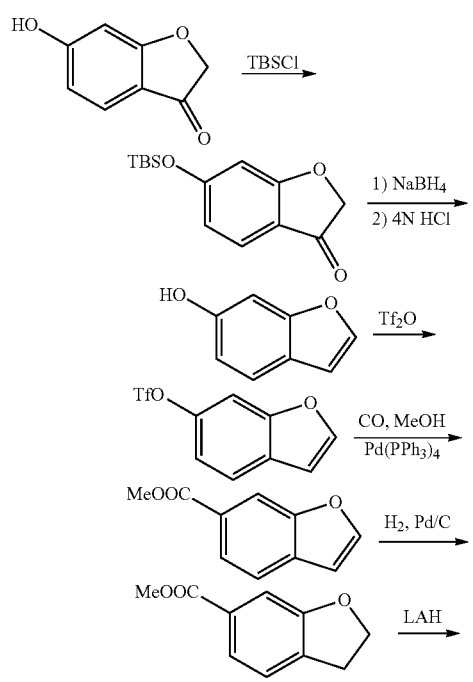

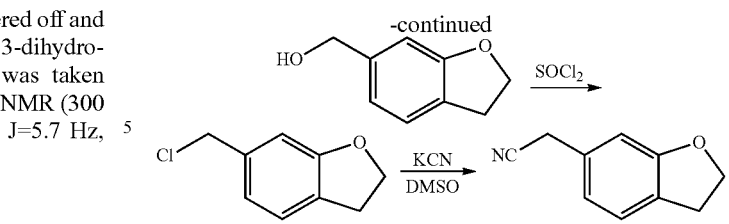

Step a:
6-(tert-Butyldimethylsilyloxy)benzofuran-3(2H)-one

To a solution of 6-hydroxybenzofuran-3(2H)-one (30.0 g, 200 mmol) in dichloromethane (500 mL) was added TBSCl (36.0 g, 240 mmol) and imidazole (16.3 g, 240 mmol) at room temperature. The reaction mixture was stirred at room temperature for 3 h. The solvent was removed under reduced pressure to afford 6-(tert-butyldimethylsilyloxy)benzofuran-3(2H)-one (40.0 g, 80% yield), that was used directly in the next step without further purification.

Step b: Benzofuran-6-ol

NaBH$_4$ (6.0 g, 160 mmol) was added to a solution of 6-(tert-butyldimethylsilyloxy)benzofuran-3(2H)-one (40.0 g, 151 mmol) in MeOH (800 mL) at room temperature. After stirring at room temperature for 2 h, the reaction mixture was treated with acetone. Subsequently 4N HCl were added to the mixture and the stirring was continued for 3 h at room temperature. The mixture was diluted with water and extracted with ethyl acetate (3×1000 mL). The extract was washed with brine, dried, concentrated in vacuo and purified by column chromatography on silica gel (5-10% ethyl acetate in petroleum ether) to afford the pure product (17.0 g, 85.5% yield). $^1$H NMR (300 MHz, CDCl$_3$) δ: 7.51 (d, J=2.1, 1H), 7.41 (d, J=8.4, 1H), 7.02 (d, J=1.8, 1H), 6.81 (dd, J=8.4, 2.1, 1H), 6.68 (dd, J=2.1, 0.9, 1H), 5.5 (br s, 1H).

Step c: Benzofuran-6-yl trifluoromethanesulfonate

To a stirred solution of benzofuran-6-ol (17.0 g, 127 mmol) in pyridine (20 g, 254 mmol) and dichloromethane (200 mL) was added Tf$_2$O (53.7 g, 190 mmol). The reaction mixture was stirred at room temperature for 16 h. The reaction mixture was diluted with water, and extracted with ethyl acetate. The combined organic layers were washed with brine, dried over Na$_2$SO$_4$, filtered and concentrated to afford a crude product that was purified by column chromatography on silica gel (5-10% ethyl acetate in petroleum ether) to afford benzofuran-6-yl trifluoromethanesulfonate (30.0 g, 88.0% yield). $^1$H NMR (300 MHz, CDCl$_3$) δ: 7.72 (d, J=2.1, 1H), 7.67 (d, J=8.7, 1H), 7.48 (d, J=1.5, 1H), 7.19 (dd, J=8.7, 2.1, 1H), 6.82-6.91 (m, 1H).

Step d: Methyl benzofuran-6-carboxylate

A mixture of benzofuran-6-yl trifluoromethanesulfonate (16.2 g, 61 mmol), 1,3-bis(diphenyl phosphino)propane (1.4 g, 3.3 mmol) and Pd(OAc)$_2$ (756 mg, 3.3 mmol) in DIEA (16.2 g, 124 mmol), MeOH (153 mL) and DMF (153 mL) was stirred at 70° C. under atmosphere of CO for 24 h. The reaction mixture was diluted with water, and extracted with ethyl acetate. The combined organic layer was then washed with brine and dried over Na$_2$SO$_4$, filtered and concentrated to afford a crude mixture that was purified by column chromatography on silica gel (5-10% ethyl acetate in petroleum ether) to yield methyl benzofuran-6-carboxylate (8.5 g, 80% yield). ¹H NMR (300 MHz, CDCl₃) δ: 8.21 (s, 1H), 7.96 (dd, J=8.1, 1.5, 1H), 7.76 (d, J=2.1, 1H), 7.63 (d, J=8.1, 1H), 6.83-6.82 (m, 1H), 3.95 (s, 1H).

Step e: Methyl 2,3-dihydrobenzofuran-6-carboxylate

A mixture of methyl benzofuran-6-carboxylate (17.8 g, 100 mmol) and 10% Pd/C (10.5 g) in MeOH was stirred under hydrogen atmosphere at 50 psi for 2 h. The catalyst was removed by filtration. The solvent was removed under reduced pressure to afford the desired methyl 2,3-dihydrobenzofuran-6-carboxylate (17.8 g, 98.5% yield). ¹H NMR (400 MHz, CDCl₃) δ: 7.57 (d, J=7.6, 1H), 7.40 (s, 1H), 7.23 (d, J=7.6, 1H), 4.61 (t, J=8.8, 2H), 3.89 (s, 3H), 3.25 (t, J=8.8, 2H).

Step f (2,3-Dihydrobenzofuran-6-yl)methanol

To a stirred solution of lithium aluminium hydride (6.1 g, 250 mmol) in THF (300 mL) was added a solution of methyl 2,3-dihydrobenzofuran-6-carboxylate (17.8 g, 100 mmol) in THF at 0° C. The mixture was stirred at room temperature for 1 h. A saturated aqueous NaOH solution was added and the mixture was extracted with ethyl acetate. The combined organic layers were washed with brine and dried over Na₂SO₄, filtered and concentrated to afford (2,3-dihydrobenzofuran-6-yl)methanol (13.8 g, 92.0% yield). ¹H NMR (400 MHz, CDCl₃) δ: 7.17 (d, J=7.2, 1H), 6.84 (d, J=7.2, 1H), 6.81 (s, 1H), 4.62 (s, 2H), 4.58 (t, J=8.4, 2H), 3.20 (t, J=8.4, 2H),) 1.67 (br s, 1H).

Step g: 6-(Chloromethyl)-2,3-dihydrobenzofuran

To a solution of (2,3-dihydrobenzofuran-6-yl)methanol (13.8 g, 92 mmol) in CHCl₃ (200 mL) was slowly added SOCl₂ at 0° C. The reaction mixture was stirred at reflux for 4 h. After the solvent was removed, saturated NaHCO₃ and ethyl acetate were added to the mixture. The organic layer was extracted with ethyl acetate. The combined organic layer was then washed with brine and dried over Na₂SO₄, filtered and concentrated to afford 6-(chloromethyl)-2,3-dihydrobenzofuran (12.3 g, 80.0% yield). ¹H NMR (400 MHz, CDCl₃) δ: 7.16 (d, J=7.5, 1H), 6.87 (d, J=7.5, 1H), 6.83 (s, 1H), 4.58 (t, J=8.7, 2H), 4.49 (s, 2H), 3.20 (t, J=8.7, 2H).

Step h: 2-(2,3-Dihydrobenzofuran-6-yl)acetonitrile

To a solution of 6-(chloromethyl)-2,3-dihydrobenzofuran (12.3 g, 73 mmol) in DMSO (100 mL) was added KCN (7.1 g, 109.5 mmol). The reaction mixture was stirred at 100° C. for 2 hours. The mixture was diluted with water and extracted with ethyl acetate (3×200 mL). The combined organic layers were washed with brine, dried, concentrated in vacuo and purified by column chromatography on silica gel (5-10% ethyl acetate in petroleum ether) to afford 2-(2,3-dihydrobenzofuran-6-yl)acetonitrile (8.4 g, 70.4% yield). ¹H NMR (400 MHz, CDCl₃) δ: 7.16 (d, J=7.6, 1H), 6.79 (d, J=7.2, 1H), 6.72 (s, 1H), 4.58 (t, J=8.4, 2H), 3.67 (s, 2H), 3.19 (t, J=8.4, 2H).

The following acids were commercially available or were prepared as described above

| Structure | Name |
| --- | --- |
| 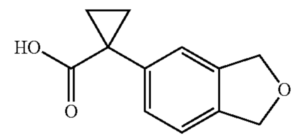 [SMILES: O=C(O)C1(c2ccc3c(c2)COC3)CC1] | 1-(1,3-dihydroisobenzofuran-5-yl)cyclopropanecarboxylic acid |
| 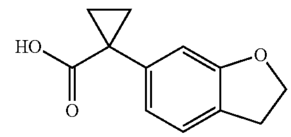 [SMILES: O=C(O)C1(c2ccc3c(c2)OCC3)CC1] | 1-(2,3-dihydrobenzofuran-6-yl)cyclopropanecarboxylic acid |
| 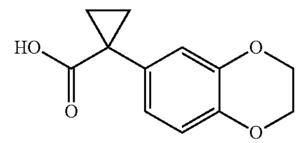 [SMILES: O=C(O)C1(c2ccc3c(c2)OCCO3)CC1] | 1-(2,3-dihydrobenzo[b][1,4]dioxin-6-yl)cyclopropanecarboxylic acid |
| 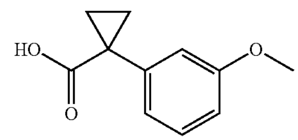 | 1-(3-methoxyphenyl)cyclopropanecarboxylic acid |
| 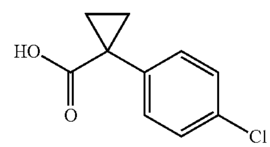 [SMILES: O=C(O)C1(c2ccc(Cl)cc2)CC1] | 1-(4-chlorophenyl)cyclopropanecarboxylic acid |
| 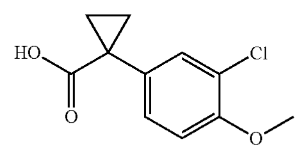 | 1-(3-chloro-4-methoxyphenyl)cyclopropanecarboxylic acid |

G. 6-Chloro-5-methylpyridin-2-amine

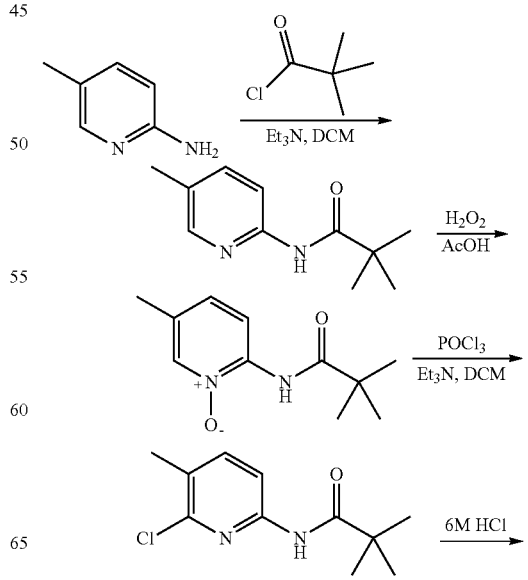

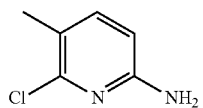

Step a: 2,2-Dimethyl-N-(5-methyl-pyridin-2-yl)-propionamide

To a stirred solution of 5-methylpyridin-2-amine (200 g, 1.85 mol) in anhydrous CH$_2$Cl$_2$ (1000 mL) was added drop wise a solution of Et$_3$N (513 mL, 3.70 mol) and 2,2-dimethyl-propionyl chloride (274 mL, 2.22 mol) at 0° C. under N$_2$. The ice bath was removed and stirring was continued at room temperature for 2 hours. The reaction was poured into ice (2000 g). The organic layer was separated and the remaining aqueous layer was extracted with CH$_2$Cl$_2$ (3×). The combined organics were dried over Na$_2$SO$_4$ and evaporated to afford 2,2-dimethyl-N-(5-methyl-pyridin-2-yl)-propionamide (350 g), which was used in the next step without further purification. $^1$H NMR (400 MHz, CDCl$_3$) δ 8.12 (d, J=8.4 Hz, 1H), 8.06 (d, J=1.2 Hz, 1H), 7.96 (s, 1H), 7.49 (dd, J=1.6, 8.4 Hz, 1H), 2.27 (s, 1H), 1.30 (s, 9H).

Step b: 2,2-Dimethyl-N-(5-methyl-1-oxy-pyridin-2-yl)-propionamide

To a stirred solution of 2,2-dimethyl-N-(5-methyl-pyridin-2-yl)-propionamide (100 g, 0.52 mol) in AcOH (500 mL) was added drop-wise 30% H$_2$O$_2$ (80 mL, 2.6 mol) at room temperature. The mixture was stirred at 80° C. for 12 hours. The reaction mixture was evaporated under vacuum to obtain 2,2-dimethyl-N-(5-methyl-1-oxy-pyridin-2-yl)-propionamide (80 g, 85% purity). $^1$H NMR (400 MHz, CDCl$_3$) δ 10.26 (br s, 1H), 8.33 (d, J=8.4 Hz, 1H), 8.12 (s, 1H), 7.17 (dd, J=0.8, 8.8 Hz, 1H), 2.28 (s, 1H), 1.34 (s, 9H).

Step c: N-(6-Chloro-5-methyl-pyridin-2-yl)-2,2-dimethyl-propionamide

To a stirred solution of 2,2-dimethyl-N-(5-methyl-1-oxy-pyridin-2-yl)-propionamide (10 g, 48 mmol) in anhydrous CH$_2$Cl$_2$ (50 mL) was added Et$_3$N (60 mL, 240 mmol) at room temperature. After being stirred for 30 min, POCl$_3$ (20 mL) was added drop-wise to the reaction mixture. The reaction was stirred at 50° C. for 15 hours. The reaction mixture was poured into ice (200 g). The organic layer was separated and the remaining aqueous layer was extracted with CH$_2$Cl$_2$ (3×). The combined organics were dried over Na$_2$SO$_4$. The solvent was evaporated under vacuum to obtain the crude product, which was purified by column chromatography (Petroleum Ether/EtOAc 100:1) to provide N-(6-chloro-5-methyl-pyridin-2-yl)-2,2-dimethyl-propionamide (0.5 g, 5%). $^1$H NMR (400 MHz, CDCl$_3$) δ 8.09 (d, J=8.0 Hz, 1H), 7.94 (br s, 1H), 7.55 (d, J=8.4 Hz, 1H), 2.33 (s, 1H), 1.30 (s, 9H).

Step d: 6-Chloro-5-methyl-pyridin-2-ylamine

To N-(6-chloro-5-methyl-pyridin-2-yl)-2,2-dimethyl-propionamide (4.00 g, 17.7 mmol) was added 6 N HCl (20 mL) at room temperature. The reaction mixture was stirred at 80° C. for 12 hours. The reaction mixture was basified with drop-wise addition of sat. NaHCO$_3$ to pH 8-9, and then the mixture was extracted with CH$_2$Cl$_2$ (3×). The organic phases were dried over Na$_2$SO$_4$ and evaporated under vacuum to obtain the 6-chloro-5-methyl-pyridin-2-ylamine (900 mg, 36%). $^1$H NMR (400 MHz, CDCl$_3$) δ 7.28 (d, J=8.0 Hz, 1H), 6.35 (d, J=8.0 Hz, 1H), 4.39 (br s, 2H), 2.22 (s, 3H). MS (ESI) m/z: 143 (M+H$^+$).

H. 6-Chloro-5-ethylpyridin-2-amine

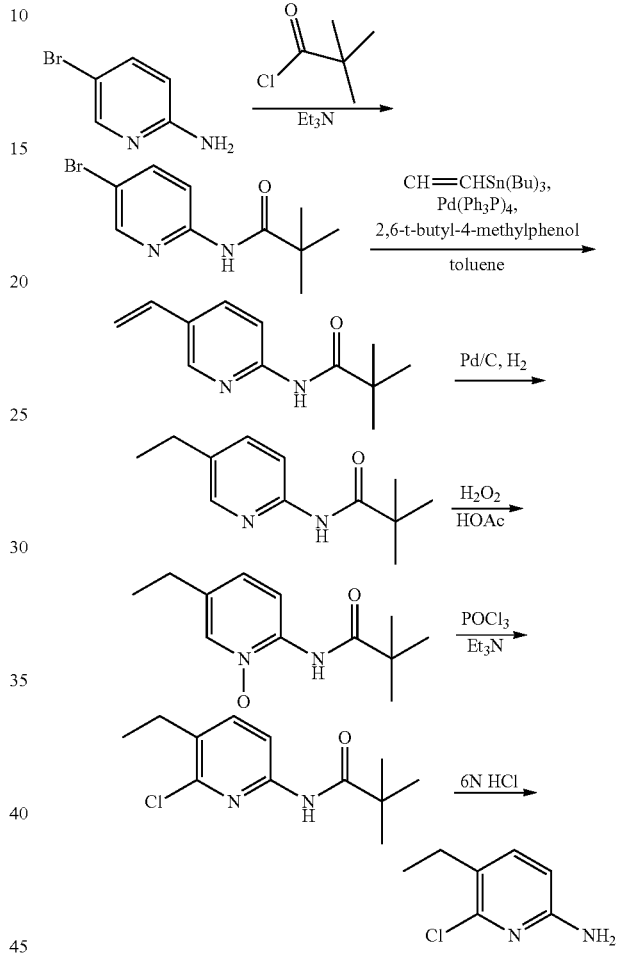

Step a: N-(5-Bromopyridin-2-yl)pivalamide

Pivaloyl chloride (85 mL, 0.69 mol) was added to a solution of 5-bromopyridin-2-amine (100 g, 0.58 mol) and Et$_3$N (120 mL, 0.87 mmol.) in CH$_2$Cl$_2$ at −78° C. The temperature was allowed to warm to room temperature and the stirring was continued overnight. The reaction mixture was poured into water, extracted with CH$_2$Cl$_2$, dried over MgSO$_4$, evaporated in vacuo and purified by silica gel column chromatography (10% EtOAc in petroleum ether) to afford N-(5-bromopyridin-2-yl)pivalamide (130 g, 87% yield). $^1$H NMR (CDCl$_3$, 400 MHz) δ 8.28 (d, J=2.0 Hz, 1H), 8.17 (d, J=9.2 Hz, 1H), 7.99 (br s, 1H), 7.77 (dd, J=9.2 and 2.0, 1H), 1.28 (s, 9H).

Step b: N-(5-Vinylpyridin-2-yl)pivalamide

Tributyl(vinyl)stannane (50 g, 0.16 mol), Pd(Ph$_3$P)$_4$ (3.3 g, 2.9 mmol) and a catalytic amount of 2,6-t-butyl-4-methylphenol was added to a solution of N-(5-bromopyridin-2- yl)pivalamide (36 g, 0.14 mol) in toluene. The reaction mixture was heated at reflux for 48 h. The solvent was evaporated in vacuo and the residue was purified by chromatography on silica gel (5% EtOAc in petroleum ether) to afford N-(5-vinylpyridin-2-yl)pivalamide (23 g, 80% yield). $^1$H NMR (CDCl$_3$, 300 MHz) δ 8.24-8.20 (m, 2H), 8.02 (br s, 1H), 7.77 (dd, J=8.7 and 2.4, 1H), 6.65 (dd, J=17.7 and 10.8, 1H), 5.73 (d, J=17.7, 1H), 5.29 (d, J=10.8, 1H), 1.32 (s, 9H).

Step c: N-(5-Ethylpyridin-2-yl)pivalamide

A catalytic amount of Pd/C was added to a solution of N-(5-vinylpyridin-2-yl)pivalamide (23 g, 0.11 mol) in EtOH (200 mL). The reaction mixture was stirred under hydrogen atmosphere overnight. The catalyst was filtrated off and the solution was concentrated in vacuo to afford N-(5-ethylpyridin-2-yl)pivalamide (22 g, 95%). $^1$H NMR (CDCl$_3$, 300 MHz) δ 8.15 (d, J=8.4, 1H), 8.09 (d, J=2.4, 1H), 7.96 (br s, 1H), 7.54 (dd, J=8.4 and 2.4, 1H), 2.61 (q, J=7.5, 2H), 1.30 (s, 9H), 1.23 (t, J=7.5, 3H).

Step d: 5-Ethyl-2-pivalamidopyridine 1-oxide

H$_2$O$_2$ (30%, 34 mL, 0.33 mol) was added to a solution of N-(5-ethylpyridin-2-yl)pivalamide (22 g, 0.11 mol) in acetic acid (200 mL). The mixture was stirred overnight at 80° C. The reaction mixture was poured into water and was extracted with EtOAc. The organics were washed with saturated Na$_2$SO$_3$ solution and NaHCO$_3$ solution before being dried over MgSO$_4$. The solvent was evaporated in vacuo to afford 5-ethyl-2-pivalamidopyridine 1-oxide (16 g, 67%), which was used for the next step without further purification.

Step e: N-(6-Chloro-5-ethylpyridin-2-yl)pivalamide

Et$_3$N (123 mL, 93.6 mmol) was added to a solution of 5-ethyl-2-pivalamidopyridine 1-oxide (16.0 g, 72.0 mmol) in POCl$_3$ (250 mL) and the reaction mixture was heated at reflux for 3 days. Excess POCl$_3$ was distilled off and the residue was poured into water. The mixture was neutralized with aqueous NaOH to pH 9. The aqueous layer was extracted with ethyl acetate. The organic layer was dried over MgSO$_4$ and the solvent was evaporated in vacuo. The residue was purified by chromatography on silica gel (10% EtOAc in petroleum ether) to afford N-(6-chloro-5-ethylpyridin-2-yl)pivalamide (900 mg, 5%) and unreacted 5-ethyl-2-pivalamidopyridine 1-oxide (4.8 g). $^1$H NMR (CDCl$_3$, 300 MHz) δ 8.12 (d, J=8.7, 1H), 7.94 (br s, 1H), 7.56 (d, J=8.7, 1H), 2.70 (q, J=7.5, 2H), 1.30 (s, 9H), 1.23 (t, J=7.5, 3H).

Step f: 6-Chloro-5-ethylpyridin-2-amine

A suspension of N-(6-chloro-5-ethylpyridin-2-yl)pivalamide (1.16 g, 4.82 mmol) in 6N HCl (20 mL) was heated at reflux overnight. The reaction mixture was cooled to room temperature and was treated with aqueous NaOH to pH 8. The aqueous layer was extracted with EtOAc. The organic layer was dried over MgSO$_4$ and the solvent was evaporated in vacuo. The residue was purified by chromatography on silica gel (5% EtOAc in petroleum ether) to afford 6-chloro-5-ethylpyridin-2-amine (650 mg, 86%). $^1$H NMR (CDCl$_3$, 400 MHz) δ 7.35 (d, J=8.4, 1H), 6.45 (d, J=8.4, 1H), 2.61 (q, J=7.6, 2H), 1.18 (t, J=7.6, 3H).

I. 6-Bromo-5-chloropyridin-2-amine

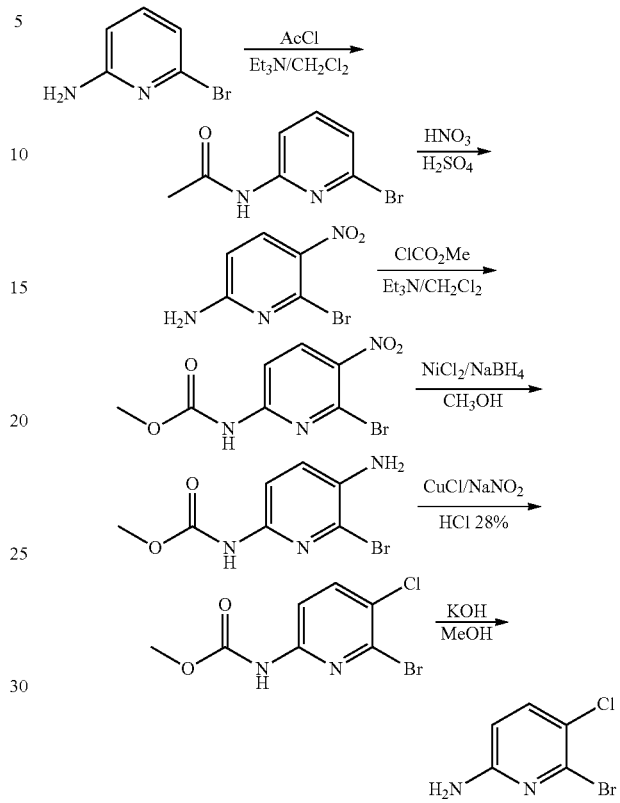

Step a: N-(6-Bromopyridin-2-yl)acetamide

To a solution of 6-bromopyridin-2-amine (10 g, 0.060 mol) and Et$_3$N (25 g, 0.27 mol) in CH$_2$Cl$_2$ (300 mL) was added AcCl (13 g, 0.17 mol) at 0° C. The mixture was stirred overnight. The reaction mixture was diluted with water and extracted with EtOAc (200 mL×3). The combined organic layers were dried over anhydrous Na$_2$SO$_4$ and evaporated under vacuum to give N-(6-bromopyridin-2-yl)acetamide (11 g, 88%). $^1$H NMR (400 MHz, CDCl$_3$) δ 8.15 (d, J=8.0 Hz, 1H), 7.97 (brs, 1H), 7.55 (t, J=8.0 Hz, 1H), 7.18 (d, J=8.0 Hz, 1H), 2.19 (s, 3H).

Step b: 6-Bromo-5-nitropyridin-2-amine

To a solution of N-(6-bromopyridin-2-yl)acetamide (9.0 g, 40 mmol) in H$_2$SO$_4$ (100 mL) was added HNO$_3$ (69%, 5.5 g, 60 mmol) dropwise at 0° C. The mixture was stirred at this temperature for 4 hours, and was then poured into ice-water. The mixture was extracted with EtOAc (100 mL×3). The combined organic layers were dried over anhydrous Na$_2$SO$_4$ and evaporated under vacuum to give 6-bromo-5-nitropyridin-2-amine (7.5 g, 82%). $^1$H NMR (400 MHz, DMSO) δ 8.10 (d, J=8.8 Hz, 1H), 7.73 (brs, 2H), 6.46 (d, J=8.8 Hz, 1H).

Step c: Methyl 6-bromo-5-nitropyridin-2-ylcarbamate

To a solution of 6-bromo-5-nitropyridin-2-amine (1.4 g, 10 mmol), Et$_3$N (2.0 g, 20 mol) and DMAP (70 mg) in $CH_2Cl_2$ (20 mL) was added $ClCO_2Me$ (1.3 g, 10 mmol) drop-wise at 0° C. The mixture was stirred overnight. The reaction mixture was diluted with water and extracted with EtOAc (20 mL×3). The combined organic layers were dried over anhydrous $Na_2SO_4$ and evaporated under vacuum to give methyl 6-bromo-5-nitropyridin-2-ylcarbamate (1.4 g, 82%). $^1$H NMR (400 MHz, DMSO) δ 10.78 (brs, 1H), 8.56 (d, J=9.2 Hz, 1H), 8.05 (d, J=8.4 Hz, 1H), 3.70 (s, 3H).

Step d: Methyl 5-amino-6-bromopyridin-2-ylcarbamate

To a solution of methyl 6-bromo-5-nitropyridin-2-ylcarbamate (700 mg, 2.5 mmol) in $CH_3OH$ (20 mL) was added $NiCl_2$ (1.2 g, 5.1 mmol) and $NaBH_4$ (300 mg, 7.6 mmol) successively at 0° C. The mixture was stirred for 20 seconds. The reaction mixture was diluted with water and extracted with EtOAc (20 mL×3). The combined organic layers were dried over anhydrous $Na_2SO_4$ and evaporated under vacuum to give methyl 5-amino-6-bromopyridin-2-ylcarbamate (600 mg, 96%). $^1$H NMR (400 MHz, $CDCl_3$) δ 7.75 (d, J=8.4 Hz, 1H), 7.13 (brs, 1H), 7.09 (d, J=8.8 Hz, 1H), 3.81 (s, 3H).

Step e: Methyl 6-bromo-5-chloropyridin-2-ylcarbamate

To a mixture of methyl 5-amino-6-bromopyridin-2-ylcarbamate (100 mg, 0.41 mmol) and CuCl (120 mg, 1.6 mmol) in HCl (28%, 10 mL) was added and $NaNO_2$ (29 mg, 0.41 mmol) at 0° C. The mixture was stirred at room temperature for 2 hr. The reaction mixture was diluted with water and extracted with ethyl acetate (20 mL×3). The combined organic layers were dried over anhydrous $Na_2SO_4$ and evaporated under vacuum to give methyl 6-bromo-5-chloropyridin-2-ylcarbamate (80 mg, 75%). $^1$H NMR (400 MHz, $CDCl_3$) δ 7.93 (d, J=8.8 Hz, 1H), 7.69 (d, J=8.8 Hz, 1H), 7.38 (brs, 1H), 3.82 (s, 3H).

Step f: 6-Bromo-5-chloropyridin-2-amine

To a solution of methyl 6-bromo-5-chloropyridin-2-ylcarbamate (1.1 g, 4.1 mmol) in methanol (50 mL) was added KOH (700 mg, 13 mmol) at room temperature. The mixture was heated at reflux for 2 hr. The reaction mixture was diluted with water and extracted with ethyl acetate (20 mL×3). The combined organic layers were dried over anhydrous $Na_2SO_4$ and evaporated under vacuum. The residue was purified by column chromatography on silica gel (5% to 10% EtOAc in petroleum ether) to give 6-bromo-5-chloropyridin-2-amine (700 mg, 81%). $^1$H NMR (400 MHz, $CDCl_3$) δ 7.54 (d, J=8.0 Hz, 1H), 6.41 (d, J=8.4 Hz, 1H).

J. 6-Chloro-4-methylpyridin-2-amine

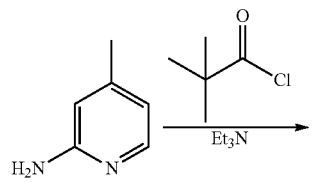

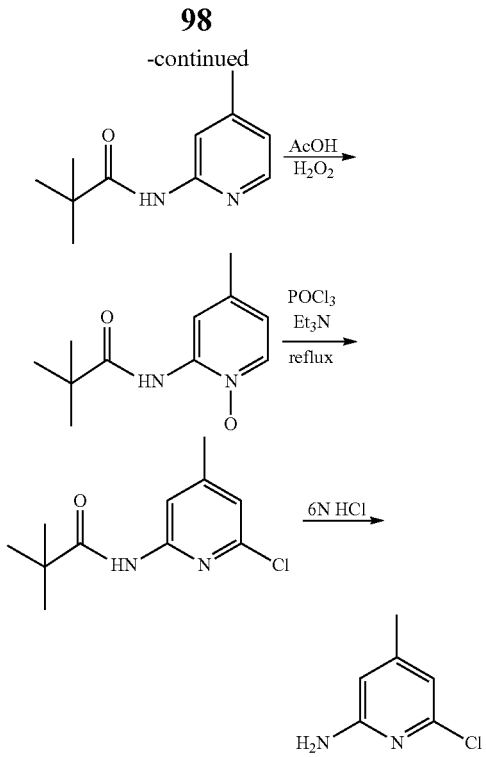

Step a: N-(4-Methylpyridin-2-yl)pivalamide

To a solution of 4-methylpyridin-2-amine (25.0 g, 0.230 mol) and $Et_3N$ (35.0 g, 0.350 mmol) in $CH_2Cl_2$ (200 ml) was added pivaloyl chloride (33.1 g, 0.270 mol) drop-wise. The mixture was stirred for 4 h under $N_2$ atmosphere. The reaction mixture was quenched with water and was extracted with ethyl acetate (200 mL×3). The combined organic extracts were dried over anhydrous $Na_2SO_4$, evaporated under vacuum and purified by chromatography on silica gel (20% ethyl acetate in petroleum ether) to afford N-(4-methylpyridin-2-yl)pivalamide (36.2 g, 82%). $^1$H NMR ($CDCl_3$, 300 MHz) δ 8.09-8.08 (m, 2H), 8.00 (br s, 1H), 6.83 (dd, J=4.8, 0.6 Hz, 1H), 2.33 (s, 3H), 1.30 (s, 9H).

Step b: 4-Methylpyridin-2-ylpivalamide-1-oxide

To a solution of N-(4-methylpyridin-2-yl)pivalamide (10 g, 52 mmol) in AcOH (300 ml) was added $H_2O_2$ (7.0 ml, 68 mmol) drop-wise at 0° C. The mixture was stirred overnight at 70° C. The reaction mixture was quenched with water, extracted with ethyl acetate (200 mL×3) and washed with saturated $Na_2SO_3$. The combined organic extracts were dried over anhydrous $Na_2SO_4$, and evaporated under vacuum. The residue was purified by chromatography on silica gel (5% ethyl acetate in petroleum ether) to afford 4-methylpyridin-2-ylpivalamide-1-oxide (8.4 g, 77%). $^1$H NMR ($CDCl_3$, 300 MHz) δ 10.38 (br s, 1H), 10.21 (br s, 1H), 8.34 (s, 1H), 8.26 (d, J=6.9 Hz, 1H), 6.83 (d, J=6.9 Hz, 1H), 2.37 (s, 3H), 1.33 (s, 9H).

Step c: N-(6-Chloro-4-methylpyridin-2-yl)pivalamide

To a solution of 4-methylpyridin-2-yl-pivalamide-1-oxide (3.0 g, 14 mmol) in $POCl_3$ (30 mL) was added $Et_3N$ (6.0 mL, 43 mmol) drop-wise at 0° C. Then mixture was stirred at 100° C. for 3 days. The mixture was quenched with water, treated with aqueous NaOH to pH 8-9, and extracted with ethyl acetate (50 mL×3). The combined organic extracts were dried over anhydrous Na$_2$SO$_4$, evaporated under vacuum and purified by chromatography on silica gel (15% ethyl acetate in petroleum ether) to afford N-(6-chloro-4-methylpyridin-2-yl)pivalamide (520 mg, 16%). $^1$H NMR (CDCl$_3$, 300 MHz) δ 8.03 (s, 1H), 7.93 (br s, 1H), 6.87 (s, 1H), 2.33 (s, 3H), 1.29 (s, 9H).

Step d: 6-Chloro-4-methylpyridin-2-amine

A solution of N-(6-chloro-4-methylpyridin-2-yl)pivalamide (500 mg, 2.21 mmol) in HCl (40 mL, 6 M) was stirred for 6 hours at 90° C. The mixture was cooled to room temperature and neutralized with NaOH to pH 10. The mixture was extracted with ethyl acetate, evaporated under vacuum, and purified by chromatography on silica gel (5% ethyl acetate in petroleum ether) to afford 6-chloro-4-methylpyridin-2-amine (257 mg, 82%). $^1$H NMR (CDCl$_3$, 300 MHz) δ 6.52 (s, 1H), 6.26 (s, 1H), 2.23 (s, 3H).

K. 6-Chloro-4,5-dimethylpyridin-2-amine

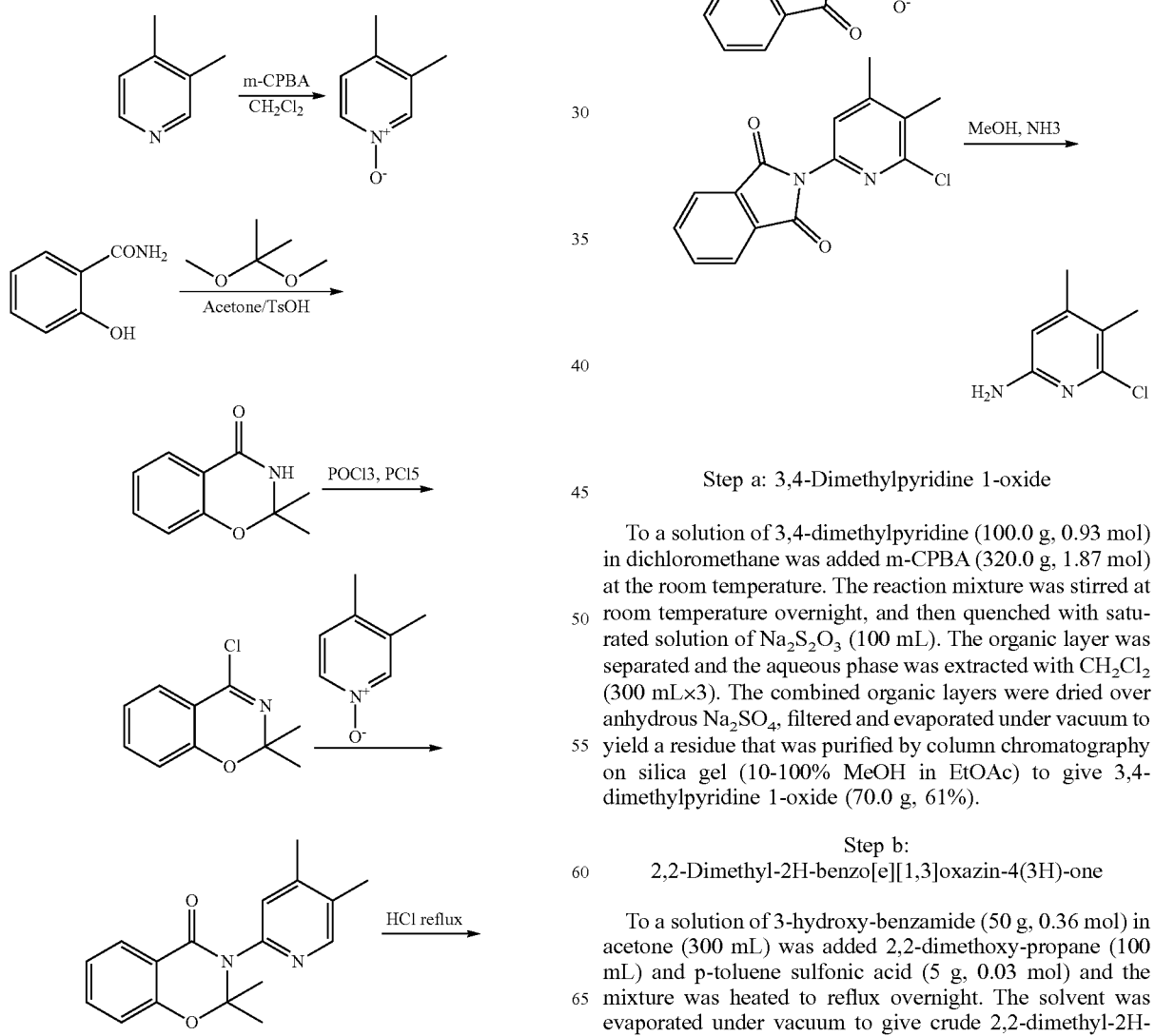

Step a: 3,4-Dimethylpyridine 1-oxide

To a solution of 3,4-dimethylpyridine (100.0 g, 0.93 mol) in dichloromethane was added m-CPBA (320.0 g, 1.87 mol) at the room temperature. The reaction mixture was stirred at room temperature overnight, and then quenched with saturated solution of Na$_2$S$_2$O$_3$ (100 mL). The organic layer was separated and the aqueous phase was extracted with CH$_2$Cl$_2$ (300 mL×3). The combined organic layers were dried over anhydrous Na$_2$SO$_4$, filtered and evaporated under vacuum to yield a residue that was purified by column chromatography on silica gel (10-100% MeOH in EtOAc) to give 3,4-dimethylpyridine 1-oxide (70.0 g, 61%).

Step b:
2,2-Dimethyl-2H-benzo[e][1,3]oxazin-4(3H)-one

To a solution of 3-hydroxy-benzamide (50 g, 0.36 mol) in acetone (300 mL) was added 2,2-dimethoxy-propane (100 mL) and p-toluene sulfonic acid (5 g, 0.03 mol) and the mixture was heated to reflux overnight. The solvent was evaporated under vacuum to give crude 2,2-dimethyl-2H-benzo[e][1,3]oxazin-4(3H)-one (55 g, 86%) that was used in the next step without further purification. $^{1}$H NMR (300 MHz, CDCl$_3$) δ 7.91 (dd, J=1.8, 7.8 Hz 1H), 7.44 (t, J=7.8 Hz 1H), 7.35 (brs, 1H), 7.05 (t, J=7.8 Hz 1H), 6.91 (d, J=8.1 Hz 1H), 1.65 (s, 6H).

Step c:
4-Chloro-2,2-dimethyl-2H-benzo[e][1,3]oxazine

To a solution of 2,2-dimethyl-2H-benzo[e][1,3]oxazin-4(3H)-one (100 g, 0.56 mol) in POCl$_3$ (500 mL) was added PCl$_5$ (170 g, 0.84 mol) at the room temperature. The mixture was hearted at 60° C. overnight. The solvent was removed by distillation under atmospheric pressure and the residue was distilled under reduced pressure (85-86° C., 2.5 mmHg) to give 4-chloro-2,2-dimethyl-2H-benzo[e][1,3]oxazine (50 g, 45%). $^{1}$H NMR (400 MHz, CDCl$_3$) δ 7.55 (dd, J=1.6, 8.4 Hz, 1H), 7.38 (dt, J=1.6, 8.0 Hz 1H), 6.95 (t, J=6.8 Hz 1H), 6.79 (d, J=8.0 Hz 1H), 1.61 (s, 6H).

Step d: 3-(4,5-dimethylpyridin-2-yl-2,2-dimethyl-2H-benzo[e][1,3]oxazin-4(3H)-one To a solution of 4-chloro-2,2-dimethyl-2H-benzo[e][1,3]oxazine (50 g, 0.26 mol) in CH$_2$Cl$_2$ (200 mL) was added 33.4-dimethylpyridine 1-oxide (65 g, 0.52 mol) at the room temperature. The mixture was heated to reflux overnight. The precipitate was filtered off and the filtrate was concentrated under vacuum to yield a residue that was purified by column chromatography on silica gel (10% ethyl acetate in petroleum ether) to give 3-(4,5-dimethylpyridin-2-yl)-2,2-dimethyl-2H-benzo[e][1,3]oxazin-4(3H)-one (9 g, 13%). $^{1}$H NMR (300 MHz, d-DMSO) δ 8.25 (s, 1H), 7.78 (d, J=6.6 Hz, 1H), 7.54-7.51 (m, 1H), 7.16-7.11 (m, 2H), 7.05 (d, J=8.4 Hz, 1H), 2.26 (s, 3H), 2.23 (s, 3H), 1.60 (s, 6H)

Step e: 4,5-Dimethylpyridin-2-amine

A solution of 3-(4,5-dimethylpyridin-2-yl)-2,2-dimethyl-2H-benzo[e][1,3]oxazin-4(3H)-one (9 g, 0.03 mol) in concentrated hydrochloric acid (100 mL) was heated at reflux overnight. The mixture was basified by saturated solution of Na$_2$CO$_3$ and extracted with CH$_2$Cl$_2$ (100 mL×3). The combined organic layers were dried over anhydrous Na$_2$SO$_4$, filtered and evaporated under vacuum to give 4,5-dimethylpyridin-2-amine (3.8 g, 97%), that was directly used in the next step without further purification.

Step f:
2-(4,5-dimethylpyridin-2-yl)-isoindoline-1,3-dione

To a solution of 4,5-dimethylpyridin-2-amine (2.1 g, 0.02 mol) in acetic acid (40 mL) was added isobenzofuran-1,3-dione (2.5 g, 0.02 mol) at the room temperature. The mixture was heated at 90° C. overnight. The resulting solution was basified by saturated solution of NaHCO$_3$ and extracted with ethyl acetate (50 mL×3). The combined organic layers were dried over anhydrous Na$_2$SO$_4$, filtered and evaporated under vacuum to give 2-(4,5-dimethylpyridin-2-yl)-isoindoline-1,3-dione (1.7 g, 40%) $^{1}$H NMR (300 MHz, DMSO) δ 8.33 (s, 1H), 7.97-7.91 (m, 4H), 7.32 (s, 1H), 2.30 (s, 3H), 2.27 (s, 3H).

Step g:
2-(1,3-Dioxoisoindolin-2-yl)-4,5-dimethylpyridine 1-oxide

To a solution of 2-(4,5-dimethylpyridin-2-yl)-isoindoline-1,3-dione (1.7 g, 0.01 mol) in CH$_2$Cl$_2$ (50 mL) was added m-CPBA (3.5 g, 0.02 mol) at the room temperature. The mixture was stirred overnight, then quenched by addition of a saturated solution of Na$_2$S$_2$O$_3$ (100 mL). The organic layer was separated and the aqueous phase was extracted with CH$_2$Cl$_2$ (50 mL×3). The combined organic layers were dried over anhydrous Na$_2$SO$_4$, filtered and evaporated under vacuum to give 2-(1,3-dioxoisoindolin-2-yl)-4,5-dimethyl-pyridine 1-oxide (1.5 g, 83%), which was used directly in the next step.

Step h: 2-(6-chloro-4,5-dimethylpyridin-2-yl)isoindoline-1,3-dione

To a solution of 2-(1,3-dioxoisoindolin-2-yl)-4,5-dimethylpyridine 1-oxide (1.5 g, 0.01 mol) in POCl$_3$ (50 mL) was added Et$_3$N (680 mg, 0.01 mol) at room temperature. The mixture was stirred at 80° C. for 2 hr, and then carefully poured into the mixture of saturation NaHCO$_3$ solution and ice water. The mixture was extracted with EtOAc (50 mL×3). The combined organic layers were dried over anhydrous Na$_2$SO$_4$, filtered and evaporated under vacuum to give a crude residue that was purified by column chromatography on silica gel (10-15% ethyl acetate in petroleum ether) to give 2-(6-chloro-4,5-dimethylpyridin-2-yl)isoindoline-1,3-dione (650 mg, 41%). $^{1}$H NMR (300 MHz, CDCl$_3$) δ 7.97-7.92 (m, 2H), 7.82-7.78 (m, 2H), 7.16 (s, 1H), 2.41 (s, 3H), 2.39 (s, 3H).

Step i: 6-Chloro-4,5-dimethylpyridin-2-amine

A solution of 2-(6-chloro-4,5-dimethylpyridin-2-yl)isoindoline-1,3-dione (650 mg, 2.27 mmol) in ammonia in methanol (2 M, 50 mL) was stirred at the room temperature overnight. The mixture was diluted with water (50 mL) and extracted with ethyl acetate (50 mL×3). The combined organic layers were dried over anhydrous Na$_2$SO$_4$, filtered and evaporated under vacuum to give a crude residue that was purified by silica gel column chromatography (10-15% ethyl acetate in petroleum ether) to give 6-chloro-4,5-dimethylpyridin-2-amine (160 mg, 46%). $^{1}$H NMR (300 MHz, d-DMSO) δ 6.21 (s, 1H), 5.93 (brs, 2H), 2.11 (s, 3H), 2.05 (s, 3H). MS (ESI) m/z (M+H$^+$): 157.2.

L. N-(6-Chloro-5-methylpyridin-2-yl)-1-(2,2-difluorobenzo[d][1,3]-dioxol-5-yl)cyclopropanecarboxamide

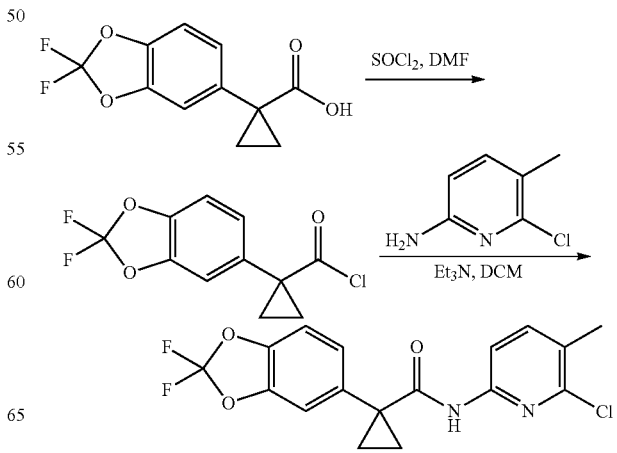

Step a: 1-(2,2-Difluorobenzo[d][1,3]dioxol-5-yl)cyclopropanecarbonyl chloride

To 1-(2,2-difluorobenzo[d][1,3]dioxol-5-yl)cyclopropanecarboxylic acid (18.8 g, 78.0 mmol) in thionyl chloride (17.0 mL, 233 mmol) was added N,N-dimethylformamide (200 µL, 2.6 mmol). The reaction mixture was stirred at room temperature for 2 hours. Excess thionyl chloride and N,N-dimethylformamide were removed in vacuo and the resulting acid chloride was used directly in next step.

Step b: N-(6-Chloro-5-methylpyridin-2-yl)-1-(2,2-difluorobenzo[d][1,3]dioxol-5-yl)cyclopropanecarboxamide To a solution of 6-chloro-5-methylpyridin-2-amine (11.1 g, 78.0 mmol) and Et₃N (22.0 mL, 156 mmol) in dichloromethane (100 mL) was added a solution of 1-(2,2-difluorobenzo[d][1,3]dioxol-5-yl)cyclopropanecarbonyl chloride (20.3 g, 78.0 mmol) in dichloromethane (50 mL). The resulting reaction mixture was allowed to stir at room temperature for 18 hours. The reaction mixture was then washed with 1N aqueous NaOH (2×200 mL), 1 N aqueous HCl (1×200 mL), and saturated aqueous NaHCO₃ (1×200 mL). The organics were dried over sodium sulfate and evaporated to yield N-(6-chloro-5-methylpyridin-2-yl)-1-(2,2-difluorobenzo[d][1,3]dioxol-5-yl)cyclopropanecarboxamide (26.9 g, 94% over two steps). ESI-MS m/z calc. 366.1. found 367.3 (M+1)⁺. Retention time 2.19 minutes. ¹H NMR (400 MHz, DMSO-d₆) δ 9.30 (s, 1H), 7.89-7.87 (m, 1H), 7.78-7.76 (m, 1H), 7.54-7.53 (m, 1H), 7.41-7.39 (m, 1H), 7.33-7.30 (m, 1H), 2.26 (s, 3H), 1.52-1.49 (m, 2H), 1.19-1.16 (m, 2H).

M. N-(6-Bromo-5-chloropyridin-2-yl)-1-(2,2-difluorobenzo[d][1,3]dioxol-5-yl)cyclopropanecarboxamide

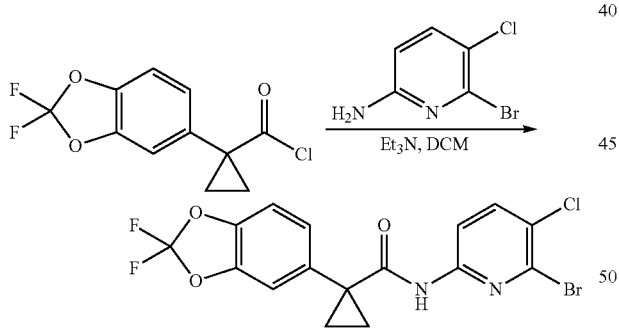

1-(2,2-Difluorobenzo[d][1,3]dioxol-5-yl)cyclopropanecarbonyl chloride (0.878 g, 3.37 mmol) was placed in an oven-dried flask which was allowed to cool under nitrogen. Dichloromethane (10 mL), triethylamine (1.42 mL, 10.1 mmol) and 6-bromo-5-chloropyridin-2-amine (10.1 mmol) were added and the reaction mixture was stirred for 16 hours. The reaction mixture was then washed with a saturated aqueous solution of sodium chloride, evaporated to near dryness, and then purified on 40 g of silica gel utilizing a gradient of 0-30% ethyl acetate in hexanes to yield N-(6-bromo-5-chloropyridin-2-yl)-1-(2,2-difluorobenzo[d][1,3]dioxol-5-yl)cyclopropanecarboxamide (1.01 g, 69%). ESI-MS m/z calc. 429.9. found; 431.3 (M+1)⁺ Retention time 2.33 minutes.

N. N-(6-Chloro-4-methylpyridin-2-yl)-1-(2,2-difluorobenzo[d][1,3]dioxol-5-yl)cyclopropanecarboxamide

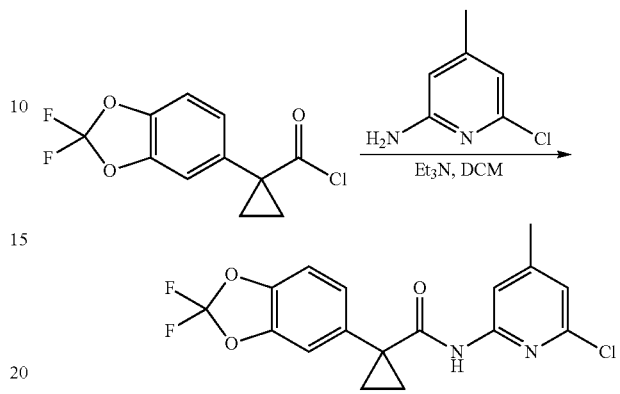

To a solution of 6-chloro-4-methylpyridin-2-amine (300 mg, 2.1 mmol) and Et₃N (1.8 mL, 13 mmol) in dichloromethane (5 mL) was added a solution of 1-(2,2-difluorobenzo[d][1,3]dioxol-5-yl)cyclopropanecarbonyl chloride (1.6 g, 6.3 mmol) in dichloromethane (5 mL). The resulting reaction mixture was allowed to stir at room temperature for 18 hours. The reaction mixture was diluted with dichloromethane (10 mL) and was washed with 1N aqueous HCl (1×20 mL) and saturated aqueous NaHCO₃ (1×20 mL). The organics were dried over sodium sulfate and evaporated to dryness. The resulting residue was purified by silica gel chromatography eluting with a gradient of 0-70% ethyl acetate in hexane to yield N-(6-chloro-4-methylpyridin-2-yl)-1-(2,2-difluorobenzo[d][1,3]dioxol-5-yl)cyclopropanecarboxamide (700 mg, 91%). ESI-MS m/z calc. 366.1. found 366.9 (M+1)⁺. Retention time 2.15 minutes.

O. 1-(Benzo[d][1,3]dioxol-5-yl)-N-(6-chloro-5-methylpyridin-2-yl)cyclopropanecarboxamide

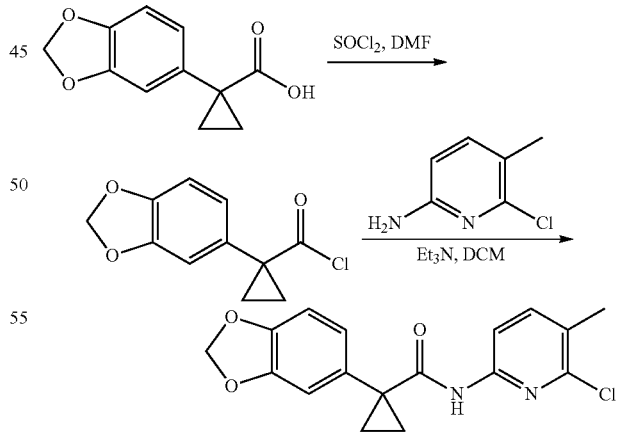

Step a: 1-(Benzo[d][1,3]-dioxol-5-yl)cyclopropanecarbonyl chloride

To 1-(benzo[d][1,3]dioxol-5-yl)cyclopropanecarboxylic acid (100 mg, 0.50 mmol) in thionyl chloride (110 µL, 1.5 mmol) was added N,N-dimethylformamide (20 μL, 0.26 mmol). The reaction mixture was stirred at room temperature for 30 minutes. Excess thionyl chloride and N,N-dimethylformamide were removed in vacuo and the resulting acid chloride was used directly in next step.

Step b: 1-(Benzo[d][1,3]-dioxol-5-yl)-N-(6-chloro-5-methylpyridin-2-yl)cyclopropanecarboxamide To a solution of 6-chloro-5-methylpyridin-2-amine (71 mg, 0.50 mmol) and Et$_3$N (140 μL, 1.0 mmol) in dichloromethane (2 mL) was added a solution of 1-(benzo[d][1,3]dioxol-5-yl)cyclopropanecarbonyl chloride (110 mg, 0.50 mmol) in dichloromethane (2 mL). The resulting reaction mixture was allowed to stir at room temperature for 18 hours. The reaction mixture was then washed with 1 N aqueous HCl (1×5 mL) and saturated aqueous NaHCO$_3$ (1×5 mL). The organic layer was dried over sodium sulfate and evaporated to yield 1-(benzo[d][1,3]dioxol-5-yl)-N-(6-chloro-5-methylpyridin-2-yl)cyclopropanecarboxamide (120 mg, 71% over 2 steps). $^1$H NMR (400 MHz, DMSO-d$_6$) δ 8.64 (s, 1H), 7.94-7.91 (m, 1H), 7.79-7.77 (m, 1H), 7.09 (m, 1H), 7.00-6.88 (m, 2H), 6.06 (s, 2H), 2.25 (s, 3H), 1.47-1.44 (m, 2H), 1.13-1.10 (m, 2H) ESI-MS m/z calc. 330.1. found 331.5 (M+1)$^+$. Retention time 1.99 minutes.

P. N-(6-chloro-4,5-dimethylpyridin-2-yl)-1-(2,2-difluorobenzo[d][1,3]dioxol-5-yl)cyclopropanecarboxamide

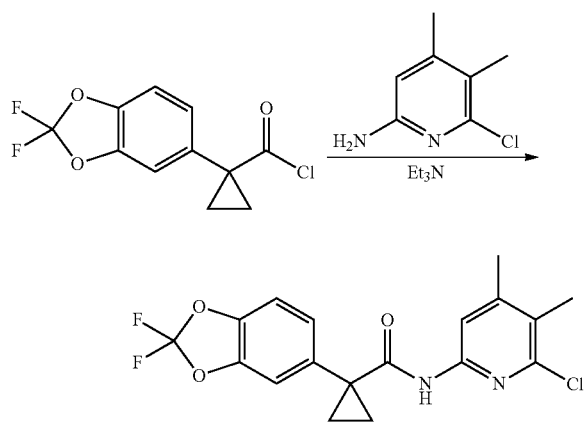

To 1-(2,2-difluorobenzo[d][1,3]dioxol-5-yl)cyclopropanecarbonyl chloride (676 mg, 2.6 mmol) and 6-chloro-4,5-dimethylpyridin-2-amine (314 mg, 2.0 mmol), dichloromethane (7.0 mL) and Et$_3$N (835 μL, 6 mmol) were added. The reaction was stirred at room temperature for 1 hour. The reaction was diluted with dichloromethane and washed with 1 N HCl (3×) and saturated aqueous NaHCO$_3$ (3×). The organic layer was dried over anhydrous Na$_2$SO$_4$ and evaporated under reduced pressure. The crude product was purified by column chromatography on silica gel to yield N-(6-chloro-4,5-dimethylpyridin-2-yl)-1-(2,2-difluorobenzo[d][1,3]dioxol-5-yl)cyclopropanecarboxamide (560 mg, 73%). ESI-MS m/z calc. 380.07. found 381.3 (M+1)$^+$. Retention time 2.18 minutes.

Q. N-(6-Chloro-4,5-dimethylpyridin-2-yl)-1-(2,3-dihydrobenzofuran-5-yl)cyclopropanecarboxamide

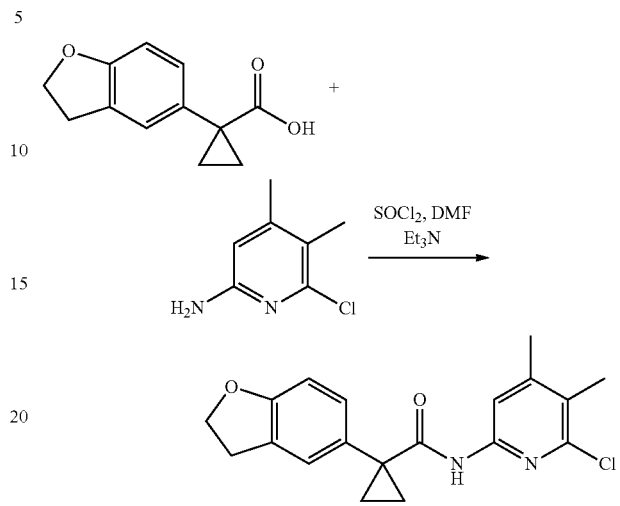

To 1-(2,3-dihydrobenzofuran-5-yl)cyclopropanecarboxylic acid (380 mg, 1.86 mmol) in thionyl chloride (406.1 μL, 5.580 mmol) was added N,N-dimethyl formamide (41 μL, 0.53 mmol). The reaction mixture was stirred at room temperature for 30 minutes before excess thionyl chloride and N,N-dimethyl formamide were removed in vacuo to yield the acid chloride. The acid chloride was then dissolved in dichloromethane (5 mL) and added slowly to a solution of 6-chloro-4,5-dimethylpyridin-2-amine (350 mg, 2.23 mmol) and triethylamine (778 μL, 5.58 mmol) in dichloromethane (5 mL). The resulting reaction mixture was stirred at room temperature for 14 hours. The reaction mixture was diluted with dichloromethane (10 mL) and washed with 1N aqueous HCl (10 mL) and a saturated aqueous NaHCO$_3$ solution (10 mL). The organic layer was dried over Na$_2$SO$_4$, filtered and evaporated under reduced pressure. The crude product was purified by column chromatography on silica gel (0-30% ethyl acetate in hexane) to yield N-(6-chloro-4,5-dimethylpyridin-2-yl)-1-(2,3-dihydrobenzofuran-5-yl)cyclopropanecarboxamide as a pale yellow solid (0.330 g, 51.76%). ESI-MS m/z calc. 342.11. found 343.3 (M+1)$^+$. Retention time 2.09 minutes.

R. N-(6-Chloro-5-cyano-4-methylpyridin-2-yl)-1-(2,2-difluorobenzo[d][1,3]-dioxol-5-yl)cyclopropanecarboxamide

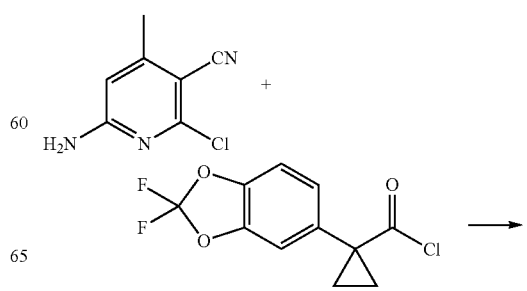

107

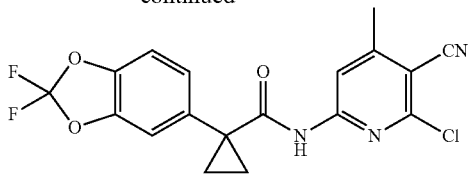

6-Amino-2-chloro-4-methylnicotinonitrile (252 mg, 1.50 mmol) was dissolved in a mixture of anhydrous N,N' dimtheylformamide (DMF, 0.5 mL) and anhydrous tetrahydrofuran (THF, 4.5 mL). The reaction tube was placed in a beaker full of room temperature water to help maintain the reaction temperature. Sodium hydride (84.23 mg, 2.106 mmol, 60% by weight in mineral oil) was added and the resulting suspension was allowed to stir for 5 minutes. 1-(2,2-Difluorobenzo[d][1,3]dioxol-5-yl)cyclopropanecarbonyl chloride (392.0 mg, 1.5 mmol) was added and the reaction mixture turned dark red. The crude material was evaporated to dryness, re-dissolved in a minimum of dichloromethane, and purified on 12 g of silica utilizing a gradient of 0-50% ethyl acetate in hexanes to yield the pure product as a pale yellow solid (0.589 g, 63%). ESI-MS m/z calc. 391.0. found 392.0 (M+1)$^+$. Retention time 2.06 minutes.

S. N-(6-Chloro-4-methylpyridin-2-yl)-1-(2,3-dihydrobenzofuran-5-yl)cyclopropanecarboxamide

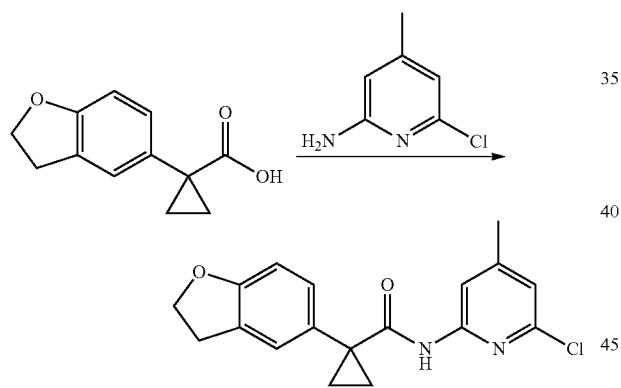

To 1-(2,3-dihydrobenzofuran-5-yl)cyclopropanecarboxylic acid (570 mg, 2.8 mmol) in thionyl chloride (0.61 mL, 8.4 mmol) was added N,N-dimethylformamide (62 μL, 0.80 mmol). The reaction mixture was stirred for one hour before the excess thionyl chloride and N,N-dimethylformamide were removed in vacuo to yield the acid chloride as an oil. The acid chloride was then dissolved in dichloromethane (5 mL) and was added slowly to a solution of 6-chloro-4-methylpyridin-2-amine (400 mg, 2.8 mmol) and triethylamine (1.2 mL, 8.4 mmol) in dichloromethane (5 mL). The resulting reaction mixture was allowed to stir at room temperature overnight. The reaction mixture was diluted with dichloromethane (5 mL) and was washed with 1N aq HCl (10 mL) and then a saturated NaHCO$_3$ solution (10 mL). The organics were dried over Na$_2$SO$_4$ and evaporated to dryness. The resulting oil was purified by silica gel chromatography eluting with 0-30% ethyl acetate in hexanes to yield the product (770 mg, 84%). ESI-MS m/z calc. 328.1. found 329.2 (M+1)$^+$. Retention time 1.91 minutes.

108

T. 6'-Methoxy-3,5'-dimethyl-2,3'-bipyridin-6-amine

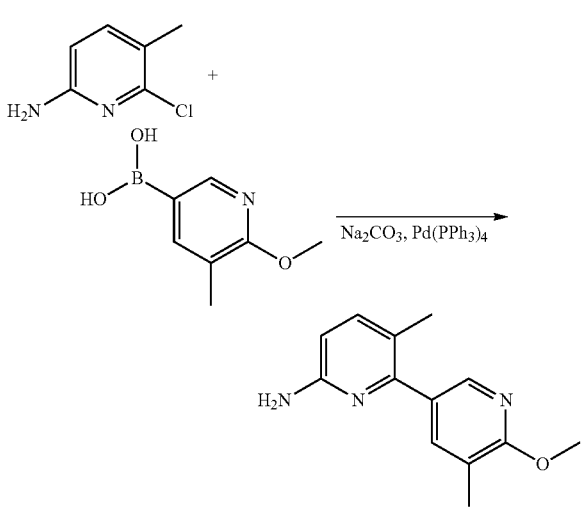

6-Chloro-5-methylpyridin-2-amine (1.426 g, 10 mmol), 6-methoxy-5-methylpyridin-3-ylboronic acid (2.0 g, 12 mmol) and Pd(PPh$_3$)$_4$ (577.8 mg, 0.5 mmol) were combined in a flask. DME (100 mL) was added followed by aqueous Na$_2$CO$_3$ (10.00 mL of 2 M, 20.0 mmol). The flask was fitted with a condenser and heated at 80° C. for 12 hours under N$_2$ atmosphere. More Pd(PPh$_3$)$_4$ (577.8 mg, 0.5 mmol) was added, the condenser was removed and the flask was fitted with a rubber stopper. N2 (g) was flushed through the flask and the reaction was stirred at 80° C. for an additional 12 hours under N$_2$ (g) balloon. The reaction mixture was filtered through a bed of Celite, the Celite was washed with ethyl acetate and the combined filtrates were concentrated. The residue was purified by column chromatography (30-100% ethyl acetate-Hexanes) to yield 680 mg of the product as an orange solid. $^1$H NMR (400 MHz, DMSO-d$_6$) δ 8.10 (s, 1H), 7.66 (s, 1H), 7.29 (d, J=8.3 Hz, 1H), 6.37 (d, J=8.3 Hz, 1H), 5.75 (s, 2H), 3.91 (s, 3H), 2.18 (s, 3H), 2.14 (s, 3H). ESI-MS m/z calc. 229.1. found 230.5 (M+1)$^+$. Retention time 0.91 minutes.

U. 2-Methoxy-3-ethyl-5-(4,4,5,5-tetramethyl-1,3,2-dioxaborolan-2-yl)pyridine

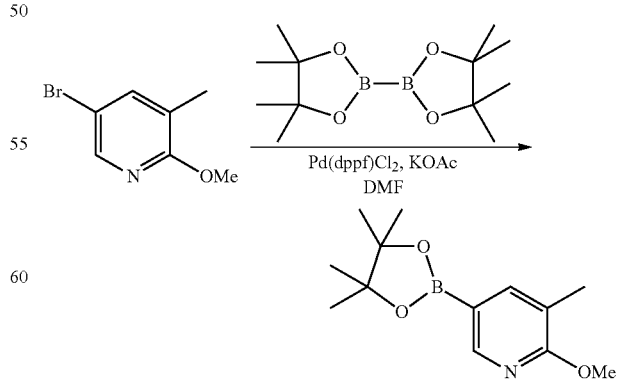

5-Bromo-2-methoxy-3-methylpyridine (400 mg, 2.0 mmol), 4,4,4',4',5,5,5',5'-octamethyl-2,2'-bi(1,3,2-dioxaborolane) (610 mg, 2.4 mmol), and Pd(dppf)Cl₂ (82 mg, 0.10 mmol) were added to a dry flask and placed under N₂. Potassium acetate (590 mg, 6.0 mmol) was weighed directly into the flask. The flask was then evacuated and back filled with N₂. Anhydrous N,N-dimethylformamide (DMF) (10 mL) was added and the reaction was heated at 80° C. in an oil bath overnight. The reaction mixture was evaporated to dryness. The residue was dissolved in ethyl acetate (20 mL) and washed with water (20 mL). The organics were dried over sodium sulfate and evaporated to dryness. The resulting material was purified by silica gel chromatography eluting with 0-70% ethyl acetate in hexane to yield 2-methoxy-3-methyl-5-(4,4,5,5-tetramethyl-1,3,2-dioxaborolan-2-yl)pyridine (360 mg, 72%). ESI-MS m/z calc. 249.1. found 168.3 (MW-C₆H₁₀+1)⁺. Retention time 0.33 minutes.

V. 6-Methoxy-2-methyl-3-(4,4,5,5-tetramethyl-1,3,2-dioxaborolan-2-yl)pyridine

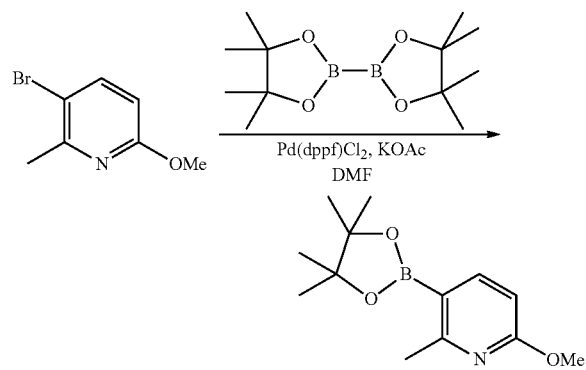

3-Bromo-6-methoxy-2-methylpyridine (400 mg, 2.0 mmol), 4,4,4',4',5,5,5',5'-octamethyl-2,2'-bi(1,3,2-dioxaborolane) (610 mg, 2.4 mmol), and Pd(dppf)Cl₂ (82 mg, 0.10 mmol) were added to a dry flask and placed under N₂. Potassium acetate (590 mg, 6.0 mmol) was weighed directly into the flask. The flask was then evacuated and back filled with N₂. Anhydrous N,N-dimethylformamide (DMF) (10 mL) was added and the reaction was heated at 80° C. in an oil bath overnight. The reaction mixture was evaporated to dryness. The residue was dissolved in ethyl acetate (20 mL) and washed with water (20 mL). The organics were dried over sodium sulfate and evaporated to dryness. The resulting material was purified by silica gel chromatography eluting with 0-70% ethyl acetate in hexane to yield 6-methoxy-2-methyl-3-(4,4,5,5-tetramethyl-1,3,2-dioxaborolan-2-yl)pyridine (300 mg, 60%). ESI-MS m/z calc. 249.1. found 168.3 (MW-C₆H₁₀+1)⁺. Retention time 0.37 minutes.

W. 2-Methoxy-5-methyl-3-(4,4,5,5-tetramethyl-1,3,2-dioxaborolan-2-yl)pyridine

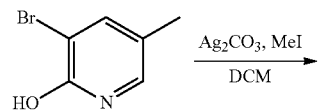

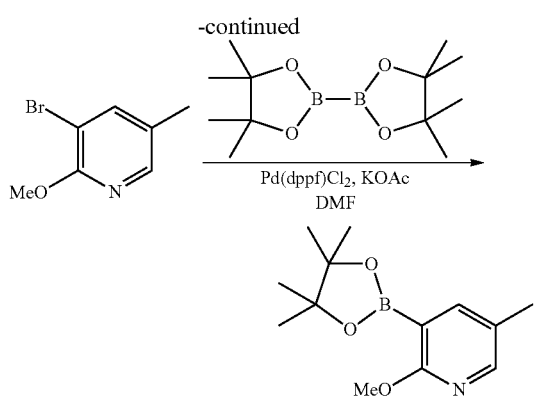

Step a: 3-Bromo-2-methoxy-5-methylpyridine

To 3-bromo-5-methylpyridin-2-ol (500 mg, 2.7 mmol) and silver carbonate (2.6 g, 9.6 mmol) suspended in dichloromethane (10 mL) was added iodomethane (0.83 mL, 13 mmol). The reaction mixture was allowed to stir at room temperature overnight. The reaction mixture was filtered through a pad of celite and the volatiles were evaporated to yield 3-bromo-2-methoxy-5-methylpyridine, which was used directly in the next step. ESI-MS m/z calc. 201.0. found 202.3 (M+1)⁺. Retention time 1.51 minutes.

Step b: 2-Methoxy-5-methyl-3-(4,4,5,5-tetramethyl-1,3,2-dioxaborolan-2-yl)pyridine 3-Bromo-2-methoxy-5-methylpyridine (540 mg, 2.7 mmol), 4,4,4',4',5,5,5',5'-octamethyl-2,2'-bi(1,3,2-dioxaborolane) (810 mg, 3.2 mmol), and Pd(dppf)Cl₂ (110 mg, 0.13 mmol) were added to a dry flask and placed under N₂. Potassium acetate (800 mg, 8.1 mmol) was weighed directly into the flask. The flask was then evacuated and back filled with N₂. Anhydrous N,N-dimethylformamide (DMF) (15 mL) was added and the reaction was heated at 80° C. in an oil bath overnight. The reaction mixture was evaporated to dryness. The residue was dissolved in ethyl acetate (20 mL) and washed with water (20 mL). The organics were dried over sodium sulfate and evaporated to dryness. The resulting material was purified by silica gel chromatography eluting with 0-100% ethyl acetate in hexane to yield 2-methoxy-5-methyl-3-(4,4,5,5-tetramethyl-1,3,2-dioxaborolan-2-yl)pyridine (450 mg, 67%). ESI-MS m/z calc. 249.1. found 168.3 (MW-C₆H₁₀+1)⁺. Retention time 0.27 minutes. ¹H NMR (400 MHz, CDCl₃) δ 8.03 (m, 1H), 7.80 (m, 1H), 3.94 (s, 3H), 2.22 (s, 3H), 1.36 (s, 12H).

X. 1-Methyl-5-(4,4,5,5-tetramethyl-1,3,2-dioxaborolan-2-yl)pyridin-2(1H)-one

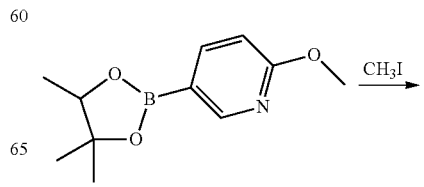

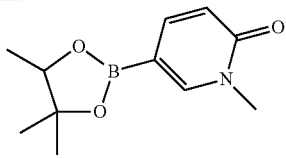

A mixture of 2-methoxy-5-(4,4,5,5-tetramethyl-1,3,2-dioxaborolan-2-yl)pyridine (235 mg, 1.00 mmol) and CH₃I (426 mg, 3.00 mmol) was heated at 80° C. for 3 hours. The mixture was partitioned between ethyl acetate and H₂O. The aqueous layer was extracted with ethyl acetate and the combined organic layers were washed with brine, dried over MgSO₄, and evaporated to dryness to afford 1-methyl-5-(4,4,5,5-tetramethyl-1,3,2-dioxaborolan-2-yl)pyridin-2(1H)-one that was directly used in next step without further purification.

Y. 1-Methyl-5-(4,4,5,5-tetramethyl-1,3,2-dioxaborolan-2-yl)pyridin-2(1H)-one

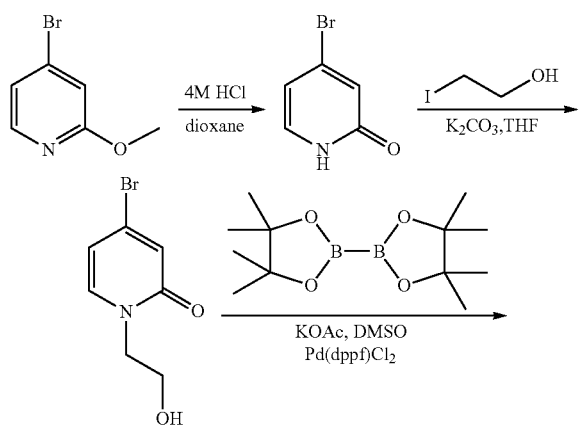

Step a: 4-Bromopyridin-2(1H)-one

To a solution of 4-bromo-2-methoxypyridine (1.0 g, 5.3 mmol) in 1,4-dioxane (26 mL) was added 4M HCl aqueous solution (13 mL). The reaction was heated at 90° C. for 5 hours and then at 50° C. overnight. The solution was neutralized with 1N NaOH solution to pH 8-9 and extracted with ethyl acetate. The organics were dried over MgSO₄ and concentrated to yield 4-bromopyridin-2(1H)— as a white solid (490 mg, 53%). The aqueous layer was also concentrated, and then the residue was stirred with CH₂Cl₂ and filtered. The filtrate was concentrated to yield additional 4-bromopyridin-2(1H)— (320 mg, 35%). ESI-MS m/z calc. 173.0. found 174.3 (M+1)⁺. Retention time 0.32 minutes. ¹H NMR (400 MHz, DMSO-d₆) δ 11.87 (s, 1H), 7.36 (d, J=7.0 Hz, 1H), 6.64 (d, J=2.0 Hz, 1H), 6.37 (dd, J=2.0, 7.0 Hz, 1H).

Step b: 4-Bromo-1-(2-hydroxyethyl)pyridin-2(1H)-one

To a solution of 4-bromopyridin-2(1H)-one (174 mg, 1.00 mmol) in THF (3.5 mL) was added K₂CO₃ (1.38 g, 10.0 mmol) and 2-iodoethanol (156 μL, 2.00 mmol). The reaction was stirred at 80° C. for 2 days before being cooled to room temperature and filtered. The filtrate was concentrated and purified by column chromatography (0-10% MeOH—CH₂Cl₂) to yield 4-bromo-1-(2-hydroxyethyl)pyridin-2(1H)-one as a pale yellow solid (30 mg, 7%). ESI-MS m/z calc. 217.0. found 218.3 (M+1)⁺. Retention time 0.33 minutes. ¹H NMR (400 MHz, DMSO-d₆) δ 7.57 (d, J=7.2 Hz, 1H), 6.70 (d, J=2.2 Hz, 1H), 6.44 (dd, J=2.2, 7.2 Hz, 1H), 4.89 (t, J=5.4 Hz, 1H), 3.91 (t, J=5.4 Hz, 2H), 3.59 (q, J=5.4 Hz, 2H).

Step c: 1-(2-Hydroxyethyl)-4-(4,4,5,5-tetramethyl-1,3,2-dioxaborolan-2-yl)pyridin-2(1H)-one A solution of 4-bromo-1-(2-hydroxyethyl)pyridin-2(1H)-one (30 mg, 0.14 mmol) in DMSO (1 mL) was added to a flask containing 4,4,4',4',5,5,5',5'-octamethyl-2,2'-bi(1,3,2-dioxaborolane) (43 mg, 0.17 mmol), potassium acetate (41 mg, 0.42 mmol) and Pd(dppf)Cl₂ (6.0 mg, 0.0070 mmol). The reaction was stirred under N₂ atmosphere at 80° C. overnight. The reaction was then stirred with ethyl acetate and water for 5 minutes before being filtered through Celite. The organic layer of the filtrate was washed with H₂O (3×). The intermediate product, 1-(2-hydroxyethyl)-4-(4,4,5,5-tetramethyl-1,3,2-dioxaborolan-2-yl)pyridin-2(1H)-one, was found to be in the aqueous layer. The combined aqueous layers were concentrated. The residue was sonicated with DME (1 mL), filtered, and concentrated to give 1-(2-hydroxyethyl)-4-(4,4,5,5-tetramethyl-1,3,2-dioxaborolan-2-yl)pyridin-2(1H)-one.

Z. Methyl 2-(3-cyano-2-oxo-5-(4,4,5,5-tetramethyl-1,3,2-dioxaborolan-2-yl)pyridin-1(2H)-yl)acetate

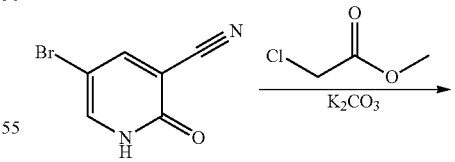

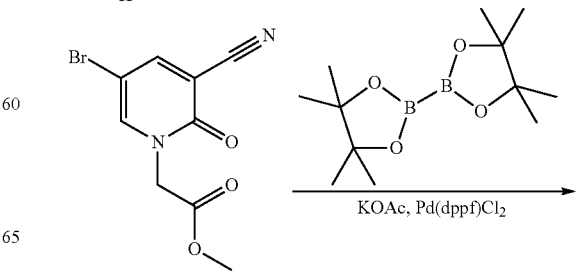

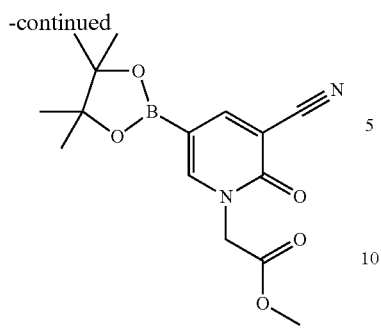

Step a: 2-(5-Bromo-3-cyano-2-oxopyridin-1(2H)-yl) acetate

To 5-bromo-3-cyano-2(1H)-pyridinone (1.4 g, 7.0 mmol) and potassium carbonate (1.9 g, 1.3 mL, 14.1 mmol), THF (26.4 mL) and methyl chloroacetate (1.53 g, 1.2 mL, 14.1 mmol) were added. The reaction was stirred at 80° C. The starting material didn't dissolve well in THF. After 3.5 hours, mainly staring material was observed. DMF (18 mL) was added and the starting material went into solution. The reaction was heated at 80° C. for 45 minutes. The desired mass was observed by LCMS. The reaction was filtered using ethyl acetate and the solvent was evaporated under reduced pressure. The crude product was separated by column chromatography on silica gel (0-100% ethyl acetate in hexane) to yield methyl 2-(5-bromo-3-cyano-2-oxopyridin-1(2H)-yl)acetate as a yellow solid (1.42 g, 74%). ESI-MS m/z calc. 271.07. found 271.3 (M+1)+. Retention time 0.59 minutes.

Step b: Methyl 2-(3-cyano-2-oxo-5-(4,4,5,5-tetramethyl-1,3,2-dioxaborolan-2-yl)pyridin-1(2H)-yl)acetate To methyl 2-(5-bromo-3-cyano-2-oxopyridin-1(2H)-yl) acetate (1.42 g, 5.23 mmol), bis(pinacol)diboron (1.73 g, 6.81 mmol), potassium acetate (1.54 g, 15.72 mmol) and anhydrous DMF (33 mL), Pd(dppf)Cl₂ (0.19 g, 0.26 mmol) was added and stirred at 80° C. for 18 hours under N₂. The solvent was evaporated under reduced pressure. To the crude product, ethyl acetate (40 mL) and water (40 mL) were added. The biphasic mixture was filtered through a plug of celite and the layers were separated. The organic layer was dried over Na₂SO₄, filtered and evaporated under reduced pressure. The crude product was purified by column chromatography on silica gel (0-100% ethyl acetate in hexane) to yield methyl 2-(3-cyano-2-oxo-5-(4,4,5,5-tetramethyl-1,3,2-dioxaborolan-2-yl)pyridin-1(2H)-yl)acetate. ESI-MS m/z calc. 318.13. found 319.3 (M+1)+. Retention time 1.41 minutes.

AA. 2-Methoxy-6-methyl-4-(4,4,5,5-tetramethyl-1,3,2-dioxaborolan-2-yl)pyridine

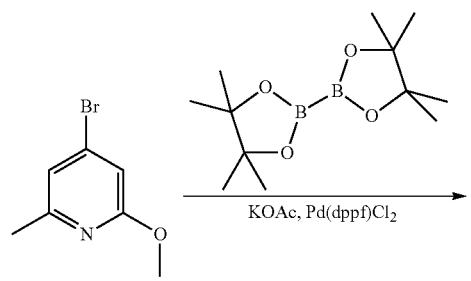

To 4-bromo-2-methoxy-6-methylpyridine (0.681 g, 3.37 mmoL), bis(pinacol)diboron (1.11 g, 4.38 mmoL), KOAc (0.992 g, 10.11 mmoL) and anhydrous DMF (21 mL), Pd(dppf)Cl₂ (0.120 g, 0.163 mmoL) was added and stirred at 80° C. for 18 hours. The solvent was evaporated under reduced pressure. To the crude product, ethyl acetate (40 mL) and water (40 mL) were added. The biphasic mixture was filtered through a plug of celite and the layers were separated. The organic layer was dried over Na₂SO₄, filtered and evaporated under reduced pressure. The crude product was purified by column chromatography on silica gel (0-50% ethyl acetate in hexane) to yield 2-methoxy-6-methyl-4-(4,4,5,5-tetramethyl-1,3,2-dioxaborolan-2-yl) pyridine. ESI-MS m/z calc. 249.11. found 250.3 (M+1)+. Retention time 0.19 minutes.

AB. 6-Methoxy-2-methyl-3-(4,4,5,5-tetramethyl-1,3,2-dioxaborolan-2-yl)pyridine

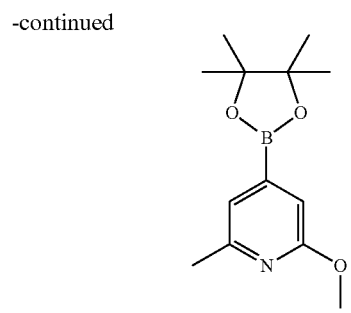

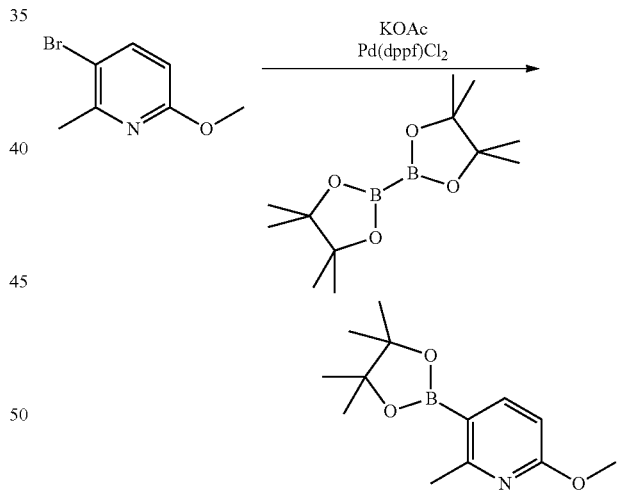

To 3-bromo-6-methoxy-2-methylpyridine (1.0 g, 4.9 mmol) in N,N-dimethyl formamide (30 mL) was added bis(pinacol)diboron (1.5 g, 5.9 mmol), potassium acetate (1.4 g, 14.8 mmol), and Pd(dppf)Cl₂ (202.1 mg, 247.5 μmol). The reaction mixture was heated to 80° C. for 18 hours. The volatiles were removed to give a black solid which was partitioned between ethyl acetate (50 mL) and water (50 mL). The biphasic mixture was filtered through a pad of celite and the layers separated. The organics were dried over Na₂SO₃ and evaporated to dryness. The resulting solid was purified by silica gel chromatography eluting with 0-30% ethyl acetate in hexane to yield 6-methoxy-2-methyl-3-(4,4,5,5-tetramethyl-1,3,2-dioxaborolan-2-yl)pyridine (0.81 g, 65.7%). ESI-MS m/z calc. 249.11. found 250.5 (M+1)⁺. Retention time 1.06 minutes.

AC. 2-Methoxy-3-methyl-5-(4,4,5,5-tetramethyl-1,3,2-dioxaborolan-2-yl)pyridine

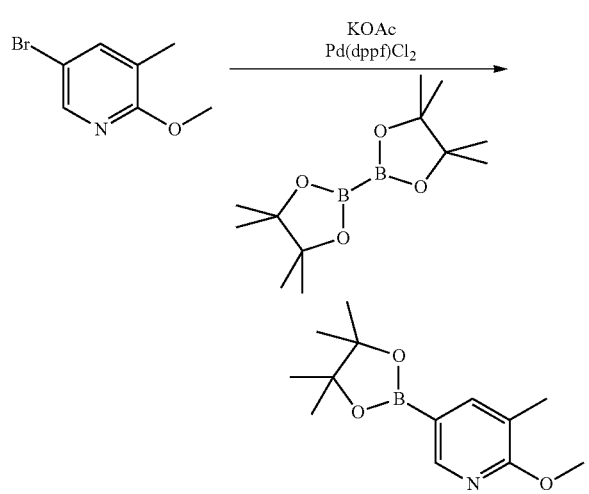

To 5-bromo-2-methoxy-3-methylpyridine (3.14 g, 15.54 mmol) in N,N-dimethyl formamide (90 mL) was added bis(pinacol)diboron (5.13 g, 20.20 mmol), potassium acetate (4.58 g, 46.62 mmol), and Pd(dppf)Cl₂ (568 mg, 777 µmol). The reaction mixture was heated to 80° C. for 18 hours. The volatiles were removed to give a solid which was partitioned between ethyl acetate and water. The biphasic mixture was filtered through a pad of celite and the layers separated. The organics were dried over Na₂SO₃ and evaporated to dryness. The resulting solid was purified by silica gel chromatography eluting with 0-30% ethyl acetate in hexane to yield 2-methoxy-3-methyl-5-(4,4,5,5-tetramethyl-1,3,2-dioxaborolan-2-yl)pyridine (1.35 g, 35%). ESI-MS m/z calc. 249.11. found 250.1 (M+1)⁺. Retention time 1.87 minutes.

AD. 1-(2-(Methylsulfonyl)ethyl)-5-(4,4,5,5-tetramethyl-1,3,2-dioxaborolan-2-yl)pyridin-2(1H)-one

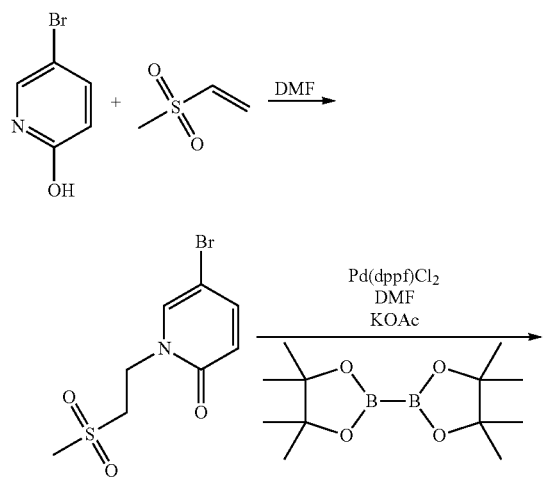

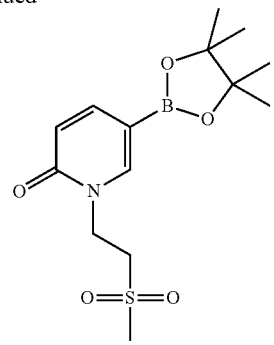

Step a: 5-Bromo-1-(2-(methylsulfonyl)ethyl)pyridin-2(1H)-one

5-Bromopyridin-2-ol (4.0 g, 23.0 mmol) and methylsulfonylethene (2.4 g, 2.0 mL, 23.0 mmol) were combined in N,N-dimethylformamide (DMF, 23 mL) and heated to 100° C. The crude reaction mixture was then evaporated to dryness. The crude material was then dissolved in a minimum of dichloromethane. The solution was then washed twice with an aqueous 1 M solution of hydrochloric acid, two times with a saturated aqueous solution of sodium bicarbonate, two times with a saturated aqueous solution of sodium chloride, and finally by two washes of water. The organic layer was dried over sodium sulfate and then evaporated to dryness to yield the product as a pale brown solid (1.87 g, 6.68 mmol, 29%). ESI-MS m/z calc. 279.0. found 280.0 (M+1)⁺. Retention time 0.34 minutes.

Step b: 1-(2-(Methylsulfonyl)ethyl)-5-(4,4,5,5-tetramethyl-1,3,2-dioxaborolan-2-yl)pyridin-2(1H)-one 5-Bromo-1-(2-(methylsulfonyl)ethyl)pyridin-2(1H)-one (1.7 g, 6.0 mmol), potassium acetate (1.8 g, 18.1 mmol), bis(pinacolato)diboron (2.0 g, 7.8 mmol), and dichloro[1,1'-bis(diphenylphosphino)ferrocene]palladium (II) dichloromethane adduct (Pd(dppf)Cl₂, 221.1 mg, 0.30 mmol) were combined in N,N-dimethylformamide (37 mL). The resulting reaction mixture was stirred and heated to 80° C. for 2 hours. The crude reaction mixture was evaporated to dryness, partitioned between 250 mL of ethyl acetate and 250 mL of water, filtered through celite, and the layers were separated. The organic layer was dried over sodium sulfate and then evaporated to dryness. The crude material was purified on silica gel (120 g) utilizing a gradient of 0-10% methanol in dichloromethane to yield the product as a semi-pure brown oil (1.78 g, 5.43 mmol, 90%). ESI-MS m/z calc. 327.1. found 328.2 (M+1)⁺. Retention time 0.90 minutes.

AE. 2-(2-oxo-5-(4,4,5,5-tetramethyl-1,3,2-dioxaborolan-2-yl)pyridin-1(2H)-yl)acetonitrile

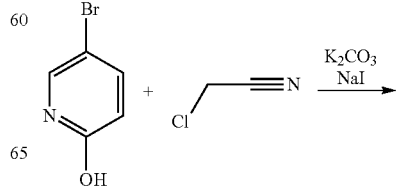

-continued

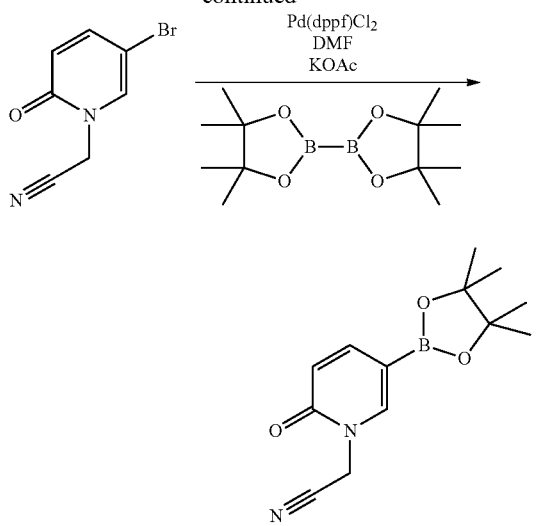

Step a: 2-(5-Bromo-2-oxopyridin-1(2H)-yl)acetonitrile

2-Hydroxy-5-bromopyridine (5.000 g, 28.74 mmol), potassium carbonate (14.30 g, 9.283 mL, 103.5 mmol), and sodium iodide (1.077 g, 7.185 mmol) were suspended in chloroacetonitrile (10.85 g, 9.095 mL, 143.7 mmol). The reaction mixture was heated to 60° C. and stirred for 2 hours. The reaction mixture was allowed to cool to room temperature, filtered, and the filter cake was washed with dichloromethane and ethyl acetate. The filtrate was concentrated and purified on 120 g of silica gel utilizing a gradient of 0-100% ethyl acetate in hexanes over 45 minutes to yield the pure product as a beige solid (4.1 g, 67%). $^1$H NMR (400.0 MHz, DMSO-$d_6$) δ 8.11 (d, J=2.7 Hz, 1H), 7.63 (dd, J=2.8, 9.8 Hz, 1H), 6.49 (d, J=9.8 Hz, 1H), 4.94 (s, 2H).

Step b: 2-(2-oxo-5-(4,4,5,5-tetramethyl-1,3,2-dioxaborolan-2-yl)pyridin-1(2H)-yl)acetonitrile 2-(5-Bromo-2-oxopyridin-1(2H)-yl)acetonitrile (2.0 g, 9.4 mmol), potassium acetate (2.77 g, 28.17 mmol), bis(pinacolato)diboron (3.1 g, 12.2 mmol), and dichloro[1,1'-bis(diphenylphosphino)ferrocene]palladium (II) dichloromethane adduct (Pd(dppf)Cl$_2$, 343.5 mg, 0.47 mmol) were combined in N,N-dimethylformamide (57 mL). The resulting reaction mixture was stirred and heated to 80° C. for 2 hours. The crude reaction mixture was evaporated to dryness, partitioned between 250 mL of ethyl acetate and 250 mL of water, filtered through celite, and the layers were separated. The organic layer was dried over sodium sulfate and then evaporated to dryness. The crude material was purified on silica gel (40 g) utilizing a gradient of 0-10% methanol in dichloromethane to yield the product as a beige solid (0.7722 g, 32%). ESI-MS m/z calc. 260.1. found 261.2 (M+1)$^+$. Retention time 1.46 minutes.

AF. 3-Chloro-2-methoxy-5-(4,4,5,5-tetramethyl-1,3,2-dioxaborolan-2-yl)pyridine

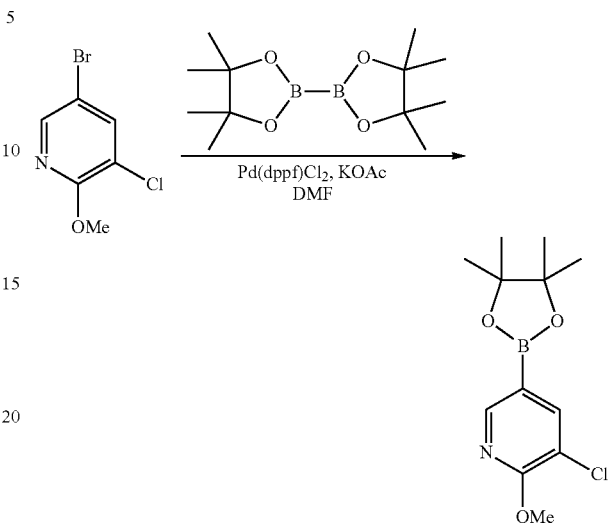

To a dry flask was added 5-bromo-3-chloro-2-methoxypyridine (0.5 g, 2.2 mmol), 4,4,4',4',5,5,5',5'-octamethyl-2,2'-bi(1,3,2-dioxaborolane) (0.70 g, 2.7 mmol), and Pd(dppf)Cl$_2$ (82 mg, 0.10 mmol). Potassium acetate (0.6 g, 6.0 mmol) was weighed directly into the flask. The flask was then evacuated and back filled with N$_2$. Anhydrous N,N-dimethylformamide (DMF) (13.0 mL) was added and the reaction was heated at 80° C. in an oil bath overnight. The reaction mixture was evaporated to dryness. The residue was dissolved in ethyl acetate (10 mL) and washed with water (10 mL). The organics were dried over sodium sulfate and evaporated to dryness. The resulting material was purified by silica gel chromatography (eluting with 0-100% ethyl acetate in hexanes) to yield the product (0.47 g, 78%). ESI-MS m/z calc. 269.53. found 270.3 (MW+1)$^+$. Retention time 2.07 minutes.

AG. 2,3-dimethoxy-5-(4,4,5,5-tetramethyl-1,3,2-dioxaborolan-2-yl)pyridine

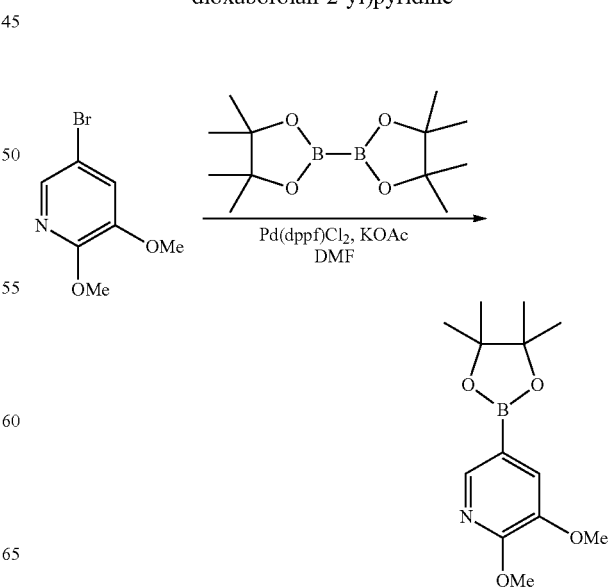

To a dry flask was added 5-bromo-2,3-dimethoxypyridine (0.1 g, 0.46 mmol), 4,4,4',4',5,5,5',5'-octamethyl-2,2'-bi(1,3,2-dioxaborolane) (0.14 g, 0.55 mmol), and Pd(dppf)Cl$_2$ (32 mg, 0.04 mmol). Potassium acetate (0.15 g, 1.5 mmol) was weighed directly into the flask. The flask was then evacuated and back filled with N$_2$. Anhydrous N,N-dimethylformamide (DMF) (2.0 mL) was added and the reaction was heated at 80° C. in an oil bath overnight. The reaction mixture was evaporated to dryness. The residue was dissolved in ethyl acetate (5 mL) and washed with water (5 mL). The organics were dried over sodium sulfate and evaporated to dryness. The resulting material was purified by silica gel chromatography (eluting with 0-100% ethyl acetate in hexanes) to yield the product (66 mg, 54%). ESI-MS m/z calc. 265.11. found 266.1 (MW+1)$^+$. Retention time 1.53 minutes.

AH. Methyl 2-methoxy-5-(4,4,5,5-tetramethyl-1,3,2-dioxaborolan-2-yl)nicotinate

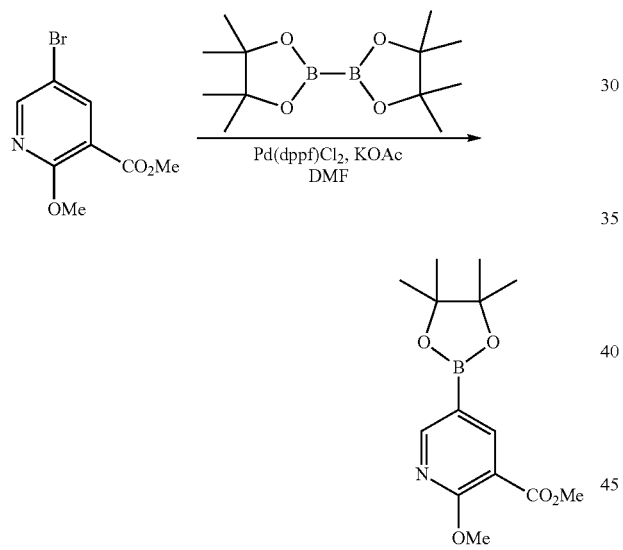

To a dry flask was added methyl 5-bromo-2-methoxynicotinate (0.5 g, 2.0 mmol), 4,4,4',4',5,5,5',5'-octamethyl-2,2'-bi(1,3,2-dioxaborolane) (0.61 g, 2.4 mmol), and Pd(dppf)Cl$_2$ (82 mg, 0.10 mmol). Potassium acetate (0.6 g, 6.0 mmol) was weighed directly into the flask. The flask was then evacuated and back filled with N$_2$. Anhydrous N,N-dimethylformamide (10.0 mL) was added and the reaction was heated at 80° C. in an oil bath overnight. The reaction mixture was evaporated to dryness. The residue was dissolved in ethyl acetate (10 mL) and washed with water (10 mL). The organics were dried over sodium sulfate and evaporated to dryness. The resulting material was purified by silica gel chromatography (eluting with 0-70% ethyl acetate in hexanes) to yield the product (0.36 g, 72%). ESI-MS m/z calc. 249.11. found 250.3 (MW+1)$^+$. Retention time 1.84 minutes.

AI. 2-Methoxy-3-nitro-5-(4,4,5,5-tetramethyl-1,3,2-dioxaborolan-2-yl)pyridine

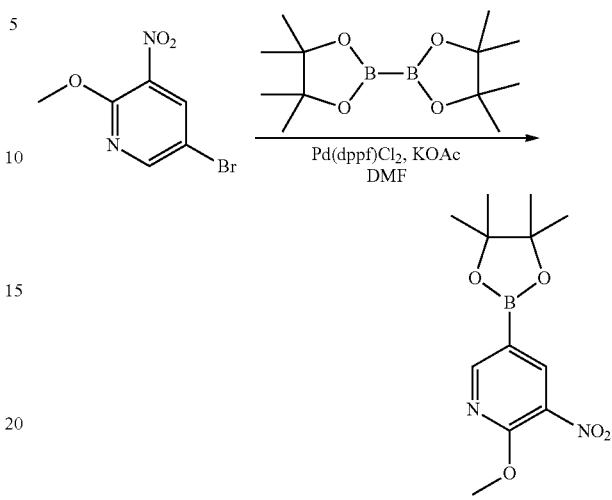

To a dry flask was added 5-bromo-2-methoxy-3-nitropyridine (1.3 g, 5.0 mmol), 4,4,4',4',5,5,5',5'-octamethyl-2,2'-bi(1,3,2-dioxaborolane) (1.6 g, 6.4 mmol), and Pd(dppf)Cl$_2$ (0.2 g, 0.25 mmol). Potassium acetate (1.5 g, 15 mmol) was weighed directly into the flask. The flask was then evacuated and back filled with N$_2$. Anhydrous N,N-dimethylformamide (30 mL) was added and the reaction was heated at 80° C. in an oil bath overnight. The reaction mixture was evaporated to dryness. The residue was dissolved in ethyl acetate (20 mL) and washed with water (20 mL). The organics were dried over sodium sulfate and evaporated to dryness. The resulting material was purified by silica gel chromatography (eluting with 0-50% ethyl acetate in hexane) to yield the product (0.2 g, 15%). ESI-MS m/z calc. 280.12. found 199.1 (MW[−C$_6$H$_{10}$]+1)$^+$. Retention time 0.7 minutes.

AJ. 5-fluoro-2-methoxy-3-(4,4,5,5-tetramethyl-1,3,2-dioxaborolan-2-yl)pyridine

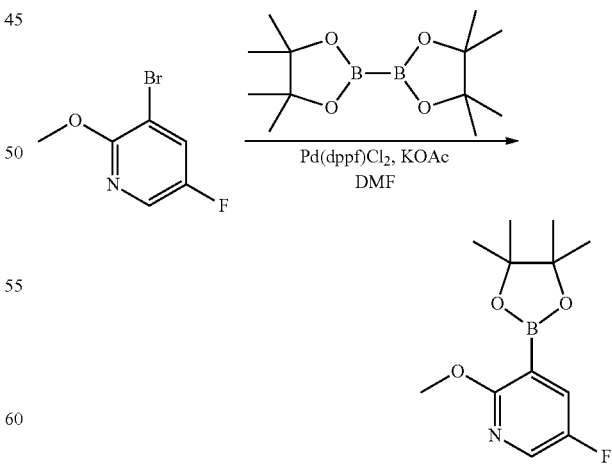

To a dry flask was added 3-bromo-5-fluoro-2-methoxypyridine (1.0 g, 5.0 mmol), 4,4,4',4',5,5,5',5'-octamethyl-2,2'-bi(1,3,2-dioxaborolane) (1.6 g, 6.4 mmol), and Pd(dppf)Cl$_2$ (0.2 g, 0.25 mmol). Potassium acetate (1.5 g, 15 mmol) was weighed directly into the flask. The flask was then evacuated and back filled with N₂. Anhydrous N,N-dimethylformamide (30 mL) was added and the reaction was heated at 80° C. in an oil bath overnight. The reaction mixture was evaporated to dryness. The residue was dissolved in ethyl acetate (20 mL) and washed with water (20 mL). The organics were dried over sodium sulfate and evaporated to dryness. The resulting material was purified by silica gel chromatography eluting with 0-50% ethyl acetate in hexane to yield the product (1.0 g, 80%). ESI-MS m/z calc. 253.13. found 254.1 (MW+1)⁺. Retention time 1.72 minutes.

AK. 5-chloro-2-methoxy-3-(4,4,5,5-tetramethyl-1,3,2-dioxaborolan-2-yl)pyridine

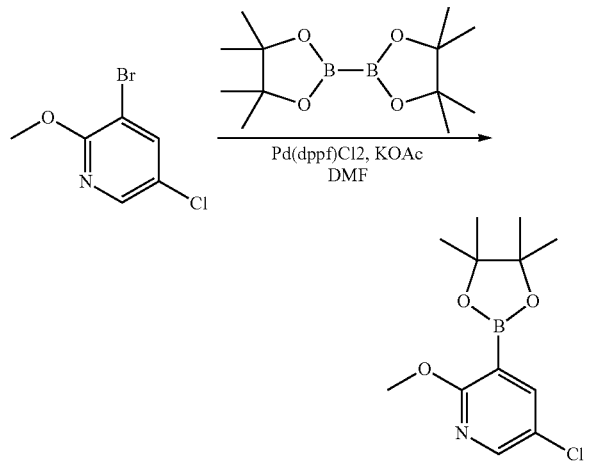

To a dry flask was added 3-bromo-5-chloro-2-methoxypyridine (1.2 g, 5.0 mmol), 4,4,4',4',5,5,5',5'-octamethyl-2,2'-bi(1,3,2-dioxaborolane) (1.6 g, 6.4 mmol), and Pd(dppf)Cl₂ (0.2 g, 0.25 mmol). Potassium acetate (1.5 g, 15 mmol) was weighed directly into the flask. The flask was then evacuated and back filled with N₂. Anhydrous N,N-dimethylformamide (30 mL) was added and the reaction was heated at 80° C. in an oil bath overnight. The reaction mixture was evaporated to dryness. The residue was dissolved in ethyl acetate (20 mL) and washed with water (20 mL). The organics were dried over sodium sulfate and evaporated to dryness. The resulting material was purified by silica gel chromatography (eluting with 0-50% ethyl acetate in hexane) to yield the product (0.8 g, 60%). ESI-MS m/z calc. 269.10. found 270.3 (MW+1)⁺. Retention time 1.95 minutes.

AL. N-(5-Chloro-6-(6-oxo-1,6-dihydropyridin-3-yl)pyridin-2-yl)-1-(2,2-difluorobenzo[d][1,3]-dioxol-5-yl)cyclopropanecarboxamide

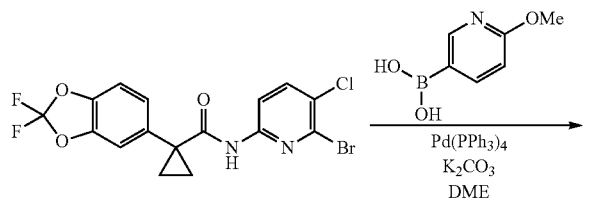

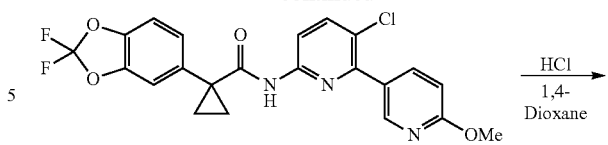

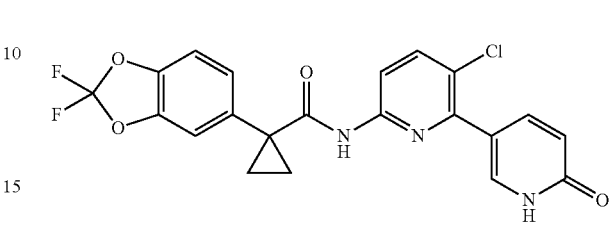

Step a: N-(3-Chloro-6'-methoxy-2,3'-bipyridin-6-yl)-1-(2,2-difluorobenzo[d][1,3]dioxol-5-yl)cyclopropanecarboxamide N-(6-Bromo-5-chloropyridin-2-yl)-1-(2,2-difluorobenzo[d][1,3]dioxol-5-yl)cyclopropanecarboxamide (259 mg, 0.600 mmol) was dissolved in 6 mL of 1,2-dimethoxyethane (DME) in a microwave reactor tube. 6-Methoxypyridin-3-ylboronic acid (138 mg, 0.900 mmol), 0.6 mL of an aqueous 2 M potassium carbonate solution, and tetrakis(triphenylphospine)palladium(0) (Pd(PPh₃)₄, 34.7 mg, 0.0300 mmol) were added and the reaction mixture was heated at 120° C. in a microwave reactor for 20 minutes. The resulting material was cooled to room temperature, filtered, and the layers were separated. The crude product was evaporated to dryness and then purified on 40 g of silica gel utilizing a gradient of 0-100% ethyl acetate in hexanes to yield N-(3-chloro-6'-methoxy-2,3'-bipyridin-6-yl)-1-(2,2-difluorobenzo[d][1,3]dioxol-5-yl)cyclopropane carboxamide (141 mg, 51%) as a colorless oil. ESI-MS m/z calc. 459.1. found; 459.9 (M+1)⁺ Retention time 2.26 minutes.

Step b: N-(5-Chloro-6-(6-oxo-1,6-dihydropyridin-3-yl)pyridin-2-yl)-1-(2,2-difluorobenzo[d][1,3]dioxol-5-yl)cyclopropanecarboxamide N-(3-Chloro-6'-methoxy-2,3'-bipyridin-6-yl)-1-(2,2-difluorobenzo[d][1,3]dioxol-5-yl)cyclopropanecarboxamide (124 mg, 0.270 mmol) was dissolved in a mixture of 1.2 mL of 1,4-dioxane and 0.6 mL of 4M aqueous hydrochloric acid. This solution was heated at 90° C. for 5 hours. The crude reaction mixture was quenched with triethylamine and then evaporated to dryness. The crude product was then partitioned between dichloromethane and water. The organic layer was separated, dried over sodium sulfate, and then purified on 4 g of silica gel utilizing a gradient of 0-5% methanol in dichloromethane to yield N-(5-chloro-6-(6-oxo-1,6-dihydropyridin-3-yl)pyridin-2-yl)-1-(2,2-difluorobenzo[d][1,3]dioxol-5-yl)cyclopropanecarboxamide as a white solid (27 mg, 22%). ESI-MS m/z calc. 445.1. found 445.9 (M+1)⁺. Retention time 1.62 minutes.

AM. 1-(2,2-Difluorobenzo[1,3]dioxol-5-yl)-N-(5-methyl-6-(2-oxo-1,2-dihydropyridin-3-yl)pyridin-2-yl)cyclopropanecarboxamide

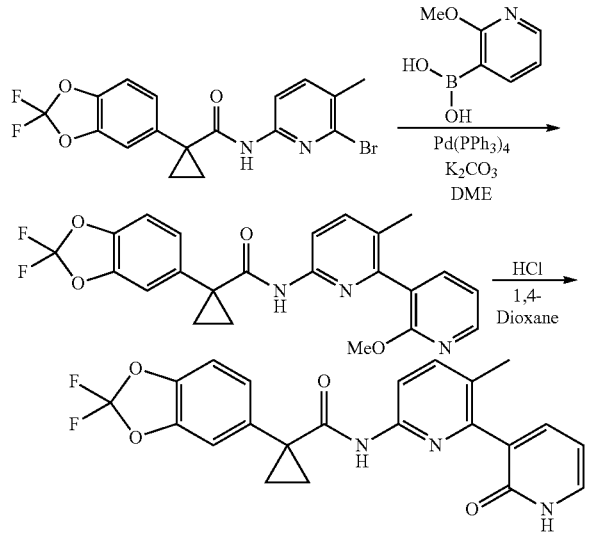

Step a: 1-(2,2-Difluorobenzo[d][1,3]dioxol-5-yl)-N-(2'-methoxy-3-methyl-2,3'-bipyridin-6-yl)cyclopropanecarboxamide N-(6-Chloro-5-methylpyridin-2-yl)-1-(2,2-difluorobenzo[d][1,3]dioxol-5-yl)cyclopropanecarboxamide (110 mg, 0.300 mmol) was dissolved in 3 mL of 1,2-dimethoxyethane (DME) in a microwave reactor tube. 2-Methoxypyridin-3-ylboronic acid (59.6 mg, 0.390 mmol), 0.4 mL of an aqueous 2 M potassium carbonate solution, and tetrakis(triphenylphospine)palladium(0) (Pd(PPh$_3$)$_4$, 34.7 mg, 0.0300 mmol) were added and the reaction mixture was heated at 120° C. in a microwave reactor for 20 minutes. The resulting material was cooled to room temperature, filtered, and the layers were separated. The crude product was evaporated to dryness, dissolved in 1 mL of N,N-dimethylformamide, and purified by reverse-phase preparative liquid chromatography utilizing a gradient of 0-99% acetonitrile in water containing 0.05% trifluoracetic acid to yield 1-(2,2-difluorobenzo[d][1,3]dioxol-5-yl)-N-(2'-methoxy-3-methyl-2,3'-bipyridin-6-yl)cyclopropanecarboxamide. ESI-MS m/z calc. 439.1. found 440.1 (M+1)$^+$. Retention time 1.94 minutes.

Step b: 1-(2,2-Difluorobenzo[d][1,3]-dioxol-5-yl)-N-(5-methyl-6-(2-oxo-1,2-dihydropyridin-3-yl)pyridin-2-yl)cyclopropanecarboxamide 1-(2,2-Difluorobenzo[d][1,3]dioxol-5-yl)-N-(2'-methoxy-3-methyl-2,3'-bipyridin-6-yl)cyclopropanecarboxamide (66 mg, 0.15 mmol) was dissolved in a mixture of 1 mL of 1,4-dioxane and 0.5 mL of 4M aqueous hydrochloric acid. This solution was heated at 90° C. for 3 hours. The crude product was then purified by reverse-phase preparative liquid chromatography utilizing a gradient of 0-99% acetonitrile in water containing 0.05% trifluoracetic acid to yield 1-(2,2-difluorobenzo[d][1,3]dioxol-5-yl)-N-(5-methyl-6-(2-oxo-1,2-dihydropyridin-3-yl)pyridin-2-yl)cyclopropanecarboxamide. ESI-MS m/z calc. 425.1. found 426.0 (M+1)$^+$. Retention time 1.33 minutes.

AN. 1-(2,2-Difluorobenzo[d][1,3]dioxol-5-yl)-N-(5-methyl-6-(6-oxo-1,6-dihydropyridin-3-yl)pyridin-2-yl)cyclopropanecarboxamide

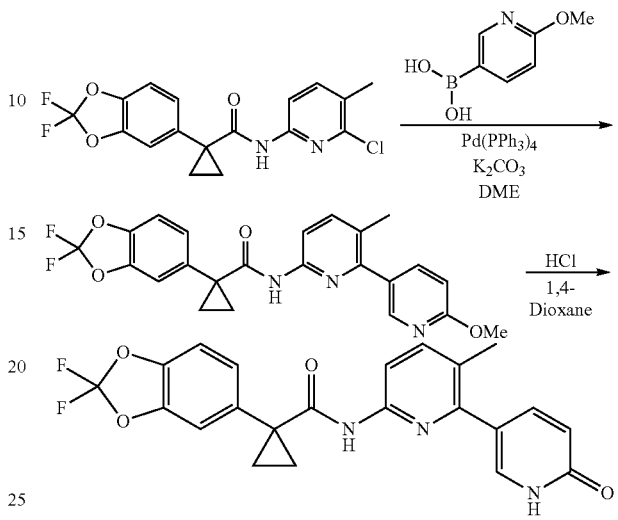

Step a: 1-(2,2-Difluorobenzo[d][1,3]dioxol-5-yl)-N-(6'-methoxy-3-methyl-2,3'-bipyridin-6-yl)cyclopropanecarboxamide N-(6-Chloro-5-methylpyridin-2-yl)-1-(2,2-difluorobenzo[d][1,3]dioxol-5-yl)cyclopropanecarboxamide (660 mg, 1.80 mmol) was dissolved in 18 mL of 1,2-dimethoxyethane (DME) in a microwave reactor tube. 6-Methoxypyridin-3-ylboronic acid (358 mg, 2.34 mmol), 2.4 mL of an aqueous 2 M potassium carbonate solution, and tetrakis(triphenylphospine)palladium(0) (Pd(PPh$_3$)$_4$, 102 mg, 0.0882 mmol) were added and the reaction mixture was heated at 120° C. in a microwave reactor for 20 minutes. The resulting material was cooled to room temperature, filtered, and the layers were separated. The crude product was evaporated to dryness and then purified on 40 g of silica gel utilizing a gradient of 0-100% ethyl acetate in hexanes to yield 1-(2,2-difluorobenzo[d][1,3]dioxol-5-yl)-N-(6'-methoxy-3-methyl-2,3'-bipyridin-6-yl)cyclopropanecarboxamide (482 mg, 61%). ESI-MS m/z calc. 439.1. found 440.1 (M+1)$^+$ Retention time 1.95 minutes.

Step b: 1-(2,2-Difluorobenzo[d][1,3]dioxol-5-yl)-N-(5-methyl-6-(6-oxo-1,6-dihydropyridin-3-yl)pyridin-2-yl)cyclopropanecarboxamide 1-(2,2-Difluorobenzo[d][1,3]dioxol-5-yl)-N-(6'-methoxy-3-methyl-2,3'-bipyridin-6-yl)cyclopropanecarboxamide (482 mg, 1.10 mmol) was dissolved in a mixture of 6 mL of 1,4-dioxane and 3 mL of 4M aqueous hydrochloric acid. This solution was heated at 90° C. for 1.5 hours. The crude reaction mixture was quenched with one equivalent of triethylamine and then evaporated to dryness. The crude product was then partitioned between dichloromethane and water. The organic layer was separated, dried over sodium sulfate, and then purified on 12 g of silica gel utilizing a gradient of 0-10% methanol in dichloromethane to yield 1-(2,2-difluorobenzo[d][1,3]dioxol-5-yl)-N-(5-methyl-6-(6-oxo-1,6-dihydropyridin-3-yl)pyridin-2-yl)cyclopropanecarboxamide as a white solid (189 mg, 40%). ESI-MS m/z calc.

425.1. found 426.3 (M+1)+. Retention time 1.53 minutes. ¹H NMR (400 MHz, DMSO-$d_6$) δ 11.78 (s, 1H), 8.91 (s, 1H), 7.81 (d, J=8.3 Hz, 1H), 7.66-7.64 (m, 2H), 7.56-7.55 (m, 2H), 7.41 (d, J=8.3 Hz, 1H), 7.34 (dd, J=1.7, 8.3 Hz, 1H), 6.36 (d, J=9.5 Hz, 1H), 2.28 (s, 3H), 1.52-1.49 (m, 2H), 1.18-1.15 (m, 2H).

AO. 1-(2,2-Difluorobenzo[1,3]dioxol-5-yl)-N-(5-methyl-6-(5-methyl-6-oxo-1,6-dihydropyridin-3-yl)pyridin-2-yl)cyclopropanecarboxamide

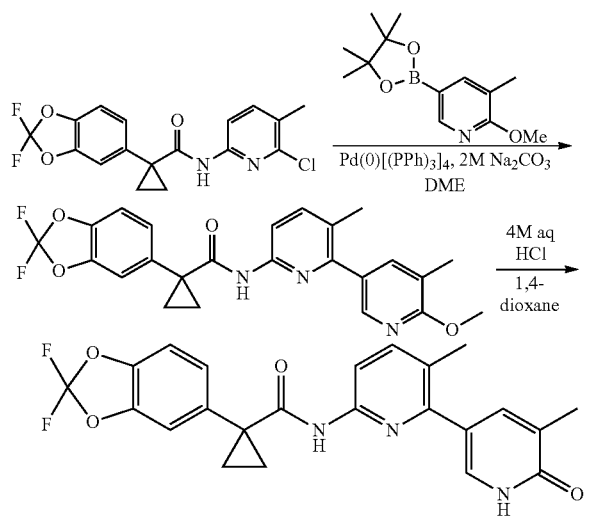

Step a: 1-(2,2-Difluorobenzo[d][1,3]dioxol-5-yl)-N-(6'-methoxy-3,5'-dimethyl-2,3'-bipyridin-6-yl)cyclopropanecarboxamide N-(6-Chloro-5-methylpyridin-2-yl)-1-(2,2-difluorobenzo[d][1,3]dioxol-5-yl)cyclopropanecarboxamide (73 mg, 0.20 mmol) was dissolved in 2 mL of 1,2-dimethoxyethane in a reaction tube. 2-Methoxy-3-methyl-5-(4,4,5,5-tetramethyl-1,3,2-dioxaborolan-2-yl)pyridine (65 mg, 0.26 mmol), 0.2 mL of an aqueous 2 M sodium carbonate solution, and tetrakis(triphenylphosphine)palladium(0) (12 mg, 0.010 mmol) were added and the reaction mixture was heated at 80° C. overnight. The reaction was diluted with ethyl acetate (5 mL) and washed with water (5 mL). The organics were dried over sodium sulfate and evaporated to dryness. The resulting residue was purified by silica gel chromatography eluting with 0-100% ethyl acetate in hexane to yield 1-(2,2-difluorobenzo[d][1,3]dioxol-5-yl)-N-(6'-methoxy-3,5'-dimethyl-2,3'-bipyridin-6-yl)cyclopropanecarboxamide (46 mg, 51%). ESI-MS m/z calc. 453.4. found 454.3 (M+1)+. Retention time 2.16 minutes.

Step b: 1-(2,2-Difluorobenzo[d][1,3]dioxol-5-yl)-N-(5-methyl-6-(5-methyl-6-oxo-1,6-dihydropyridin-3-yl)pyridin-2-yl)cyclopropanecarboxamide To 1-(2,2-difluorobenzo[d][1,3]dioxol-5-yl)-N-(6'-methoxy-3,5'-dimethyl-2,3'-bipyridin-6-yl)cyclopropanecarboxamide (46 mg, 0.11 mmol) in 1,4-dioxane (1 mL) was added 0.5 mL of an aqueous 4 M hydrochloric acid solution. The reaction mixture was heated at 90° C. for 2 hours before being quenched with triethylamine (0.5 mL). The reaction mixture was diluted with dichloromethane (3 mL) and washed with water (3 mL). The organics were dried over sodium sulfate and evaporated to dryness. The residue was dissolved in N,N-dimethylformamide (1 mL) and purified by reverse-phase preparative liquid chromatography to yield 1-(2,2-difluorobenzo[d][1,3]dioxol-5-yl)-N-(5-methyl-6-(5-methyl-6-oxo-1,6-dihydropyridin-3-yl)pyridin-2-yl)cyclopropane carboxamide as a trifluoroacetic acid salt. ESI-MS m/z calc. 439.4. found 440.3 (M+1)+. Retention time 1.64 minutes. ¹H NMR (parent) (400 MHz, DMSO-$d_6$) δ 11.68 (s, 1H), 8.93 (s, 1H), 7.80 (d, J=8.3 Hz, 1H), 7.64 (d, J=8.4 Hz, 1H), 7.55-7.54 (m, 1H), 7.52-7.51 (m, 1H), 7.41-7.39 (m, 2H), 7.34-7.31 (m, 1H), 2.27 (s, 3H), 1.98 (s, 3H), 1.51-1.48 (m, 2H), 1.17-1.15 (m, 2H).

AP. 1-(2,2-Difluorobenzo[d][1,3]dioxol-5-yl)-N-(5-methyl-6-(2-methyl-6-oxo-1,6-dihydropyridin-3-yl)pyridin-2-yl)pyridin-2-yl)cyclopropanecarboxamide

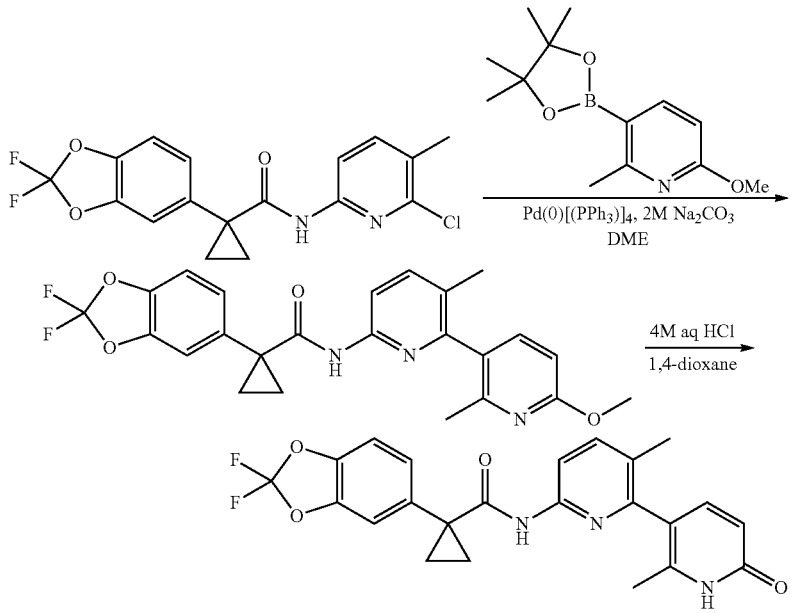

Step a: 1-(2,2-Difluorobenzo[d][1,3]dioxol-5-yl)-N-(6'-methoxy-2',3-dimethyl-2,3'-bipyridin-6-yl)cyclopropanecarboxamide N-(6-Chloro-5-methylpyridin-2-yl)-1-(2,2-difluorobenzo[d][1,3]dioxol-5-yl)cyclopropanecarboxamide (73 mg, 0.20 mmol) was dissolved in 2 mL of 1,2-dimethoxyethane in a reaction tube. 6-Methoxy-2-methyl-3-(4,4,5,5-tetramethyl-1,3,2-dioxaborolan-2-yl)pyridine (65 mg, 0.26 mmol), 0.2 mL of an aqueous 2 M sodium carbonate solution, and tetrakis(triphenylphosphine)palladium(0) (12 mg, 0.010 mmol) were added and the reaction mixture was heated at 80° C. overnight. The reaction was diluted with ethyl acetate (5 mL) and washed with water (5 mL). The organics were dried over sodium sulfate and evaporated to dryness. The resulting residue was purified by silica gel chromatography eluting with 0-100% ethyl acetate in hexane to yield 1-(2,2-difluorobenzo[d][1,3]dioxol-5-yl)-N-(6'-methoxy-2',3-dimethyl-2,3'-bipyridin-6-yl)cyclopropanecarboxamide (69 mg, 76%). ESI-MS m/z calc. 453.4. found 454.3 (M+1)$^+$. Retention time 1.98 minutes.

Step b: 1-(2,2-Difluorobenzo[d][1,3]-dioxol-5-yl)-N-(5-methyl-6-(2-methyl-6-oxo-1,6-dihydropyridin-3-yl)pyridin-2-yl)cyclopropanecarboxamide To 1-(2,2-difluorobenzo[d][1,3]dioxol-5-yl)-N-(6'-methoxy-2',3-dimethyl-2,3'-bipyridin-6-yl)cyclopropanecarboxamide (69 mg, 0.15 mmol) in 1,4-dioxane (1 mL) was added 0.5 mL of an aqueous 4 M hydrochloric acid solution. The reaction mixture was heated at 90° C. for 2 hours before being quenched with triethylamine (0.5 mL). The reaction mixture was diluted with dichloromethane (3 mL) and washed with water (3 mL). The organics were dried over sodium sulfate and evaporated to dryness. The residue was dissolved in N,N-dimethylformamide (1 mL) and purified by reverse-phase preparative liquid chromatography to yield 1-(2,2-difluorobenzo[d][1,3]dioxol-5-yl)-N-(5-methyl-6-(2-methyl-6-oxo-1,6-dihydropyridin-3-yl)pyridin-2-yl)cyclopropane carboxamide as a trifluoroacetic acid salt. ESI-MS m/z calc. 439.4. found 440.3 (M+1)$^+$. Retention time 1.56 minutes. $^1$H NMR (parent) (400 MHz, DMSO) δ 11.69 (s, 1H), 8.91 (s, 1H), 7.88 (d, J=8.4 Hz, 1H), 7.68 (d, J=8.5 Hz, 1H), 7.55 (d, J=1.5 Hz, 1H), 7.39 (d, J=8.3 Hz, 1H), 7.33 (dd, J=1.7, 8.3 Hz, 1H), 7.22 (d, J=9.3 Hz, 1H), 6.17 (d, J=9.3 Hz, 1H), 2.05 (s, 3H), 1.90 (s, 3H), 1.51-1.48 (m, 2H), 1.17-1.14 (m, 2H).

AQ. 1-(2,2-Difluorobenzo[d][1,3]dioxol-5-yl)-N-(5-methyl-6-(5-methyl-2-oxo-1,2-dihydropyridin-3-yl)pyridin-2-yl)cyclopropanecarboxamide

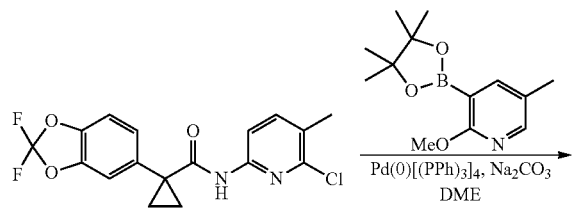

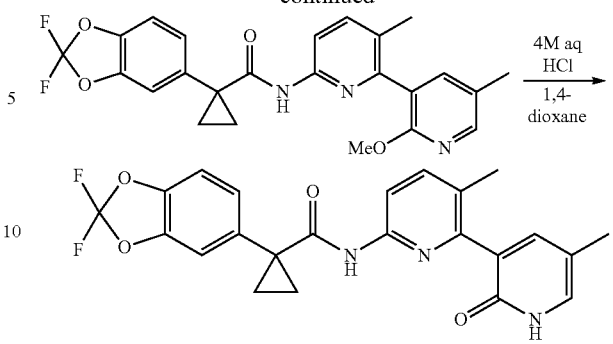

Step a: 1-(2,2-Difluorobenzo[d][1,3]-dioxol-5-yl)-N-(2'-methoxy-3,5'-dimethyl-2,3'-bipyridin-6-yl)cyclopropanecarboxamide N-(6-Chloro-5-methylpyridin-2-yl)-1-(2,2-difluorobenzo[d][1,3]dioxol-5-yl)cyclopropanecarboxamide (73 mg, 0.20 mmol) was dissolved in 2 mL of 1,2-dimethoxyethane in a reaction tube. 2-Methoxy-5-methyl-3-(4,4,5,5-tetramethyl-1,3,2-dioxaborolan-2-yl)pyridine (65 mg, 0.26 mmol), 0.2 mL of an aqueous 2 M sodium carbonate solution, and tetrakis(triphenylphosphine)palladium(0) (12 mg, 0.010 mmol) were added and the reaction mixture was heated at 120° C. for 20 minutes under microwave irradiation. The reaction was diluted with ethyl acetate (5 mL) and washed with water (5 mL). The organics were dried over sodium sulfate and evaporated to dryness. The resulting residue was purified by silica gel chromatography eluting with 0-100% ethyl acetate in hexane to yield 1-(2,2-difluorobenzo[d][1,3]dioxol-5-yl)-N-(2'-methoxy-3,5'-dimethyl-2,3'-bipyridin-6-yl)cyclopropanecarboxamide (49 mg, 72%). ESI-MS m/z calc. 453.4. found 454.3 (M+1)$^+$. Retention time 2.10 minutes.

Step b: 1-(2,2-Difluorobenzo[d][1,3]dioxol-5-yl)-N-(5-methyl-6-(5-methyl-2-oxo-1,2-dihydropyridin-3-yl)pyridin-2-yl)cyclopropanecarboxamide To 1-(2,2-difluorobenzo[d][1,3]dioxol-5-yl)-N-(2'-methoxy-3,5'-dimethyl-2,3'-bipyridin-6-yl)cyclopropanecarboxamide (49 mg, 0.11 mmol) in 1,4-dioxane (0.5 mL) was added 0.5 mL of an aqueous 4 M hydrochloric acid solution. The reaction mixture was heated at 90° C. for 2 hours before being quenched with triethylamine (0.5 mL). The reaction mixture was diluted with dichloromethane (3 mL) and washed with water (3 mL). The organics were dried over sodium sulfate and evaporated to dryness. The residue was dissolved in N,N-dimethylformamide (1 mL) and purified by reverse-phase preparative liquid chromatography to yield 1-(2,2-difluorobenzo[d][1,3]dioxol-5-yl)-N-(5-methyl-6-(5-methyl-2-oxo-1,2-dihydropyridin-3-yl)pyridin-2-yl)cyclopropane carboxamide as a trifluoroacetic acid salt. ESI-MS m/z calc. 439.4. found 440.3 (M+1)$^+$. Retention time 1.55 minutes.

129

AR. 1-(2,2-Difluorobenzo[d][1,3]dioxol-5-yl)-N-(2'-methoxy-3,6'-dimethyl-2,4'-bipyridin-6-yl)cyclopropanecarboxamide

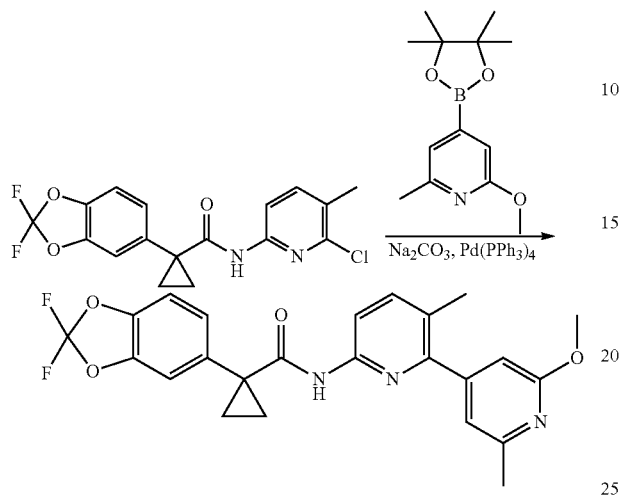

To N-(6-chloro-5-methylpyridin-2-yl)-1-(2,2-difluorobenzo[d][1,3]dioxol-5-yl)cyclopropanecarboxamide (200 mg, 0.54 mmol), 2-methoxy-6-methyl-4-(4,4,5,5-tetramethyl-1,3,2-dioxaborolan-2-yl)pyridine (408 mg, 1.64 mmol) and tetrakis(triphenylphosphine)palladium (0) (64 mg, 0.055 mmol) in 1,2-dimethoxyethane (3.3 mL), 2 M Na$_2$CO$_3$ (818.0 µL, 1.636 mmol) was added. The reaction mixture was stirred and heated at 80° C. for 68 hours under N$_2$ atmosphere. The reaction mixture was diluted with ethyl acetate (5 mL), dried over Na$_2$SO$_4$, filtered and evaporated under reduced pressure. The crude product was purified by column chromatography on silica gel (0-15% ethyl acetate in hexane) to yield 1-(2,2-difluorobenzo[d][1,3]dioxol-5-yl)-N-(2'-methoxy-3,6'-dimethyl-2,4'-bipyridin-6-yl)cyclopropanecarboxamide (0.214 g, 86.5%). ESI-MS m/z calc. 453.4. found 454.5 (M+1)$^+$. Retention time 1.81 minutes.

AS. 1-(2,2-Difluorobenzo[d][1,3]dioxol-5-yl)-N-(5-methyl-6-(6-methyl-2-oxo-1,2-dihydropyridin-4-yl)pyridin-2-yl)cyclopropanecarboxamide

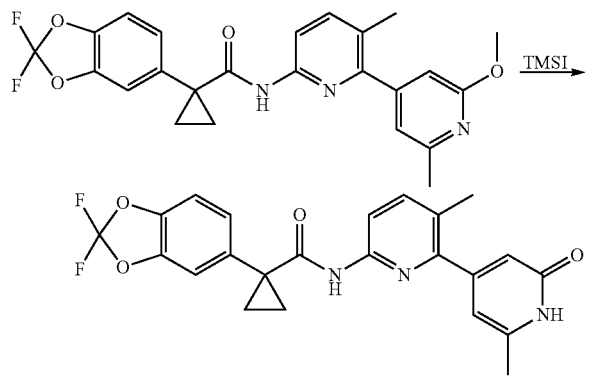

130

To a suspension of 1-(2,2-difluorobenzo[d][1,3]dioxol-5-yl)-N-(2'-methoxy-3,6'-dimethyl-2,4'-bipyridin-6-yl)cyclopropanecarboxamide (12 mg, 26.5 µmol) in CH$_3$CN (0.5 mL) was added TMSI (7.5 µL, 52.9 µmol) drop wise. The reaction was stirred at 55° C. for 1 hour. MeOH (1.0 mL) was added followed by ethyl acetate (3 mL) and water (1 mL). The organic layer was separated and washed with NaHSO$_3$ (2×), and brine (1×). The organic layer was then dried over Na$_2$SO$_4$, filtered and evaporated under reduced pressure to yield 1-(2,2-difluorobenzo[d][1,3]dioxol-5-yl)-N-(5-methyl-6-(6-methyl-2-oxo-1,2-dihydropyridin-4-yl)pyridin-2-yl)cyclopropanecarboxamide as a white solid (9.5 g, 81.7%); ESI-MS m/z calc. 439.4. found 440.5 (M+1)$^+$. Retention time 1.60 minutes.

AT. Methyl 2-(3-cyano-5-(6-(1-(2,2-difluorobenzo[d][1,3]dioxol-5-yl)cyclopropanecarboxamido)-3-methylpyridin-2-yl)-2-oxopyridin-1(2H)-yl)acetate

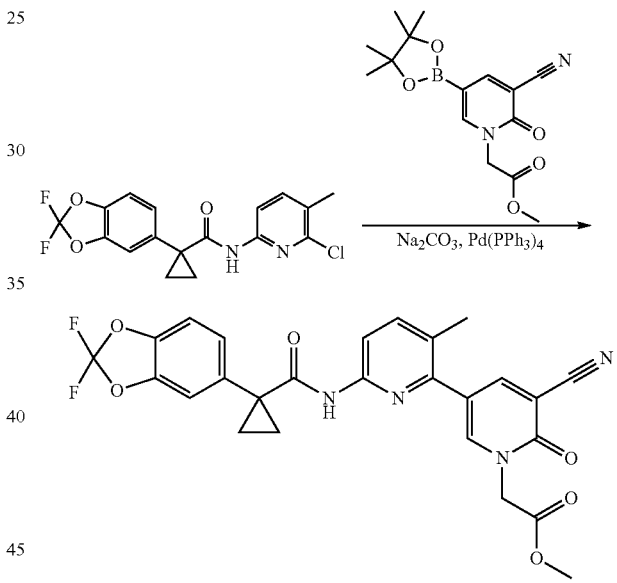

To N-(6-chloro-5-methylpyridin-2-yl)-1-(2,2-difluorobenzo[d][1,3]dioxol-5-yl)cyclopropanecarboxamide (150 mg, 0.41 mmol), methyl 2-(3-cyano-2-oxo-5-(4,4,5,5-tetramethyl-1,3,2-dioxaborolan-2-yl)pyridin-1(2H)-yl)acetate (244 mg, 0.61 mmol) and tetrakis(triphenylphosphine)palladium (0) (47 mg, 0.041 mmol) in 1,2-dimethoxyethane (4.5 mL), 2 M Na$_2$CO$_3$ (613.5 µL, 1.23 mmol) was added. The reaction mixture was stirred and heated at 80° C. for 22 hours under N$_2$ atmosphere. The reaction mixture was diluted with ethyl acetate (5 mL), dried over Na$_2$SO$_4$, filtered and evaporated under reduced pressure. The crude product was purified by column chromatography on silica gel (0-100% ethyl acetate in hexane) to yield methyl 2-(3-cyano-5-(6-(1-(2,2-difluorobenzo[d][1,3]dioxol-5-yl)cyclopropanecarboxamido)-3-methylpyridin-2-yl)-2-oxopyridin-1(2H)-yl)acetate (100 mg, 46.8%). ESI-MS m/z calc. 522.5. found 532.5 (M+1)$^+$. Retention time 1.86 minutes.

AQ. 1-(4-Methoxyphenyl)-N-(5-methyl-6-(2-oxo-1,2-dihydropyridin-4-yl)pyridin-2-yl)cyclopropanecarboxamide

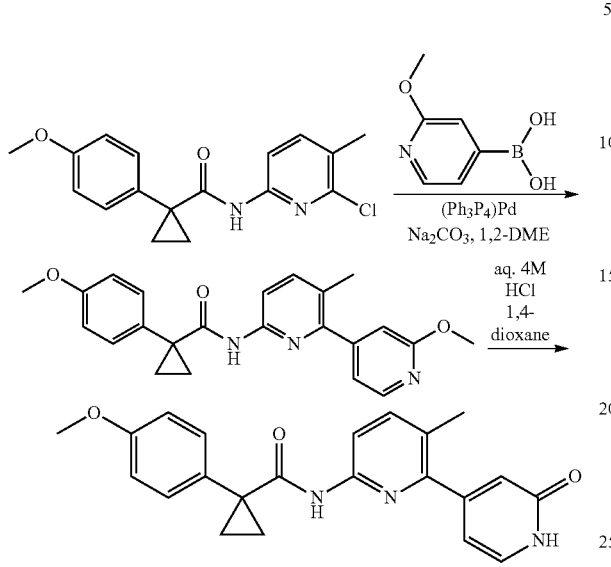

Step a: N-(2'-Methoxy-3-methyl-2,4'-bipyridin-6-yl)-1-(4-methoxyphenyl)-cyclopropanecarboxamide N-(6-Chloro-5-methylpyridin-2-yl)-1-(4-methoxyphenyl) cyclopropane carboxamide (63 mg, 0.20 mmol) was dissolved in 1,2-dimethoxyethane (2.0 mL) in a reaction tube. 2-Methoxypyridin-4-ylboronic acid (46 mg, 0.30 mmol), aqueous 2 M sodium carbonate (0.20 mL), and $(Ph_3P)_4Pd$ (12 mg, 0.010 mmol) were added and the reaction mixture was heated at 80° C. under $N_2$ atmosphere for 18 hours. Since the reaction was incomplete, it was re-treated with same amount of boronic acid, base and Pd catalyst and heated at 80° C. for 18 hours. The resulting material was cooled to room temperature, filtered, and evaporated under reduced pressure. The crude product was dissolved in DMSO (2 mL), filtered, and purified by reverse phase preparative HPLC to yield N-(2'-methoxy-3-methyl-2,4'-bipyridin-6-yl)-1-(4-methoxyphenyl)cyclopropane carboxamide. ESI-MS m/z calc. 389.2. found 390.5 $(M+1)^+$. Retention time 1.84 minutes.

Step b: 1-(4-Methoxyphenyl)-N-(5-methyl-6-(2-oxo-1,2-dihydropyridin-4-yl)pyridin-2-yl)cyclopropanecarboxamide N-(2'-Methoxy-3-methyl-2,4'-bipyridin-6-yl)-1-(4-methoxyphenyl)cyclopropanecarboxamide (TFA salt) (~39 mg, ~0.10 mmol) was dissolved in chloroform (1 mL) in a reaction tube. Trimethylsilyliodide (56 µL, 0.40 mmol was added and the reaction mixture was stirred at room temperature for 4 hours. The resulting material was filtered and evaporated under reduced pressure. The crude product was dissolved in DMSO (1 mL), filtered, and purified by reverse phase preparative HPLC to yield 1-(4-methoxyphenyl)-N-(5-methyl-6-(2-oxo-1,2-dihydropyridin-4-yl)pyridin-2-yl) cyclo-propanecarboxamide. ESI-MS m/z calc. 375.2. found 376.5 $(M+1)^+$. Retention time 1.45 minutes.

AR. 1-(4-Methoxyphenyl)-N-(5-methyl-6-(2-oxo-1,2-dihydropyridin-3-yl)pyridin-2-yl)cyclopropanecarboxamide

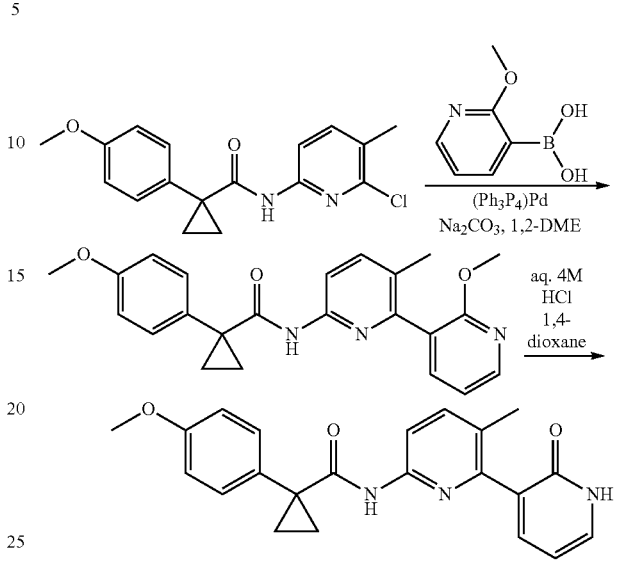

Step a: N-(2'-Methoxy-3-methyl-2,3'-bipyridin-6-yl)-1-(4-methoxyphenyl)cyclopropanecarboxamide N-(6-Chloro-5-methylpyridin-2-yl)-1-(4-methoxyphenyl) cyclopropane carboxamide (63 mg, 0.20 mmol) was dissolved in 1,2-dimethoxyethane (2.0 mL) in a reaction tube. 2-Methoxypyridin-3-ylboronic acid (46 mg, 0.30 mmol), aqueous 2 M sodium carbonate (0.20 mL), and $(Ph_3P)_4Pd$ (12 mg, 0.010 mmol) were added and the reaction mixture was heated at 80° C. under $N_2$ atmosphere for 18 hours. Since the reaction was incomplete, it was re-treated with same amount of boronic acid, base and Pd catalyst and was heated at 80° C. for 18 hours. The resulting material was cooled to room temperature, filtered, and evaporated under reduced pressure. The crude product was dissolved in DMSO (2 mL), filtered and purified by reverse phase preparative HPLC to yield N-(2'-methoxy-3-methyl-2,3'-bipyridin-6-yl)-1-(4-methoxyphenyl)cyclopropane carboxamide. ESI-MS m/z calc. 389.2. found 390.5 $(M+1)^+$. Retention time 1.76 minutes.

Step b: 1-(4-Methoxyphenyl)-N-(5-methyl-6-(2-oxo-1,2-dihydropyridin-3-yl)pyridin-2-yl)cyclopropanecarboxamide N-(2'-Methoxy-3-methyl-2,3'-bipyridin-6-yl)-1-(4-methoxyphenyl)cyclopropane carboxamide (TFA salt) (~39 mg, ~0.10 mmol) was dissolved in 1,4-dioxane (0.6 mL) in a reaction tube. An aqueous 4M HCl (0.27 mL, 1.1 mmol) was added and the reaction mixture was stirred at 90° C. for 1 hour. The resulting material was cooled to room temperature, filtered, and purified by reverse phase preparative HPLC to yield 1-(4-methoxyphenyl)-N-(5-methyl-6-(2-oxo-1,2-dihydropyridin-3-yl)pyridin-2-yl)cyclo-propanecarboxamide. ESI-MS m/z calc. 375.2. found 376.7 $(M+1)^+$. Retention time 1.26 minutes. $^1$H NMR (400 MHz, DMSO-$d_6$) δ 8.14 (s, 1H), 7.94 (d, J=8.4 Hz, 1H), 7.66 (d, J=8.4 Hz, 1H), 7.47-7.42 (m, 3H), 7.38 (dd, J=6.8, 2.1 Hz, 1H), 6.98 (d, J=8.7 Hz, 2H), 6.25 (t, J=6.6 Hz, 1H), 3.77 (s, 3H), 2.08 (s, 3H), 1.52-1.49 (m, 2H), 1.13-1.11 (m, 2H).

133

AM. 1-(Benzo[d][1,3]dioxol-5-yl)-N-(5-methyl-6-(6-oxo-1,6-dihydropyridin-3-yl)pyridin-2-yl)cyclopropanecarboxamide

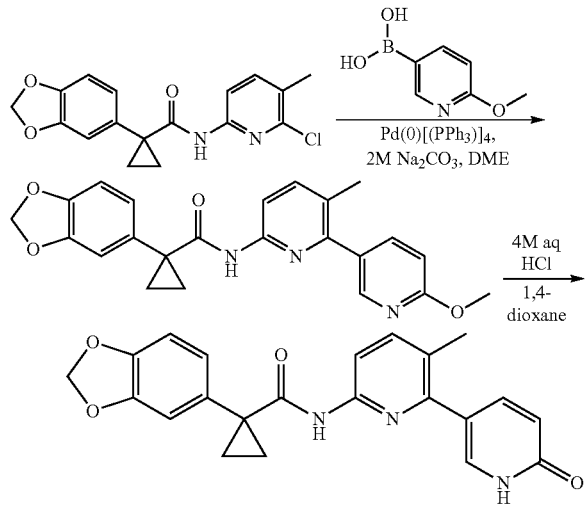

Step a: 1-(Benzo[d][1,3]-dioxol-5-yl)-N-(6'-methoxy-3-methyl-2,3'-bipyridin-6-yl)cyclopropanecarboxamide 1-(Benzo[d][1,3]dioxol-5-yl)-N-(6-chloro-5-methylpyridin-2-yl)cyclopropanecarboxamide (66 mg, 0.20 mmol) was dissolved in 2 mL of 1,2-dimethoxyethane in a reaction tube. 6-Methoxypyridin-3-ylboronic acid (37 mg, 0.24 mmol), 0.2 mL of an aqueous 2 M sodium carbonate solution, and tetrakis(triphenylphosphine)palladium(0) (12 mg, 0.010 mmol) were added and the reaction mixture was heated at 80° C. overnight. The reaction was diluted with ethyl acetate (5 mL) and washed with water (5 mL). The organics were dried over sodium sulfate and evaporated to dryness. The resulting residue was purified by silica gel chromatography eluting with a gradient of 0-100% ethyl acetate in hexane to yield 1-(benzo[d][1,3]dioxol-5-yl)-N-(6'-methoxy-3-methyl-2,3'-bipyridin-6-yl)cyclo-propanecarboxamide (34 mg, 51%). ESI-MS m/z calc. 403.2. found 404.7 (M+1)$^+$. Retention time 1.84 minutes.

Step b: 1-(Benzo[d][1,3]-dioxol-5-yl)-N-(5-methyl-6-(6-oxo-1,6-dihydropyridin-3-yl)pyridin-2-yl)cyclopropanecarboxamide To 1-(benzo[d][1,3]dioxol-5-yl)-N-(6'-methoxy-3-methyl-2,3'-bipyridin-6-yl)cyclopropanecarboxamide (34 mg, 0.080 mmol) in 1,4-dioxane (1 mL) was added 0.5 mL of an aqueous 4 M hydrochloric acid solution. The reaction mixture was heated at 90° C. for 4 hours before being quenched with triethylamine (0.5 mL) and evaporated to dryness. The residue was dissolved in N,N-dimethylformamide (1 mL) and purified by reverse-phase preparative liquid chromatography to yield 1-(benzo[d][1,3]dioxol-5-yl)-N-(5-methyl-6-(6-oxo-1,6-dihydropyridin-3-yl)pyridin-2-yl)cyclopropanecarboxamide as a trifluoroacetic acid salt. ESI-MS m/z calc. 389.1. found 390.3 (M+1)$^+$. Retention time 2.00 minutes.

134

AN. 1-(2,2-Difluorobenzo[d][1,3]dioxol-5-yl)-N-(4-methyl-6-(2-oxo-1,2-dihydropyridin-4-yl)pyridin-2-yl)cyclopropanecarboxamide

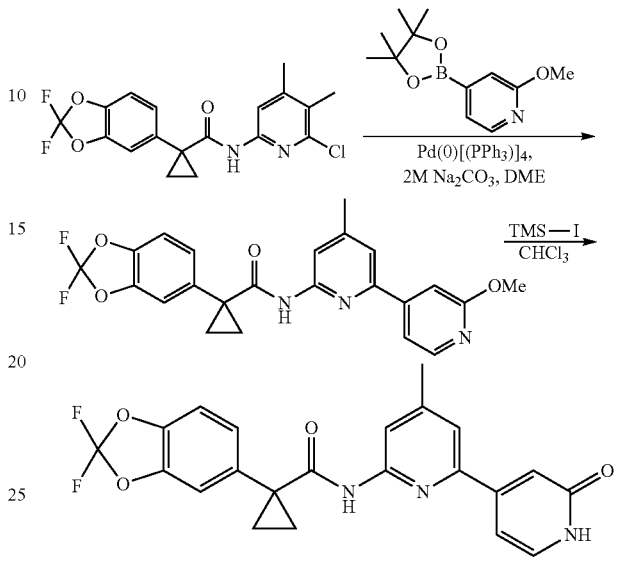

Step a: 1-(2,2-Difluorobenzo[d][1,3]dioxol-5-yl)-N-(2'-methoxy-4-methyl-2,4'-bipyridin-6-yl)cyclopropanecarboxamide N-(6-Chloro-4-methylpyridin-2-yl)-1-(2,2-difluorobenzo[d][1,3]dioxol-5-yl)cyclopropanecarboxamide (73 mg, 0.20 mmol) was dissolved in 2 mL of 1,2-dimethoxyethane in a reaction tube. 2-Methoxy-4-(4,4,5,5-tetramethyl-1,3,2-dioxaborolan-2-yl)pyridine (55 mg, 0.36 mmol), 0.3 mL of an aqueous 2 M sodium carbonate solution, and tetrakis(triphenylphosphine)palladium(0) (18 mg, 0.015 mmol) were added and the reaction mixture was heated at 80° C. overnight. The reaction mixture was diluted with dichloromethane (5 mL) and washed with water (5 mL). The organics were dried over sodium sulfate and evaporated to dryness. The resulting residue was purified by silica gel chromatography eluting with a gradient of 0-100% ethyl acetate in hexane to yield 1-(2,2-difluorobenzo[d][1,3]dioxol-5-yl)-N-(2'-methoxy-4-methyl-2,4'-bipyridin-6-yl)cyclopropanecarboxamide (31 mg, 35%). ESI-MS m/z calc. 439.1. found 440.3 (M+1)$^+$. Retention time 2.12 minutes.

Step b: 1-(2,2-Difluorobenzo[d][1,3]dioxol-5-yl)-N-(4-methyl-6-(2-oxo-1,2-dihydropyridin-4-yl)pyridin-2-yl)cyclopropanecarboxamide To 1-(2,2-difluorobenzo[d][1,3]dioxol-5-yl)-N-(2'-methoxy-4-methyl-2,4'-bipyridin-6-yl)cyclopropanecarboxamide (31 mg, 0.070 mmol) in chloroform (1 mL) was added iodotrimethylsilane (30 μL, 0.21 mmol). The reaction mixture was stirred at room temperature overnight. The reaction mixture was evaporated to dryness and the residue was dissolved in N,N-dimethylformamide (1 mL) and purified by reverse-phase preparative liquid chromatography to yield 1-(2,2-difluorobenzo[d][1,3]dioxol-5-yl)-N-(4-methyl-6-(2-oxo-1,2-dihydropyridin-4-yl)pyridin-2-yl)cyclopropanecarboxamide as the trifluoroacetic acid salt. ESI-MS m/z calc. 425.1. found 426.3 (M+1)⁺. Retention time 1.70 minutes.

AO. 1-(2,2-Difluorobenzo[d][1,3]dioxol-5-yl)-N-(5-methyl-6-(1-methyl-6-oxo-1,6-dihydropyridin-3-yl)pyridin-2-yl)cyclopropanecarboxamide

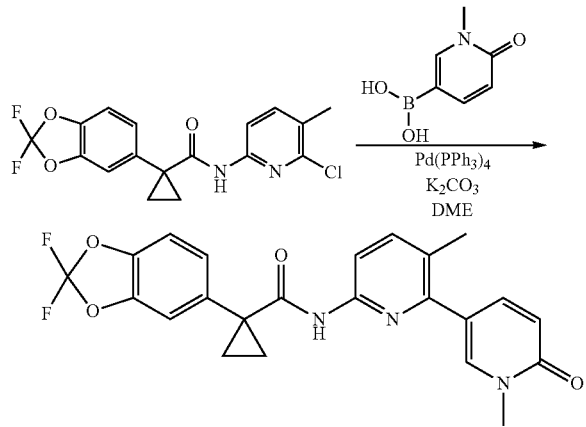

To a mixture of 1-methyl-5-(4,4,5,5-tetramethyl-1,3,2-dioxaborolan-2-yl)pyridin-2(1H)-one (68 mg, 0.30 mmol), N-(6-chloro-5-methylpyridin-2-yl)-1-(2,2-difluorobenzo[d][1,3]dioxol-5-yl)cyclopropanecarboxamide (88 mg, 0.24 mmol) in DME (1.5 mL) and 2 M Na₂CO₃ (0.24 mL) was added Pd(PPh₃)₄ (14 mg, 0.0030 mmol). The mixture was heated in microwave oven at 120° C. for 30 min. The mixture was partitioned between ethyl acetate and H₂O before the aqueous layer was extracted with ethyl acetate (3×). The combined organic layers were washed with brine and dried over MgSO₄. After the removal solvent, the residue was purified by column chromatography (10-20% EtOAc-Hexane) to afford 1-(2,2-difluorobenzo[d][1,3]dioxol-5-yl)-N-(5-methyl-6-(1-methyl-6-oxo-1,6-dihydropyridin-3-yl)pyridin-2-yl)cyclopropanecarboxamide (67 mg, 72%). ¹H-NMR (400 MHz, CDCl₃) δ 8.06 (d, J=8.4 Hz, 1H), 7.63 (s, 1H), 7.57 (d, J=8.4 Hz, 1H), 7.53-7.48 (m, 2H), 7.24 (td, J=10.0, 1.7 Hz, 2H), 7.12 (d, J=8.2 Hz, 1H), 6.61 (d, J=9.2 Hz, 1H), 3.60 (s, 3H), 2.33 (s, 3H), 1.77 (q, J=3.6 Hz, 2H), 1.19 (q, J=3.6 Hz, 2H). MS (ESI) m/e (M+H⁺) 440.2.

AP. 1-(2,2-Difluorobenzo[d][1,3]dioxol-5-yl)-N-(6-(1-(2-hydroxyethyl)-2-oxo-1,2-dihydropyridin-4-yl)-5-methylpyridin-2-yl)cyclopropanecarboxamide

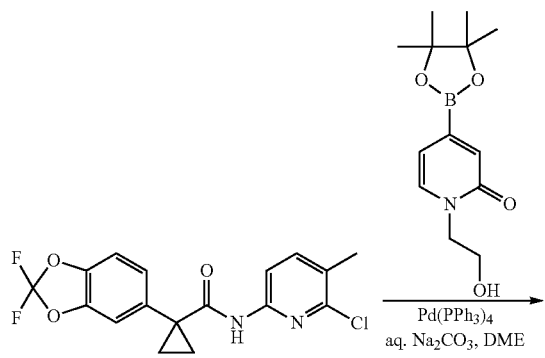

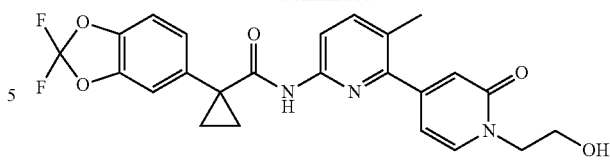

1-(2-Hydroxyethyl)-4-(4,4,5,5-tetramethyl-1,3,2-dioxaborolan-2-yl)pyridin-2(1H)-one (0.14 mmol) was added to a microwave vial containing N-(6-chloro-5-methylpyridin-2-yl)-1-(2,2-difluorobenzo[d][1,3]dioxol-5-yl)cyclopropanecarboxamide (51 mg, 0.14 mmol) and Pd(PPh₃)₄ (8.0 mg, 0.0070 mmol). Saturated aqueous Na₂CO₃ (70 μL) was added and the reaction vial was flushed with N₂ (g) and sealed. The reaction was heated in the microwave at 120° C. for 20 minutes before being filtered and concentrated. The residue was dissolved in DMSO and purified by reverse-phase HPLC to yield 1-(2,2-difluorobenzo[d][1,3]dioxol-5-yl)-N-(6-(1-(2-hydroxyethyl)-2-oxo-1,2-dihydropyridin-4-yl)-5-methylpyridin-2-yl)cyclopropanecarboxamide. ESI-MS m/z calc. 469.1. found 470.5 (M+1)⁺. Retention time 1.58 minutes. ¹H NMR (400 MHz, DMSO-d₆) δ 8.87 (s, 1H), 7.91 (d, J=8.4 Hz, 1H), 7.73 (d, J=8.5 Hz, 1H), 7.63 (d, J=6.9 Hz, 1H), 7.56 (d, J=1.6 Hz, 1H), 7.41 (d, J=8.3 Hz, 1H), 7.34 (dd, J=1.7, 8.3 Hz, 1H), 6.39 (d, J=1.8 Hz, 1H), 6.26 (dd, J=1.9, 6.9 Hz, 1H), 3.96 (t, J=5.4 Hz, 2H), 3.63 (t, J=5.5 Hz, 2H), 2.26 (s, 3H), 1.52-1.50 (m, 2H), 1.19-1.16 (m, 2H).

AQ. 1-(2,3-dihydro-1H-inden-5-yl)-N-(5-methyl-6-(6-oxo-1,6-dihydropyridin-3-yl)pyridin-2-yl)cyclopropanecarboxamide

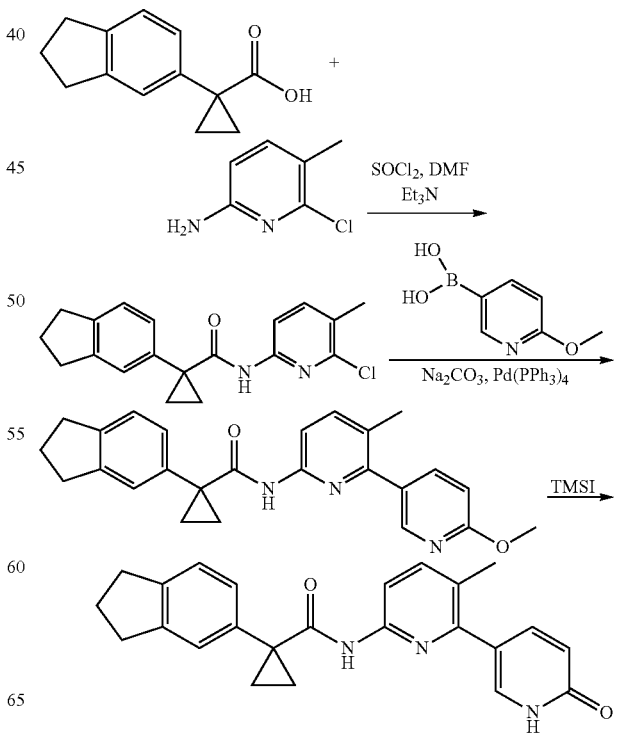

Step a: N-(6-chloro-5-methylpyridin-2-yl)-1-(2,3-dihydro-1H-inden-5-yl)cyclopropanecarboxamide To 1-(2,3-dihydro-1H-inden-5-yl)cyclopropanecarboxylic acid (0.2 g, 0.9889 mmol) in thionyl chloride (215.9 µL, 2.967 mmol) was added N,N-dimethyl formamide (21.79 µL, 0.2826 mmol). The reaction mixture was stirred at room temperature for 30 minutes before excess thionyl chloride and N,N-dimethyl formamide were removed in vacuo to yield the acid chloride. The acid chloride was then dissolved in dichloromethane (3 mL) and added slowly to a solution of 6-chloro-5-methylpyridin-2-amine (0.169 g, 1.187 mmol) and triethylamine (413.5 µL, 2.967 mmol) in dichloromethane (3 mL). The resulting reaction mixture was stirred at room temperature for 17.5 hours. The reaction mixture was diluted with dichloromethane (10 mL) and washed first with 1N aqueous HCl (10 mL) and then with a saturated aqueous NaHCO$_3$ solution (10 mL). The organic layer was dried over Na$_2$SO$_4$, filtered and evaporated under reduced pressure. The crude product was purified by column chromatography on silica gel (0-30% ethyl acetate in hexane) to yield N-(6-chloro-5-methylpyridin-2-yl)-1-(2,3-dihydro-1H-inden-5-yl)cyclopropanecarboxamide (0.135 g, 41.77%). ESI-MS m/z calc. 326.12. found 327.5 (M+1)$^+$. Retention time 2.33 minutes.

Step b: 1-(2,3-Dihydro-1H-inden-5-yl)-N-(6'-methoxy-3-methyl-2,3'-bipyridin-6-yl)cyclopropanecarboxamide To N-(6-chloro-5-methylpyridin-2-yl)-1-(2,3-dihydro-1H-inden-5-yl)cyclopropanecarboxamide (0.132 g, 0.4030 mmol), 6-methoxypyridin-3-ylboronic acid (0.092 g, 0.6045 mmol) and tetrakis(triphenylphosphine)palladium (0) (0.046 g, 0.04030 mmol) in 1,2-dimethoxyethane (4.4 mL), 2 M Na$_2$CO$_3$ (600 µL) was added. The reaction mixture was stirred and heated at 80° C. for 22 hours under N$_2$ atmosphere. The reaction mixture was diluted with ethyl acetate (5 mL), dried over Na$_2$SO$_4$, filtered and evaporated under reduced pressure. The crude product was purified by column chromatography on silica gel (0-30% ethyl acetate in hexane) to yield 1-(2,3-dihydro-1H-inden-5-yl)-N-(6'-methoxy-3-methyl-2,3'-bipyridin-6-yl)cyclopropanecarboxamide as a white solid (0.150 g, 93.17%). ESI-MS m/z calc. 399.48, found 400.5 (M+1)$^+$. Retention time 2.17 minutes.

Step c: 1-(2,3-dihydro-1H-inden-5-yl)-N-(5-methyl-6-(6-oxo-1,6-dihydropyridin-3-yl)pyridin-2-yl)cyclopropanecarboxamide To a suspension of 1-(2,3-dihydro-1H-inden-5-yl)-N-(6'-methoxy-3-methyl-2,3'-bipyridin-6-yl)cyclopropanecarboxamide (0.127 g, 0.3172 mmol) in CH$_3$CN (6.7 mL) was added TMSI (254 mg, 180.5 µL, 1.27 mmol) drop-wise. The suspension became a clear solution upon TMSI addition. The reaction was stirred at 55° C. for 6.5 hours. The reaction was allowed to cool down to room temperature. Methanol (2.0 mL) was added followed by ethyl acetate (6 mL). The organic layer was washed with NaHSO$_3$ (2×), and brine (1×). The organic layer was dried over Na$_2$SO$_4$, filtered and evaporated under reduced pressure. The crude product was purified by column chromatography on silica gel (0-10% methanol in dichloromethane) to yield 1-(2,3-dihydro-1H-inden-5-yl)-N-(5-methyl-6-(6-oxo-1,6-dihydropyridin-3-yl)pyridin-2-yl)cyclopropanecarboxamide as a yellow solid (0.096 g, 78.5%). ESI-MS m/z calc. 385.46. found 386.5 (M+1)$^+$. Retention time 1.58 minutes.

AR. 1-(2,2-Difluorobenzo[d][1,3]dioxol-5-yl)-N-(6-(1-(2-hydroxyethyl)-5-methyl-2-oxo-1,2-dihydropyridin-3-yl)-5-methylpyridin-2-yl)cyclopropanecarboxamide

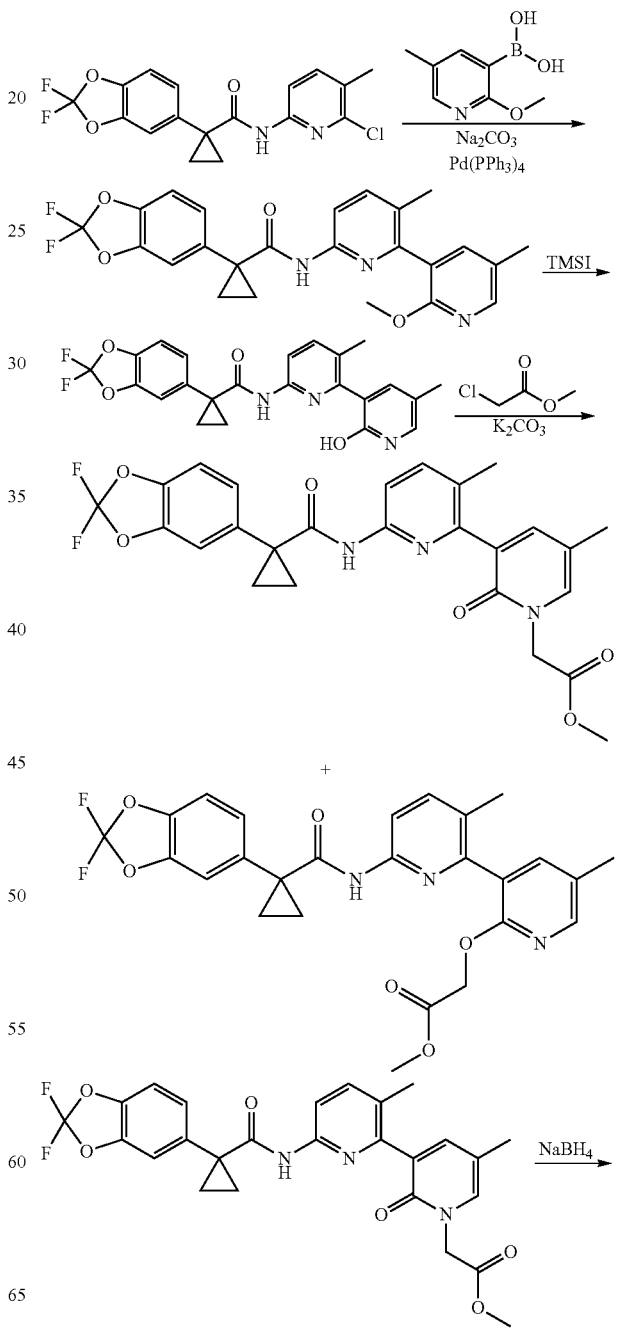

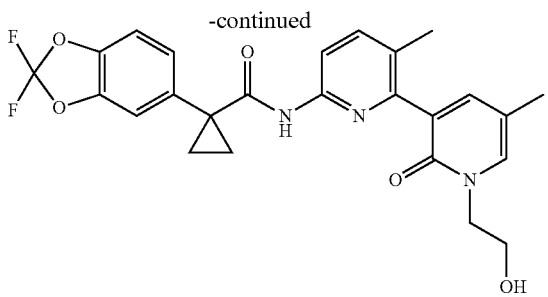

Step a: 1-(2,2-Difluorobenzo[d][1,3]dioxol-5-yl)-N-(2'-methoxy-3,5'-dimethyl-2,3'-bipyridin-6-yl)cyclopropanecarboxamide To a mixture of N-(6-chloro-5-methylpyridin-2-yl)-1-(2,2-difluorobenzo[d][1,3]dioxol-5-yl)cyclopropanecarboxamide (0.550 g, 1.5 mmol) and 6-methoxy-4-methylpyridin-3-ylboronic acid (0.376 g, 2.25 mmol) in DME (10 mL) and Na$_2$CO$_3$ (2 M, 1.5 mL, 3.0 mmol) was added Pd(PPh$_3$)$_4$ (0.087 g, 0.075 mmol). The mixture was heated in microwave oven at 120° C. for 30 minutes. The reaction was partitioned between ethyl acetate and water and the aqueous layer was extracted with ethyl acetate twice. The combined organic layers were washed with brine and dried over MgSO$_4$. After the removal of solvent, the residue was purified by column chromatography (0-20% EtOAc-Hexane) to yield 1-(2,2-difluorobenzo[d][1,3]dioxol-5-yl)-N-(2'-methoxy-3,5'-dimethyl-2,3'-bipyridin-6-yl)cyclopropanecarboxamide (0.554 g, 81%). ESI-MS m/z calc. 453.44. found 454.2 (M+1)$^+$. Retention time 2.08 minutes.

Step b: 1-(2,2-Difluorobenzo[d][1,3]dioxol-5-yl)-N-(2'-hydroxy-3,5'-dimethyl-2,3'-bipyridin-6-yl)cyclopropanecarboxamide To a mixture of 1-(2,2-difluorobenzo[d][1,3]dioxol-5-yl)-N-(2'-methoxy-3,5'-dimethyl-2,3'-bipyridin-6-yl)cyclopropanecarboxamide (0.181 g, 0.05 mmol) in CH$_3$CN (0.5 mL) was added TMSI (114, 0.80 mmol) drop wise at 0° C. The reaction was stirred at 50° C. for 3 hours. The reaction was partitioned between ethyl acetate and H$_2$O and the aqueous layer was extracted with ethyl acetate. The combined organic layers were washed with brine and dried over MgSO$_4$. After the removal of solvent, the residue was purified by column chromatography (0-10% MeOH-EtOAc) to yield a yellow solid. The solid was re-dissolved in DCM-EtOAc, washed with NaHSO$_3$ (2×), brine, dried over MgSO$_4$ and evaporated to dryness to yield 1-(2,2-difluorobenzo[d][1,3]dioxol-5-yl)-N-(2'-hydroxy-3,5'-dimethyl-2,3'-bipyridin-6-yl)cyclopropanecarboxamide as a white solid (0.148 g, 84%). ESI-MS m/z calc. 439.41. found 440.2 (M+1)$^+$. Retention time 1.51 minutes.

Step c: Methyl 2-(3-(6-(1-(2,2-difluorobenzo[d][1,3]dioxol-5-yl)cyclopropanecarboxamido)-3-methylpyridin-2-yl)-5-methyl-2-oxopyridin-1(2H)-yl)acetate To a solution of 1-(2,2-difluorobenzo[d][1,3]dioxol-5-yl)-N-(2'-hydroxy-3,5'-dimethyl-2,3'-bipyridin-6-yl)cyclopropanecarboxamide (0.029 g, 0.06556 mmol) in DMF (1 mL) was added K$_2$CO$_3$ (0.091 mg, 0.6556 mmol) and methyl chloroacetate (28.82 µL, 0.3278 mmol). The reaction was stirred at 80° C. for 21 hours to yield a mixture of N-alkylated product and O-alkylated product. The reaction was filtered using ethyl acetate and the solvent was evaporated under reduced pressure. The crude products were separated by column chromatography on silica gel (0-100% ethyl acetate in hexane) to yield methyl 2-(3-(6-(1-(2,2-difluorobenzo[d][1,3]dioxol-5-yl)cyclopropanecarboxamido)-3-methylpyridin-2-yl)-5-methyl-2-oxopyridin-1(2H)-yl)acetate [20 mg, 59.3%; ESI-MS m/z calc. 511.47. found 512.5 (M+1)$^+$, retention time 1.74 minutes] and methyl 2-(6-(1-(2,2-difluorobenzo[d][1,3]dioxol-5-yl)cyclopropanecarboxamido)-3,5'-dimethyl-2,3'-bipyridin-2'-yloxy)acetate [8 mg, 24%; ESI-MS m/z calc. 511.47. found 512.5 (M+1)$^+$, retention time 2.13 minutes].

Step d: 1-(2,2-Difluorobenzo[d][1,3]dioxol-5-yl)-N-(6-(1-(2-hydroxyethyl)-5-methyl-2-oxo-1,2-dihydropyridin-3-yl)-5-methylpyridin-2-yl)cyclopropanecarboxamide To a solution of methyl 2-(3-(6-(1-(2,2-difluorobenzo[d][1,3]dioxol-5-yl)cyclopropanecarboxamido)-3-methylpyridin-2-yl)-5-methyl-2-oxopyridin-1(2H)-yl)acetate (17 mg, 0.034 mmol) in THF (1.6 mL) was added NaBH$_4$ (7 mg, 0.17 mmol) and stirred at 50° C. for 3 hours and 15 minutes. The reaction was filtered using ethyl acetate and the solvent was evaporated under reduced pressure. The crude product was purified by column chromatography on silica gel (0-100% ethyl acetate in hexane) to yield 1-(2,2-difluorobenzo[d][1,3]dioxol-5-yl)-N-(6-(1-(2-hydroxyethyl)-5-methyl-2-oxo-1,2-dihydropyridin-3-yl)-5-methylpyridin-2-yl)cyclopropanecarboxamide as a white solid (5.5 g, 33.6%). ESI-MS m/z calc. 483.46. found 484.5 (M+1)$^+$, retention time 1.49 minutes.

AS. 1-(2,2-Difluorobenzo[d][1,3]dioxol-5-yl)-N-(2'-methoxy-3,6'-dimethyl-2,4'-bipyridin-6-yl)cyclopropanecarboxamide

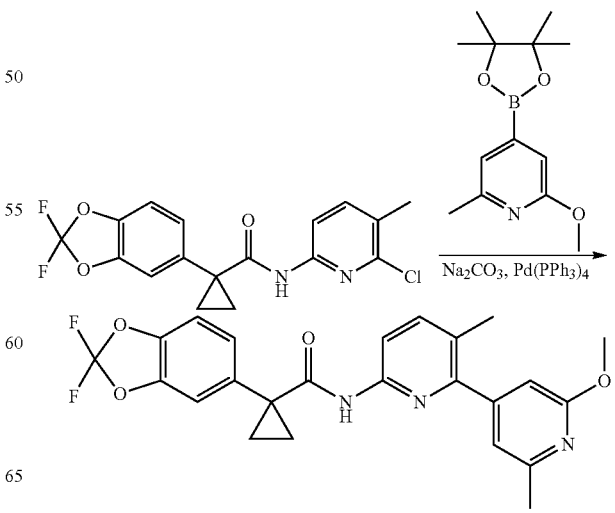

To N-(6-chloro-5-methylpyridin-2-yl)-1-(2,2-difluorobenzo[d][1,3]dioxol-5-yl)cyclopropanecarboxamide (200 mg, 0.545 mmol), 2-methoxy-6-methyl-4-(4,4,5,5-tetramethyl-1,3,2-dioxaborolan-2-yl)pyridine (408 mg, 1.636 mmol) and tetrakis(triphenylphosphine)palladium (0) (64 mg, 0.055 mmol) in 1,2-dimethoxyethane (3.3 mL), 2 M Na$_2$CO$_3$ (818.0 μL, 1.63 mmol) was added. The reaction mixture was stirred and heated at 80° C. for 68 hours under N$_2$ atmosphere. The reaction mixture was diluted with ethyl acetate (5 mL), dried over Na$_2$SO$_4$, filtered and evaporated under reduced pressure. The crude product was purified by column chromatography on silica gel (0-15% ethyl acetate in hexane) to yield 1-(2,2-difluorobenzo[d][1,3]dioxol-5-yl)-N-(2'-methoxy-3,6'-dimethyl-2,4'-bipyridin-6-yl)cyclopropanecarboxamide (214 mg, 86.5%). ESI-MS m/z calc. 453.4. found 454.5 (M+1)$^+$, retention time 1.81 minutes.

AT. 1-(2,2-Difluorobenzo[d][1,3]dioxol-5-yl)-N-(5-methyl-6-(6-methyl-2-oxo-1,2-dihydropyridin-4-yl)pyridin-2-yl)cyclopropanecarboxamide

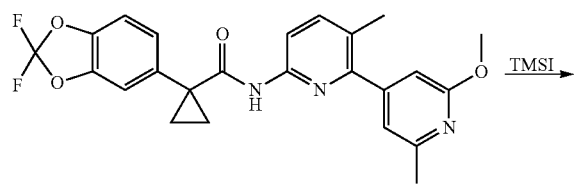

To a suspension of 1-(2,2-difluorobenzo[d][1,3]dioxol-5-yl)-N-(2'-methoxy-3,6'-dimethyl-2,4'-bipyridin-6-yl)cyclopropanecarboxamide (0.012 g, 26.46 μmol) in CH$_3$CN (0.5 mL) was added TMSI (7.5 μL, 52.9 μmol) drop wise. The reaction was stirred at 55° C. for 1 hour. MeOH (1.0 mL) was added followed by ethyl acetate (3 mL) and water (1 mL). The organic layer was separated and washed with NaHSO$_3$ (2×) and brine (1×). The organic layer was then dried over Na$_2$SO$_4$, filtered and evaporated under reduced pressure to yield 1-(2,2-difluorobenzo[d][1,3]dioxol-5-yl)-N-(5-methyl-6-(6-methyl-2-oxo-1,2-dihydropyridin-4-yl)pyridin-2-yl)cyclopropanecarboxamide as a white solid (9.5 mg, 81.7%). ESI-MS m/z calc. 439.4. found 440.5 (M+1)$^+$, retention time 1.60 minutes.

AU. 1-(2,2-Difluorobenzo[d][1,3]dioxol-5-yl)-N-(4-methyl-6-(2-methyl-6-oxo-1,6-dihydropyridin-3-yl)pyridin-2-yl)cyclopropanecarboxamide

Step a: 1-(2,2-Difluorobenzo[d][1,3]dioxol-5-yl)-N-(6'-methoxy-2',4-dimethyl-2,3'-bipyridin-6-yl)cyclopropanecarboxamide To N-(6-chloro-4-methylpyridin-2-yl)-1-(2,2-difluorobenzo[d][1,3]dioxol-5-yl)cyclopropanecarboxamide (88 mg, 0.24 mmol) in 1,2-dimethoxyethane (2.5 mL) was added 6-methoxy-2-methyl-3-(4,4,5,5-tetramethyl-1,3,2-dioxaborolan-2-yl)pyridine (144 mg, 0.29 mmol), tetrakis(triphenylphosphine)palladium (0) (28 mg, 0.024 mmol), and 2 M $Na_2CO_3$ (361.2 μL, 0.72 mmol). The reaction mixture was irradiated in the microwave at 120° C. for 20 minutes. The reaction mixture was evaporated to dryness and purified by silica gel chromatography eluting with (0-20% ethyl acetate in hexane) to yield 1-(2,2-difluorobenzo[d][1,3]dioxol-5-yl)-N-(6'-methoxy-2',4-dimethyl-2,3'-bipyridin-6-yl)cyclopropanecarboxamide (70 mg, 61%). ESI-MS m/z calc. 453.44. found 454.3 $(M+1)^+$. Retention time 1.89 minutes.

Step b: 1-(2,2-Difluorobenzo[d][1,3]dioxol-5-yl)-N-(4-methyl-6-(2-methyl-6-oxo-1,6-dihydropyridin-3-yl)pyridin-2-yl)cyclopropanecarboxamide To 1-(2,2-difluorobenzo[d][1,3]dioxol-5-yl)-N-(6'-methoxy-2',4-dimethyl-2,3'-bipyridin-6-yl)cyclopropanecarboxamide (70 mg, 0.154 mmol) in 1,4-dioxane (1.9 mL) was added aqueous 4 M HCl (417 μL, 1.67 mmol) dropwise. The reaction was stirred at 90° C. for 1.5 hours. The reaction was allowed to cool down to room temperature and then quenched with $Et_3N$. The solvent was evaporated under reduced pressure. The crude compound was dissolved in ethyl acetate and washed with water (2×) and brine (1×). The organic layer was dried over $Na_2SO_4$, filtered and evaporated under reduced pressure. The crude product was purified by column chromatography on silica gel (0-100% ethyl acetate in hexane) to yield 1-(2,2-difluorobenzo[d][1,3]dioxol-5-yl)-N-(4-methyl-6-(2-methyl-6-oxo-1,6-dihydropyridin-3-yl)pyridin-2-yl)cyclopropanecarboxamide as a yellow solid (13 mg, 20%); ESI-MS m/z calc. 439.41. found 440.5 $(M+1)^+$. Retention time 1.58 minutes.

AV. 1-(2,2-Difluorobenzo[d][1,3]dioxol-5-yl)-N-(4-methyl-6-(4-methyl-6-oxo-1,6-dihydropyridin-3-yl)pyridin-2-yl)cyclopropanecarboxamide

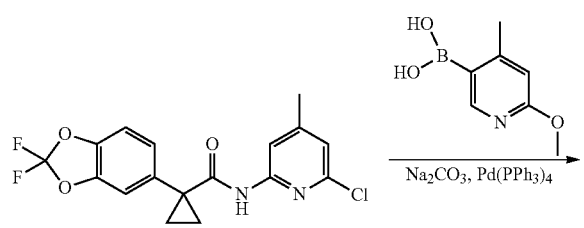

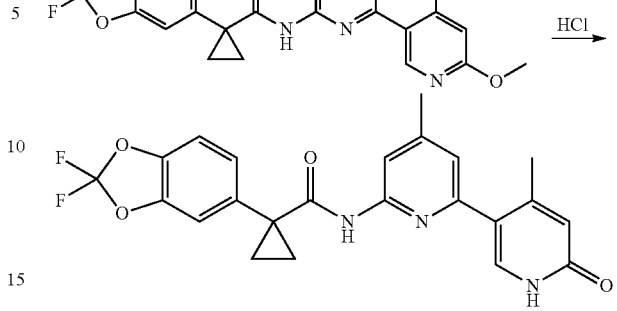

Step a: 1-(2,2-Difluorobenzo[d][1,3]dioxol-5-yl)-N-(6'-methoxy-4,4'-dimethyl-2,3'-bipyridin-6-yl)cyclopropanecarboxamide To N-(6-chloro-4-methylpyridin-2-yl)-1-(2,2-difluorobenzo[d][1,3]dioxol-5-yl)cyclopropanecarboxamide (59 mg, 0.16 mmol), 6-methoxy-4-methylpyridin-3-ylboronic acid (40 mg, 0.24 mmol) and tetrakis(triphenylphosphine) palladium (0) (9 mg, 0.008 mmol) in 1,2-dimethoxyethane (1.63 mL), aqueous saturated $Na_2CO_3$ (163 uL) was added. The reaction mixture was stirred and heated at 80° C. for 18 hours under $N_2$ atmosphere. The reaction mixture was diluted with 1,2-dimethoxyethane, dried over $Na_2SO_4$, filtered and evaporated under reduced pressure. The crude product was purified by column chromatography on silica gel (0-30% ethyl acetate in hexane) to yield 1-(2,2-difluorobenzo[d][1,3]dioxol-5-yl)-N-(6'-methoxy-4,4'-dimethyl-2,3'-bipyridin-6-yl)cyclopropanecarboxamide (38 mg, 52%). ESI-MS m/z calc. 453.44. found 454.5 $(M+1)^+$. Retention time 2.01 minutes.

Step b: 1-(2,2-Difluorobenzo[d][1,3]dioxol-5-yl)-N-(4-methyl-6-(4-methyl-6-oxo-1,6-dihydropyridin-3-yl)pyridin-2-yl)cyclopropanecarboxamide To 1-(2,2-difluorobenzo[d][1,3]dioxol-5-yl)-N-(6'-methoxy-4,4'-dimethyl-2,3'-bipyridin-6-yl)cyclopropanecarboxamide (38 mg, 0.083 mmol) in 1,4-dioxane (1.5 mL) was added aqueous 4 M HCl (225 μL, 0.899 mmol) dropwise. The reaction was stirred at 90° C. for 1.5 hours. The reaction was allowed to cool down to room temperature and then quenched with $Et_3N$. The solvent was evaporated under reduced pressure. The crude compound was dissolved in ethyl acetate and washed with water (2×) and brine (1×). The organic layer was dried over $Na_2SO_4$, filtered and evaporated under reduced pressure. The crude product was purified by column chromatography on silica gel (0-10% methanol in dichloromethans) to yield 1-(2,2-difluorobenzo[d][1,3]dioxol-5-yl)-N-(4-methyl-6-(4-methyl-6-oxo-1,6-dihydropyridin-3-yl)pyridin-2-yl)cyclopropanecarboxamide as a white solid (7 mg, 19%). ESI-MS m/z calc. 439.41. found 440.5 $(M+1)^+$. Retention time 1.60 minutes.

AW. 1-(2,2-Difluorobenzo[d][1,3]dioxol-5-yl)-N-(4-methyl-6-(5-methyl-6-oxo-1,6-dihydropyridin-3-yl)pyridin-2-yl)cyclopropanecarboxamide

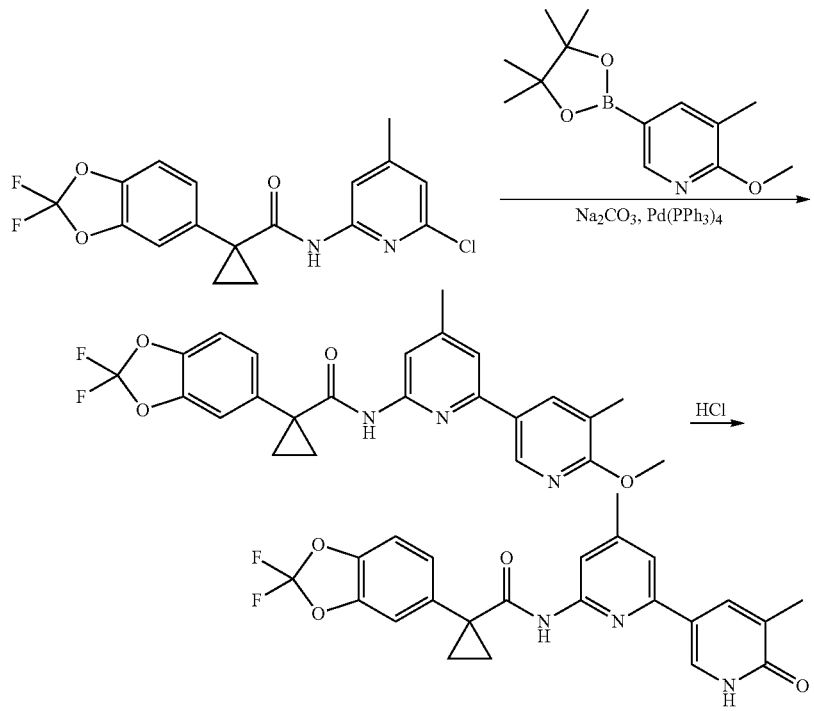

Step a: 1-(2,2-Difluorobenzo[d][1,3]dioxol-5-yl)-N-(6'-methoxy-4,5'-dimethyl-2,3'-bipyridin-6-yl)cyclopropanecarboxamide To N-(6-chloro-4-methylpyridin-2-yl)-1-(2,2-difluorobenzo[d][1,3]dioxol-5-yl)cyclopropanecarboxamide (0.15 g, 0.41 mmol), 2-methoxy-3-methyl-5-(4,4,5,5-tetramethyl-1,3,2-dioxaborolan-2-yl)pyridine (0.15 g, 0.61 mmol) and tetrakis(triphenylphosphine)palladium (0) (0.024 g, 0.02 mmol) in 1,2-dimethoxyethane (2.46 mL), aqueous saturated Na$_2$CO$_3$ (410 uL) was added. The reaction mixture was stirred and heated at 80° C. for 18 hours under N$_2$ atmosphere. The reaction mixture was diluted with 1,2-dimethoxyethane, dried over Na$_2$SO$_4$, filtered and evaporated under reduced pressure. The crude product was purified by column chromatography on silica gel (0-30% ethyl acetate in hexane) to yield 1-(2,2-difluorobenzo[d][1,3]dioxol-5-yl)-N-(6'-methoxy-4,5'-dimethyl-2,3'-bipyridin-6-yl)cyclopropanecarboxamide (0.075 g, 40%). ESI-MS m/z calc. 453.44. found 454.5 (M+1)$^+$. Retention time 2.24 minutes.

Step b: 1-(2,2-Difluorobenzo[d][1,3]dioxol-5-yl)-N-(4-methyl-6-(5-methyl-6-oxo-1,6-dihydropyridin-3-yl)pyridin-2-yl)cyclopropanecarboxamide To 1-(2,2-difluorobenzo[d][1,3]dioxol-5-yl)-N-(6'-methoxy-4,5'-dimethyl-2,3'-bipyridin-6-yl)cyclopropanecarboxamide (0.075 g, 0.165 mmol) in 1,4-dioxane (2 mL) was added aqueous 4 M HCl (447 µL, 1.79 mmol) dropwise. The reaction was stirred at 90° C. for 1.5 hours. The reaction was allowed to cool down to room temperature and then quenched with Et$_3$N. The solvent was evaporated under reduced pressure. The crude compound was dissolved in ethyl acetate and washed with water (2×) and brine (1×). The organic layer was dried over Na$_2$SO$_4$, filtered and evaporated under reduced pressure. The crude product was purified by column chromatography on silica gel (0-100% ethyl acetate in hexane) to yield 1-(2,2-difluorobenzo[d][1,3]dioxol-5-yl)-N-(4-methyl-6-(5-methyl-6-oxo-1,6-dihydropyridin-3-yl)pyridin-2-yl)cyclopropanecarboxamide as a white solid (33 mg, 46%); ESI-MS m/z calc. 439.41. found 440.5 (M+1)$^+$. Retention time 1.72 minutes.

AX. 1-(2,2-Difluorobenzo[d][1,3]dioxol-5-yl)-N-(6'-methoxy-2',3,4-trimethyl-2,3'-bipyridin-6-yl)cyclopropanecarboxamide

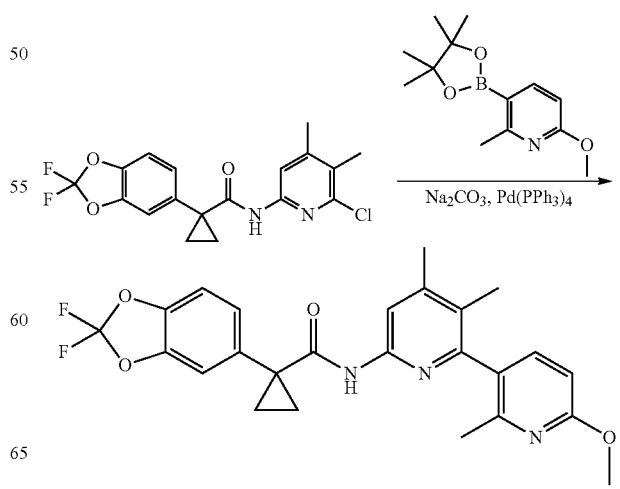

To N-(6-chloro-4,5-dimethylpyridin-2-yl)-1-(2,2-difluorobenzo[d][1,3]dioxol-5-yl)cyclopropanecarboxamide (70 mg, 0.18 mmol), 6-methoxy-2-methyl-3-(4,4,5,5-tetramethyl-1,3,2-dioxaborolan-2-yl)pyridine (69 mg, 0.27 mmol) and tetrakis(triphenylphosphine)-palladium (0) (21 mg, 0.018 mmol) in 1,2-dimethoxyethane (2.0 mL), 2 M Na$_2$CO$_3$ (276 µL, 0.55 mmol) was added. The reaction mixture was stirred and heated at 80° C. for 20 hours under N$_2$ atmosphere. The reaction mixture was diluted with ethyl acetate (5 mL), dried over Na$_2$SO$_4$, filtered and evaporated under reduced pressure. The crude product was purified by column chromatography on silica gel (0-30% ethyl acetate in hexane) to yield 1-(2,2-difluorobenzo[d][1,3]dioxol-5-yl)-N-(6'-methoxy-2',3,4-trimethyl-2,3'-bipyridin-6-yl)cyclopropanecarboxamide (45 mg, 52%). ESI-MS m/z calc. 467.5. found 468.3 (M+1)$^+$. Retention time 1.80 minutes.

AY. 1-(2,2-Difluorobenzo[d][1,3]dioxol-5-yl)-N-(4,5-dimethyl-6-(2-methyl-6-oxo-1,6-dihydropyridin-3-yl)pyridin-2-yl)cyclopropanecarboxamide

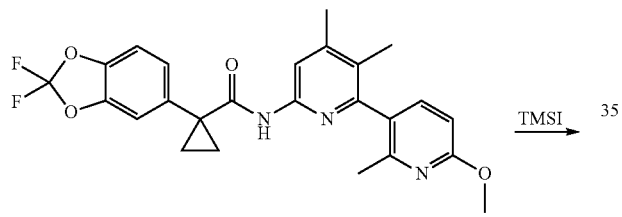

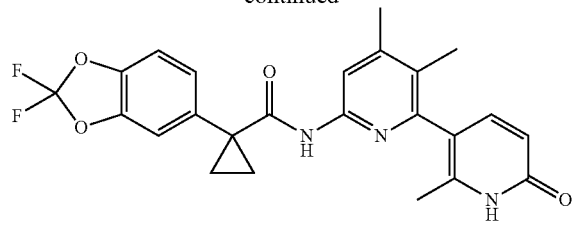

To a suspension of 1-(2,2-difluorobenzo[d][1,3]dioxol-5-yl)-N-(6'-methoxy-2',3,4-trimethyl-2,3'-bipyridin-6-yl)cyclopropanecarboxamide (41.6 mg, 0.09 mmol) in CH$_3$CN (1.8 mL) was added TMSI (25.3 µL, 0.18 mmol) drop wise. The suspension became clear solution on TMSI addition. The reaction was stirred at 55° C. for 2 hours and 30 minutes. The reaction was allowed to cool down to room temperature. Methanol (1.0 mL) was added followed by ethyl acetate (6 mL). The organic layer was washed with NaHSO$_3$ (2×), and brine (1×). The organic layer was dried over Na$_2$SO$_4$, filtered and evaporated under reduced pressure. The crude product was purified by column chromatography on silica gel (0-10% methanol in dichloromethane) to yield 1-(2,2-difluorobenzo[d][1,3]dioxol-5-yl)-N-(4,5-dimethyl-6-(2-methyl-6-oxo-1,6-dihydropyridin-3-yl)pyridin-2-yl)cyclopropanecarboxamide as a white solid (30 mg, 74%). ESI-MS m/z calc. 453.4. found 454.3 (M+1)$^+$. Retention time 1.50 minutes.

AZ. 1-(2,2-Difluorobenzo[d][1,3]dioxol-5-yl)-N-(6'-methoxy-3,4,5'-trimethyl-2,3'-bipyridin-6-yl)cyclopropanecarboxamide

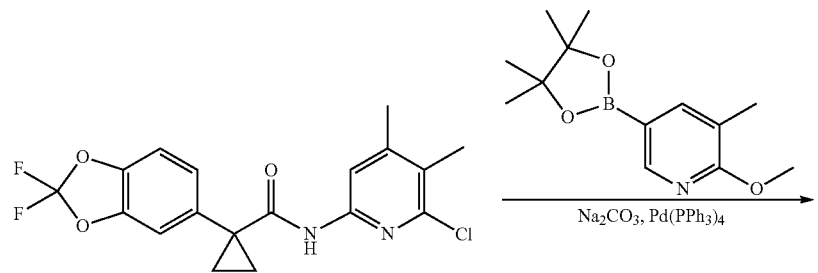

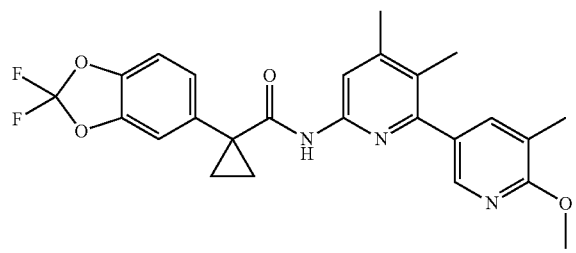

To N-(6-chloro-4,5-dimethylpyridin-2-yl)-1-(2,2-difluorobenzo[d][1,3]dioxol-5-yl)cyclopropanecarboxamide (70 mg, 0.18 mmol), 2-methoxy-3-methyl-5-(4,4,5,5-tetramethyl-1,3,2-dioxaborolan-2-yl)pyridine (69 mg, 0.27 mmol) and tetrakis(triphenylphosphine)palladium (0) (21 mg, 0.018 mmol) in 1,2-dimethoxyethane (2.0 mL), 2 M $Na_2CO_3$ (276 μL, 0.55 mmol) was added. The reaction mixture was stirred and heated at 80° C. for 20 hours under $N_2$ atmosphere. The reaction mixture was diluted with ethyl acetate (5 mL), dried over $Na_2SO_4$, filtered and evaporated under reduced pressure. The crude product was purified by column chromatography on silica gel (0-30% ethyl acetate in hexane) to yield 1-(2,2-difluorobenzo[d][1,3]dioxol-5-yl)-N-(6'-methoxy-3,4,5'-trimethyl-2,3'-bipyridin-6-yl)cyclopropanecarboxamide (50 mg, 58%). ESI-MS m/z calc. 467.4. found 468.7 (M+1)$^+$. Retention time 1.96 minutes.

BA. 1-(2,2-Difluorobenzo[d][1,3]dioxol-5-yl)-N-(4,5-dimethyl-6-(5-methyl-6-oxo-1,6-dihydropyridin-3-yl)pyridin-2-yl)cyclopropanecarboxamide

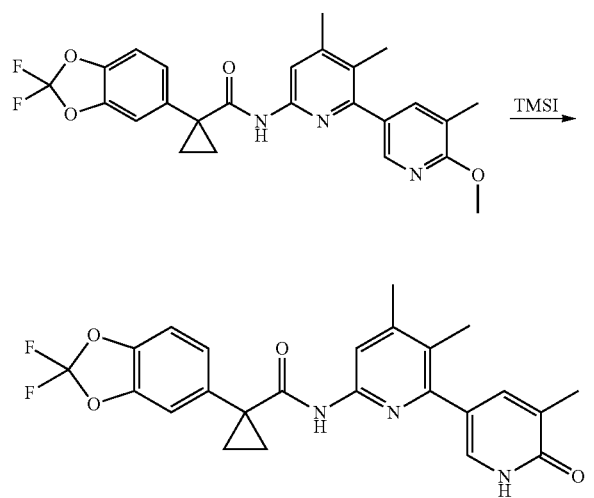

To a suspension of 1-(2,2-difluorobenzo[d][1,3]dioxol-5-yl)-N-(6'-methoxy-3,4,5'-trimethyl-2,3'-bipyridin-6-yl)cyclopropanecarboxamide (44 mg, 0.09 mmol) in $CH_3CN$ (2.0 mL) was added TMSI (27 μL, 0.19 mmol) drop wise. The reaction was stirred at 55° C. for 2 hours and 30 minutes. The reaction was allowed to cool down to room temperature. Methanol (1.0 mL) was added followed by ethyl acetate (6 mL). The organic layer was washed with $NaHSO_3$ (2×), and brine (1×). The organic layer was dried over $Na_2SO_4$, filtered and evaporated under reduced pressure. The crude product was purified by column chromatography on silica gel (0-10% methanol in dichloromethane) to yield 1-(2,2-difluorobenzo[d][1,3]dioxol-5-yl)-N-(4,5-dimethyl-6-(5-methyl-6-oxo-1,6-dihydropyridin-3-yl)pyridin-2-yl)cyclopropanecarboxamide as a white solid (37 mg, 86%). ESI-MS m/z calc. 453.4. found 454.5 (M+1)$^+$. Retention time 1.58 minutes.

BB. 1-(2,3-Dihydrobenzofuran-5-yl)-N-(2'-methoxy-3,4-dimethyl-2,3'-bipyridin-6-yl)cyclopropanecarboxamide

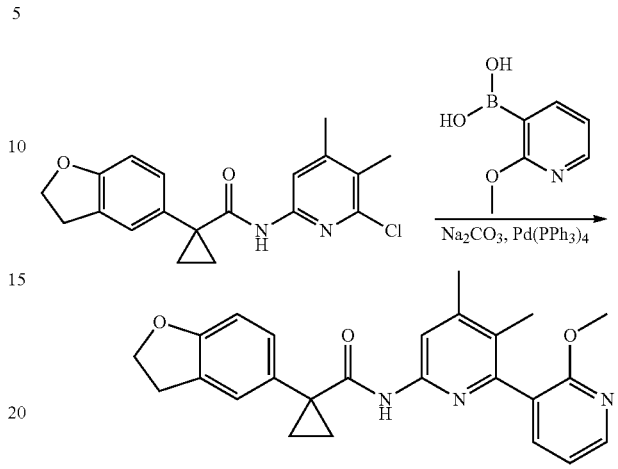

To N-(6-chloro-4,5-dimethylpyridin-2-yl)-1-(2,3-dihydrobenzofuran-5-yl)cyclopropanecarboxamide (100 mg, 0.29 mmol), 2-methoxypyridin-3-ylboronic acid (67 mg, 0.44 mmol) and tetrakis(triphenylphosphine)palladium (0) (34 mg, 0.029 mmol) in 1,2-dimethoxyethane (3.0 mL), 2 M $Na_2CO_3$ (438 μL, 0.88 mmol) was added. The reaction mixture was stirred and heated at 80° C. for 68 hours under $N_2$ atmosphere. The reaction mixture was diluted with ethyl acetate (5 mL), dried over $Na_2SO_4$, filtered and evaporated under reduced pressure. The crude product was purified by column chromatography on silica gel (0-30% ethyl acetate in hexane) to yield 1-(2,3-dihydrobenzofuran-5-yl)-N-(2'-methoxy-3,4-dimethyl-2,3'-bipyridin-6-yl)cyclopropanecarboxamide as a pale yellow solid (112 mg, 92.4%). ESI-MS m/z calc. 415.5. found 416.5 (M+1)$^+$. Retention time 1.68 minutes.

BC. 1-(2,3-Dihydrobenzofuran-5-yl)-N-(4,5-dimethyl-6-(2-oxo-1,2-dihydropyridin-3-yl)pyridin-2-yl)cyclopropanecarboxamide

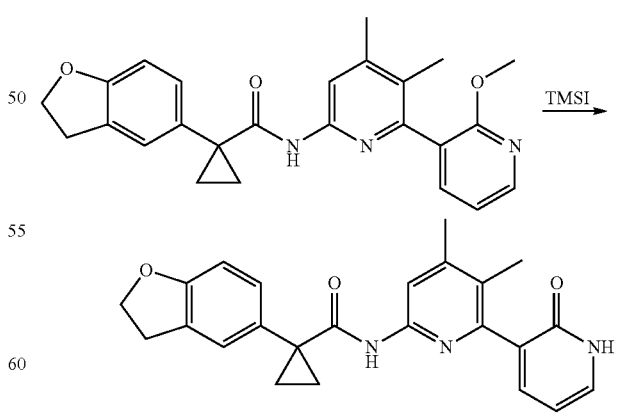

To a suspension of 1-(2,3-dihydrobenzofuran-5-yl)-N-(2'-methoxy-3,4-dimethyl-2,3'-bipyridin-6-yl)cyclopropanecarboxamide (105 mg, 0.25 mmol) in $CH_3CN$ (5.0 mL) was added TMSI (71.7 μL, 0.50 mmol) drop wise. The reaction was stirred at 55° C. for 1 hour. Methanol (1.0 mL) was added followed by ethyl acetate (6 mL). The organic layer was washed with NaHSO₃ (2×), and brine (1×). The organic layer was dried over Na₂SO₄, filtered and evaporated under reduced pressure. The crude product was purified by column chromatography on silica gel (0-10% methanol in dichloromethane) to yield 1-(2,3-dihydrobenzofuran-5-yl)-N-(4,5-dimethyl-6-(2-oxo-1,2-dihydropyridin-3-yl)pyridin-2-yl)cyclopropanecarboxamide as a white solid (82 mg, 81%). ESI-MS m/z calc. 401.5. found 402.5 (M+1)⁺. Retention time 1.18 minutes.

BD. 1-(2,3-Dihydrobenzofuran-5-yl)-N-(6'-methoxy-3,4-dimethyl-2,3'-bipyridin-6-yl)cyclopropanecarboxamide

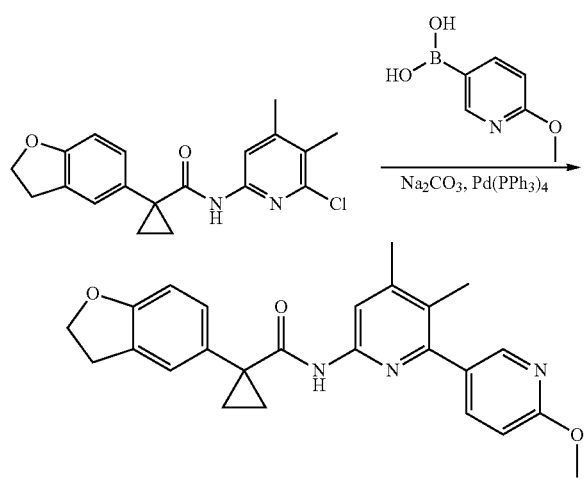 [SMILES: Cc1cc(NC(=O)C2(c3ccc4c(c3)CCO4)CC2)nc(Cl)c1C ; COc1ccc(B(O)O)cn1 ; COc1ccc(-c2nc(NC(=O)C3(c4ccc5c(c4)CCO5)CC3)cc(C)c2C)cn1]

To N-(6-chloro-4,5-dimethylpyridin-2-yl)-1-(2,3-dihydrobenzofuran-5-yl)cyclopropanecarboxamide (100 mg, 0.29 mmol), 6-methoxypyridin-3-ylboronic acid (67 mg, 0.44 mmol) and tetrakis(triphenylphosphine)palladium (0) (34 mg, 0.029 mmol) in 1,2-dimethoxyethane (3.0 mL), 2 M Na₂CO₃ (438 µL, 0.87 mmol) was added. The reaction mixture was stirred and heated at 80° C. for 15 hours under N₂ atmosphere. The reaction mixture was diluted with ethyl acetate (5 mL), dried over Na₂SO₄, filtered and evaporated under reduced pressure. The crude product was purified by column chromatography on silica gel (0-30% ethyl acetate in hexane) to yield 1-(2,3-dihydrobenzofuran-5-yl)-N-(6'-methoxy-3,4-dimethyl-2,3'-bipyridin-6-yl)cyclopropanecarboxamide as a white solid (105 mg, 86.6%). ESI-MS m/z calc. 415.5. found 416.5 (M+1)⁺. Retention time 1.66 minutes.

BE. 1-(2,3-Dihydrobenzofuran-5-yl)-N-(4,5-dimethyl-6-(6-oxo-1,6-dihydropyridin-3-yl)pyridin-2-yl)cyclopropanecarboxamide

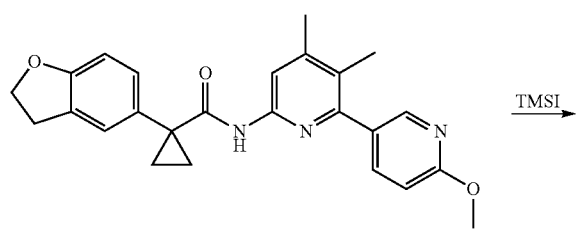

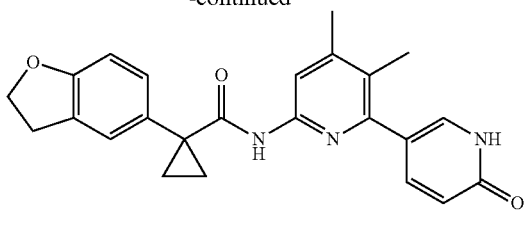

To a suspension of 1-(2,3-dihydrobenzofuran-5-yl)-N-(6'-methoxy-3,4-dimethyl-2,3'-bipyridin-6-yl)cyclopropanecarboxamide (100 mg, 0.24 mmol) in CH₃CN (4.75 mL) was added TMSI (68.4 µL, 0.48 mmol) drop wise. The reaction was stirred at 55° C. After 65 minutes, mainly starting material and some product observed. Two more equivalents of TMSI were added and the heating at 55° C. was continued for 3 hours 20 minutes. The reaction was allowed to cool down to room temperature. Methanol (1.0 mL) was added followed by ethyl acetate (6 mL). The organic layer was washed with NaHSO₃ (2×: until the yellow colour disappeared), and brine (1×). The organic layer was dried over Na₂SO₄, filtered and evaporated under reduced pressure. The crude product was purified by column chromatography on silica gel (0-10% methanol in dichloromethane) to yield 1-(2,3-dihydrobenzofuran-5-yl)-N-(4,5-dimethyl-6-(6-oxo-1,6-dihydropyridin-3-yl)pyridin-2-yl)cyclopropanecarboxamide as a white solid (60 mg, 62%). ESI-MS m/z calc. 401.5. found 402.3 (M+1)⁺. Retention time 1.33 minutes.

BF. 1-(2,3-Dihydrobenzofuran-5-yl)-N-(2'-methoxy-3,4-dimethyl-2,4'-bipyridin-6-yl)cyclopropanecarboxamide

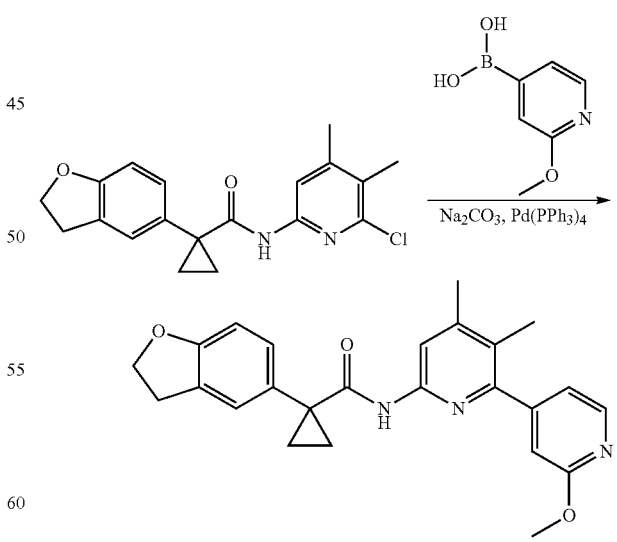

To N-(6-chloro-4,5-dimethylpyridin-2-yl)-1-(2,3-dihydrobenzofuran-5-yl)cyclopropanecarboxamide (100 mg, 0.29 mmol), 2-methoxypyridin-4-ylboronic acid (67 mg, 0.44 mmol) and tetrakis(triphenylphosphine)palladium (0) (34 mg, 0.029 mmol) in 1,2-dimethoxyethane (3.0 mL), 2 M Na₂CO₃ (438 μL, 0.87 mmol) was added. The reaction mixture was stirred and heated at 80° C. for 16 hours under N₂ atmosphere. Product and starting material were observed. 0.5 Equivalents of 2-methoxypyridin-4-ylboronic acid and 0.05 equivalents of tetrakis(triphenylphosphine)palladium (0) were added and continued heating for 40 hours. The reaction mixture was diluted with ethyl acetate (5 mL), dried over Na₂SO₄, filtered and evaporated under reduced pressure. The crude product was purified by column chromatography on silica gel (0-30% ethyl acetate in hexane) to yield 1-(2,3-dihydrobenzofuran-5-yl)-N-(2'-methoxy-3,4-dimethyl-2,4'-bipyridin-6-yl)cyclopropanecarboxamide as a yellow solid (107 mg, 88%). ESI-MS m/z calc. 415.5. found 416.7 (M+1)⁺. Retention time 1.74 minutes.

BG. 1-(2,3-Dihydrobenzofuran-5-yl)-N-(4,5-dimethyl-6-(2-oxo-1,2-dihydropyridin-4-yl)pyridin-2-yl)cyclopropanecarboxamide

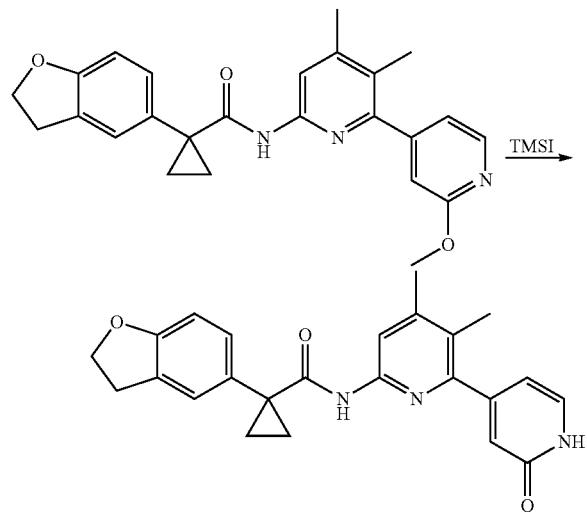

To a suspension of 1-(2,3-dihydrobenzofuran-5-yl)-N-(2'-methoxy-3,4-dimethyl-2,4'-bipyridin-6-yl)cyclopropanecarboxamide (96 mg, 0.23 mmol) in CH₃CN (4.8 mL) was added TMSI (65.6 μL, 0.46 mmol) drop wise. The suspension became a clear solution on TMSI addition. The reaction was stirred at 55° C. for 5 hours. The reaction was allowed to cool down to room temperature. Methanol (1.0 mL) was added followed by ethyl acetate (6 mL). The organic layer was washed with NaHSO₃ (2×), and brine (1×). The organic layer was dried over Na₂SO₄, filtered and evaporated under reduced pressure. The crude product was purified by column chromatography on silica gel (0-10% methanol in dichloromethane) to yield 1-(2,3-dihydrobenzofuran-5-yl)-N-(4,5-dimethyl-6-(2-oxo-1,2-dihydropyridin-4-yl)pyridin-2-yl)cyclopropanecarboxamide as a white solid (50 mg, 54%). ESI-MS m/z calc. 401.5. found 402.5 (M+1)⁺. Retention time 1.41 minutes.

BH. 1-(2,2-difluorobenzo[d][1,3]dioxol-5-yl)-N-(2'-methoxy-4,5'-dimethyl-2,3'-bipyridin-6-yl)cyclopropanecarboxamide

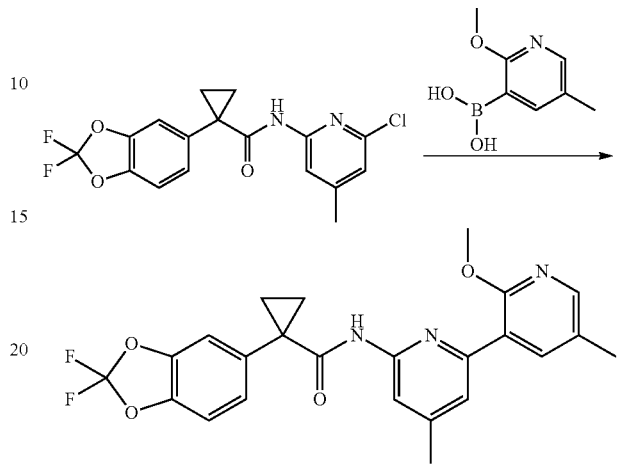

To a mixture of N-(6-chloro-4-methylpyridin-2-yl)-1-(2,2-difluorobenzo[d][1,3]dioxol-5-yl)cyclopropanecarboxamide (60 mg, 0.16 mmol) and 2-methoxy-5-methylpyridin-3-ylboronic acid (41 mg, 0.25 mmol) in DME (2 mL) and Na₂CO₃ (2M, 0.165 mL, 0.32 mmol) was added Pd(PPh₃)₄ (9.5 mg, 0.008 mmol). The mixture was heated in microwave oven at 120° C. for 30 min. The reaction was re-partitioned between EtOAc and H₂O and the aqueous layer was extracted with ethyl acetate twice. The combined organic layers were washed with brine and dried over MgSO₄. After the removal of solvent, the residue was purified by column chromatography (0-20% EtOAc-Hexane) to yield 1-(2,2-difluorobenzo[d][1,3]dioxol-5-yl)-N-(2'-methoxy-4,5'-dimethyl-2,3'-bipyridin-6-yl)cyclopropanecarboxamide (72 mg, 97%). ¹H NMR (400 MHz, CDCl3) 7.98 (s, 1H), 7.96 (dd, J=0.7, 2.4 Hz, 1H), 7.77 (d, J=2.3 Hz, 1H), 7.68 (s, 1H), 7.48 (d, J=9.0 Hz, 1H), 7.23 (dd, J=1.7, 9.4 Hz, 2H), 7.10 (d, J=8.2 Hz, 1H), 3.96 (s, 3H), 2.40 (s, 3H), 2.26 (s, 3H), 1.77-1.70 (m, 2H), 1.19-1.11 (m, 2H). Retention time: 2.01 min; ESI-MS m/z calc. 453.4. found 454.2 (M+H)⁺.

BI. 1-(2,2-Difluorobenzo[d][1,3]dioxol-5-yl)-N-(2'-hydroxy-4,5'-dimethyl-2,3'-bipyridin-6-yl)cyclopropanecarboxamide

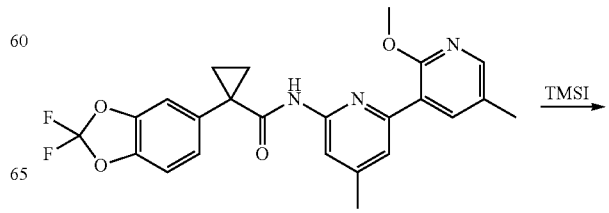

-continued

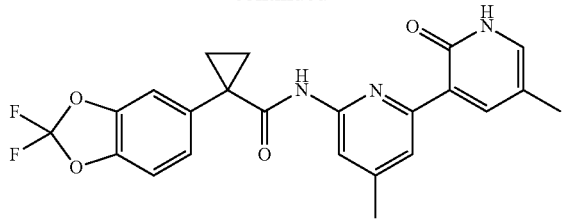

To a suspension of 1-(2,2-difluorobenzo[d][1,3]dioxol-5-yl)-N-(2'-methoxy-4,5'-dimethyl-2,3'-bipyridin-6-yl)cyclopropanecarboxamide (70 mg, 0.15 mmol) in CH₃CN (3 mL) was added TMSI (44 uL, 0.30 mmol) dropwise at 20° C. The reaction was stirred at 50° C. for 30 min. MeOH (1.0 mL) was added and the solution was re-partitioned between EtOAc and H₂O, washed with NaHSO₃ (2×), brine, dried over MgSO₄ and evaporated to dryness to yield a white solid. The crude material was further purified by column chromatography (0-10% MeOH-EtOAc) to yield 1-(2,2-difluorobenzo[d][1,3]dioxol-5-yl)-N-(2'-hydroxy-4,5'-dimethyl-2,3'-bipyridin-6-yl)cyclopropanecarboxamide (62 mg, 91%). H NMR (400 MHz, MeOD) 7.81 (s, 2H), 7.65 (s, 1H), 7.31 (d, J=1.5 Hz, 1H), 7.25 (dd, J=1.7, 8.3 Hz, 1H), 7.17-7.14 (m, 2H), 2.29 (s, 3H), 2.03 (s, 3H), 1.57 (dd, J=4.0, 7.0 Hz, 2H), 1.15 (dd, J=4.0, 7.0 Hz, 2H). Retention time: 1.42 min; ESI-MS m/z calc. 439.4. found 440.5 (M+H)⁺.

BG. 1-(2,2-Difluorobenzo[d][1,3]dioxol-5-yl)-N-(2'-methoxy-3,4,5'-trimethyl-2,3'-bipyridin-6-yl)cyclopropanecarboxamide

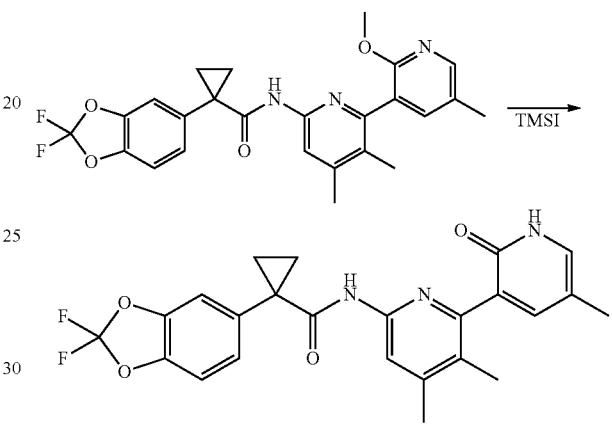

To a mixture of N-(6-chloro-4,5-dimethylpyridin-2-yl)-1-(2,2-difluorobenzo[d][1,3]dioxol-5-yl)cyclopropanecarboxamide (114 mg, 0.3 mmol) and 2-methoxy-5-methylpyridin-3-ylboronic acid (75 mg, 0.45 mmol) in DME (3 mL) and Na₂CO₃ (2M, 0.3 mL, 0.6 mmol) was added Pd(PPh₃)₄ (17 mg, 0.015 mmol). The mixture was heated in microwave oven at 120° C. for 30 min. The reaction was re-partitioned between EtOAc and H₂O and the aqueous layer was extracted with EtOAc twice. The combined organic layers were washed with brine and dried over MgSO₄. After the removal of solvent, the residue was purified by column chromatography (0-20% EtOAc-Hexane) to yield 1-(2,2-difluorobenzo[d][1,3]dioxol-5-yl)-N-(2'-methoxy-3,4,5'-trimethyl-2,3'-bipyridin-6-yl)cyclopropanecarboxamide (80 mg, 57%). 1H NMR (400 MHz, CDCl3) 8.02 (s, 1H), 7.99 (d, J=1.6 Hz, 1H), 7.59 (s, 1H), 7.31 (d, J=2.1 Hz, 1H), 7.20-7.16 (m, 2H), 7.04 (d, J=8.1 Hz, 1H), 3.85 (s, 3H), 2.33 (s, 3H), 2.26 (s, 3H), 1.95 (s, 3H), 1.73 (dd, J=3.8, 6.9 Hz, 2H), 1.14 (dd, J=3.9, 7.0 Hz, 2H). Retention time: 2.02 min; ESI-MS m/z calc. 467.5. found 468.2 (M+H)⁺.

BK. 1-(2,2-Difluorobenzo[d][1,3]dioxol-5-yl)-N-(2'-hydroxy-3,4,5'-trimethyl-2,3'-bipyridin-6-yl)cyclopropanecarboxamide

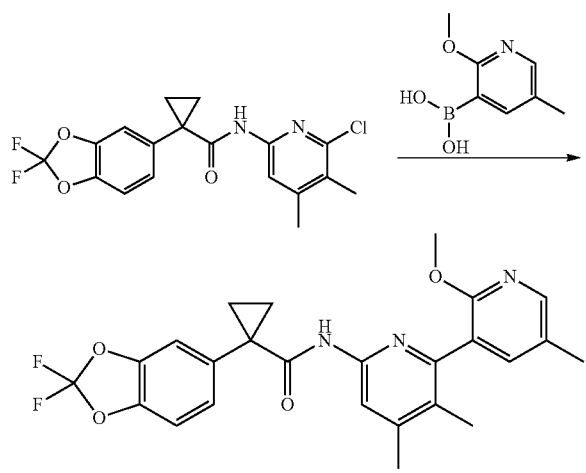

To a suspension of 1-(2,2-difluorobenzo[d][1,3]dioxol-5-yl)-N-(2'-methoxy-3,4,5'-trimethyl-2,3'-bipyridin-6-yl)cyclopropanecarboxamide (75 mg, 0.16 mmol) in CH₃CN (3 mL) was added TMSI (46 uL, 0.30 mmol) dropwise at 20° C. The reaction was stirred at 50° C. for 30 min) MeOH (1.0 mL) was added and the solution was re-partitioned between EtOAc and H₂O, washed with NaHSO₃ (2×), brine, dried over MgSO₄ and evaporated to dryness to yield a white solid. The crude material was further purified by column chromatography (0-10% MeOH-EtOAc) to yield 1-(2,2-difluorobenzo[d][1,3]dioxol-5-yl)-N-(2'-hydroxy-3,4,5'-trimethyl-2,3'-bipyridin-6-yl)cyclopropanecarboxamide (67 mg, 92%). 1H NMR (400 MHz, MeOD) 7.89 (s, 1H), 7.31-7.27 (m, 2H), 7.23-7.19 (m, 2H), 7.12 (d, J=8.3 Hz, 1H), 2.25 (s, 3H), 2.03 (s, 3H), 1.97 (s, 3H), 1.56 (dd, J=3.9, 7.0 Hz, 2H), 1.13 (dd, J=3.8, 6.9 Hz, 2H). Retention time: 1.52 min; ESI-MS m/z calc. 453.4. found 454.5 (M+H)+.

BL. 1-(2,2-Difluorobenzo[d][1,3]dioxol-5-yl)-N-(6'-methoxy-3,4,4'-trimethyl-2,3'-bipyridin-6-yl)cyclopropanecarboxamide

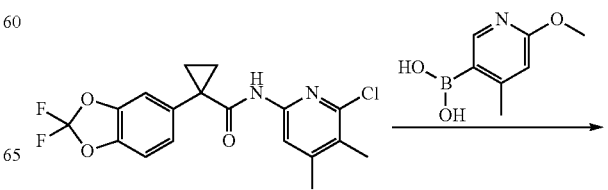

-continued

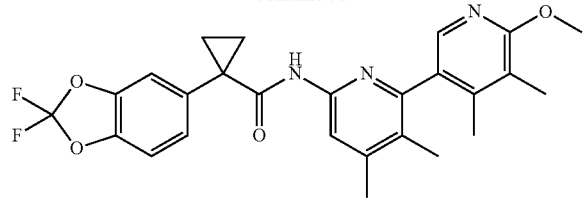

To a mixture of N-(6-chloro-4,5-dimethylpyridin-2-yl)-1-(2,2-difluorobenzo[d][1,3]dioxol-5-yl)cyclopropanecarboxamide (25 mg, 0.067 mmol) and 2-methoxy-4-methylpyridin-5-ylboronic acid (21 mg, 0.1 mmol) in DME (0.7 mL) and Na₂CO₃ (2M, 0.065 mL, 0.13 mmol) was added Pd(PPh₃)₄ (4 mg, 0.003 mmol). The mixture was heated in microwave oven at 120° C. for 30 min. The reaction was re-partitioned between EtOAc and H₂O and the aqueous layer was extracted with EtOAc twice. The combined organic layers were washed with brine and dried over MgSO₄. After the removal of solvent, the residue was purified by column chromatography (0-20% EtOAc-Hexane) to yield 1-(2,2-difluorobenzo[d][1,3]dioxol-5-yl)-N-(6'-methoxy-3,4,4'-trimethyl-2,3'-bipyridin-6-yl)cyclopropanecarboxamide (20 mg, 65%). 1H NMR (400 MHz, CDCl3) 8.05 (s, 1H), 7.86 (s, 1H), 7.59 (d, J=1.5 Hz, 1H), 7.21-7.16 (m, 2H), 7.04 (d, J=8.2 Hz, 1H), 6.62 (s, 1H), 3.92 (s, 3H), 2.34 (s, 3H), 2.00 (s, 3H), 1.96 (s, 3H), 1.74 (dd, J=3.9, 6.9 Hz, 2H), 1.15 (dd, J=3.9, 7.0 Hz, 2H). Retention time: 2.00 min; ESI-MS m/z calc. 467.5. found 468.2 (M+H)⁺.

BM. 1-(2,2-Difluorobenzo[d][1,3]dioxol-5-yl)-N-(6'-hydroxy-3,4,4'-trimethyl-2,3'-bipyridin-6-yl)cyclopropanecarboxamide

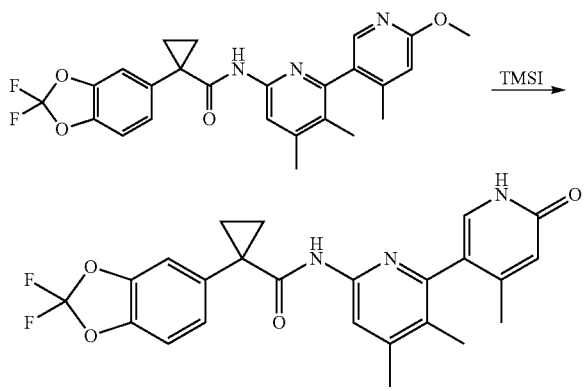

To a suspension of 1-(2,2-difluorobenzo[d][1,3]dioxol-5-yl)-N-(6'-methoxy-3,4,4'-trimethyl-2,3'-bipyridin-6-yl)cyclopropanecarboxamide (17 mg, 0.036 mmol) in CH₃CN (0.7 mL) was added TMSI (10 uL, 0.072 mmol) dropwise at 20° C. The reaction was stirred at 50° C. for 30 min. Additional TMSI (10 uL, 0.072 mmol) was added and the reaction was heated at 50° C. for 2 h. Additional TMSI (10 uL, 0.072 mmol) was added and the reaction was heated at 70° C. for 2 h. MeOH (1.0 mL) was added and the solution was re-partitioned between EtOAc and H₂O. The organic layer was washed with NaHSO₃ (2×), brine, dried over MgSO₄ and evaporated to dryness to yield a white solid that was further purified by preparative TLC (10% MeOH-EtOAc) to yield 1-(2,2-difluorobenzo[d][1,3]dioxol-5-yl)-N-(6'-hydroxy-3,4,4'-trimethyl-2,3'-bipyridin-6-yl)cyclopropanecarboxamide (8 mg, 49%). 1H NMR (400 MHz, MeOD) 7.92 (s, 1H), 7.28 (d, J=1.6 Hz, 1H), 7.22 (dd, J=1.7, 8.3 Hz, 1H), 7.14-7.10 (m, 2H), 6.36 (s, 1H), 2.27 (s, 3H), 1.95 (s, 3H), 1.81 (d, J=0.6 Hz, 3H), 1.56 (dd, J=3.9, 7.0 Hz, 2H), 1.14 (dd, J=3.9, 7.0 Hz, 2H). Retention time: 1.49 min; ESI-MS m/z calc. 453.4. found 454.2 (M+H)⁺.

BN. 1-(Benzo[d][1,3]dioxol-5-yl)-N-(2'-methoxy-2,3'-bipyridin-6-yl)cyclopropanecarboxamide

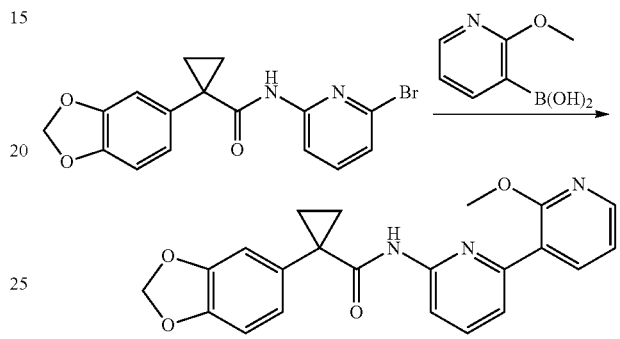

1-(Benzo[d][1,3]dioxol-5-yl)-N-(6-bromopyridin-2-yl)cyclopropanecarboxamide (36 mg, 0.10 mmol) was dissolved in 1 mL of ethanol containing 0.12 mL of a 2 M aqueous solution of potassium carbonate, 2-methoxypyridin-3-ylboronic acid (18 mg, 0.12 mmol) and 6 mg of Fibre-Cat 1007. The reaction mixture was then heated to 110° C. for 10 minutes in a microwave reactor. The resulting material was cooled to room temperature, filtered, and purified by reverse-phase preparative liquid chromatography utilizing a gradient of 0-99% acetonitrile in water containing 0.05% trifluoroacetic acid to yield the pure product. ESI-MS m/z calc. 389.1. found 390.1 (M+1)⁺. Retention time 3.09 minutes.

BO. 1-(Benzo[d][1,3]dioxol-5-yl)-N-(6'-methoxy-2,3'-bipyridin-6-yl)cyclopropanecarboxamide

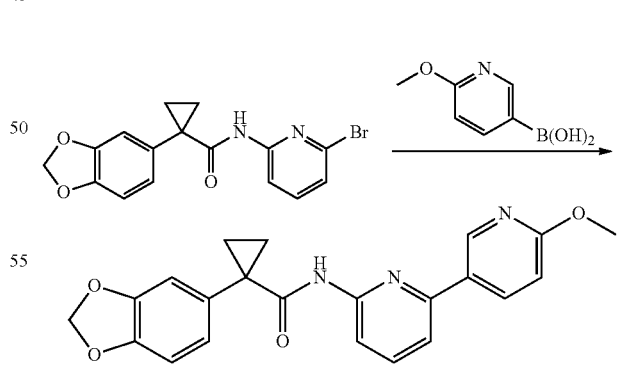

1-(Benzo[d][1,3]dioxol-5-yl)-N-(6-bromopyridin-2-yl)cyclopropanecarboxamide (36 mg, 0.10 mmol) and 6-methoxypyridin-3-ylboronic acid (19 mg, 0.12 mmol) were dissolved in 1 mL of N,N-dimethylformamide (DMF) containing 0.2 mL of a 2M aqueous solution of potassium carbonate potassium carbonate and dichloro[1,1'-bis(diphenylphosphino)ferrocene]palladium (II) dichloromethane adduct (Pd(dppf)Cl$_2$, 7.1 mg, 0.010 mmol). The resulting solution was stirred and heated to 80° C. for 16 hours. The resulting material was cooled to room temperature, filtered, and purified by reverse-phase preparative liquid chromatography utilizing a gradient of 0-99% acetonitrile in water containing 0.05% trifluoroacetic acid to yield the pure product. ESI-MS m/z calc. 389.1. found 390.1 (M+1)$^+$. Retention time 3.57 minutes.

BP. 1-(2,2-Difluorobenzo[d][1,3]-dioxol-5-yl)-N-(5-methyl-6-(1-(2-(methylsulfonyl)ethyl)-6-oxo-1,6-dihydropyridin-3-yl)pyridin-2-yl)cyclopropanecarboxamide

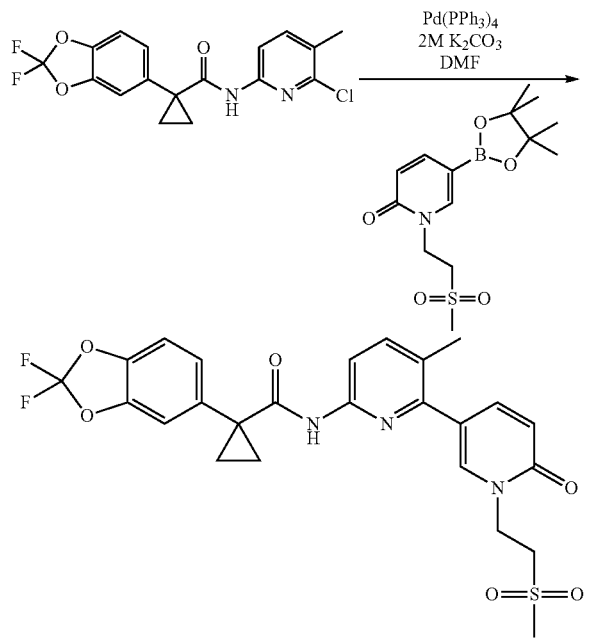

N-(6-Chloro-5-methylpyridin-2-yl)-1-(2,2-difluorobenzo[d][1,3]dioxol-5-yl)cyclopropanecarboxamide (325 mg, 0.886 mmol), tetrakis(triphenylphosphine)palladium (0) (51.20 mg, 0.044 mmol), potassium carbonate (1.1 mL of 2 M, 2.21 mmol), and 1-(2-(methylsulfonyl)ethyl)-5-(4,4,5,5-tetramethyl-1,3,2-dioxaborolan-2-yl)pyridin-2(1H)-one (377 mg, 1.15 mmol) were combined in a scintillation vial containing 1,2-dimethoxyethane (8 mL). The reaction mixture was then stirred and heated to 80 degrees C. for 16 hours. The reaction was then allowed to cool to room temperature. The layers were then separated and the organic layer was evaporated to dryness, re-dissolved in 1 mL of N,N-dimethylformamide, and purified by reverse-phase preparative liquid chromatography utilizing a gradient of 0-99% acetonitrile (containing 0.035% trifluoroacetic acid (v/v)) in water (containing 0.05% trifluoroacetic acid (v/v)) to yield the product. The resulting trifluoroacetic acid salt was then dissolved in a minimum of dichloromethane (5 mL). This solution was then washed two times with a saturated aqueous solution of sodium bicarbonate, followed by two washes of a saturated aqueous solution of sodium chloride, followed by two washes of water. The organic layer was dried over sodium sulfate and then evaporated to dryness. The product was then further purified on 4 g of silica utilizing a gradient of 0-10% methanol in dichloromethane to yield the pure product (16.7 mg, 3.5%). ESI-MS m/z calc. 531.1. found 532.1 (M+1)$^+$. Retention time 1.52 minutes. $^1$H NMR (400 MHz, CD$_3$CN) δ 7.94 (d, J=8.4 Hz, 1H), 7.77 (s, 1H), 7.65 (d, J=2.3 Hz, 1H), 7.62-7.55 (m, 2H), 7.36-7.32 (m, 2H), 7.22 (d, J=8.2 Hz, 1H), 6.42 (d, J=9.4 Hz, 1H), 4.29 (t, J=6.7 Hz, 2H), 3.49 (t, J=6.7 Hz, 2H), 2.90 (s, 3H), 2.32 (s, 3H), 1.62-1.58 (m, 2H), 1.19-1.15 (m, 2H).

BQ. N-(6-(1-(cyanomethyl)-6-oxo-1,6-dihydropyridin-3-yl)-5-methylpyridin-2-yl)-1-(2,2-difluorobenzo[d][1,3]dioxol-5-yl)cyclopropanecarboxamide

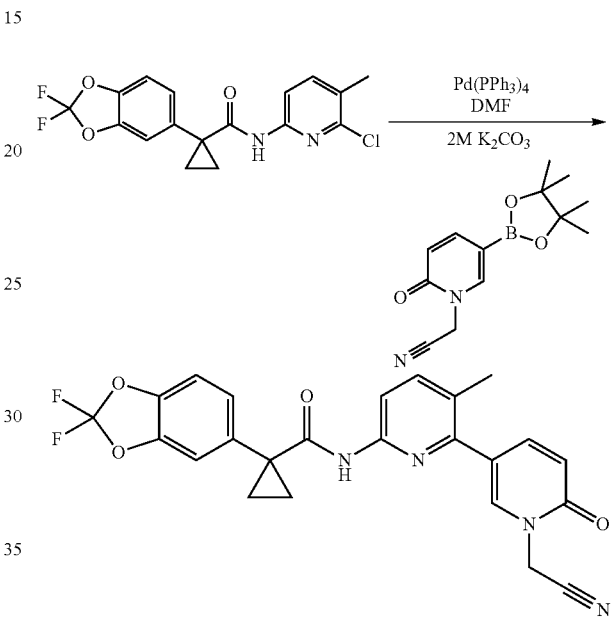

N-(6-chloro-5-methylpyridin-2-yl)-1-(2,2-difluorobenzo[d][1,3]dioxol-5-yl)cyclopropanecarboxamide (325.2 mg, 0.89 mmol), 2-(2-oxo-5-(4,4,5,5-tetramethyl-1,3,2-dioxaborolan-2-yl)pyridin-1(2H)-yl)acetonitrile (0.300 g, 1.15 mmol), tetrakis(triphenylphosphine)palladium (0) (51 mg, 0.044 mmol) and potassium carbonate (1.71 g, 1.11 mL of 2 M, 2.21 mmol) were combined in a scintillation vial containing 1,2-dimethoxyethane (8 mL). The reaction mixture was then stirred and heated to 80° C. overnight. The crude reaction mixture was purified by reverse-phase preparative liquid chromatography to yield the product (25.3 mg, 6.1%) as a trifluoracetic acid salt. ESI-MS m/z calc. 464.1. found 465.1 (M+1)$^+$. Retention time 2.00 minutes.

BR. N-(5-Cyano-4-methyl-6-(6-oxo-1,6-dihydropyridin-3-yl)pyridin-2-yl)-1-(2,2-difluorobenzo[d][1,3]dioxol-5-yl)cyclopropanecarboxamide

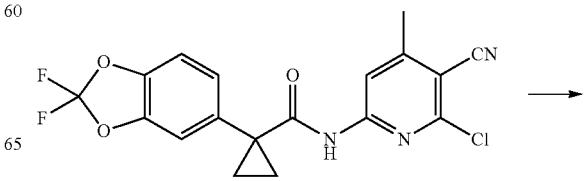

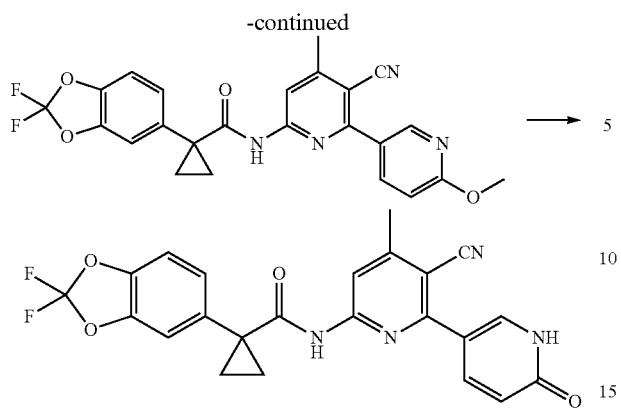

Step a: N-(3-Cyano-6'-methoxy-4-methyl-2,3'-bipyridin-6-yl)-1-(2,2-difluorobenzo[d][1,3]dioxol-5-yl)cyclopropanecarboxamide N-(6-chloro-5-cyano-4-methylpyridin-2-yl)-1-(2,2-difluorobenzo[d][1,3]dioxol-5-yl)cyclopropanecarboxamide (369 mg, 0.94 mmol), potassium carbonate (1.45 g, 942.0 μL of 2 M, 1.88 mmol), tetrakis(triphenylphosphine)palladium (0) (54 mg, 0.047 mmol), 1,2-dimethoxyethane (9 mL), and 2-methoxypyridine-5-boronic acid (230.5 mg, 1.51 mmol) were combined in a 40 mL scintillation vial. The reaction mixture was heated to 80° C. for 6 hours. The reaction mixture was allowed to cool to room temperature, the layers were separated, and the crude material was purified on 40 g of silica gel utilizing a gradient of 0-80% ethyl acetate in hexanes to yield the pure product (0.437 g, 71%). ESI-MS m/z calc. 464.1. found 465.1 (M+1)+. Retention time 2.08 minutes.

Step b: N-(5-Cyano-4-methyl-6-(6-oxo-1,6-dihydropyridin-3-yl)pyridin-2-yl)-1-(2,2-difluorobenzo[d][1,3]dioxol-5-yl)cyclopropanecarboxamide N-(3-cyano-6'-methoxy-4-methyl-2,3'-bipyridin-6-yl)-1-(2,2-difluorobenzo[d][1,3]dioxol-5-yl)cyclopropanecarboxamide (0.150 g, 0.323 mmol) was dissolved in acetonitrile (7.2 mL). Iodotrimethylsilane (129.3 mg, 92 μL, 0.65 mmol) was added and the reaction mixture was heated to 55° C. for 5 hours. The crude reaction mixture was then evaporated to dryness, re-dissolved in a minimum of dichloromethane and purified on 12 g of silica gel utilizing a gradient of 0-100% ethyl acetate in hexanes (0.125 g, 86%). ESI-MS m/z calc. 450.1. found 451.1 (M+1)+. Retention time 1.60 minutes. $^1$H NMR (400 MHz, CDCl$_3$) 8.17 (s, 1H), 8.07-8.03 (m, 2H), 7.82 (s, 1H), 7.26 (dd, J=1.7, 8.2 Hz, 1H), 7.19-7.16 (m, 2H), 6.69 (d, J=10.4 Hz, 1H), 2.58 (s, 3H), 1.80-1.75 (m, 2H), 1.27-1.22 (m, 2H).

BS. 1-(2,3-Dihydrobenzofuran-5-yl)-N-(4-methyl-6-(2-oxo-1,2-dihydropyridin-3-yl)pyridin-2-yl)cyclopropanecarboxamide

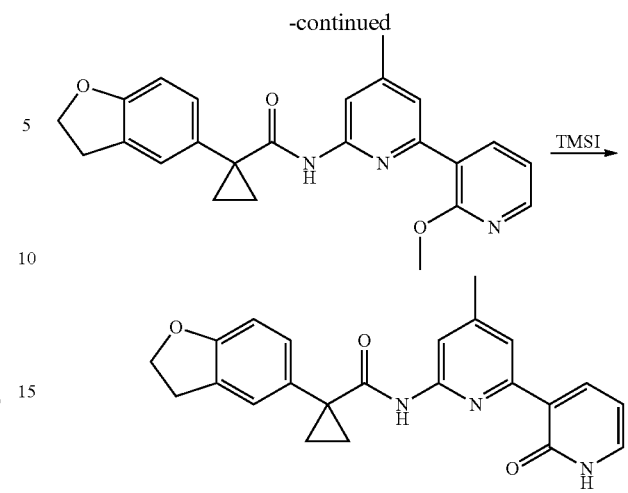

Step a: 1-(2,3-Dihydrobenzofuran-5-yl)-N-(2'-methoxy-4-methyl-2,3'-bipyridin-6-yl)cyclopropanecarboxamide To N-(6-chloro-4-methylpyridin-2-yl)-1-(2,3-dihydrobenzofuran-5-yl)cyclopropanecarboxamide (150 mg, 0.46 mmol) in 1,2-dimethoxyethane (4 mL) was added 2-methoxypyridin-3-ylboronic acid (84 mg, 0.55 mmol), tetrakis(triphenylphosphine)palladium (0) (53 mg, 0.046 mmol), and 2 M Na$_2$CO$_3$ (680 μL, 1.4 mmol). The reaction mixture was irradiated in the microwave at 120° C. for 20 minutes. The reaction mixture was evaporated to dryness and the residue was purified by silica gel chromatography eluting with (0-20% ethyl acetate/hexanes) to yield 1-(2,3-dihydrobenzofuran-5-yl)-N-(2'-methoxy-4-methyl-2,3'-bipyridin-6-yl)cyclopropanecarboxamide (69 mg, 38%).

Step b: 1-(2,3-Dihydrobenzofuran-5-yl)-N-(4-methyl-6-(2-oxo-1,2-dihydropyridin-3-yl)pyridin-2-yl)cyclopropanecarboxamide To a suspension of 1-(2,3-dihydrobenzofuran-5-yl)-N-(2'-methoxy-4-methyl-2,3'-bipyridin-6-yl)cyclopropanecarboxamide (69 mg, 0.17 mmol) in CH$_3$CN (2.5 mL) was added TMSI (49 uL, 0.34 mmol) dropwise at 20° C. The reaction was stirred at 50° C. for 30 min. MeOH (1.0 mL) was added and the solution was evaporated to dryness. The residue was re-dissolved in DCM-EtOAc (1:3) before it was washed with NaHSO$_3$ (2×) and brine. The organics were dried over MgSO$_4$ and evaporated to dryness. The crude material was purified by column chromatography (0-10% MeOH-EtOAc) to yield 1-(2,3-dihydrobenzofuran-5-yl)-N-(4-methyl-6-(2-oxo-1,2-dihydropyridin-3-yl)pyridin-2-yl)cyclopropanecarboxamide. ESI-MS m/z calc. 387.2. found 388.1 (M+1)+. Retention time 1.38 minutes.

BT. 1-(2,3-Dihydrobenzofuran-5-yl)-N-(4-methyl-6-(6-oxo-1,6-dihydropyridin-3-yl)pyridin-2-yl)cyclopropanecarboxamide

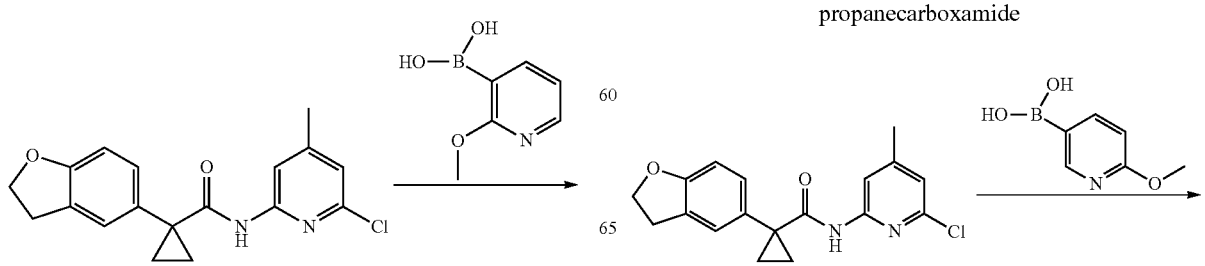

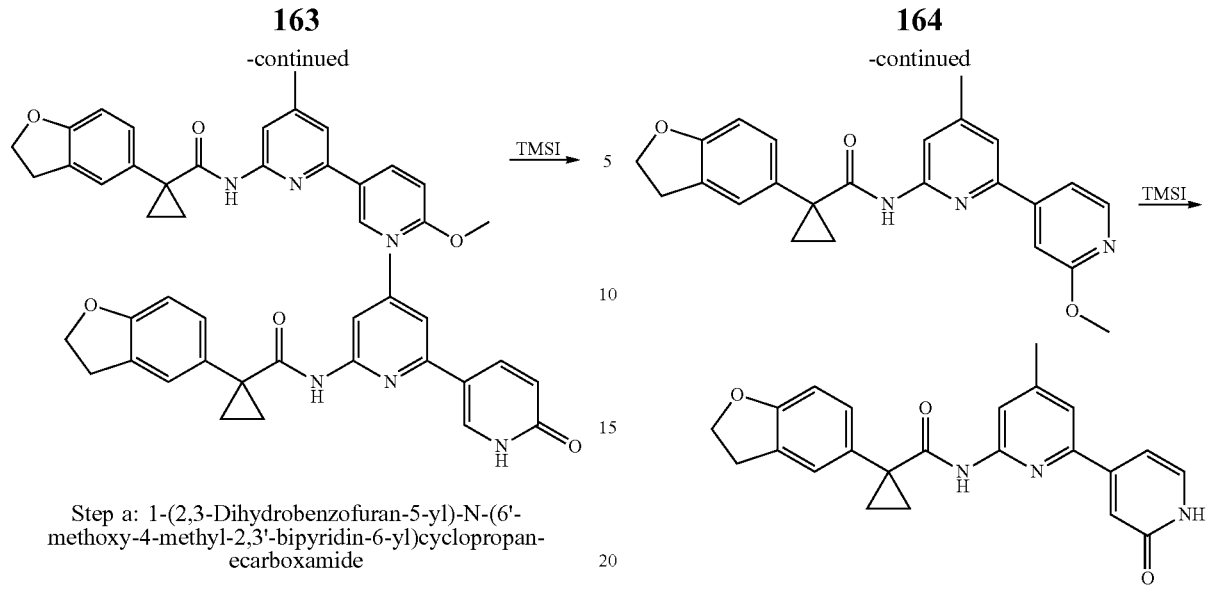

Step a: 1-(2,3-Dihydrobenzofuran-5-yl)-N-(6'-methoxy-4-methyl-2,3'-bipyridin-6-yl)cyclopropanecarboxamide To N-(6-chloro-4-methylpyridin-2-yl)-1-(2,3-dihydrobenzofuran-5-yl)cyclopropanecarboxamide (200 mg, 0.61 mmol) in 1,2-dimethoxyethane (3 mL) was added 6-methoxypyridin-3-ylboronic acid (110 mg, 0.73 mmol), tetrakis(triphenylphosphine)-palladium (0) (70 mg, 0.061 mmol), and 2 M $Na_2CO_3$ (910 µL, 1.8 mmol). The reaction mixture was irradiated in the microwave at 120° C. for 20 minutes. The reaction mixture was evaporated to dryness and the residue was purified by silica gel chromatography eluting with (0-20% ethyl acetate/hexanes) to yield 1-(2,3-dihydrobenzofuran-5-yl)-N-(6'-methoxy-4-methyl-2,3'-bipyridin-6-yl)cyclopropanecarboxamide (147 mg, 60%). ESI-MS m/z calc. 401.2. found 402.3 (M+1)⁺. Retention time 1.90 minutes.

Step b: 1-(2,3-Dihydrobenzofuran-5-yl)-N-(4-methyl-6-(6-oxo-1,6-dihydropyridin-3-yl)pyridin-2-yl)cyclopropanecarboxamide To a suspension of 1-(2,3-dihydrobenzofuran-5-yl)-N-(6'-methoxy-4-methyl-2,3'-bipyridin-6-yl)cyclopropanecarboxamide (180 mg, 0.45 mmol) in $CH_3CN$ (7 mL) was added TMSI (130 uL, 0.90 mmol) dropwise at 20° C. The reaction was stirred at 50° C. for 30 min. MeOH (1.0 mL) was added and the solution was evaporated to dryness. The residue was re-dissolved in DCM-EtOAc (1:3) before it was washed with $NaHSO_3$ (2×) and brine. The organics were dried over $MgSO_4$ and evaporated to dryness. The crude material was purified by HPLC to yield 1-(2,3-dihydrobenzofuran-5-yl)-N-(4-methyl-6-(6-oxo-1,6-dihydropyridin-3-yl)pyridin-2-yl)cyclopropanecarboxamide. ESI-MS m/z calc. 387.2. found 388.1 (M+1)⁺. Retention time 1.35 minutes.

BU. 1-(2,3-Dihydrobenzofuran-5-yl)-N-(4-methyl-6-(2-oxo-1,2-dihydropyridin-4-yl)pyridin-2-yl)cyclopropanecarboxamide

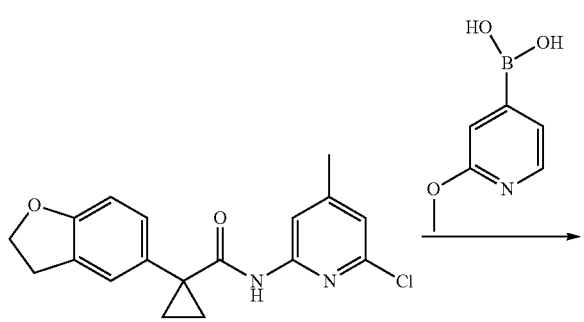

Step a: 1-(2,3-Dihydrobenzofuran-5-yl)-N-(2'-methoxy-4-methyl-2,4'-bipyridin-6-yl)cyclopropanecarboxamide To N-(6-chloro-4-methylpyridin-2-yl)-1-(2,3-dihydrobenzofuran-5-yl)cyclopropanecarboxamide (150 mg, 0.46 mmol) in 1,2-dimethoxyethane (4 mL) was added 2-methoxypyridin-4-ylboronic acid (84 mg, 0.55 mmol), tetrakis(triphenylphosphine)palladium (0) (53 mg, 0.046 mmol), and 2 M $Na_2CO_3$ (680 µL, 1.4 mmol). The reaction mixture was irradiated in the microwave at 120° C. for 20 minutes. The reaction mixture was evaporated to dryness and the residue was purified by silica gel chromatography eluting with (0-20% ethyl acetate/hexanes) to yield 1-(2,3-dihydrobenzofuran-5-yl)-N-(2'-methoxy-4-methyl-2,4'-bipyridin-6-yl)cyclopropanecarboxamide (76 mg, 42%). ESI-MS m/z calc. 401.2. found 402.3 (M+1)⁺. Retention time 1.88 minutes.

Step b: 1-(2,3-Dihydrobenzofuran-5-yl)-N-(4-methyl-6-(2-oxo-1,2-dihydropyridin-4-yl)pyridin-2-yl)cyclopropanecarboxamide To a suspension of 1-(2,3-dihydrobenzofuran-5-yl)-N-(2'-methoxy-4-methyl-2,4'-bipyridin-6-yl)cyclopropanecarboxamide (78 mg, 0.19 mmol) in $CH_3CN$ (3 mL) was added TMSI (55 uL, 0.39 mmol) dropwise at 20° C. The reaction was stirred at 50° C. for 30 min. MeOH (1.0 mL) was added and the solution was evaporated to dryness. The residue was re-dissolved in DCM-EtOAc (1:3) before it was washed with $NaHSO_3$ (2×) and brine. The organics were dried over $MgSO_4$ and evaporated to dryness. The crude material was purified by column chromatography (0-10% MeOH-EtOAc) to yield 1-(2,3-dihydrobenzofuran-5-yl)-N-(4-methyl-6-(2-oxo-1,2-dihydropyridin-4-yl)pyridin-2-yl)cyclopropanecarboxamide. ESI-MS m/z calc. 387.2. found 388.3 (M+1)⁺. Retention time 1.36 minutes.

BV. N-(5'-chloro-6'-methoxy-3-methyl-2,3'-bipyridin-6-yl)-1-(2,2-difluorobenzo[d][1,3]dioxol-5-yl)cyclopropanecarboxamide

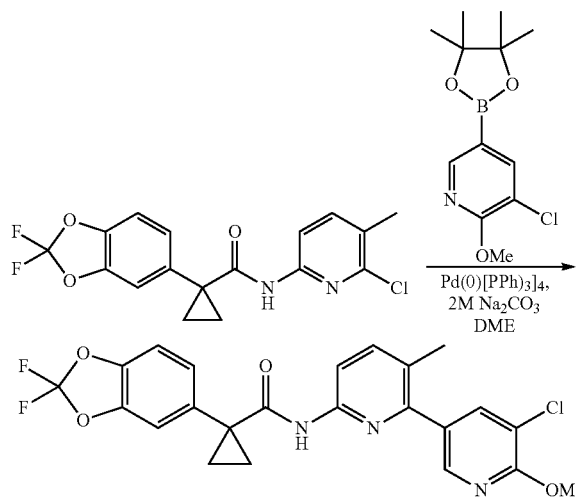

To N-(6-chloro-5-methylpyridin-2-yl)-1-(2,2-difluorobenzo[d][1,3]dioxol-5-yl)cyclopropanecarboxamide (73 mg, 0.2 mmol) in 1,2-dimethoxyethane (2 mL) was added 3-chloro-2-methoxy-5-(4,4,5,5-tetramethyl-1,3,2-dioxaborolan-2-yl)pyridine (65 mg, 0.24 mmol), tetrakis(triphenylphosphine)palladium (0) (12 mg, 0.01 mmol), and 2 M sodium carbonate (0.20 mL, 0.4 mmol). The reaction mixture was heated to 80° C. in an oil bath overnight. The reaction mixture was diluted with dichloromethane (5 mL) and washed with water (5 mL). The organics were dried over sodium sulfate and evaporated to dryness. The crude reaction mixture was purified by silica gel chromatography (eluting with 0-100% ethyl acetate in hexanes) to yield the product (26 mg, 27%). ESI-MS m/z calc. 473.86. found 474.3 (M+1)$^+$. Retention time 2.27 minutes.

BW. 1-(2,2-difluorobenzo[d][1,3]dioxol-5-yl)-N-(5',6'-dimethoxy-3-methyl-2,3'-bipyridin-6-yl)cyclopropanecarboxamide

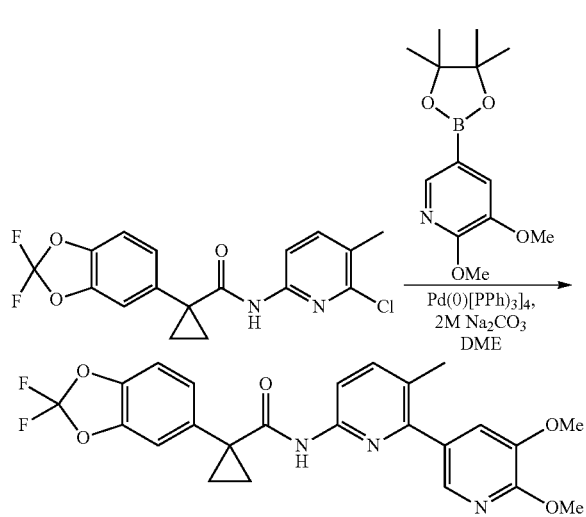

To N-(6-chloro-5-methylpyridin-2-yl)-1-(2,2-difluorobenzo[d][1,3]dioxol-5-yl)cyclopropanecarboxamide (73 mg, 0.2 mmol) in 1,2-dimethoxyethane (2 mL) was added 2,3-dimethoxy-5-(4,4,5,5-tetramethyl-1,3,2-dioxaborolan-2-yl)pyridine (63 mg, 0.24 mmol), tetrakis(triphenylphosphine)palladium (0) (12 mg, 0.01 mmol), and 2 M sodium carbonate (0.20 mL, 0.4 mmol). The reaction mixture was irradiated in the microwave at 120° C. for twenty minutes. The reaction mixture was diluted with ethyl acetate (5 mL) and washed with water (5 mL). The organics were dried over sodium sulfate and evaporated to dryness. The crude reaction mixture was purified by silica gel chromatography (eluting with 0-100% ethyl acetate in hexanes) to yield the product (51 mg, 55%). ESI-MS m/z calc. 469.44. found 470.5 (M+1)$^+$. Retention time 2.03 minutes.

BX. 6-(1-(2,2-difluorobenzo[d][1,3]dioxol-5-yl)cyclopropanecarboxamido)-6'-methoxy-N,N,3-trimethyl-2,3'-bipyridine-5'-carboxamide

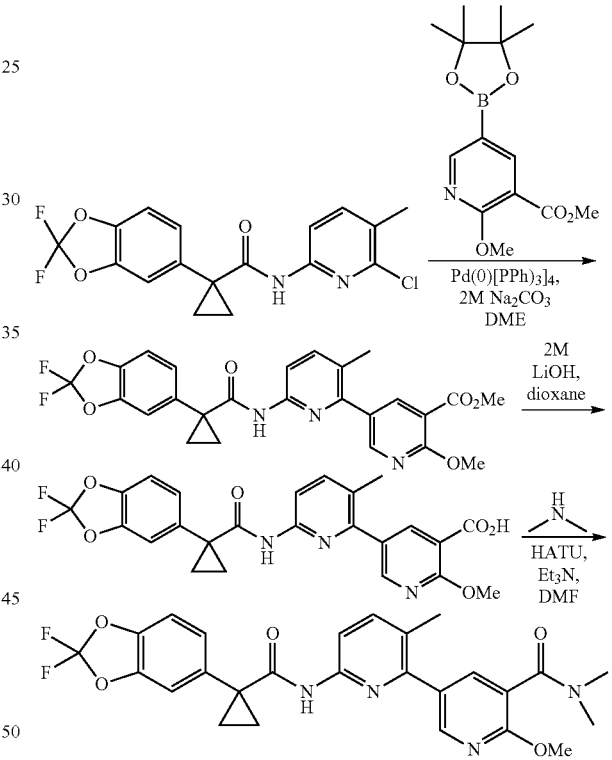

Step a: Methyl 6-(1-(2,2-difluorobenzo[d][1,3]dioxol-5-yl)cyclopropanecarboxamido)-6'-methoxy-3-methyl-2,3'-bipyridine-5'-carboxylate To N-(6-chloro-5-methylpyridin-2-yl)-1-(2,2-difluorobenzo[d][1,3]dioxol-5-yl)cyclopropanecarboxamide (0.26 g, 0.7 mmol) in 1,2-dimethoxyethane (7 mL) was added methyl 2-methoxy-5-(4,4,5,5-tetramethyl-1,3,2-dioxaborolan-2-yl)nicotinate (0.25 g, 0.86 mmol), tetrakis(triphenylphosphine)palladium (0) (42 mg, 0.04 mmol), and 2 M sodium carbonate (0.70 mL, 1.4 mmol). The reaction mixture was irradiated in the microwave at 120° C. for twenty minutes. The reaction mixture was diluted with ethyl acetate (5 mL) and washed with water (5 mL). The organics were dried over sodium sulfate and evaporated to dryness. The crude reaction mixture was purified by silica gel chromatography (eluting with 0-100% ethyl acetate in hexanes) to yield the product (0.29 g, 81%). ESI-MS m/z calc. 497.45. found 498.3 (M+1)⁺. Retention time 2.14 minutes.

Step b: 6-(1-(2,2-difluorobenzo[d][1,3]-dioxol-5-yl)cyclopropanecarboxamido)-6'-methoxy-3-methyl-2,3'-bipyridine-5'-carboxylic acid To a flask containing methyl 6-(1-(2,2-difluorobenzo[d][1,3]dioxol-5-yl)cyclopropanecarboxamido)-6'-methoxy-3-methyl-2,3'-bipyridine-5'-carboxylate (0.22 g, 0.45 mmol) was added a mixture of 2M Lithium hydroxide (2.5 mL of 2 M, 5.0 mmol) and 1,4-dioxane (2.5 mL) and the reaction mixture was stirred at room temperature for two hours. The reaction mixture was evaporated and residue was suspended between dichloromethane (10 mL) and 1 N hydrochloric acid (10 mL). The organics were dried over sodium sulfate and evaporated to give the product (0.20 g, 95%). ESI-MS m/z calc. 483.12. found 484.5 (M+1)⁺. Retention time 1.85 minutes.

Step c: 6-(1-(2,2-difluorobenzo[d][1,3]dioxol-5-yl)cyclopropanecarboxamido)-6'-methoxy-N,N,3-trimethyl-2,3'-bipyridine-5'-carboxamide To a solution of 6-(1-(2,2-difluorobenzo[d][1,3]dioxol-5-yl)cyclopropanecarboxamido)-6'-methoxy-3-methyl-2,3'-bipyridine-5'-carboxylic acid (72 mg, 0.15 mmol), dimethyl amine (10 mg, 0.23 mmol), and triethylamine (42 µL, 0.30 mmol) in N,N-dimethylformamide (1 mL) was added O-(7-azabenzotriazol-1-yl)-N,N,N',N'-tetramethyluronium hexafluorophosphate (68 mg, 0.18 mmol) and the reaction mixture was stirred at 80° C. overnight. The crude reaction mixture was purified by silica gel chromatography (eluting with 0-100% ethyl acetate in hexanes) to yield the product (51 mg, 67%). ESI-MS m/z calc. 510.49. found 511.5 (M+1)⁺. Retention time 1.81 minutes.

BY. N-(6-(1-(2-cyanamido-2-oxoethyl)-6-oxo-1,6-dihydropyridin-3-yl)-5-methylpyridin-2-yl)-1-(2,2-difluorobenzo[d][1,3]dioxol-5-yl)cyclopropanecarboxamide

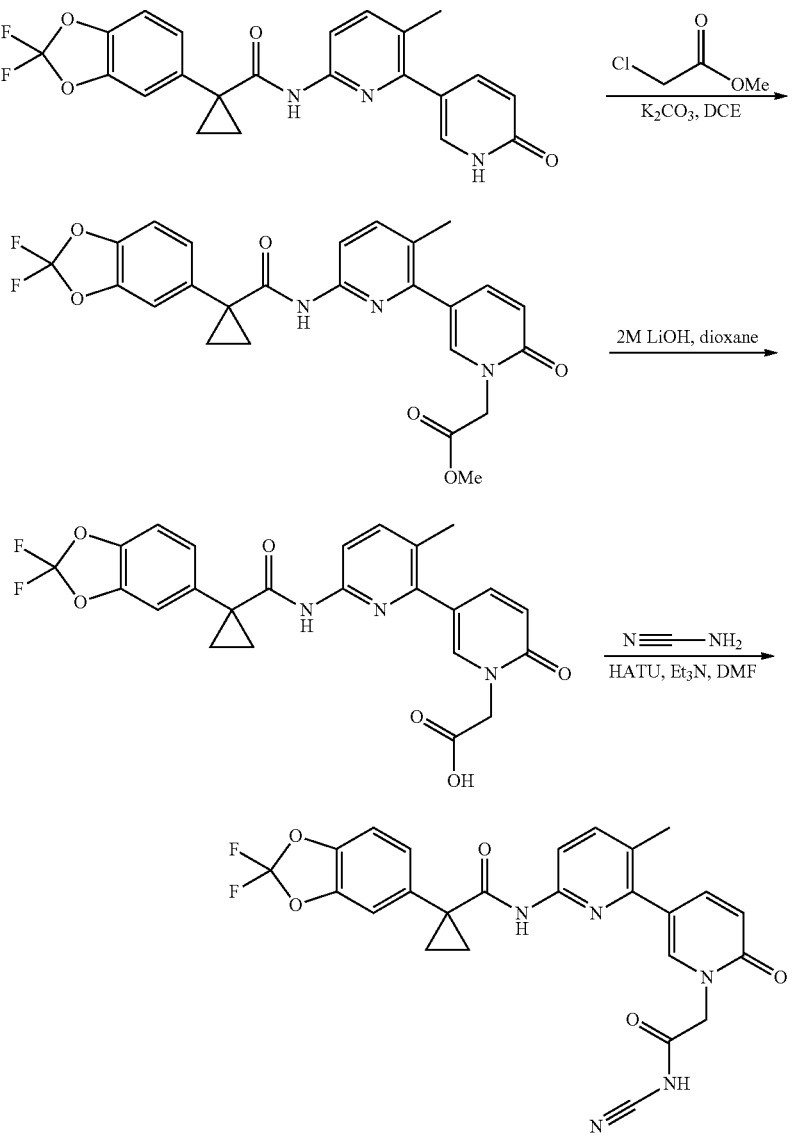

Step a: Methyl 2-(5-(6-(1-(2,2-difluorobenzo[d][1,3]dioxol-5-yl)cyclopropanecarboxamido)-3-methylpyridin-2-yl)-2-oxopyridin-1(2H)-yl)acetate To a flask containing 1-(2,2-difluorobenzo[d][1,3]dioxol-5-yl)-N-(5-methyl-6-(6-oxo-1,6-dihydropyridin-3-yl)pyridin-2-yl)cyclopropanecarboxamide (0.15 g, 0.35 mmol), methyl chloroacetate (0.19 g, 1.8 mmol), and potassium carbonate (0.5 g, 3.5 mmol) was added dichloroethane (7 mL) and the reaction mixture was heated to 100° C. in a sealed tube overnight. The reaction was diluted with dichloromethane (15 mL) and washed with water (10 mL). The organics were dried over sodium sulfate and evaporated to dryness. The crude reaction was purified by silica gel chromatography (eluting with 0-10% methanol in dichloromethane) to give the product (0.13 g, 76%). ESI-MS m/z calc. 497.14. found 498.3 (M+1)⁺. Retention time 1.73 minutes.

Step b: 2-(5-(6-(1-(2,2-difluorobenzo[d][1,3]-dioxol-5-yl)cyclopropanecarboxamido)-3-methylpyridin-2-yl)-2-oxopyridin-1(2H)-yl)acetic acid To a flask containing methyl 2-(5-(6-(1-(2,2-difluorobenzo[d][1,3]dioxol-5-yl)cyclopropanecarboxamido)-3-methylpyridin-2-yl)-2-oxopyridin-1(2H)-yl)acetate (0.13 g, 0.27 mmol) was added a mixture of 2M Lithium hydroxide (1 mL of 2 M, 2.0 mmol) and 1,4-dioxane (4 mL) and the reaction mixture was heated to 60° C. for 2 hrs. The reaction mixture was evaporated and the resulting residue was suspended between ethyl acetate (10 mL) and 1 N hydrochloric acid (10 mL). The organics were dried over sodium sulfate and evaporated to give the product (0.13 g, 98%). ESI-MS m/z calc. 483.12. found 484.5 (M+1)⁺. Retention time 1.59 minutes.

Step c: N-(6-(1-(2-cyanamido-2-oxoethyl)-6-oxo-1,6-dihydropyridin-3-yl)-5-methylpyridin-2-yl)-1-(2,2-difluorobenzo[d][1,3]dioxol-5-yl)cyclopropanecarboxamide To 2-(5-(6-(1-(2,2-difluorobenzo[d][1,3]dioxol-5-yl)cyclopropanecarboxamido)-3-methylpyridin-2-yl)-2-oxopyridin-1(2H)-yl)acetic acid (0.13 g, 0.27 mmol), cyanamide (27 μL, 0.32 mmol), and triethylamine (75 μL, 0.54 mmol) in N,N-dimethylformamide (3 mL) was added O-(7-azabenzotriazol-1-yl)-N,N,N',N'-tetramethyluronium hexafluorophosphate (0.12 g, 0.33 mmol) and the reaction mixture was stirred at room temperature for 1 hour. At this point the reaction mixture was filtered and purified by reverse-phase HPLC. The resulting trifluoroacetic acid salt was dissolved in dichloromethane and washed with a saturated sodium bicarbonate solution and 1 N Hydrochloric acid. The organics were dried over sodium sulfate and evaporated to dryness to give the product (45 mg, 31%). ESI-MS m/z calc. 507.14. found 508.4 (M+1)⁺. Retention time 1.63 minutes.

BZ. 1-(2,2-difluorobenzo[d][1,3]dioxol-5-yl)-N-(6-(5-fluoro-2-oxo-1,2-dihydropyridin-4-yl)-5-methylpyridin-2-yl)cyclopropanecarboxamide

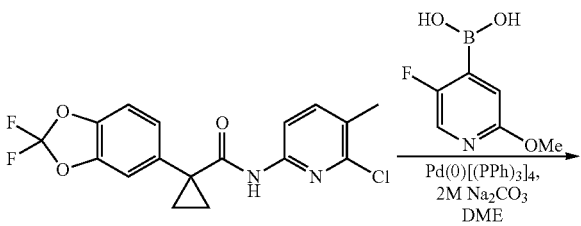

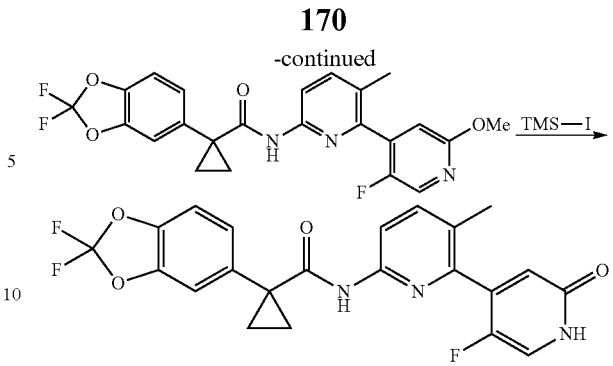

Step a: 1-(2,2-difluorobenzo[d][1,3]dioxol-5-yl)-N-(5'-fluoro-2'-methoxy-3-methyl-2,4'-bipyridin-6-yl)cyclopropanecarboxamide To N-(6-chloro-5-methylpyridin-2-yl)-1-(2,2-difluorobenzo[d][1,3]dioxol-5-yl)cyclopropanecarboxamide (73 mg, 0.2 mmol) in 1,2-dimethoxyethane (2 mL) was added 5-fluoro-2-methoxypyridin-4-ylboronic acid (44 mg, 0.26 mmol), tetrakis(triphenylphosphine)palladium (0) (12 mg, 0.01 mmol), and 2 M sodium carbonate (0.20 mL, 0.4 mmol). The reaction mixture was irradiated in the microwave at 120° C. for twenty minutes. The reaction mixture was diluted with ethyl acetate (5 mL) and washed with water (5 mL). The organics were dried over sodium sulfate and evaporated to dryness. The crude reaction mixture was purified by silica gel chromatography (eluting with 0-100% ethyl acetate in hexanes) to yield the product (19 mg, 20%). ESI-MS m/z calc. 457.12. found 458.3 (M+1)⁺. Retention time 2.17 minutes.

Step b: 1-(2,2-difluorobenzo[d][1,3]dioxol-5-yl)-N-(6-(5-fluoro-2-oxo-1,2-dihydropyridin-4-yl)-5-methylpyridin-2-yl)cyclopropanecarboxamide To 1-(2,2-difluorobenzo[d][1,3]dioxol-5-yl)-N-(5'-fluoro-2'-methoxy-3-methyl-2,4'-bipyridin-6-yl)cyclopropanecarboxamide (19 mg, 0.04 mmol) in chloroform (0.5 mL) was added iodotrimethylsilane (32 mg, 0.16 mmol). The reaction mixture was stirred at room temperature for three hours. At this point the reaction mixture was purified directly by silica gel chromatography (eluting with 0-100% ethyl acetate in hexanes) to yield the product (5.1 mg, 47%). ESI-MS m/z calc. 443.38. found 444.3 (M+1)⁺. Retention time 1.63 minutes.

CA. 1-(2,3-dihydrobenzofuran-5-yl)-N-(5-methyl-6-(5-methyl-6-oxo-1,6-dihydropyridin-3-yl)pyridin-2-yl)cyclopropanecarboxamide

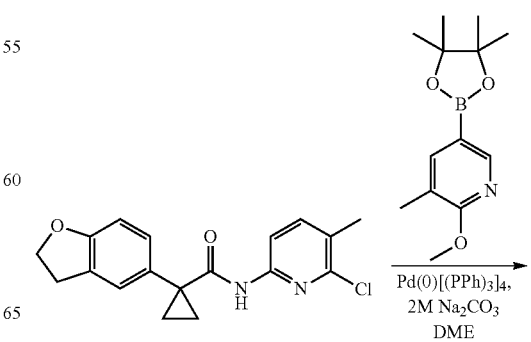

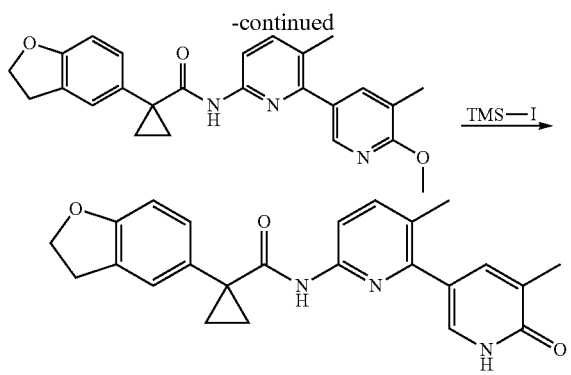

Step a: 1-(2,3-dihydrobenzofuran-5-yl)-N-(6'-methoxy-3,5'-dimethyl-2,3'-bipyridin-6-yl)cyclopropanecarboxamide To N-(6-chloro-5-methylpyridin-2-yl)-1-(2,3-dihydrobenzofuran-5-yl)cyclopropanecarboxamide (0.1 g, 0.3 mmol) in 1,2-dimethoxyethane (3 mL) was added 2-methoxy-3-methyl-5-(4,4,5,5-tetramethyl-1,3,2-dioxaborolan-2-yl)pyridine (98 mg, 0.4 mmol), tetrakis(triphenylphosphine)palladium (0) (35 mg, 0.03 mmol), and 2 M sodium carbonate (0.45 mL, 0.9 mmol) and the reaction mixture was heated to 80° C. overnight. The reaction was diluted with ethyl acetate (5 mL) and washed with water (5 mL). The aqueous layer was back extracted with ethyl acetate (5 mL). The organics were dried over sodium sulfate and evaporated. The resulting crude material was purified by silica gel chromatography (eluting with 0-30% ethyl acetate in hexanes) to yield the product (0.1 g, 84%). ESI-MS m/z calc. 415.48. found 416.1 (M+1)⁺. Retention time 2.03 minutes.

Step b: 1-(2,3-dihydrobenzofuran-5-yl)-N-(5-methyl-6-(5-methyl-6-oxo-1,6-dihydropyridin-3-yl)pyridin-2-yl)cyclopropanecarboxamide To 1-(2,3-dihydrobenzofuran-5-yl)-N-(6'-methoxy-3,5'-dimethyl-2,3'-bipyridin-6-yl)cyclopropanecarboxamide (98 mg, 0.24 mmol) in acetonitrile (4 mL) at 50° C. was added iodotrimethylsilane (95 mg, 0.5 mmol). The reaction was heated for one hour before being quenched with methanol (1 mL). The reaction was diluted with dichloromethane (15 mL) and washed with an aqueous saturated sodium bisulfite solution (2×15 mL). The organics were dried over sodium sulfate and evaporated to dryness. The resulting white solid was purified by silica gel chromatography (eluting with 0-10% methanol in ethyl acetate) to yield the product (74 mg, 76%) as a white solid. ESI-MS m/z calc. 401.46. found 402.5 (M+1)⁺. Retention time 1.47 minutes.

CB. N-(6-(5-amino-6-oxo-1,6-dihydropyridin-3-yl)-5-methylpyridin-2-yl)-1-(2,2-difluorobenzo[d][1,3]dioxol-5-yl)cyclopropanecarboxamide

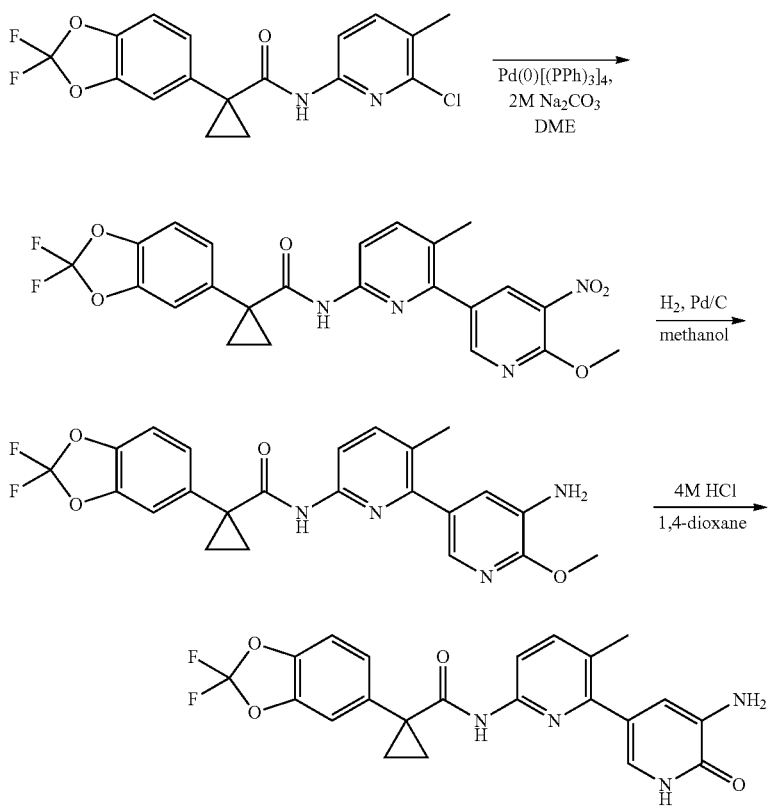

Step a: 1-(2,2-Difluorobenzo[d][1,3]dioxol-5-yl)-N-(6'-methoxy-3-methyl-5'-nitro-2,3'-bipyridin-6-yl)cyclopropanecarboxamide To N-(6-chloro-5-methylpyridin-2-yl)-1-(2,2-difluorobenzo[d][1,3]dioxol-5-yl)cyclopropanecarboxamide (0.11 g, 0.3 mmol) in 1,2-dimethoxyethane (3 mL) was added 2-methoxy-3-nitro-5-(4,4,5,5-tetramethyl-1,3,2-dioxaborolan-2-yl)pyridine (0.11 g, 0.39 mmol), tetrakis(triphenylphosphine)palladium (0) (17 mg, 0.015 mmol), and 2 M sodium carbonate (0.3 mL, 0.6 mmol) and the reaction mixture was heated to 80° C. overnight. The crude material was purified by silica gel chromatography (eluting with 0-35% ethyl acetate in hexanes) to yield the product (71 mg, 50%). ESI-MS m/z calc. 484.12. found 485.0 (M+1)$^+$. Retention time 2.17 minutes.

Step b: N-(5'-amino-6'-methoxy-3-methyl-2,3'-bipyridin-6-yl)-1-(2,2-difluorobenzo[d][1,3]dioxol-5-yl)cyclopropanecarboxamide To 1-(2,2-difluorobenzo[d][1,3]dioxol-5-yl)-N-(6'-methoxy-3-methyl-5'-nitro-2,3'-bipyridin-6-yl)cyclopropanecarboxamide (71 mg, 0.15 mmol) in methanol (10 mL) was added Pd/C (15 mg, 0.015 mmol) The reaction was stirred at room temperature under a balloon of hydrogen for one hour before being filtered and evaporated to yield the product (53 mg, 77%). ESI-MS m/z calc. 454.15. found 455.1 (M+1)$^+$. Retention time 1.75 minutes.

Step c: N-(6-(5-amino-6-oxo-1,6-dihydropyridin-3-yl)-5-methylpyridin-2-yl)-1-(2,2-difluorobenzo[d][1,3]dioxol-5-yl)cyclopropanecarboxamide To N-(5'-amino-6'-methoxy-3-methyl-2,3'-bipyridin-6-yl)-1-(2,2-difluorobenzo[d][1,3]dioxol-5-yl)cyclopropanecarboxamide (53 mg, 0.1166 mmol) in 1,4-dioxane (2 mL) was added 4M aq hydrochloric acid (0.5 mL, 2.0 mmol) and the reaction mixture was heated to 90° C. After one hour the reaction was quenched with triethylamine (0.5 mL). The reaction mixture was evaporated to dryness and the residue was dissolved in N,N-dimethylformamide (2 mL) and purified by reverse phase HPLC. The fractions from the HPLC purification were neutralized with saturated sodium bicarbonate and extracted with ethyl acetate (3×10 mL). The organics were dried over sodium sulfate and evaporated to yield the product (26 mg, 48%). ESI-MS m/z calc. 440.4. found 441.3 (M+1)$^+$. Retention time 1.39 minutes.

CC. 1-(2,3-dihydrobenzofuran-5-yl)-N-(5-methyl-6-(6-oxo-1,6-dihydropyridin-3-yl)pyridin-2-yl)cyclopropanecarboxamide

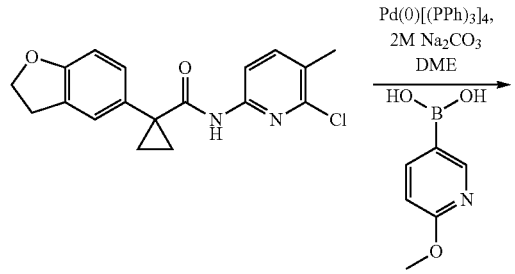

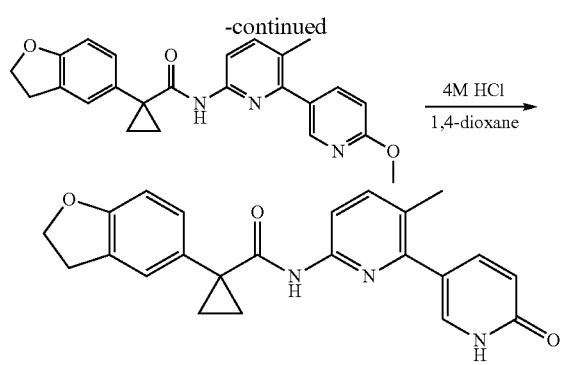

Step a: 1-(2,3-dihydrobenzofuran-5-yl)-N-(6'-methoxy-3-methyl-2,3'-bipyridin-6-yl)cyclopropanecarboxamide To N-(6-chloro-5-methylpyridin-2-yl)-1-(2,3-dihydrobenzofuran-5-yl)cyclopropanecarboxamide (95 mg, 0.3 mmol) in 1,2-dimethoxyethane (3 mL) was added 6-methoxypyridin-3-ylboronic acid (66 mg, 0.4 mmol), tetrakis(triphenylphosphine)palladium (0) (33 mg, 0.03 mmol), and 2 M sodium carbonate (0.45 mL, 0.9 mmol). The reaction mixture was irradiated in the microwave at 120° C. for twenty minutes. The reaction mixture was diluted with ethyl acetate (5 mL) and washed with water (5 mL). The organics were dried over sodium sulfate and evaporated to dryness. The crude reaction mixture was purified by silica gel chromatography (eluting with 0-50% ethyl acetate in hexanes) to yield the product (72 mg, 62%). ESI-MS m/z calc. 401.17. found 402.5 (M+1)$^+$. Retention time 1.86 minutes.

Step b: 1-(2,3-dihydrobenzofuran-5-yl)-N-(5-methyl-6-(6-oxo-1,6-dihydropyridin-3-yl)pyridin-2-yl)cyclopropanecarboxamide To 1-(2,3-dihydrobenzofuran-5-yl)-N-(6'-methoxy-3-methyl-2,3'-bipyridin-6-yl)cyclopropanecarboxamide (72 mg, 0.18 mmol) in 1,4-dioxane (2 mL) was added 0.5 mL of an aqueous 4 M hydrochloric acid solution. The reaction mixture was heated to 90° C. for 30 minutes before being quenched with triethylamine (0.5 mL) and evaporated to dryness. The residue was dissolved in N,N-dimethylformamide (1 mL) and purified by reverse-phase preparative liquid chromatography. The resulting trifluoroacetic acid salt was dissolved in dichloromethane (5 mL) and washed with a saturated sodium bicarbonate solution (5 mL). The organics were dried over sodium sulfate and evaporated to dryness to yield the product (30 mg, 44%) ESI-MS m/z calc. 387.43. found 388.3 (M+1)$^+$. Retention time 1.39 minutes. $^1$H NMR (400 MHz, DMSO-d6) δ 11.75 (s, 1H), 8.18 (s, 1H), 7.89 (d, J=8.3 Hz, 1H), 7.67 (d, J=8.4 Hz, 1H), 7.61-7.58 (m, 1H), 7.51 (m, 1H), 7.37 (m, 1H), 7.26-7.23 (m, 1H), 6.81 (d, J=8.2 Hz, 1H), 6.36 (d, J=9.5 Hz, 1H), 4.55 (t, J=8.7 Hz, 2H), 3.19 (t, J=8.7 Hz, 2H), 2.27 (s, 3H), 1.49-1.46 (m, 2H), 1.11-1.09 (m, 2H).

CC. 1-(2,3-Dihydrobenzofuran-5-yl)-N-(5-methyl-6-(2-oxo-1,2-dihydropyridin-4-yl)pyridin-2-yl)cyclopropanecarboxamide

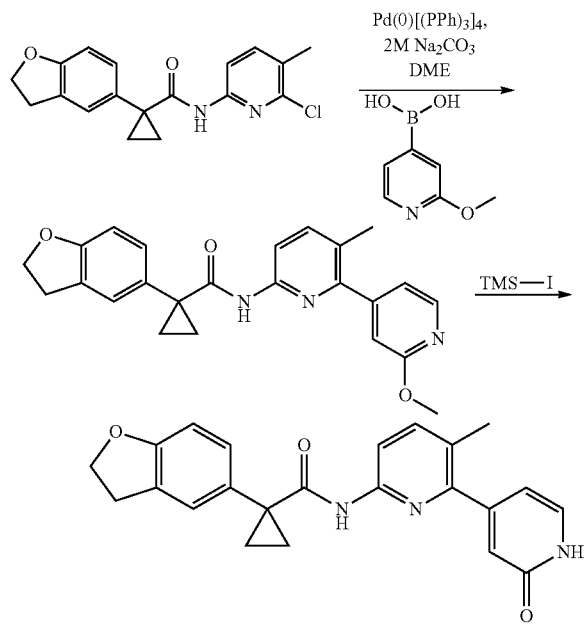

Step a: 1-(2,3-Dihydrobenzofuran-5-yl)-N-(2'-methoxy-3-methyl-2,4'-bipyridin-6-yl)cyclopropanecarboxamide To N-(6-chloro-5-methylpyridin-2-yl)-1-(2,3-dihydrobenzofuran-5-yl)cyclopropanecarboxamide (95 mg, 0.3 mmol) in 1,2-dimethoxyethane (3 mL) was added 2-methoxypyridin-4-ylboronic acid (66 mg, 0.4 mmol), tetrakis(triphenylphosphine)palladium (0) (33 mg, 0.03 mmol), and 2 M sodium carbonate (0.45 mL, 0.9 mmol). The reaction mixture was irradiated in the microwave at 120° C. for twenty minutes. The reaction mixture was diluted with ethyl acetate (5 mL) and washed with water (5 mL). The organics were dried over sodium sulfate and evaporated to dryness. The crude reaction mixture was purified by silica gel chromatography eluting with (0-50% ethyl acetate/hexanes) to yield the product (42 mg, 34%). ESI-MS m/z calc. 401.17. found 402.5 (M+1)+. Retention time 1.88 minutes.

Step b: 1-(2,3-Dihydrobenzofuran-5-yl)-N-(5-methyl-6-(2-oxo-1,2-dihydropyridin-4-yl)pyridin-2-yl)cyclopropanecarboxamide To 1-(2,3-dihydrobenzofuran-5-yl)-N-(2'-methoxy-3-methyl-2,4'-bipyridin-6-yl)cyclopropanecarboxamide (42 mg, 0.1 mmol) in chloroform (2 mL) was added iodotrimethylsilane (63 mg, 0.3 mmol). The reaction mixture was heated to 60° C. for one hour. The reaction was evaporated to dryness and the residue was dissolved in N,N-dimethylformamide (1 mL) and purified by reverse-phase preparative liquid chromatography. The resulting trifluoroacetic acid salt was dissolved in dichloromethane (5 mL) and washed with a saturated sodium bicarbonate solution (5 mL). The organics were dried over sodium sulfate and evaporated to dryness to yield the product (14 mg, 36%) ESI-MS m/z calc. 387.43. found 388.5 (M+1)+. Retention time 1.41 minutes. $^1$H NMR (400 MHz, DMSO-d6) δ 11.66 (s, 1H), 8.19 (s, 1H), 7.99 (d, J=8.4 Hz, 1H), 7.73 (d, J=8.5 Hz, 1H), 7.40-7.37 (m, 2H), 7.26-7.24 (m, 1H), 6.80 (d, J=8.2 Hz, 1H), 6.28 (m, 1H), 6.18-6.15 (m, 1H), 4.55 (t, J=8.7 Hz, 2H), 3.19 (t, J=8.6 Hz, 2H), 2.22 (s, 3H), 1.49-1.47 (m, 2H), 1.11-1.09 (m, 2H)

CD. (R)-1-(2,2-difluorobenzo[d][1,3]dioxol-5-yl)-N-(6-(1-(2,3-dihydroxypropyl)-6-oxo-1,6-dihydropyridin-3-yl)-5-methylpyridin-2-yl)cyclopropanecarboxamide

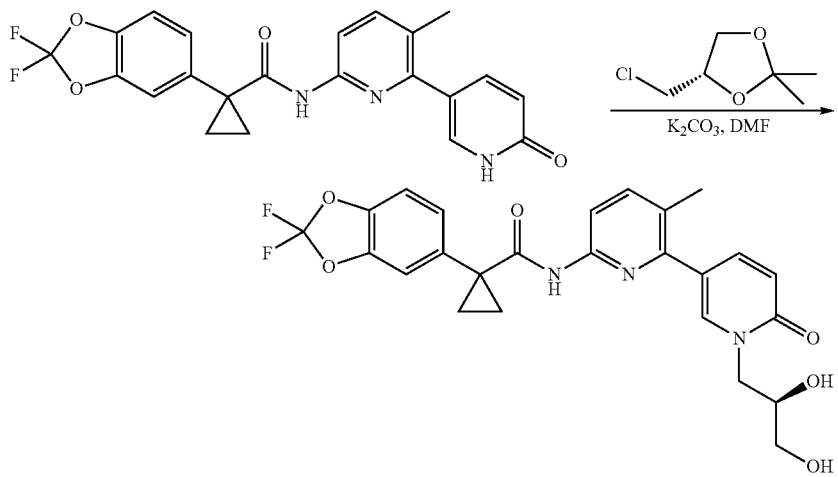

To 1-(2,2-difluorobenzo[d][1,3]dioxol-5-yl)-N-(5-methyl-6-(6-oxo-1,6-dihydropyridin-3-yl)pyridin-2-yl)cyclopropanecarboxamide (0.15 g, 0.35 mmol), (S)-4-(chloromethyl)-2,2-dimethyl-1,3-dioxolane (0.27 g, 1.8 mmol), and potassium carbonate (0.5 g, 3.5 mmol) was added N,N-dimethylformamide and the reaction mixture was heated to 100° C. overnight. The reaction was diluted with dichloromethane (20 mL) and washed with 1N hydrochloric acid (10 mL) and a saturated aqueous sodium bicarbonate solution (10 mL). The organics were dried over sodium sulfate and evaporated. The crude residue was purified by silica gel chromatography (eluting with 0-10% methanol in dichloromethane) to yield the product (47 mg, 27%). ESI-MS m/z calc. 499.16. found 500.2 (M+1)$^+$. Retention time 1.53 minutes.

CE. Ethyl 2-(5-(6-(1-(2,2-difluorobenzo[d][1,3]di-oxol-5-yl)cyclopropanecarboxamido)-3-methylpyri-din-2-yl)-2-oxopyridin-1(2H)-yl)ethylcarbamate

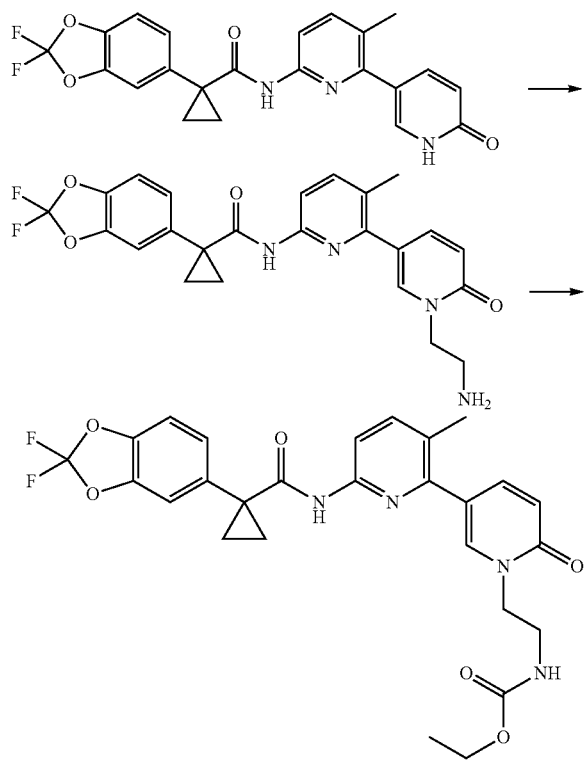

Step a: N-(6-(1-(2-aminoethyl)-6-oxo-1,6-dihydro-pyridin-3-yl)-5-methylpyridin-2-yl)-1-(2,2-difluo-robenzo[d][1,3]dioxol-5-yl)cyclopropanecarboxam-ide To a flask containing 1-(2,2-difluorobenzo[d][1,3]dioxol-5-yl)-N-(5-methyl-6-(6-oxo-1,6-dihydropyridin-3-yl)pyridin-2-yl)cyclopropanecarboxamide (0.13 g, 0.3 mmol), ten-butyl 2-bromoethylcarbamate (0.35 g, 1.6 mmol), and potassium carbonate (0.5 g, 3.1 mmol) was added N,N-dimethylformamide (5 mL) and the reaction mixture was heated to 100° C. for 2 hours. The reaction was purified by reverse-phase preparative liquid chromatography to give the product (24 mg, 17%). ESI-MS m/z calc. 468.16. found 469.5 (M+1)$^+$. Retention time 1.37 minutes.

Step b: Ethyl 2-(5-(6-(1-(2,2-difluorobenzo[d][1,3] dioxol-5-yl)cyclopropanecarboxamido)-3-methyl-pyridin-2-yl)-2-oxopyridin-1(2H)-yl)ethylcarbamate To a flask containing N-(6-(1-(2-aminoethyl)-6-oxo-1,6-dihydropyridin-3-yl)-5-methylpyridin-2-yl)-1-(2,2-difluo-robenzo[d][1,3]dioxol-5-yl)cyclopropanecarboxamide (36 mg, 0.08 mmol), ethyl chloroformate (10 mg, 0.09 mmol), and triethylamine (32 µL, 0.23 mmol) was added N,N-dimethyl formamide (1 mL) and the reaction mixture was stirred at room temperature overnight. The reaction mixture was filtered and purified by reverse-phase preparative liquid chromatography to give the product (11 mg, 25%). ESI-MS m/z calc. 540.18. found 541.7 (M+1)$^+$. Retention time 1.72 minutes.

CF. 1-(2,2-difluorobenzo[d][1,3]dioxol-5-yl)-N-(6-(5-fluoro-2-oxo-1,2-dihydropyridin-3-yl)-5-methyl-pyridin-2-yl)cyclopropanecarboxamide

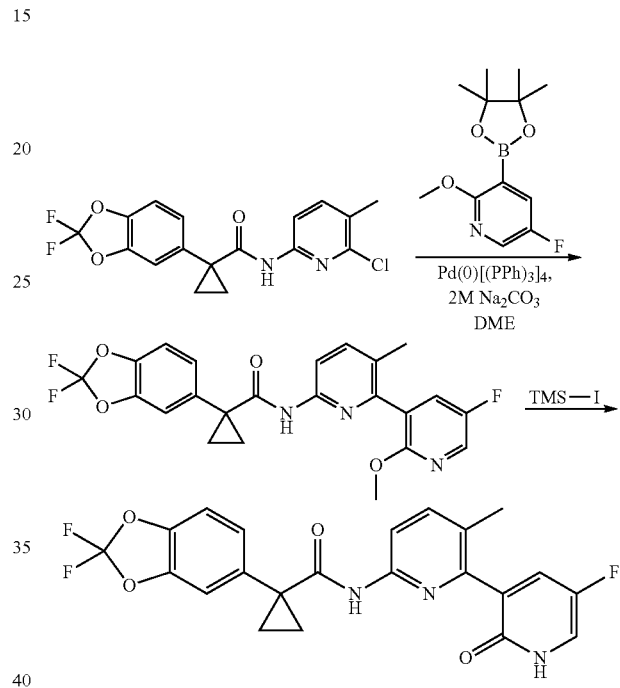

Step a: 1-(2,2-difluorobenzo[d][1,3]dioxol-5-yl)-N-(5'-fluoro-2'-methoxy-3-methyl-2,3'-bipyridin-6-yl) cyclopropanecarboxamide To N-(6-chloro-5-methylpyridin-2-yl)-1-(2,2-difluo-robenzo[d][1,3]dioxol-5-yl)cyclopropanecarboxamide (0.1 g, 0.3 mmol) in 1,2-dimethoxyethane (3 mL) was added 5-fluoro-2-methoxy-3-(4,4,5,5-tetramethyl-1,3,2-dioxa-borolan-2-yl)pyridine (0.1 g, 0.39 mmol), tetrakis(triphenyl-phosphine)palladium (0) (17 mg, 0.015 mmol), and 2 M sodium carbonate (0.3 mL, 0.6 mmol) and the reaction mixture was heated to 80° C. overnight. The crude material was purified by silica gel chromatography (eluting with 0-35% ethyl acetate in hexanes) to yield the product (42 mg, 31%). ESI-MS m/z calc. 457.4. found 458.3 (M+1)$^+$. Retention time 2.20 minutes.

Step b: 1-(2,2-difluorobenzo[d][1,3]dioxol-5-yl)-N-(6-(5-fluoro-2-oxo-1,2-dihydropyridin-3-yl)-5-meth-ylpyridin-2-yl)cyclopropanecarboxamide To 1-(2,2-difluorobenzo[d][1,3]dioxol-5-yl)-N-(5'-fluoro-2'-methoxy-3-methyl-2,3'-bipyridin-6-yl)cyclopro-panecarboxamide (42 mg, 0.09 mmol) in chloroform (1 mL) was added iodotrimethylsilane (55 mg, 0.3 mmol). The reaction mixture was stirred at room temperature for three hours. At this point the reaction mixture was purified directly by silica gel chromatography (eluting with 0-100% ethyl acetate in hexanes) to yield the product (19 mg, 47%). ESI-MS m/z calc. 443.38. found 443.96 (M+1)+. Retention time 1.56 minutes.

CG. 1-(2,3-dihydrobenzofuran-5-yl)-N-(5-methyl-6-(5-methyl-2-oxo-1,2-dihydropyridin-3-yl)pyridin-2-yl)cyclopropanecarboxamide

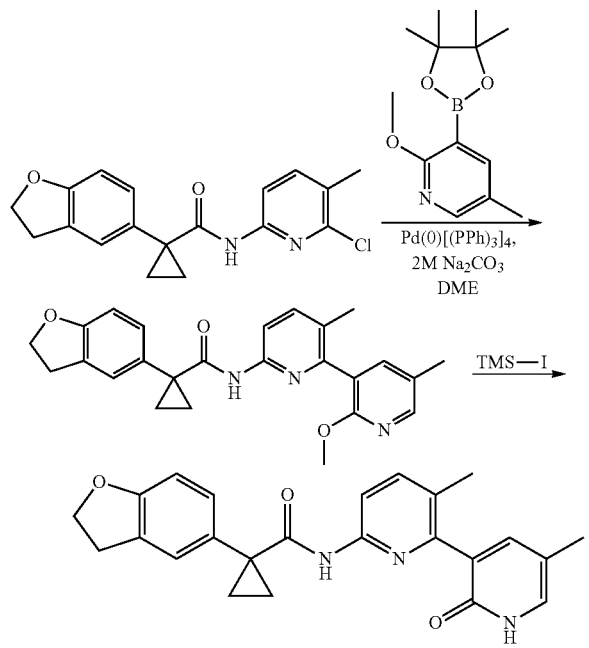

Step a: 1-(2,3-dihydrobenzofuran-5-yl)-N-(2'-methoxy-3,5'-dimethyl-2,3'-bipyridin-6-yl)cyclopropanecarboxamide To N-(6-chloro-5-methylpyridin-2-yl)-1-(2,3-dihydrobenzofuran-5-yl)cyclopropanecarboxamide (0.1 g, 0.3 mmol) in 1,2-dimethoxyethane (3 mL) was added 2-methoxy-5-methyl-3-(4,4,5,5-tetramethyl-1,3,2-dioxaborolan-2-yl)pyridine (98 mg, 0.4 mmol), tetrakis(triphenylphosphine)palladium (0) (35 mg, 0.03 mmol), and 2 M sodium carbonate (0.45 mL, 0.9 mmol) and the reaction mixture was heated to 80° C. overnight. The reaction was diluted with ethyl acetate (5 mL) and washed with water (5 mL). The aqueous layer was back extracted with ethyl acetate (5 mL). The organics were dried over sodium sulfate and evaporated. The resulting crude material was purified by silica gel chromatography (eluting with 0-30% ethyl acetate in hexanes) to yield the product (95 mg, 76%). ESI-MS m/z calc. 415.48. found 416.1 (M+1)+. Retention time 1.92 minutes.

Step b: 1-(2,3-dihydrobenzofuran-5-yl)-N-(5-methyl-6-(5-methyl-2-oxo-1,2-dihydropyridin-3-yl)pyridin-2-yl)cyclopropanecarboxamide To 1-(2,3-dihydrobenzofuran-5-yl)-N-(2'-methoxy-3,5'-dimethyl-2,3'-bipyridin-6-yl)cyclopropanecarboxamide (90 mg, 0.2 mmol) in acetonitrile (4 mL) at 50° C. was added iodotrimethylsilane (87 mg, 0.4 mmol). The reaction was heated for one hour before being quenched with methanol (1 mL). The reaction was diluted with dichloromethane (15 mL) and washed with an aqueous saturated sodium bisulfite solution (2×15 mL). The organics were dried over sodium sulfate and evaporated to dryness. The resulting white solid was purified by silica gel chromatography (eluting with 0-10% methanol in ethyl acetate) to yield the product (49 mg, 55%) as a white solid. ESI-MS m/z calc. 401.46. found 402.5 (M+1)+. Retention time 1.32 minutes.

CH. 1-(2,3-dihydrobenzofuran-5-yl)-N-(5-methyl-6-(2-oxo-1,2-dihydropyridin-3-yl)pyridin-2-yl)cyclopropanecarboxamide

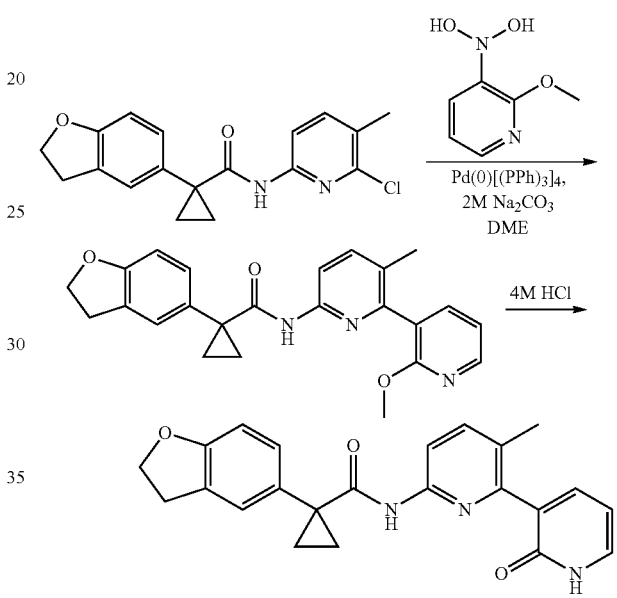

Step a: 1-(2,3-dihydrobenzofuran-5-yl)-N-(2'-methoxy-3-methyl-2,3'-bipyridin-6-yl)cyclopropanecarboxamide To N-(6-chloro-5-methylpyridin-2-yl)-1-(2,3-dihydrobenzofuran-5-yl)cyclopropanecarboxamide (95 mg, 0.3 mmol) in 1,2-dimethoxyethane (3 mL) was added 2-methoxypyridin-3-ylboronic acid (66 mg, 0.4 mmol), tetrakis(triphenylphosphine)palladium (0) (33 mg, 0.03 mmol), and 2 M sodium carbonate (0.45 mL, 0.9 mmol). The reaction mixture was irradiated in the microwave at 120° C. for twenty minutes. The reaction mixture was diluted with ethyl acetate (5 mL) and washed with water (5 mL). The organics were dried over sodium sulfate and evaporated to dryness. The crude reaction mixture was purified by silica gel chromatography (eluting with 0-50% ethyl acetate in hexanes) to yield the product (87 mg, 75%). ESI-MS m/z calc. 401.17. found 402.1 (M+1)+. Retention time 1.79 minutes.

Step b: 1-(2,3-dihydrobenzofuran-5-yl)-N-(5-methyl-6-(2-oxo-1,2-dihydropyridin-3-yl)pyridin-2-yl)cyclopropanecarboxamide To 1-(2,3-dihydrobenzofuran-5-yl)-N-(2'-methoxy-3-methyl-2,3'-bipyridin-6-yl)cyclopropanecarboxamide (87 mg, 0.2 mmol) in 1,4-dioxane (1 mL) was added 0.5 mL of an aqueous 4 M hydrochloric acid solution. The reaction mixture was heated to 90° C. for 30 minutes before being quenched with triethlyamine (0.5 mL) and evaporated to dryness. The residue was dissolved in N,N-dimethylformamide (1 mL) and purified by reverse-phase preparative liquid chromatography. The resulting trifluoroacetic acid salt was dissolved in dichloromethane (5 mL) and washed with a saturated sodium bicarbonate solution. The organics were dried over sodium sulfate and evaporated to dryness to yield the product (27 mg, 32%) ESI-MS m/z calc. 387.43. found 388.5 (M+1)$^+$. Retention time 1.23 minutes. $^1$H NMR (400 MHz, DMSO-d6) δ 11.81 (s, 1H), 8.02 (s, 1H), 7.94 (d, J=8.3 Hz, 1H), 7.62 (d, J=8.4 Hz, 1H), 7.45 (m, 1H), 7.37-7.35 (m, 2H), 7.24 (m, 1H), 6.80 (d, J=8.2 Hz, 1H), 6.24 (m, 1H), 4.54 (t, J=8.7 Hz, 2H), 3.19 (t, J=8.7 Hz, 2H), 2.07 (s, 3H), 1.50-1.47 (m, 2H), 1.11-1.08 (m, 2H).

CI. N-(6-(5-chloro-2-oxo-1,2-dihydropyridin-3-yl)-5-methylpyridin-2-yl)-1-(2,2-difluorobenzo[d][1,3]dioxol-5-yl)cyclopropanecarboxamide

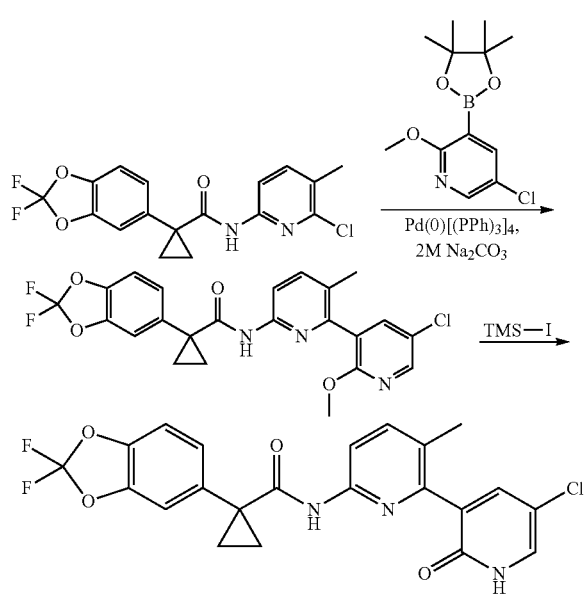

Step a: N-(5'-chloro-2'-methoxy-3-methyl-2,3'-bipyridin-6-yl)-1-(2,2-difluorobenzo[d][1,3]dioxol-5-yl)cyclopropanecarboxamide To N-(6-chloro-5-methylpyridin-2-yl)-1-(2,2-difluorobenzo[d][1,3]dioxol-5-yl)cyclopropanecarboxamide (0.11 g, 0.3 mmol) in 1,2-dimethoxyethane (3 mL) was added 5-chloro-2-methoxy-3-(4,4,5,5-tetramethyl-1,3,2-dioxaborolan-2-yl)pyridine (0.11 g, 0.39 mmol), tetrakis(triphenylphosphine)palladium (0) (17 mg, 0.015 mmol), and 2 M sodium carbonate (0.3 mL, 0.6 mmol) and the reaction mixture was heated to 80° C. overnight. The crude material was purified by silica gel chromatography (eluting with 0-35% ethyl acetate in hexanes) to yield the product (55 mg, 39%). ESI-MS m/z calc. 473.1. found 474.0 (M+1)$^+$. Retention time 2.33 minutes.

Step b: N-(6-(5-chloro-2-oxo-1,2-dihydropyridin-3-yl)-5-methylpyridin-2-yl)-1-(2,2-difluorobenzo[d][1,3]dioxol-5-yl)cyclopropanecarboxamide To N-(5'-chloro-2'-methoxy-3-methyl-2,3'-bipyridin-6-yl)-1-(2,2-difluorobenzo[d][1,3]dioxol-5-yl)cyclopropanecarboxamide (55 mg, 0.12 mmol) in chloroform (1 mL) was added iodotrimethylsilane (70 mg, 0.35 mmol). The reaction mixture was stirred at room temperature overnight. At this point the reaction mixture was purified directly by silica gel chromatography (eluting with a gradient of 0-5% methanol in dichloromethane) to yield the product (24 mg, 41%). ESI-MS m/z calc. 459.08. found 459.95 (MW+1)$^+$. Retention time 1.62 minutes.

CJ. N-(6-(3-chloro-2-oxo-1,2-dihydropyridin-4-yl)-5-methylpyridin-2-yl)-1-(2,2-difluorobenzo[d][1,3]dioxol-5-yl)cyclopropanecarboxamide

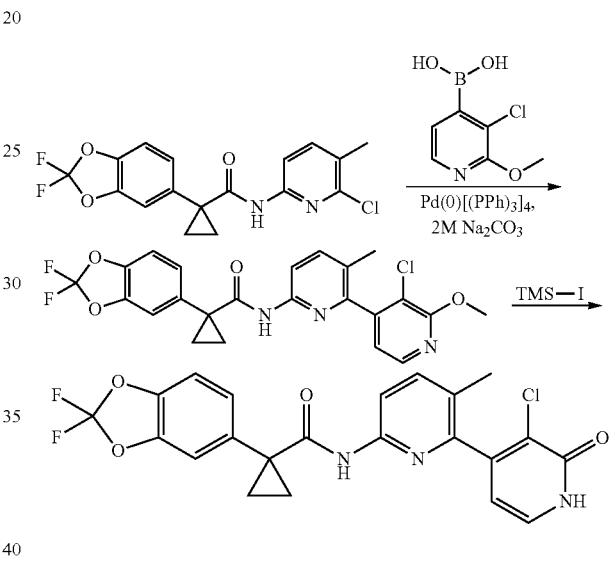

Step a: N-(3'-chloro-2'-methoxy-3-methyl-2,4'-bipyridin-6-yl)-1-(2,2-difluorobenzo[d][1,3]dioxol-5-yl)cyclopropanecarboxamide To N-(6-chloro-5-methylpyridin-2-yl)-1-(2,2-difluorobenzo[d][1,3]dioxol-5-yl)cyclopropanecarboxamide (0.11 g, 0.3 mmol) in 1,2-dimethoxyethane (3 mL) was added 3-chloro-2-methoxypyridin-4-ylboronic acid (73 mg, 0.39 mmol), tetrakis(triphenylphosphine)-palladium (0) (17 mg, 0.015 mmol), and 2 M sodium carbonate (0.3 mL, 0.6 mmol) and the reaction mixture was heated to 80° C. overnight. The crude material was purified by silica gel chromatography (eluting with 0-20% ethyl acetate in hexanes) to yield the product (72 mg, 50%). ESI-MS m/z calc. 473.10. found 474.3 (M+1)$^+$. Retention time 2.19 minutes.

Step b: N-(6-(3-chloro-2-oxo-1,2-dihydropyridin-4-yl)-5-methylpyridin-2-yl)-1-(2,2-difluorobenzo[d][1,3]dioxol-5-yl)cyclopropanecarboxamide To N-(3'-chloro-2'-methoxy-3-methyl-2,4'-bipyridin-6-yl)-1-(2,2-difluorobenzo[d][1,3]dioxol-5-yl)cyclopropanecarboxamide (71 mg, 0.15 mmol) in chloroform (2 mL) was added iodotrimethylsilane (90 mg, 0.45 mmol). The reaction mixture was stirred at room temperature for six hours. The reaction mixture was evaporated to dryness and purified by reverse phase preparative liquid chromatography to yield the product as a trifluoroacetic acid salt. The salt was dissolved in dichloromethane (5 mL) and washed with a saturated sodium bicarbonate solution (2×5 mL). The organics were dried over sodium sulfate and evaporated to yield the product (23 mg, 33%). ESI-MS m/z calc. 459.08. found 460.3 (M+1)⁺. Retention time 1.11 minutes. ¹H NMR (400 MHz, DMSO-d6) δ 12.26 (s, 1H), 9.11 (s, 1H), 7.97 (d, J=8.5 Hz, 1H), 7.75 (d, J=8.6 Hz, 1H), 7.55 (m, 1H), 7.44 (d, J=6.6 Hz, 1H), 7.40-7.38 (m, 1H), 7.35-7.32 (m, 1H), 6.11 (d, J=6.6 Hz, 1H), 2.06 (s, 3H), 1.51-1.50 (m, 2H), 1.17-1.15 (m, 2H).

CK. 1-(2,3-dihydrobenzofuran-6-yl)-N-(5-methyl-6-(6-oxo-1,6-dihydropyridin-3-yl)pyridin-2-yl)cyclopropanecarboxamide

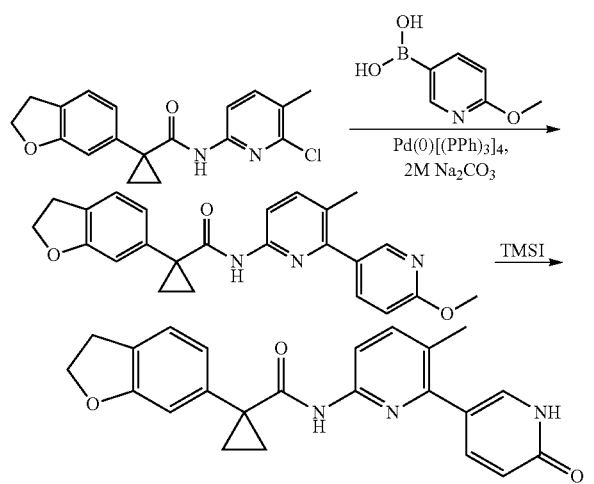

Step a: 1-(2,3-dihydrobenzofuran-6-yl)-N-(2'-methoxy-3-methyl-2,4'-bipyridin-6-yl)cyclopropanecarboxamide A mixture of N-(6-chloro-5-methylpyridin-2-yl)-1-(2,3-dihydrobenzofuran-6-yl)cyclopropanecarboxamide (50.0 mg, 0.15 mmol), 2-methoxypyridine-5-boronic acid (23.26 mg, 0.15 mmol), and tetrakis(triphenylphosphine)palladium (0) (9.0 mg, 0.0076 mmol) in 1,2-dimethoxyethane (1.5 mL) and 2 M Na₂CO₃ (0.3 mL) was stirred at 80° C. for 16 hours under N₂ atmosphere. The reaction mixture was diluted with ethyl acetate (5 mL), dried over Na₂SO₄, filtered and evaporated under reduced pressure. The crude product was purified by column chromatography on silica gel (0-30% ethyl acetate in hexane) to yield 30 mg (49%) of 1-(2,3-dihydrobenzofuran-6-yl)-N-(2'-methoxy-3-methyl-2,4'-bipyridin-6-yl)cyclopropanecarboxamide. ESI-MS m/z calc. 401.2. found 402.0 (M+1)⁺. Retention time 1.83 minutes.

Step b: 1-(2,3-dihydrobenzofuran-6-yl)-N-(5-methyl-6-(6-oxo-1,6-dihydropyridin-3-yl)pyridin-2-yl)cyclopropanecarboxamide To a slurry of 1-(2,3-dihydrobenzofuran-6-yl)-N-(2'-methoxy-3-methyl-2,4'-bipyridin-6-yl)cyclopropanecarboxamide (25 mg, 0.062 mmol) in AcCN (1.5 mL) was added TMS-I (35.45 μL, 0.24 mmol) and stirred at 55° C. for 7 h. The reaction was diluted with methanol (1.0 mL) and stirred at room temperature for 2 h. The resulting mixture was concentrated under vacuum, and taken into ethyl acetate (10 mL. The organic solution washed with sodium bisulphate (2×2 ml) water (2×3 mL), dried over sodium sulphate and concentrated under vacuum. The solid was stirred with methanol (1.0 mL) at 40° C. for 10 min and collected by filtration, washed with methanol (1.0 mL) and dried under vacuum to yield 18.0 mg (74%) of the desired product. ESI-MS m/z calc. 387.4. found 388.2 (M+1)⁺. Retention time 1.32 minutes.

CL. 1-(2,3-dihydrobenzofuran-6-yl)-N-(4-methyl-6-(6-oxo-1,6-dihydropyridin-3-yl)pyridin-2-yl)cyclopropanecarboxamide

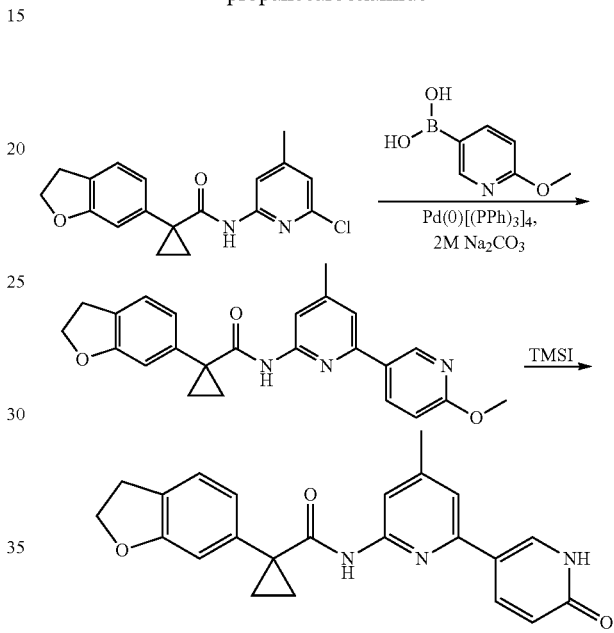

Step a: 1-(2,3-Dihydrobenzofuran-6-yl)-N-(6'-methoxy-4-methyl-2,3'-bipyridin-6-yl)cyclopropanecarboxamide A mixture of N-(6-chloro-4-methylpyridin-2-yl)-1-(2,3-dihydrobenzofuran-6-yl)cyclopropanecarboxamide (50.0 mg, 0.15 mmol), 2-methoxypyridine-5-boronic acid (23.0 mg, 0.15 mmol), and tetrakis(triphenylphosphine)palladium (0) (8.8 mg, 0.0076 mmol) in 1,2-dimethoxyethane (1.0 mL) and 2 M Na₂CO₃ (0.2 mL) was stirred at 80° C. for 16 hours under N₂ atmosphere. The reaction mixture was diluted with ethyl acetate (5 mL), dried over Na₂SO₄, filtered and evaporated under reduced pressure. The crude product was purified by column chromatography on silica gel (0-30% ethyl acetate in hexane) to yield 20 mg (32%) of 1-(2,3-dihydrobenzofuran-6-yl)-N-(6'-methoxy-4-methyl-2,3'-bipyridin-6-yl)cyclopropanecarboxamide. ESI-MS m/z calc. 401.2. found 402.0 (M+1)⁺. Retention time 1.94 minutes.

Step b: 1-(2,3-dihydrobenzofuran-6-yl)-N-(4-methyl-6-(6-oxo-1,6-dihydropyridin-3-yl)pyridin-2-yl)cyclopropanecarboxamide To a slurry of 1-(2,3-dihydrobenzofuran-6-yl)-N-(6'-methoxy-4-methyl-2,3'-bipyridin-6-yl)cyclopropanecarboxamide (20 mg, 0.049 mmol) in acetonitrile (1.5 mL) was added TMS-I (28.4 μL, 0.19 mmol) and the mixture was stirred at 55° C. for 7 h. The reaction was diluted with methanol (1.0 mL) and stirred at room temperature for 2 h. The resulting mixture was concentrated under vacuum, and taken into ethyl acetate (10 mL). The organic solution was washed with sodium bisulphate (2×2 ml), water (2×3 mL), dried over sodium sulphate and concentrated under vacuum. The solid was stirred with methanol (1.0 mL) at 40° C. for 10 min and collected by filtration, washed with methanol (1.0 mL) and dried under vacuum to yield the product (8.0 mg, 41%). ESI-MS m/z calc. 387.4. found 388.2 (M+1)⁺. Retention time 1.44 minutes.

CM. 1-(4-chlorophenyl)-N-(5-methyl-6-(5-methyl-6-oxo-1,6-dihydropyridin-3-yl)pyridin-2-yl)cyclopropanecarboxamide

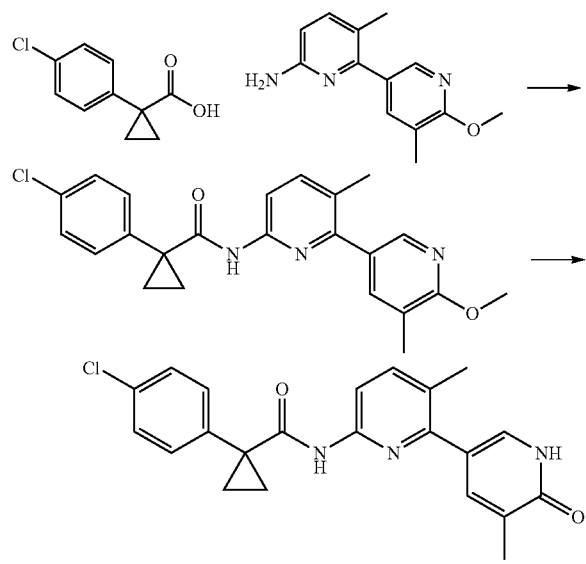

Step a: 1-(4-chlorophenyl)-N-(5-methyl-6-(5-methyl-6-oxo-1,6-dihydropyridin-3-yl)pyridin-2-yl) cyclopropanecarboxamide To a solution of 1-(4-chlorophenyl)cyclopropanecarboxylic acid (39.3 mg, 0.2 mmol) in dichloromethane (2 mL) was added thionyl chloride (43.8 µL, 0.6 mmol) followed by DMF (1 drop) and the reaction was stirred at room temperature for 30 minutes and then the solvent was removed. Toluene (~1 mL) was added, mixed with the residue and then removed by evaporation. The residue was then dissolved in dichloromethane (1 mL) and a solution of 6'-methoxy-3,5'-dimethyl-2,3'-bipyridin-6-amine (46 mg, 0.2 mmol) and triethyl amine (83.6 µL, 0.60 mmol) in dichloromethane (1 mL) was added. The reaction was stirred at room temperature for 12 hors. The reaction was then concentrated. The residue was dissolved in DMSO and purified by reverse phase HPLC (10-99% acetonitrile/water) to yield 62 mg of the product. ESI-MS m/z calc. 407.1. found 408.2 (M+1)⁺. Retention time 2.07 minutes.

Step b: 1-(4-chlorophenyl)-N-(5-methyl-6-(5-methyl-6-oxo-1,6-dihydropyridin-3-yl)pyridin-2-yl) cyclopropanecarboxamide To a solution of 1-(4-chlorophenyl)-N-(5-methyl-6-(5-methyl-6-oxo-1,6-dihydropyridin-3-yl)pyridin-2-yl)cyclopropanecarboxamide (62 mg, 0.15 mmol) in acetonitrile (3 mL) was added TMS-Iodide (86.6 µL, 0.61 mmol). The reaction was stirred at 50° C. for 2 hours. The reaction solution was diluted with dichloromethane and washed with saturated NaHSO3 (2×), brine, dried over MgSO4 and concentrated. The crude product was dissolved in DMSO (2 mL) and purified by HPLC ((10-99% acetonitrile/water). ESI-MS m/z calc. 393.1. found 394.3 (M+1)⁺. Retention time 1.55 minutes. 1H NMR (400.0 MHz, DMSO-d6) δ 8.87 (s, 1H), 7.85 (d, J=8.3 Hz, 1H), 7.66 (d, J=8.4 Hz, 1H), 7.51-7.44 (m, 5H), 7.40 (d, J=2.4 Hz, 1H), 2.28 (s, 3H), 2.00 (s, 3H), 1.51-1.49 (m, 2H) and 1.16-1.13 (m, 2H) ppm CN. 1-(3-chloro-4-methoxyphenyl)-N-(5-methyl-6-(5-methyl-6-oxo-1,6-dihydropyridin-3-yl)pyridin-2-yl)cyclopropanecarboxamide

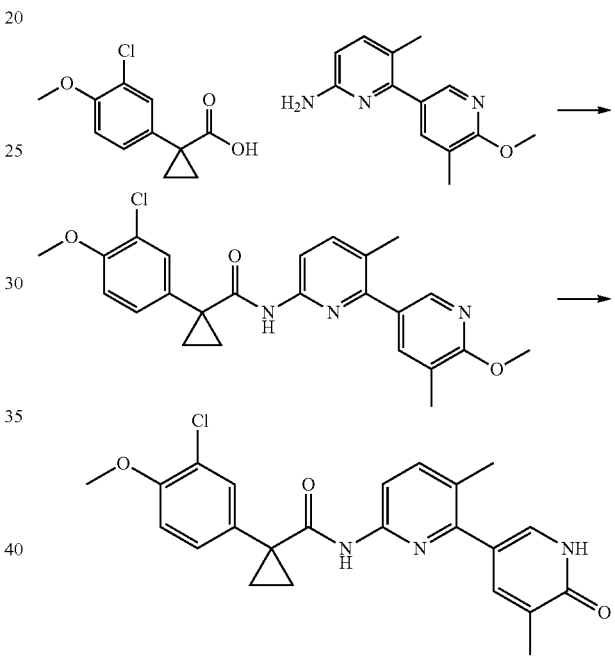

Step a: 1-(3-chloro-4-methoxyphenyl)-N-(6'-methoxy-3,5'-dimethyl-2,3'-bipyridin-6-yl)cyclopropanecarboxamide To a solution of 1-(3-chloro-4-methoxyphenyl)cyclopropanecarboxylic acid (45.3 mg, 0.2 mmol) in dichloromethane (2 mL) was added thionyl chloride (43.8 µL, 0.60 mmol) followed by DMF (1 drop) and the reaction was stirred at room temperature for 30 minutes and then the solvent was evaporated. Toluene (~1 mL) was added and mixed with the residue and then evaporated. The residue was then dissolved in dichloromethane (1 mL) and a solution of 6'-methoxy-3,5'-dimethyl-2,3'-bipyridin-6-amine (45.9 mg, 0.20 mmol) and Et₃N (83.6 µL, 0.60 mmol) in dichloromethane (1 mL) was added. The reaction was stirred at room temperature for 12 hours and then the reaction was then concentrated. The residue was dissolved in DMSO and purified by HPLC (10-99% acetonitrile in water) to yield 44 mg of the product. ESI-MS m/z calc. 437.1. found 438.1 (M+1)⁺. Retention time 2.10 minutes.

Step b: 1-(3-Chloro-4-methoxyphenyl)-N-(5-methyl-6-(5-methyl-6-oxo-1,6-dihydropyridin-3-yl)pyridin-2-yl)cyclopropanecarboxamide To a solution of 1-(3-chloro-4-methoxyphenyl)-N-(6'-methoxy-3,5'-dimethyl-2,3'-bipyridin-6-yl)cyclopropanecarboxamide (44 mg, 0.10 mmol) in acetonitrile (2 mL) was added TMS-Iodide (57.2 µL, 0.40 mmol). The reaction was stirred at 50° C. for 20 min. The reaction solution was diluted with dichloromethane and washed with saturated NaHSO$_3$ (2×), brine, dried over MgSO$_4$ and concentrated. The crude product was dissolved in DMSO (1 mL) and purified by reverse phase HPLC (10-99% CH$_3$CN in water). ESI-MS m/z calc. 423.1. found 424.3 (M+1)$^+$. Retention time 1.52 minutes.

CO. 1-(1,3-dihydroisobenzofuran-5-yl)-N-(5-methyl-6-(5-methyl-6-oxo-1,6-dihydropyridin-3-yl)pyridin-2-yl)cyclopropanecarboxamide

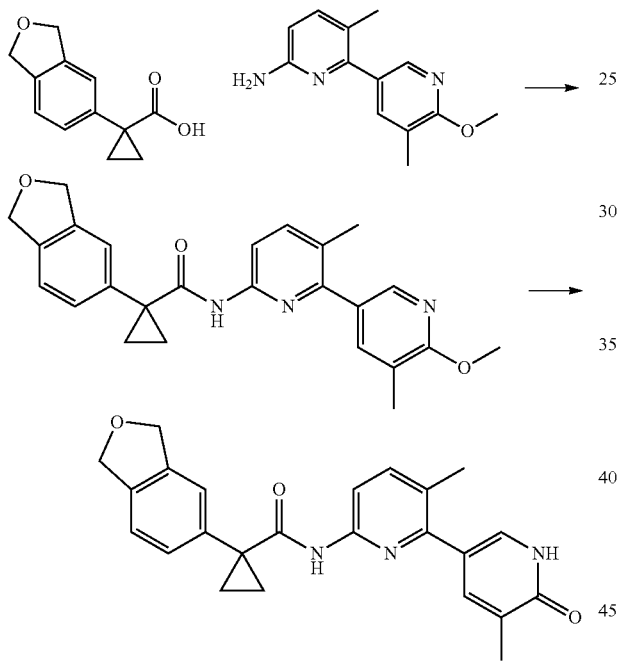

Step a: 1-(1,3-Dihydroisobenzofuran-5-yl)-N-(6'-methoxy-3,5'-dimethyl-2,3'-bipyridin-6-yl)cyclopropanecarboxamide To a solution of 1-(1,3-dihydroisobenzofuran-5-yl)cyclopropanecarboxylic acid (40.8 mg, 0.2 mmol) in dichloromethane (2 mL) was added thionyl chloride (43.8 µL, 0.60 mmol) followed by DMF (1 drop) and the reaction was stirred at room temperature for 30 minutes and then the solvent was evaporated. Toluene (~1 mL) was added and mixed with the residue and then removed by rotovap. The residue was then dissolved in dichloromethane (1 mL) and a solution of 6'-methoxy-3,5'-dimethyl-2,3'-bipyridin-6-amine (45.8 mg, 0.20 mmol) and Et$_3$N (83.6 µL, 0.60 mmol) in dichloromethane (1 mL) was added. The reaction was stirred at room temperature for 12 hours. The reaction was then concentrated. The residue was dissolved in DMSO and purified by reverse phase HPLC (10-99% CH$_3$CN in water) to yield 40 mg of the desired product. ESI-MS m/z calc. 415.2. found 416.5 (M+1)$^+$. Retention time 1.87 minutes.

Step b: 1-(1,3-dihydroisobenzofuran-5-yl)-N-(5-methyl-6-(5-methyl-6-oxo-1,6-dihydropyridin-3-yl)pyridin-2-yl)cyclopropanecarboxamide To a solution of 1-(1,3-dihydroisobenzofuran-5-yl)-N-(6'-methoxy-3,5'-dimethyl-2,3'-bipyridin-6-yl)cyclopropanecarboxamide (40 mg, 0.1 mmol) in acetonitrile (2 mL) was added TMS-Iodide (54.8 µL, 0.39 mmol). The reaction was stirred at 50° C. for 20 min. The reaction solution was diluted with CH$_2$Cl$_2$ and washed with saturated NaHSO$_3$ (2×), brine, dried over MgSO$_4$ and concentrated. The crude product was dissolved in DMSO (1 mL) and purified by reverse phase HPLC (10-99% CH$_3$CN/water). ESI-MS m/z calc. 401.1. found 402.5 (M+1)$^+$. Retention time 1.29 minutes.

CP. 1-(2,3-Dihydrobenzo[b][1,4]dioxin-6-yl)-N-(5-methyl-6-(5-methyl-6-oxo-1,6-dihydropyridin-3-yl)pyridin-2-yl)cyclopropanecarboxamide

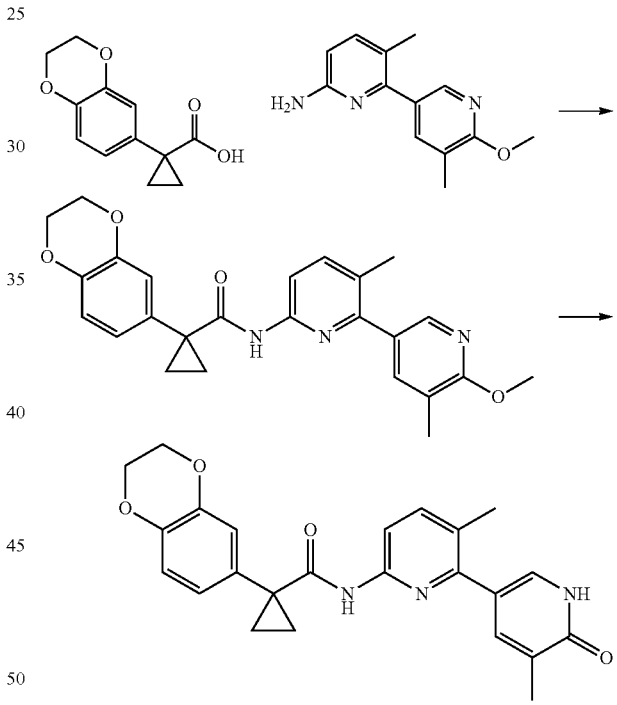

Step a: 1-(2,3-dihydrobenzo[b][1,4]dioxin-6-yl)-N-(6'-methoxy-3,5'-dimethyl-2,3'-bipyridin-6-yl)cyclopropanecarboxamide To a solution of 1-(2,3-dihydrobenzo[b][1,4]dioxin-6-yl)cyclopropanecarboxylic acid (44.04 mg, 0.2 mmol) in dichloromethane (2 mL) was added thionyl chloride (14.6 µL, 0.20 mmol) followed by DMF (1 drop) and the reaction was stirred at room temperature for 30 minutes. The solvent was removed by rotovap. Toluene (~1 mL) was added and mixed with the residue and then removed by rotovap. The toluene step was repeated once more and then the residue was placed under high vacuum for 10 minutes. It was then dissolved in dichloromethane (1 mL) and a solution of 6'-methoxy-3,5'-dimethyl-2,3'-bipyridin-6-amine (46 mg, 0.20 mmol) and triethylamine (83.6 µL, 0.60 mmol) in dichloromethane (1 mL) was added. The reaction was stirred at room temperature for 12 hours. The reaction was then concentrated. The residue was dissolved in DMSO and purified by reverse phase HPLC (10-99% CH₃CN in water) to yield 16 mg of the product. ESI-MS m/z calc. 431.2. found 432.5 (M+1)⁺. Retention time 1.98 minutes.

Step b: 1-(2,3-dihydrobenzo[b][1,4]dioxin-6-yl)-N-(5-methyl-6-(5-methyl-6-oxo-1,6-dihydropyridin-3-yl)pyridin-2-yl)cyclopropanecarboxamide To a solution of 1-(2,3-dihydrobenzo[b][1,4]dioxin-6-yl)-N-(6'-methoxy-3,5'-dimethyl-2,3'-bipyridin-6-yl)cyclopropanecarboxamide (16 mg, 0.037 mmol) in acetonitrile (1 mL) was added TMS-Iodide (21.10 µL, 0.148 mmol). The reaction was stirred at 50° C. for 20 minutes. The reaction solution was diluted with dichloromethane and washed with saturated NaHSO₃ (2×), brine, dried over MgSO₄ and concentrated. The crude product was dissolved in DMSO (1 mL) and purified by reverse phase HPLC (10-99% CH₃CN in water). ESI-MS m/z calc. 417.5. found 418.3 (M+1)⁺. Retention time 1.40 minutes.

CQ. 1-(3-methoxyphenyl)-N-(5-methyl-6-(5-methyl-6-oxo-1,6-dihydropyridin-3-yl)pyridin-2-yl)cyclopropanecarboxamide Step a: N-(6'-methoxy-3,5'-dimethyl-2,3'-bipyridin-6-yl)-1-(3-methoxyphenyl)cyclopropanecarboxamide 1-(3-Methoxyphenyl)cyclopropanecarboxylic acid (38.4 mg, 0.2 mmol) was dissolved in dichloromethane (2 mL) and thionyl chloride (43.8 µL, 0.60 mmol) was added followed by DMF (1 drop) and the reaction was stirred at room temperature for 30 minutes. Then the solvent was removed by evaporation, toluene (~1 mL) was added twice, mixed with the residue and removed by evaporation and then the residue was placed under high vacuum for 10 minutes. It was then dissolved in dichloromethane (1 mL) and a solution of 6'-methoxy-3,5'-dimethyl-2,3'-bipyridin-6-amine (45.9 mg, 0.20 mmol) and triethyl amine (83.6 µL, 0.60 mmol) in dichloromethane (1 mL) was added. The reaction was stirred at room temperature for 12 hours. The reaction was then concentrated. The residue was dissolved in DMSO and purified by reverse phase HPLC (10-99% CH₃CN in water) to yield 41 mg (50% yield) of the product. ESI-MS m/z calc. 403.5. found 404.5 (M+1)⁺. Retention time 2.03 minutes.

Step b: 1-(3-Methoxyphenyl)-N-(5-methyl-6-(5-methyl-6-oxo-1,6-dihydropyridin-3-yl)pyridin-2-yl)cyclopropanecarboxamide To a solution of N-(6'-methoxy-3,5'-dimethyl-2,3'-bipyridin-6-yl)-1-(3-methoxyphenyl)cyclopropanecarboxamide (41 mg, 0.10 mmol) in acetonitrile (2 mL) was added TMS-Iodide (28.0 µL, 0.20 mmol). The reaction was stirred at 50° C. for 20 min. The reaction solution was diluted with dichloromethane and washed with saturated NaHSO₃ (2×), brine, dried over MgSO₄ and concentrated. The crude product was dissolved in DMSO (1 mL) and purified by reverse phase HPLC (Gilson, 10-99% CH₃CN in water) to yield the desired product. ESI-MS m/z calc. 389.4. found 390.5 (M+1)⁺. Retention time 1.41 minutes.

CR. 1-(2,2-Difluorobenzo[d][1,3]-dioxol-5-yl)-N-(6 (1 (2 hydroxyethyl)-2-oxo-1,2-dihydropyridin-4-yl)-4-methylpyridin-2-yl)cyclopropanecarboxamide

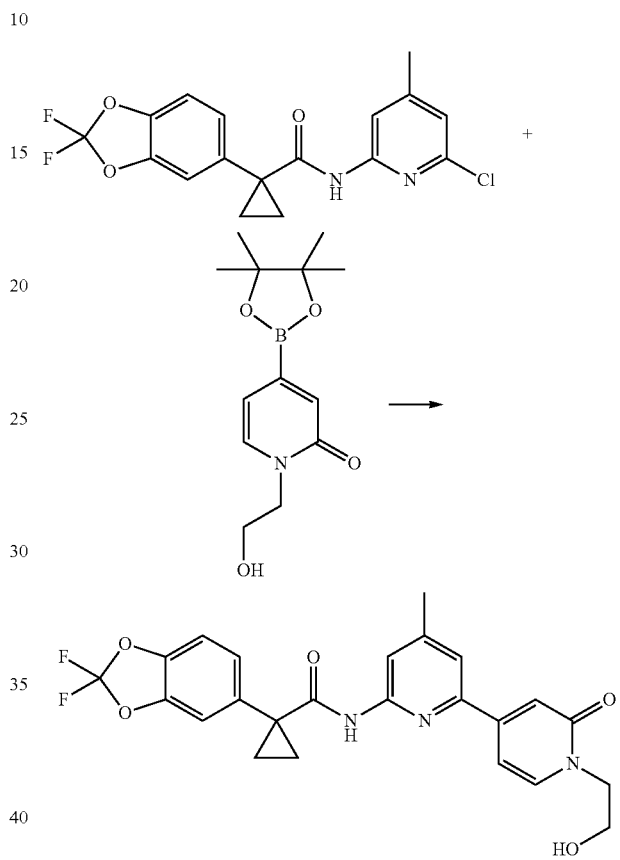

A solution of N-(6-chloro-4-methylpyridin-2-yl)-1-(2,2-difluorobenzo[d][1,3]dioxol-5-yl)cyclopropanecarboxamide (217 mg, 409.0 µmol) in DME (4 mL) was added to a reaction tube containing 1-(2-hydroxyethyl)-4-(4,4,5,5-tetramethyl-1,3,2-dioxaborolan-2-yl)pyridin-2(1H)-one (150 mg, 409.0 µmol) and Pd(PPh₃)₄ (24 mg, 20.5 µmol). Saturated Na₂CO₃ solution was added (400 µL) and the reaction was stirred at 80° C. overnight. The reaction was filtered and concentrated and purified twice by column chromatography (first column: 0-5% MeOH—CH₂Cl₂; second column: 75-100% Ethyl acetate—hexanes then 0-20% EtOH—ethyl acetate) to obtain the product as a brown oil (12 mg) that was redissolved in DMSO and further purified by reverse phase HPLC (10-99% CH₃CN in water) to obtain 4 mg of clean product as a white solid. ESI-MS m/z calc. 469.4. found 470.5 (M+1)⁺. Retention time 1.66 minutes. H NMR (400 MHz, CD₃CN) 8.02 (s, 1H), 7.87 (s, 1H), 7.47-7.43 (m, 2H), 7.39-7.35 (m, 2H), 7.26 (d, J=8.2 Hz, 1H), 6.94 (d, J=1.7 Hz, 1H), 6.69 (dd, J=1.9, 7.1 Hz, 1H), 3.99 (t, J=5.2 Hz, 2H), 3.74 (q, J=5.2 Hz, 2H), 3.29 (t, J=5.6 Hz, 1H), 2.39 (s, 3H), 1.62 (dd, J=3.9, 7.0 Hz, 2H), 1.20 (dd, J=4.0, 7.0 Hz, 2H).

CS. 1-(2,2-difluorobenzo[d][1,3]dioxol-5-yl)-N-(2'-methoxy-3,4-dimethyl-2,3'-bipyridin-6-yl)cyclopropanecarboxamide

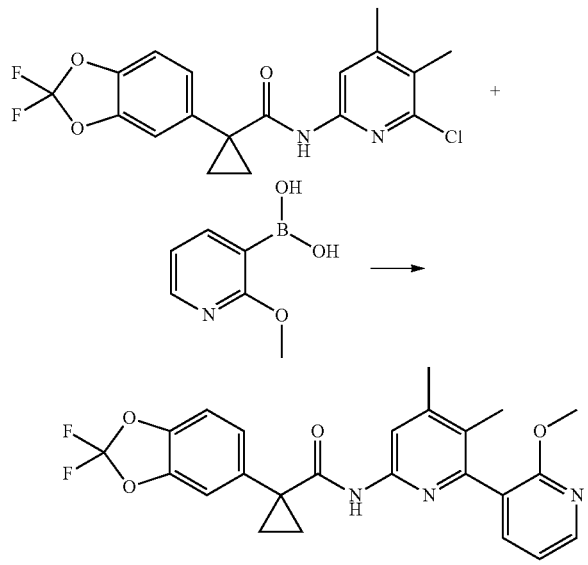

A solution of N-(6-chloro-4,5-dimethylpyridin-2-yl)-1-(2,2-difluorobenzo[d][1,3]dioxol-5-yl)cyclopropanecarboxamide (38 mg, 0.1 mmol) in DME (1 mL) was added to a reaction tube containing 2-methoxypyridin-3-ylboronic acid (46 mg, 0.15 mmol) and Pd(PPh$_3$)$_4$ (6 mg, 0.005 mmol). Saturated Na$_2$CO$_3$ solution was added (100 µL) and the reaction was stirred at 80° C. overnight. The reaction was filtered, concentrated and purified by column chromatography (0-50% ethyl acetate in hexanes) to obtain 50 mg (55%) of a clear oil. ESI-MS m/z calc. 453.4. found 454.5 (M+1)$^+$. Retention times: 1.9 minutes. H NMR (400 MHz, DMSO) 8.81 (s, 1H), 8.22 (dd, J=1.9, 5.0 Hz, 1H), 7.84 (s, 1H), 7.57-7.53 (m, 2H), 7.38-7.31 (m, 2H), 7.05 (dd, J=5.0, 7.2 Hz, 1H), 3.78 (s, 3H), 2.29 (s, 3H), 1.89 (s, 3H), 1.50-1.47 (m, 2H), 1.16-1.13 (m, 2H)

CT. 1-(2,2-difluorobenzo[d][1,3]dioxol-5-yl)-N-(2'-methoxy-3,4-dimethyl-2,4'-bipyridin-6-yl)cyclopropanecarboxamide

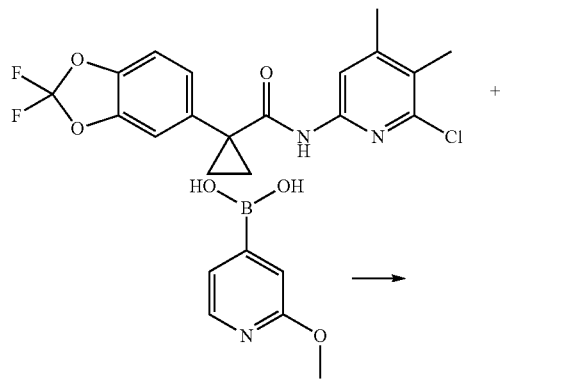

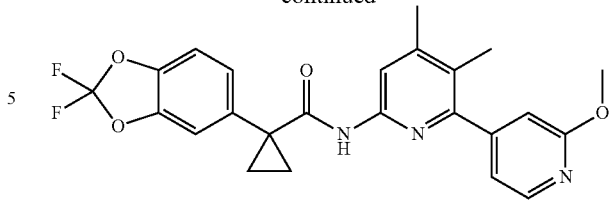

A solution of N-(6-chloro-4,5-dimethylpyridin-2-yl)-1-(2,2-difluorobenzo[d][1,3]dioxol-5-yl)cyclopropanecarboxamide (38 mg, 0.1 mmol) in DME (1 mL) was added to a reaction tube containing 2-methoxypyridin-4-ylboronic acid (46 mg, 0.15 mmol) and Pd(PPh$_3$)$_4$ (6 mg, 0.005 mmol). Saturated Na$_2$CO$_3$ solution was added (100 µL) and the reaction was stirred at 80° C. overnight. The reaction was filtered, concentrated and purified by column chromatography (0-50% ethyl acetate in hexanes) to obtain 40 mg (44%) of a clear oil. ESI-MS m/z calc. 453.4. found 454.3 (M+1)$^+$. Retention times: 2.06 minutes. H NMR (400 MHz, DMSO) 8.85 (s, 1H), 8.20 (d, J=5.2 Hz, 1H), 7.86 (s, 1H), 7.54 (d, J=1.5 Hz, 1H), 7.39 (d, J=8.3 Hz, 1H), 7.32 (dd, J=1.6, 8.3 Hz, 1H), 6.97 (dd, J=1.2, 5.2 Hz, 1H), 6.77 (s, 1H), 3.87 (s, 3H), 2.31 (s, 3H), 2.09 (s, 3H), 1.51-1.48 (m, 2H), 1.17-1.15 (m, 2H).

CU. 1-(2,2-Difluorobenzo[d][1,3]dioxol-5-yl)-N-(6'-methoxy-3,4-dimethyl-2,3'-bipyridin-6-yl)cyclopropanecarboxamide

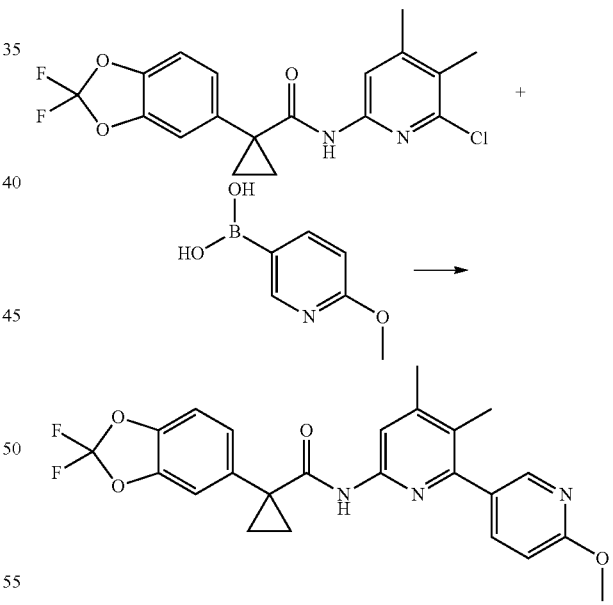

A solution of N-(6-chloro-4,5-dimethylpyridin-2-yl)-1-(2,2-difluorobenzo[d][1,3]dioxol-5-yl)cyclopropanecarboxamide (38 mg, 0.1 mmol) in DME (1 mL) was added to a reaction tube containing 6-methoxypyridin-3-ylboronic acid (46 mg, 0.15 mmol) and Pd(PPh$_3$)$_4$ (6 mg, 0.005 mmol). Saturated Na$_2$CO$_3$ solution was added (100 µL) and the reaction was stirred at 80° C. overnight. The reaction was filtered, concentrated and purified by column chromatography (0-50% ethyl acetate in hexanes) to obtain 40 mg (44%) of a clear oil. ESI-MS m/z calc. 453.4. found 454.3 (M+1)$^+$.

Retention times: 2.06 minutes. H NMR (400 MHz, DMSO) 8.76 (s, 1H), 8.19 (d, J=2.4 Hz, 1H), 7.82 (s, 1H), 7.74 (dd, J=2.4, 8.5 Hz, 1H), 7.55 (d, J=1.3 Hz, 1H), 7.40 (d, J=8.3 Hz, 1H), 7.33 (dd, J=1.5, 8.3 Hz, 1H), 6.87 (d, J=8.5 Hz, 1H), 3.88 (s, 3H), 2.31 (s, 3H), 2.13 (s, 3H), 1.51-1.49 (m, 2H), 1.18-1.15 (m, 2H).

CV. 1-(2,2-difluorobenzo[d][1,3]dioxol-5-yl)-N-(4,5-dimethyl-6-(2-oxo-1,2-dihydropyridin-3-yl)pyridin-2-yl)cyclopropanecarboxamide

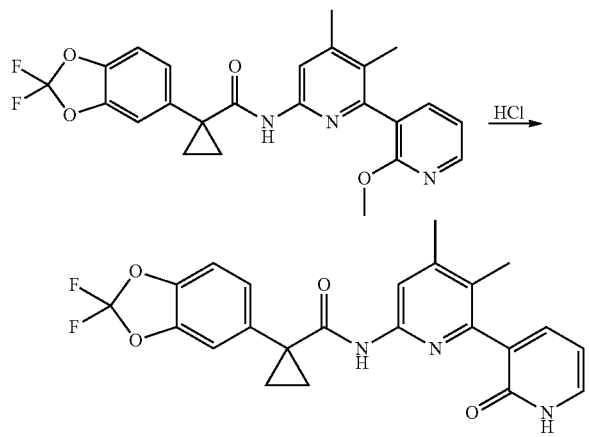

To a solution of 1-(2,2-difluorobenzo[d][1,3]dioxol-5-yl)-N-(2'-methoxy-3,4-dimethyl-2,3'-bipyridin-6-yl)cyclopropanecarboxamide (40 mg, 0.09 mmol) in dioxane (1 mL) was added 4M HCl and the reaction was stirred at 90° C. for 3 hours. To the mixture at room temperature, 0.5 mL of triethyl amine was added and the reaction was concentrated under reduced pressure. The crude residue was purified by column chromatography using a gradient of ethyl acetate in hexanes (50-100%). ESI-MS m/z calc. 439.4. found 440.3 (M+1)$^+$. Retention times: 1.39 minutes. H NMR (400 MHz, DMSO) 8.67 (s, 1H), 7.80 (s, 1H), 7.55 (d, J=1.5 Hz, 1H), 7.44-7.32 (m, 4H), 6.23 (t, J=6.6 Hz, 1H), 2.27 (s, 3H), 1.96 (s, 3H), 1.51-1.48 (m, 2H), 1.16-1.14 (m, 2H).

CW. 1-(2,2-Difluorobenzo[d][1,3]dioxol-5-yl)-N-(4,5-dimethyl-6-(6-oxo-1,6-dihydropyridin-3-yl)pyridin-2-yl)cyclopropanecarboxamide

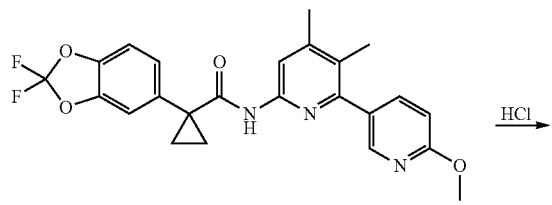

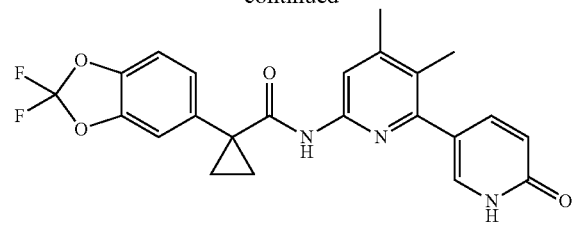

To a solution of 1-(2,2-difluorobenzo[d][1,3]dioxol-5-yl)-N-(6'-methoxy-3,4-dimethyl-2,3'-bipyridin-6-yl)cyclopropanecarboxamide (40 mg, 0.09 mmol) in dioxane (1 mL) was added 4M HCl and the reaction was stirred at 90° C. for 3 hours. To the mixture at room temperature, 0.5 mL of triethyl amine was added and the reaction was concentrated under reduced pressure. The crude residue was purified by column chromatography using a gradient of ethyl acetate in hexanes (50-100%). ESI-MS m/z calc. 439.4. found 440.3 (M+1)$^+$. Retention times: 1.53 minutes. H NMR (400 MHz, DMSO) 8.79 (s, 1H), 7.76 (s, 1H), 7.56-7.53 (m, 2H), 7.44-7.32 (m, 3H), 6.35 (d, J=9.4 Hz, 1H), 2.28 (s, 3H), 2.15 (s, 3H), 1.50-1.48 (m, 2H), 1.17-1.15 (m, 2H).

CX. 1-(2,2-Difluorobenzo[d][1,3]dioxol-5-yl)-N-(4,5-dimethyl-6-(2-oxo-1,2-dihydropyridin-4-yl)pyridin-2-yl)cyclopropanecarboxamide

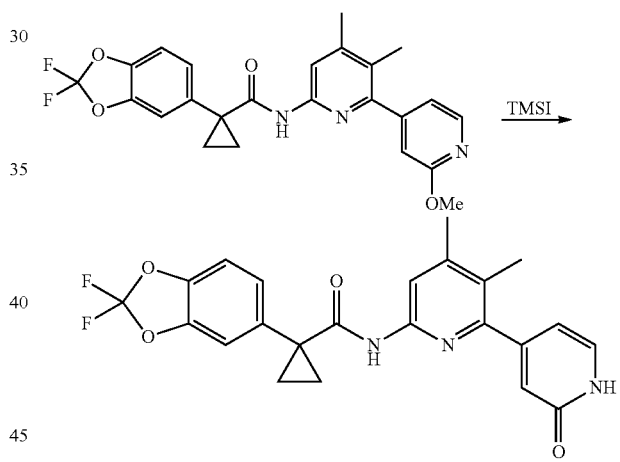

To a solution of 1-(2,2-difluorobenzo[d][1,3]dioxol-5-yl)-N-(2'-methoxy-3,4-dimethyl-2,4'-bipyridin-6-yl)cyclopropanecarboxamide (20 mg, 0.044 mmol) in chloroform (1 mL) was added TMS-Iodide (25.6 μL, 0.18 mmol). The reaction was stirred at 55° C. for one hour. The reaction solution was diluted with dichloromethane and washed with saturated NaHSO$_3$ (2×), brine, dried over MgSO$_4$ and concentrated. The crude product purified by reverse phase HPLC (10-99% CH$_3$CN in water) to yield the desired product. ESI-MS m/z calc. 439.4. found 440.5 (M+1)$^+$. Retention time 1.61 minutes.

The analytical data for the compounds of Table 1 are shown below in Table 2:

TABLE 2

| Cmpd # | LC/MS M + 1 | LC/RT min | NMR ($^1$H) δ |
|---|---|---|---|
| 1 | 456.5 | 1.44 | |
| 2 | 390.5 | 1.8 | |

TABLE 2-continued

| Cmpd # | LC/MS M + 1 | LC/RT min | NMR (¹H) δ |
|---|---|---|---|
| 3 | 440.3 | 2.19 | |
| 4 | 483.3 | 1.58 | |
| 5 | 440 | 1.79 | |
| 6 | 440.3 | 1.64 | H NMR (400 MHz, DMSO) 11.67 (s, 1H), 8.93 (s, 1H), 7.80 (d, J = 8.3 Hz, 1H), 7.64 (d, J = 8.4 Hz, 1H), 7.57-7.48 (m, 2H), 7.41-7.39 (m, 2H), 7.43-7.31 (m, 1H), 2.27 (s, 3H), 1.98 (s, 3H), 1.51-1.47 (m, 2H), 1.17-1.14 (m, 2H) |
| 7 | 390.5 | 1.76 | |
| 8 | 454.3 | 2.12 | |
| 9 | 455.5 | 1.76 | |
| 10 | 376.7 | 1.26 | |
| 11 | 440 | 1.95 | |
| 12 | 426 | 1.45 | H NMR (400 MHz, DMSO) 11.78 (s, 1H), 8.91 (s, 1H), 7.81 (d, J = 8.3 Hz, 1H), 7.66-7.64 (m, 2H), 7.56-7.55 (m, 2H), 7.41 (d, J = 8.3 Hz, 1H), 7.34 (dd, J = 1.7, 8.3 Hz, 1H), 6.36 (d, J = 9.5 Hz, 1H), 2.28 (s, 3H), 1.52-1.49 (m, 2H), 1.18-1.15 (m, 2H) |
| 13 | 484.5 | 1.62 | |
| 14 | 440 | 1.41 | |
| 15 | 440.1 | 1.94 | |
| 16 | 498.3 | 1.76 | H NMR (400 MHz, DMSO) 9.01 (s, 1H), 7.92 (d, J = 8.4 Hz, 1H), 7.75-7.70 (m, 2H), 7.55 (d, J = 1.6 Hz, 1H), 7.40 (d, J = 8.3 Hz, 1H), 7.34 (dd, J = 1.7, 8.3 Hz, 1H), 6.44 (d, J = 1.6 Hz, 1H), 6.35 (dd, J = 1.9, 7.0 Hz, 1H), 4.74 (s, 2H), 3.69 (s, 3H), 2.26 (s, 3H), 1.52-1.50 (m, 2H), 1.19-1.16 (m, 2H) |
| 17 | 426.3 | 1.32 | |
| 18 | 454 | 1.9 | |
| 19 | 426.3 | 1.7 | |
| 20 | 470.5 | 1.66 | |
| 21 | 456.3 | 1.54 | |
| 22 | 446.3 | 1.62 | |
| 23 | 470.3 | 1.72 | |
| 24 | 459.9 | 2.26 | |
| 25 | 460.3 | 1.74 | |
| 26 | 376.5 | 1.45 | |
| 27 | 426.3 | 1.68 | |
| 28 | 442.3 | 1.42 | |
| 29 | 470.5 | 1.58 | H NMR (400 MHz, DMSO-d6) 8.87 (s, 1H), 7.91 (d, J = 8.4 Hz, 1H), 7.73 (d, J = 8.5 Hz, 1H), 7.63 (d, J = 6.9 Hz, 1H), 7.56 (d, J = 1.6 Hz, 1H), 7.41 (d, J = 8.3 Hz, 1H), 7.34 (dd, J = 1.7, 8.3 Hz, 1H), 6.39 (d, J = 1.8 Hz, 1H), 6.26 (dd, J = 1.9, 6.9 Hz, 1H), 3.96 (t, J = 5.4 Hz, 2H), 3.63 (t, J = 5.5 Hz, 2H), 2.26 (s, 3H), 1.52-1.50 (m, 2H), 1.19-1.16 (m, 2H). |
| 30 | 454 | 2.12 | |
| 31 | 440.3 | 1.55 | |
| 32 | 483.5 | 1.57 | |
| 33 | 497.5 | 1.83 | |
| 34 | 469.3 | 1.5 | |
| 35 | 440 | 1.75 | |
| 36 | 454.3 | 1.97 | |
| 37 | 440 | 2 | |
| 38 | 440.3 | 2.21 | |
| 39 | 444 | 1.58 | |
| 40 | 440.3 | 1.56 | H NMR (400 MHz, DMSO) 11.69 (s, 1H), 8.91 (s, 1H), 7.88 (d, J = 8.4 Hz, 1H), 7.68 (d, J = 8.5 Hz, 1H), 7.55 (d, J = 1.5 Hz, 1H), 7.39 (d, J = 8.3 Hz, 1H), 7.33 (dd, J = 1.7, 8.3 Hz, 1H), 7.22 (d, J = 9.3 Hz, 1H), 6.17 (d, J = 9.3 Hz, 1H), 2.05 (s, 3H), 1.90 (s, 3H), 1.51-1.48 (m, 2H), 1.17-1.14 (m, 2H) |
| 41 | 440.5 | 1.65 | H NMR (400 MHz, DMSO) 8.92 (s, 1H), 7.91 (d, J = 8.4 Hz, 1H), 7.73-7.71 (m, 2H), 7.56 (d, J = 1.5 Hz, 1H), 7.41 (d, J = 8.3 Hz, 1H), 7.34 (dd, J = 1.7, 8.3 Hz, 1H), 6.40 (d, J = 1.6 Hz, 1H), 6.27 (dd, J = 1.9, 6.9 Hz, 1H), 3.45 (s, 3H), 2.24 (s, 3H), 1.52-1.49 (m, 2H), 1.19-1.16 (m, 2H) |
| 42 | 451.3 | 1.7 | |
| 43 | 458.5 | 2.25 | |
| 44 | 426.3 | 1.57 | |
| 45 | 390.5 | 1.84 | |
| 46 | 426 | 1.33 | |

TABLE 2-continued

| Cmpd # | LC/MS M + 1 | LC/RT min | NMR ($^1$H) δ |
|---|---|---|---|
| 47 | 484.5 | 1.62 | H NMR (400 MHz, DMSO) 8.98 (s, 1H), 7.92 (d, J = 8.4 Hz, 1H), 7.74-7.68 (m, 2H), 7.55 (d, J = 1.6 Hz, 1H), 7.41-7.32 (m, 2H), 6.43 (d, J = 1.7 Hz, 1H), 6.32 (dd, J = 1.9, 7.0 Hz, 1H), 4.64 (s, 2H), 2.26 (s, 3H), 1.52-1.50 (m, 2H), 1.18-1.16 (m, 2H) |
| 48 | 440.3 | 1.91 | |
| 49 | 390.3 | 2.02 | |
| 50 | 426.3 | 1.67 | |
| 51 | 412.5 | 1.31 | |
| 52 | 440.5 | 1.61 | |
| 53 | 484.5 | 1.84 | |
| 54 | 427.5 | 1.48 | H NMR (400 MHz, DMSO) 9.37 (s, 1H), 9.02 (s, 1H), 7.55-7.51 (m, 3H), 7.38 (d, J = 8.3 Hz, 1H), 7.32 (dd, J = 1.7, 8.3 Hz, 1H), 6.30 (t, J = 6.6 Hz, 1H), 2.33 (s, 3H), 1.55-1.52 (m, 2H), 1.21-1.18 (m, 2H) |
| 55 | 427.5 | 1.49 | H NMR (400 MHz, DMSO) 9.44 (s, 1H), 8.97 (s, 1H), 7.75-7.70 (m, 2H), 7.54 (d, J = 1.6 Hz, 1H), 7.39 (d, J = 8.3 Hz, 1H), 7.32 (dd, J = 1.7, 8.3 Hz, 1H), 6.41 (d, J = 9.4 Hz, 1H), 2.52 (s, 3H), 1.55-1.52 (m, 2H), 1.22-1.19 (m, 2H) |
| 56 | 454.5 | 1.9 | H NMR (400 MHz, DMSO) 8.81 (s, 1 H), 8.22 (dd, J = 1.9, 5.0 Hz, 1H), 7.84 (s, 1H), 7.57-7.53 (m, 2H), 7.38-7.31 (m, 2H), 7.05 (dd, J = 5.0, 7.2 Hz, 1H), 3.78 (s, 3H), 2.29 (s, 3H), 1.89 (s, 3H), 1.50-1.47 (m, 2H), 1.16-1.13 (m, 2H) |
| 57 | 454.3 | 2.06 | H NMR (400 MHz, DMSO) 8.76 (s, 1H), 8.19 (d, J = 2.4 Hz, 1H), 7.82 (s, 1H), 7.74 (dd, J = 2.4, 8.5 Hz, 1H), 7.55 (d, J = 1.3 Hz, 1H), 7.40 (d, J = 8.3 Hz, 1H), 7.33 (dd, J = 1.5, 8.3 Hz, 1H), 6.87 (d, J = 8.5 Hz, 1H), 3.88 (s, 3H), 2.31 (s, 3H), 2.13 (s, 3H), 1.51-1.49 (m, 2H), 1.18-1.15 (m, 2H) |
| 58 | 454.3 | 2.06 | H NMR (400 MHz, DMSO) 8.85 (s, 1H), 8.20 (d, J = 5.2 Hz, 1H), 7.86 (s, 1H), 7.54 (d, J = 1.5 Hz, 1H), 7.39 (d, J = 8.3 Hz, 1H), 7.32 (dd, J = 1.6, 8.3 Hz, 1H), 6.97 (dd, J = 1.2, 5.2 Hz, 1H), 6.77 (s, 1H), 3.87 (s, 3H), 2.31 (s, 3H), 2.09 (s, 3H), 1.51-1.48 (m, 2H), 1.17-1.15 (m, 2H) |
| 59 | 402.5 | 1.32 | |
| 60 | 418.3 | 1.42 | |
| 61 | 394.3 | 1.57 | |
| 62 | 424.3 | 1.54 | |
| 63 | 390.5 | 1.44 | |
| 64 | 470.5 | 1.66 | H NMR (400 MHz, CD3CN) 8.02 (s, 1H), 7.87 (s, 1H), 7.47-7.43 (m, 2H), 7.39-7.35 (m, 2H), 7.26 (d, J = 8.2 Hz, 1H), 6.94 (d, J = 1.7 Hz, 1H), 6.69 (dd, J = 1.9, 7.1 Hz, 1H), 3.99 (t, J = 5.2 Hz, 2H), 3.74 (q, J = 5.2 Hz, 2H), 3.29 (t, J = 5.6 Hz, 1H), 2.39 (s, 3H), 1.62 (dd, J = 3.9, 7.0 Hz, 2H), 1.20 (dd, J = 4.0, 7.0 Hz, 2H) |
| 65 | 440.3 | 1.53 | H NMR (400 MHz, DMSO) 8.79 (s, 1H), 7.76 (s, 1H), 7.56-7.53 (m, 2H), 7.44-7.32 (m, 3H), 6.35 (d, J = 9.4 Hz, 1H), 2.28 (s, 3H), 2.15 (s, 3H), 1.50-1.48 (m, 2H), 1.17-1.15 (m, 2H) |
| 66 | 440.3 | 1.39 | H NMR (400 MHz, DMSO) 8.67 (s, 1H), 7.80 (s, 1H), 7.55 (d, J = 1.5 Hz, 1H), 7.44-7.32 (m, 4H), 6.23 (t, J = 6.6 Hz, 1H), 2.27 (s, 3H), 1.96 (s, 3H), 1.51-1.48 (m, 2H), 1.16-1.14 (m, 2H) |
| 67 | 440.5 | 1.61 | |
| 68 | 388.1 | 1.35 | |
| 69 | 388.3 | 1.38 | |
| 70 | 388.3 | 1.36 | |
| 71 | 474.3 | 2.35 | |
| 72 | 470.5 | 1.97 | |
| 73 | 511.5 | 1.82 | |
| 74 | 508.5 | 1.6 | |
| 75 | 440 | 1.56 | |
| 76 | 402.5 | 1.47 | |
| 77 | 441.3 | 1.39 | |
| 78 | 388.3 | 1.39 | H NMR (400 MHz, DMSO-d6) 11.75 (s, 1H), 8.18 (s, 1H), 7.89 (d, J = 8.3 Hz, 1H), 7.67 (d, J = 8.4 Hz, 1H), 7.61-7.58 (m, 1H), 7.51 (m, 1H), 7.37 (m, 1H), 7.26-7.23 (m, 1H), 6.81 (d, J = 8.2 Hz, 1H), 6.36 (d, J = 9.5 Hz, 1H), 4.55 (t, J = 8.7 Hz, 2H), 3.19 (t, J = 8.7 Hz, 2H), 2.27 (s, 3H), 1.49-1.46 (m, 2H), 1.11-1.09 (m, 2H) |
| 79 | 500.3 | 1.46 | |

TABLE 2-continued

| Cmpd # | LC/MS M + 1 | LC/RT min | NMR ($^1$H) δ |
|---|---|---|---|
| 80 | 388.5 | 1.41 | H NMR (400 MHz, DMSO-d6) 11.66 (s, 1H), 8.19 (s, 1H), 7.99 (d, J = 8.4 Hz, 1H), 7.73 (d, J = 8.5 Hz, 1H), 7.40-7.37 (m, 2H), 7.26-7.24 (m, 1H), 6.80 (d, J = 8.2 Hz, 1H), 6.28 (m, 1H), 6.18-6.15 (m, 1H), 4.55 (t, J = 8.7 Hz, 2H), 3.19 (t, J = 8.6 Hz, 2H), 2.22 (s, 3H), 1.49-1.47 (m, 2H), 1.11-1.09 (m, 2H) |
| 81 | 541.7 | 1.69 | |
| 82 | 443.96 | 1.52 | |
| 83 | 402.5 | 1.32 | |
| 84 | 388.5 | 1.23 | H NMR (400 MHz, DMSO-d6) 11.81 (s, 1H), 8.02 (s, 1H), 7.94 (d, J = 8.3 Hz, 1H), 7.62 (d, J = 8.4 Hz, 1H), 7.45 (m, 1H), 7.37-7.35 (m, 2H), 7.24 (m, 1H), 6.80 (d, J = 8.2 Hz, 1H), , 6.24 (m, 1H), 4.54 (t, J = 8.7 Hz, 2H), 3.19 (t, J = 8.7 Hz, 2H), 2.07 (s, 3H), 1.50-1.47 (m, 2H), 1.11-1.08 (m, 2H) |
| 85 | 459.9 | 1.69 | |
| 86 | 460.3 | 1.68 | H NMR (400 MHz, DMSO-d6) 12.26 (s, 1H), 9.11 (s, 1H), 7.97 (d, J = 8.5 Hz, 1H), 7.75 (d, J = 8.6 Hz, 1H), 7.55 (m, 1H), 7.44 (d, J = 6.6 Hz, 1H), 7.40-7.38 (m, 1H), 7.35-7.32 (m, 1H), 6.11 (d, J = 6.6 Hz, 1H), 2.06 (s, 3H), 1.51-1.50 (m, 2H), 1.17-1.15 (m, 2H) |
| 87 | 454.2 | 1.96 | |
| 88 | 468.2 | 2.02 | |
| 89 | 468.2 | 1.94 | |
| 90 | 454.2 | 1.49 | |
| 91 | 454.5 | 1.52 | |
| 92 | 440.5 | 1.43 | |
| 93 | 390.1 | 3.09 | |
| 94 | 390.1 | 3.57 | |
| 95 | 532.1 | 1.52 | H NMR (400 MHz, CD3CN) 7.94 (d, J = 8.4 Hz, 1H), 7.77 (s, 1 H), 7.65 (d, J = 2.3 Hz, 1H), 7.62-7.55 (m, 2H), 7.36-7.32 (m, 2H), 7.22 (d, J = 8.2 Hz, 1H), 6.42 (d, J = 9.4 Hz, 1H), 4.29 (t, J = 6.7 Hz, 2H), 3.49 (t, J = 6.7 Hz, 2H), 2.90 (s, 3H), 2.32 (s, 3H), 1.62-1.58 (m, 2H), 1.19-1.15 (m, 2H) |
| 96 | 451.1 | 1.6 | H NMR (400 MHz, CDCl3) 8.17 (s, 1H), 8.07-8.03 (m, 2H), 7.82 (s, 1H), 7.26 (dd, J = 1.7, 8.2 Hz, 1H), 7.19-7.16 (m, 2H), 6.69 (d, J = 10.4 Hz, 1H), 2.58 (s, 3H), 1.80-1.75 (m, 2 H), 1.27-1.22 (m, 2H). |
| 97 | 465.1 | 2 | |
| 98 | 388.2 | 1.44 | |
| 99 | 388.2 | 1.32 | 1H NMR, DMSO-d6: 1.11 (ABq, 2H, J = 3.0, 6.0 Hz), 1.46 (ABq, 2H, J = 3.0, 6.0 Hz), 2.26 (s, 3H), 3.18 (t, 2H, J = 6.0 Hz), 4.55 (t, 2H, J = 6.0 Hz), 6.35 (d, 1H, J = 9.0 Hz), 6.89 (d, 1H, J = 3.0 Hz), 6.96 (dd, 1H, J = 3.0, 6.0 Hz), 7.26 (d, 1H, J = 6.0 Hz), 7.50 (d, 1H, J = 3.0 Hz), 7.59 (dd, 1H, 3.0, 6.0 Hz), 7.66(d, 1H, J = 6.0 Hz), 7.89 (d, 1H, J = 6.0 Hz), 8.27 (s, 1H), 11.76 (s, 1H). |
| 100 | 416.5 | 1.68 | 1H NMR (400.0 MHz, DMSO-d6) d 8.22 (dd, J = 1.9, 5.0 Hz, 1H), 8.01 (s, 1H), 7.92 (s, 1H), 7.52 (dd, J = 1.9, 7.2 Hz, 1H), 7.35 (s, 1 H), 7.22 (d, J = 8.2 Hz, 1H), 7.07-7.03 (m, 1H), 6.77 (d, J = 8.2 Hz, 1H), 4.50 (t, J = 8.8 Hz, 2H), 3.80 (s, 3H), 3.15 (t, J = 8.7 Hz, 2H), 2.30 (s, 3H), 1.90 (s, 3H), 1.48-1.40 (m, 2H) and 1.10-1.05 (m, 2H) ppm |
| 101 | 416.5 | 1.66 | 1H NMR (400.0 MHz, DMSO-d6) d 8.16 (d, J = 2.4 Hz, 1H), 8.03 (s, 1H), 7.91 (s, 1H), 7.71 (dd, J = 2.5, 8.5 Hz, 1H), 7.36 (s, 1H), 7.23 (d, J = 8.2 Hz, 1H), 6.86 (d, J = 8.5 Hz, 1H), 6.79 (d, J = 8.2 Hz, 1H), 4.55 (t, J = 8.8 Hz, 2H), 3.90 (s, 3H), 3.15 (t, J = 8.7 Hz, 2H), 2.30 (s, 3H), 2.10 (s, 3H), 1.48-1.45 (m, 2H) and 1.10-1.08 (m, 2H) ppm |
| 102 | 416.7 | 1.74 | 1H NMR (400.0 MHz, DMSO-d6) d 8.20 (d, J = 5.2 Hz, 1H), 8.07 (s, 1H), 7.95 (s, 1H), 7.36 (s, 1H), 7.23 (d, J = 8.2 Hz, 1H), 6.94 (d, J = 5.2 Hz, 1H), 6.79 (d, J = 8.2 Hz, 1H), 6.74 (s, 1H), 4.53 (t, J = 8.8 Hz, 2H), 3.87 (s, 3H), 3.17 (t, J = 8.7 Hz, 2H), 2.31 (s, 3H), 2.08 (s, 3H), 1.48-1.46 (m, 2H) and 1.11-1.09 (m, 2H) ppm |
| 103 | 468.3 | 1.8 | 1H NMR (400.0 MHz, DMSO-d6) d 8.81 (s, 1H), 7.85 (s, 1H), 7.54 (s, 1H), 7.42-7.31 (m, 3H), 6.67 (d, J = 8.4 Hz, 1H), 3.86 (s, 3H), 2.30 (s, 3H), 2.08 (s, 3H), 1.92 (s, 3H), 1.51-1.48 (m, 2H) and 1.17-1.15 (m, 2H) ppm |
| 104 | 468.7 | 1.96 | 1H NMR (400.0 MHz, DMSO-d6) d 8.78 (s, 1H), 8.01 (s, 1H), 7.81 (s, 1H), 7.58-7.56 (m, 2H), 7.41-7.34 (m, 2H), 3.91 (s, 3H), 2.30 (s, 3H), 2.17 (s, 3H), 2.13 (s, 3H), 1.50-1.48 (m, 2H) and 1.18-1.16 (m, 2H) ppm |

TABLE 2-continued

| Cmpd # | LC/MS M + 1 | LC/RT min | NMR ($^1$H) δ |
|---|---|---|---|
| 105 | 454.5 | 1.81 | 1H NMR (400.0 MHz, DMSO-d6) d 8.98 (s, 1H), 7.92 (d, J = 8.4 Hz, 1H), 7.73 (d, J = 8.5 Hz, 1H), 7.55 (s, 1H), 7.40 (d, J = 8.3 Hz, 1H), 7.34 (d, J = 8.3 Hz, 1H), 6.88 (s, 1H), 6.64 (s, 1H), 3.85 (s, 3H), 2.42 (s, 3H), 2.21 (s, 3H), 1.52-1.49 (m, 2H) and 1.18-1.16 (m, 2H) ppm |
| 106 | 440.5 | 1.6 | 1H NMR (400.0 MHz, DMSO-d6) d 11.66 (s, 1H), 8.96 (s, 1H), 7.90 (d, J = 8.4 Hz, 1H), 7.71 (d, J = 8.5 Hz, 1H), 7.56 (s, 1H), 7.41 (d, J = 8.3 Hz, 1H), 7.34 (d, J = 8.3 Hz, 1H), 6.10 (s, 1H), 6.01 (s, 1H), 2.22 (s, 3H), 2.18 (s, 3H), 1.52-1.49 (m, 2H) and 1.18-1.15 (m, 2H) ppm |
| 107 | 440.5 | 1.72 | 1H NMR (400.0 MHz, DMSO-d6) d 11.78 (s, 1H), 8.84 (s, 1H), 7.97 (s, 1H), 7.91 (s, 1H), 7.69 (s, 1H), 7.58 (s, 1H), 7.44 (d, J = 8.3 Hz, 1H), 7.38 (s, 1H), 7.36 (d, J = 8.4 Hz, 1H), 2.32 (s, 3H), 2.02 (s, 3H), 1.53-1.50 (m, 2H) and 1.20-1.18 (m, 2H) ppm |
| 108 | 454.3 | 1.5 | 1H NMR (400.0 MHz, DMSO-d6) d 11.66 (s, 1H), 8.81 (s, 1H), 7.81 (s, 1H), 7.54 (s, 1H), 7.39 (d, J = 8.3 Hz, 1H), 7.33 (d, J = 8.3 Hz, 1H), 7.19 (d, J = 9.3 Hz, 1H), 6.17 (d, J = 9.3 Hz, 1H), 2.28 (s, 3H), 1.98 (s, 3H), 1.89 (s, 3H), 1.50-1.48 (m, 2H) and 1.17-1.14 (m, 2H) ppm |
| 109 | 402.5 | 1.41 | 1H NMR (400.0 MHz, DMSO-d6) d 11.66 (s, 1H), 8.06 (s, 1H), 7.93 (s, 1H), 7.39 (d, J = 6.6 Hz, 1H), 7.36 (s, 1H), 7.23 (d, J = 8.2 Hz, 1H), 6.80 (d, J = 8.2 Hz, 1H), 6.19 (s, 1H), 6.10 (d, J = 6.6 Hz, 1H), 4.55 (t, J = 8.8 Hz, 2H), 3.19 (t, J = 8.7 Hz, 2H), 2.30 (s, 3H), 2.10 (s, 3H), 1.49-1.46 (m, 2H) and 1.11-1.08 (m, 2H) ppm |
| 110 | 523.5 | 1.86 | 1H NMR (400.0 MHz, DMSO-d6) d 9.13 (s, 1H), 8.46 (s, 1 H), 8.34 (s, 1 H), 7.89 (d, J = 8.4 Hz, 1H), 7.72 (d, J = 8.5 Hz, 1H), 7.54 (s, 1H), 7.41 (d, J = 8.3 Hz, 1H), 7.32 (d, J = 8.3 Hz, 1H), 4.88 (s, 2H), 3.71 (s, 3H), 2.30 (s, 3H), 1.52-1.49 (m, 2H) and 1.19-1.16 (m, 2H) ppm |
| 111 | 454.5 | 1.58 | 1H NMR (400.0 MHz, DMSO-d6) d 11.60 (s, 1H), 8.82 (s, 1H), 7.75 (s, 1H), 7.55 (s, 1H), 7.42-7.29 (m, 4H), 2.28 (s, 3H), 2.16 (s, 3H), 1.99 (s, 3H), 1.49-1.48 (m, 2H) and 1.17-1.16 (m, 2H) ppm |
| 112 | 402.3 | 1.33 | 1H NMR (400.0 MHz, DMSO-d6) d 11.72 (s, 1H), 8.06 (s, 1H), 7.85 (s, 1H), 7.50 (d, J = 9.4 Hz, 1H), 7.41 (s, 1H), 7.36 (s, 1H), 7.24 (d, J = 8.2 Hz, 1H), 6.80 (d, J = 8.2 Hz, 1H), 6.35 (d, J = 9.4 Hz, 1H), 4.55 (t, J = 8.8 Hz, 2H), 3.21-3.17 (m, 2H), 2.28 (s, 3H), 2.14 (s, 3H), 1.48-1.45 (m, 2H) and 1.10-1.08 (m, 2H) ppm |
| 113 | 440.5 | 1.6 | |
| 114 | 402.5 | 1.18 | 1H NMR (400.0 MHz, DMSO-d6) d 11.78 (s, 1H), 7.91 (s, 1H), 7.88 (s, 1H), 7.43 (d, J = 6.3 Hz, 1H), 7.36 (s, 1H), 7.32 (d, J = 6.7 Hz, 1H), 7.23 (d, J = 8.1 Hz, 1H), 6.79 (d, J = 8.2 Hz, 1H), 6.23 (t, J = 6.6 Hz, 1H), 4.54 (t, J = 8.7 Hz, 2H), 3.19 (t, J = 8.7 Hz, 2H), 2.27 (s, 3H), 1.95 (s, 3H), 1.48-1.47 (m, 2H) and 1.09-1.08 (m, 2H) ppm |
| 115 | 386.5 | 1.58 | 1H NMR (400.0 MHz, DMSO-d6) d 11.76 (s, 1H), 8.24 (s, 1H), 7.89 (d, J = 8.3 Hz, 1H), 7.67 (d, J = 8.5 Hz, 1H), 7.58 (d, J = 9.5 Hz, 1H), 7.50 (s, 1H), 7.36 (s, 1H), 7.27 (s, 2H), 6.35 (d, J = 9.5 Hz, 1H), 2.87 (t, J = 7.4 Hz, 4H), 2.26 (s, 3H), 2.03 (qn, J = 7.4 Hz, 2H), 1.49-1.47 (m, 2H) and 1.13-1.12 (m, 2H) ppm |
| 116 | 484.5 | 1.49 | 1H NMR (400.0 MHz, DMSO-d6) d 8.76 (s, 1H), 7.86 (d, J = 8.3 Hz, 1H), 7.61 (d, J = 8.4 Hz, 1H), 7.56 (s, 1H), 7.49 (s, 1H), 7.40 (d, J = 8.3 Hz, 1H), 7.34 (d, J = 8.3 Hz, 1H), 7.26 (s, 1H), 4.88 (t, J = 5.3 Hz, 1H), 3.95-3.92 (m, 2H), 3.62-3.58 (m, 2H), 2.06 (s, 3H), 2.04 (s, 3H), 1.51-1.48 (m, 2H), and 1.17-1.14 (m, 2H) ppm |
| 117 | 440.5 | 1.58 | 1H NMR (400.0 MHz, DMSO-d6) d 11.68 (s, 1H), 8.75 (s, 1H), 7.74 (s, 1H), 7.58 (s, 1H), 7.51 (d, J = 9.4 Hz, 1H), 7.43 (d, J = 8.3 Hz, 1H), 7.35 (d, J = 8.3 Hz, 1H), 7.04 (s, 1H), 6.20 (d, J = 9.5 Hz, 1H), 2.33 (s, 3H), 2.24 (s, 3H), 1.52-1.50 (m, 2H) and 1.21-1.18 (m, 2H) ppm |

Assays

Assays for Detecting and Measuring ΔF508-CFTR Correction Properties of Compounds Membrane Potential Optical Methods for Assaying ΔF508-CFTR Modulation Properties of Compounds The optical membrane potential assay utilized voltage-sensitive FRET sensors described by Gonzalez and Tsien (See Gonzalez, J. E. and R. Y. Tsien (1995) "Voltage sensing by fluorescence resonance energy transfer in single cells" *Biophys J* 69(4): 1272-80, and Gonzalez, J. E. and R. Y. Tsien (1997) "Improved indicators of cell membrane potential that use fluorescence resonance energy transfer" *Chem Biol* 4(4): 269-77) in combination with instrumentation for measuring fluorescence changes such as the Voltage/Ion Probe Reader (VIPR) (See, Gonzalez, J. E., K. Oades, et al. (1999) "Cell-based assays and instrumentation for screening ion-channel targets" *Drug Discov Today* 4(9): 431-439).

These voltage sensitive assays are based on the change in fluorescence resonant energy transfer (FRET) between the membrane-soluble, voltage-sensitive dye, DiSBAC$_2$(3), and a fluorescent phospholipid, CC2-DMPE, which is attached to the outer leaflet of the plasma membrane and acts as a FRET donor. Changes in membrane potential ($V_m$) cause the negatively charged DiSBAC$_2$(3) to redistribute across the plasma membrane and the amount of energy transfer from CC2-DMPE changes accordingly. The changes in fluorescence emission were monitored using VIPR™ II, which is an integrated liquid handler and fluorescent detector designed to conduct cell-based screens in 96- or 384-well microtiter plates.

1. Identification of Correction Compounds

To identify small molecules that correct the trafficking defect associated with ΔF508-CFTR; a single-addition HTS assay format was developed. The cells were incubated in serum-free medium for 16 hrs at 37° C. in the presence or absence (negative control) of test compound. As a positive control, cells plated in 384-well plates were incubated for 16 hrs at 27° C. to "temperature-correct" ΔF508-CFTR. The cells were subsequently rinsed 3× with Krebs Ringers solution and loaded with the voltage-sensitive dyes. To activate ΔF508-CFTR, 10 μM forskolin and the CFTR potentiator, genistein (20 μM), were added along with Cl⁻-free medium to each well. The addition of Cl⁻-free medium promoted Cl⁻ efflux in response to ΔF508-CFTR activation and the resulting membrane depolarization was optically monitored using the FRET-based voltage-sensor dyes.

2. Identification of Potentiator Compounds

To identify potentiators of ΔF508-CFTR, a double-addition HTS assay format was developed. During the first addition, a Cl⁻-free medium with or without test compound was added to each well. After 22 sec, a second addition of Cl⁻-free medium containing 2-10 μM forskolin was added to activate ΔF508-CFTR. The extracellular Cl⁻ concentration following both additions was 28 mM, which promoted Cl⁻ efflux in response to ΔF508-CFTR activation and the resulting membrane depolarization was optically monitored using the FRET-based voltage-sensor dyes. *Solutions* Bath Solution #1: (in mM) NaCl 160, KCl 4.5, CaCl$_2$ 2, MgCl$_2$ 1, HEPES 10, pH 7.4 with NaOH.

Chloride-free bath solution: Chloride salts in Bath Solution #1 are substituted with gluconate salts.
CC2-DMPE: Prepared as a 10 mM stock solution in DMSO and stored at −20° C.
DiSBAC$_2$(3): Prepared as a 10 mM stock in DMSO and stored at −20° C.

4. Cell Culture

NIH3T3 mouse fibroblasts stably expressing ΔF508-CFTR are used for optical measurements of membrane potential. The cells are maintained at 37° C. in 5% CO$_2$ and 90% humidity in Dulbecco's modified Eagle's medium supplemented with 2 mM glutamine, 10% fetal bovine serum, 1×NEAA, β-ME, 1× pen/strep, and 25 mM HEPES in 175 cm² culture flasks. For all optical assays, the cells were seeded at 30,000/well in 384-well matrigel-coated plates and cultured for 2 hrs at 37° C. before culturing at 27° C. for 24 hrs for the potentiator assay. For the correction assays, the cells are cultured at 27° C. or 37° C. with and without compounds for 16-24 hours *Electrophysiological Assays for assaying ΔF508-CFTR modulation properties of compounds*

2. Using Chamber Assay

Using chamber experiments were performed on polarized epithelial cells expressing ΔF508-CFTR to further characterize the ΔF508-CFTR modulators identified in the optical assays. FRT$^{\Delta F508\text{-}CFTR}$ epithelial cells grown on Costar Snapwell cell culture inserts were mounted in an Using chamber (Physiologic Instruments, Inc., San Diego, Calif.), and the monolayers were continuously short-circuited using a Voltage-clamp System (Department of Bioengineering, University of Iowa, IA, and, Physiologic Instruments, Inc., San Diego, Calif.). Transepithelial resistance was measured by applying a 2-mV pulse. Under these conditions, the FRT epithelia demonstrated resistances of 4 KΩ/cm² or more. The solutions were maintained at 27° C. and bubbled with air. The electrode offset potential and fluid resistance were corrected using a cell-free insert. Under these conditions, the current reflects the flow of Cl⁻ through ΔF508-CFTR expressed in the apical membrane. The $I_{SC}$ was digitally acquired using an MP100A-CE interface and AcqKnowledge software (v3.2.6; BIOPAC Systems, Santa Barbara, Calif.).

2. Identification of Correction Compounds

Typical protocol utilized a basolateral to apical membrane Cl⁻ concentration gradient. To set up this gradient, normal ringer was used on the basolateral membrane, whereas apical NaCl was replaced by equimolar sodium gluconate (titrated to pH 7.4 with NaOH) to give a large Cl⁻ concentration gradient across the epithelium. All experiments were performed with intact monolayers. To fully activate ΔF508-CFTR, forskolin (10 μM) and the PDE inhibitor, IBMX (100 μM), were applied followed by the addition of the CFTR potentiator, genistein (50 μM).

As observed in other cell types, incubation at low temperatures of FRT cells stably expressing ΔF508-CFTR increases the functional density of CFTR in the plasma membrane. To determine the activity of correction compounds, the cells were incubated with 10 μM of the test compound for 24 hours at 37° C. and were subsequently washed 3× prior to recording. The cAMP- and genistein-mediated $I_{SC}$ in compound-treated cells was normalized to the 27° C. and 37° C. controls and expressed as percentage activity. Preincubation of the cells with the correction compound significantly increased the cAMP- and genistein-mediated $I_{SC}$ compared to the 37° C. controls.

3. Identification of Potentiator Compounds

Typical protocol utilized a basolateral to apical membrane Cl⁻ concentration gradient. To set up this gradient, normal ringers was used on the basolateral membrane and was permeabilized with nystatin (360 μg/ml), whereas apical NaCl was replaced by equimolar sodium gluconate (titrated to pH 7.4 with NaOH) to give a large Cl⁻ concentration gradient across the epithelium. All experiments were performed 30 min after nystatin permeabilization. Forskolin (10 μM) and all test compounds were added to both sides of the cell culture inserts. The efficacy of the putative ΔF508-CFTR potentiators was compared to that of the known potentiator, genistein.

4. Solutions

Basolateral solution (in mM): NaCl (135), CaCl$_2$ (1.2), MgCl$_2$ (1.2), K$_2$HPO$_4$ (2.4), KHPO$_4$ (0.6), N-2-hydroxyethylpiperazine-N'-2-ethanesulfonic acid (HEPES) (10), and dextrose (10). The solution was titrated to pH 7.4 with NaOH.

Apical solution (in mM): Same as basolateral solution with NaCl replaced with Na Gluconate (135).

5. Cell Culture

Fisher rat epithelial (FRT) cells expressing ΔF508-CFTR (FRT$^{\Delta F508\text{-}CFTR}$) were used for Using chamber experiments for the putative ΔF508-CFTR modulators identified from our optical assays. The cells were cultured on Costar Snapwell cell culture inserts and cultured for five days at 37° C. and 5% $CO_2$ in Coon's modified Ham's F-12 medium supplemented with 5% fetal calf serum, 100 U/ml penicillin, and 100 µg/ml streptomycin. Prior to use for characterizing the potentiator activity of compounds, the cells were incubated at 27° C. for 16-48 hrs to correct for the ΔF508-CFTR. To determine the activity of corrections compounds, the cells were incubated at 27° C. or 37° C. with and without the compounds for 24 hours.

6. Whole-Cell Recordings

The macroscopic ΔF508-CFTR current ($I_{\Delta F508}$) in temperature- and test compound-corrected NIH3T3 cells stably expressing ΔF508-CFTR were monitored using the perforated-patch, whole-cell recording. Briefly, voltage-clamp recordings of $I_{\Delta F508}$ were performed at room temperature using an Axopatch 200B patch-clamp amplifier (Axon Instruments Inc., Foster City, Calif.). All recordings were acquired at a sampling frequency of 10 kHz and low-pass filtered at 1 kHz. Pipettes had a resistance of 5-6 MΩ when filled with the intracellular solution. Under these recording conditions, the calculated reversal potential for Cl⁻ ($E_{Cl}$) at room temperature was −28 mV. All recordings had a seal resistance >20 GΩ and a series resistance <15 MΩ. Pulse generation, data acquisition, and analysis were performed using a PC equipped with a Digidata 1320 A/D interface in conjunction with Clampex 8 (Axon Instruments Inc.). The bath contained <250 µl of saline and was continuously perifused at a rate of 2 ml/min using a gravity-driven perfusion system.

7. Identification of Correction Compounds

To determine the activity of correction compounds for increasing the density of functional ΔF508-CFTR in the plasma membrane, we used the above-described perforated-patch-recording techniques to measure the current density following 24-hr treatment with the correction compounds. To fully activate ΔF508-CFTR, 10 µM forskolin and 20 µM genistein were added to the cells. Under our recording conditions, the current density following 24-hr incubation at 27° C. was higher than that observed following 24-hr incubation at 37° C. These results are consistent with the known effects of low-temperature incubation on the density of ΔF508-CFTR in the plasma membrane. To determine the effects of correction compounds on CFTR current density, the cells were incubated with 10 µM of the test compound for 24 hours at 37° C. and the current density was compared to the 27° C. and 37° C. controls (% activity). Prior to recording, the cells were washed 3× with extracellular recording medium to remove any remaining test compound. Preincubation with 10 µM of correction compounds significantly increased the cAMP- and genistein-dependent current compared to the 37° C. controls.

8. Identification of Potentiator Compounds

The ability of ΔF508-CFTR potentiators to increase the macroscopic ΔF508-CFTR Cl⁻ current ($I_{\Delta F508}$) in NIH3T3 cells stably expressing ΔF508-CFTR was also investigated using perforated-patch-recording techniques. The potentiators identified from the optical assays evoked a dose-dependent increase in $I_{\Delta F508}$ with similar potency and efficacy observed in the optical assays. In all cells examined, the reversal potential before and during potentiator application was around −30 mV, which is the calculated $E_{Cl}$ (−28 mV).

9. Solutions

Intracellular solution (in mM): Cs-aspartate (90), CsCl (50), $MgCl_2$ (1), HEPES (10), and 240 µg/ml amphotericin-B (pH adjusted to 7.35 with CsOH).

Extracellular solution (in mM): N-methyl-D-glucamine (NMDG)-Cl (150), $MgCl_2$ (2), $CaCl_2$ (2), HEPES (10) (pH adjusted to 7.35 with HCl).

10. Cell Culture

NIH3T3 mouse fibroblasts stably expressing ΔF508-CFTR are used for whole-cell recordings. The cells are maintained at 37° C. in 5% $CO_2$ and 90% humidity in Dulbecco's modified Eagle's medium supplemented with 2 mM glutamine, 10% fetal bovine serum, 1× NEAA, β-ME, 1× pen/strep, and 25 mM HEPES in 175 cm² culture flasks. For whole-cell recordings, 2,500-5,000 cells were seeded on poly-L-lysine-coated glass coverslips and cultured for 24-48 hrs at 27° C. before use to test the activity of potentiators; and incubated with or without the correction compound at 37° C. for measuring the activity of correctors.

11. Single-Channel Recordings

The single-channel activities of temperature-corrected ΔF508-CFTR stably expressed in NIH3T3 cells and activities of potentiator compounds were observed using excised inside-out membrane patch. Briefly, voltage-clamp recordings of single-channel activity were performed at room temperature with an Axopatch 200B patch-clamp amplifier (Axon Instruments Inc.). All recordings were acquired at a sampling frequency of 10 kHz and low-pass filtered at 400 Hz. Patch pipettes were fabricated from Corning Kovar Sealing #7052 glass (World Precision Instruments, Inc., Sarasota, Fla.) and had a resistance of 5-8 MΩ when filled with the extracellular solution. The ΔF508-CFTR was activated after excision, by adding 1 mM Mg-ATP, and 75 nM of the cAMP-dependent protein kinase, catalytic subunit (PKA; Promega Corp. Madison, Wis.). After channel activity stabilized, the patch was perifused using a gravity-driven microperfusion system. The inflow was placed adjacent to the patch, resulting in complete solution exchange within 1-2 sec. To maintain ΔF508-CFTR activity during the rapid perifusion, the nonspecific phosphatase inhibitor F⁻ (10 mM NaF) was added to the bath solution. Under these recording conditions, channel activity remained constant throughout the duration of the patch recording (up to 60 min). Currents produced by positive charge moving from the intra- to extracellular solutions (anions moving in the opposite direction) are shown as positive currents. The pipette potential ($V_p$) was maintained at 80 mV.

Channel activity was analyzed from membrane patches containing ≤2 active channels. The maximum number of simultaneous openings determined the number of active channels during the course of an experiment. To determine the single-channel current amplitude, the data recorded from 120 sec of ΔF508-CFTR activity was filtered "off-line" at 100 Hz and then used to construct all-point amplitude histograms that were fitted with multigaussian functions using Bio-Patch Analysis software (Bio-Logic Comp. France). The total microscopic current and open probability ($P_o$) were determined from 120 sec of channel activity. The $P_o$ was determined using the Bio-Patch software or from the relationship $P_o=I/i(N)$, where I=mean current, i=single-channel current amplitude, and N=number of active channels in patch.

12. Solutions

Extracellular solution (in mM): NMDG (150), aspartic acid (150), $CaCl_2$ (5), $MgCl_2$ (2), and HEPES (10) (pH adjusted to 7.35 with Tris base).

Intracellular solution (in mM): NMDG-Cl (150), MgCl$_2$ (2), EGTA (5), TES (10), and Tris base (14) (pH adjusted to 7.35 with HCl).

13. Cell Culture

NIH3T3 mouse fibroblasts stably expressing ΔF508-CFTR are used for excised-membrane patch-clamp recordings. The cells are maintained at 37° C. in 5% CO$_2$ and 90% humidity in Dulbecco's modified Eagle's medium supplemented with 2 mM glutamine, 10% fetal bovine serum, 1×NEAA, β-ME, 1× pen/strep, and 25 mM HEPES in 175 cm$^2$ culture flasks. For single channel recordings, 2,500-5,000 cells were seeded on poly-L-lysine-coated glass coverslips and cultured for 24-48 hrs at 27° C. before use.

The exemplified compounds of Table 3 have an activity as shown below in Table 3.

TABLE 3

| Cmpd # | EC50 | % Efficacy |
|---|---|---|
| 1 | +++ | ++ |
| 2 | +++ | ++ |
| 3 | +++ | +++ |
| 4 | +++ | ++ |
| 5 | +++ | ++ |
| 6 | +++ | +++ |
| 7 | +++ | ++ |
| 8 | +++ | ++ |
| 9 | +++ | +++ |
| 10 | +++ | ++ |
| 11 | +++ | +++ |
| 12 | +++ | ++ |
| 13 | + | ++ |
| 14 | +++ | ++ |
| 15 | +++ | +++ |
| 16 | +++ | ++ |
| 17 | +++ | +++ |
| 18 | +++ | +++ |
| 19 | +++ | +++ |
| 20 | +++ | +++ |
| 21 | +++ | ++ |
| 22 | +++ | ++ |
| 23 | ++ | ++ |
| 24 | +++ | +++ |
| 25 | +++ | +++ |
| 26 | +++ | ++ |
| 27 | +++ | +++ |
| 28 | +++ | ++ |
| 29 | +++ | +++ |
| 30 | +++ | ++ |
| 31 | +++ | ++ |
| 32 | ++ | ++ |
| 33 | +++ | +++ |
| 34 | ++ | ++ |
| 35 | +++ | ++ |
| 36 | +++ | +++ |
| 37 | +++ | +++ |
| 38 | +++ | +++ |
| 39 | +++ | ++ |
| 40 | +++ | +++ |
| 41 | +++ | +++ |
| 42 | +++ | ++ |
| 43 | +++ | +++ |
| 44 | +++ | ++ |
| 45 | +++ | +++ |
| 46 | +++ | ++ |
| 47 | +++ | + |
| 48 | +++ | +++ |
| 49 | +++ | ++ |
| 50 | +++ | ++ |
| 51 | +++ | +++ |
| 52 | +++ | ++ |
| 53 | +++ | +++ |
| 54 | +++ | ++ |
| 55 | +++ | ++ |
| 56 | +++ | +++ |
| 57 | +++ | +++ |
| 58 | +++ | +++ |
| 59 | ++ | ++ |
| 60 | +++ | ++ |
| 61 | +++ | ++ |
| 62 | +++ | ++ |
| 63 | +++ | ++ |
| 64 | +++ | +++ |
| 65 | +++ | ++ |
| 66 | +++ | +++ |
| 67 | +++ | +++ |
| 68 | +++ | ++ |
| 69 | +++ | ++ |
| 70 | +++ | ++ |
| 71 | +++ | +++ |
| 72 | +++ | +++ |
| 73 | +++ | ++ |
| 74 | ++ | + |
| 75 | +++ | +++ |
| 76 | +++ | ++ |
| 77 | +++ | +++ |
| 78 | +++ | ++ |
| 79 | +++ | +++ |
| 80 | +++ | ++ |
| 81 | +++ | +++ |
| 82 | +++ | +++ |
| 83 | +++ | ++ |
| 84 | +++ | ++ |
| 85 | +++ | +++ |
| 86 | +++ | +++ |
| 87 | +++ | +++ |
| 88 | +++ | +++ |
| 89 | +++ | +++ |
| 90 | +++ | +++ |
| 91 | +++ | +++ |
| 92 | +++ | ++ |
| 93 | +++ | +++ |
| 94 | ++ | +++ |
| 95 | +++ | +++ |
| 96 | +++ | +++ |
| 97 | +++ | ++ |
| 98 | +++ | ++ |
| 99 | +++ | +++ |
| 100 | +++ | +++ |
| 101 | +++ | +++ |
| 102 | +++ | ++ |
| 103 | +++ | +++ |
| 104 | +++ | ++ |
| 105 | +++ | ++ |
| 106 | +++ | +++ |
| 107 | +++ | +++ |
| 108 | +++ | +++ |
| 109 | +++ | ++ |
| 110 | +++ | ++ |
| 111 | +++ | +++ |
| 112 | +++ | ++ |
| 113 | +++ | +++ |
| 114 | +++ | ++ |
| 115 | +++ | ++ |
| 116 | +++ | +++ |
| 117 | +++ | +++ |

EC50: +++ <= 2.0 μM < ++ <= 5.0 μM < +
Percent Efficacy: + <= 50.0% < ++ <= 100.0% < +++

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

We claim:

1. A compound of formula VI:

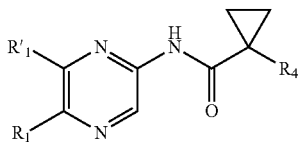

or a pharmaceutically acceptable salt thereof, wherein:

each $R'_1$ is:

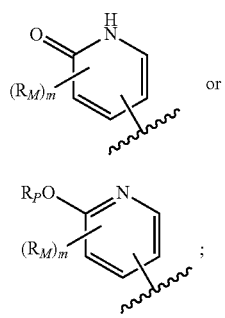

m is 0-3;

$R_P$ is optionally substituted C1-C6 aliphatic, wherein up to two carbon units therein are optionally and independently replaced by —CO—, —CONR$^N$—, —CO$_2$—, —OCO$_2$—, —NR$^N$CO$_2$—, —O—, —OCONR$^N$—, —NR$^N$CO—, —S—, —SO—, —SO$_2$—, —NR$^N$—;

$R_M$ is independently —Z$^M$R$_{11}$, wherein each $Z^M$ is independently a bond or an optionally substituted branched or straight C1-C6 aliphatic chain wherein up to two carbon units of $Z^M$ are optionally and independently replaced by —CO—, —CONR$^N$—, —CO$_2$—, —OCO—, —CHR$^N$—, —NR$^N$CO$_2$—, —O—, —OCONR$^N$—, —NR$^N$CO—, —S—, —SO—, —SO$_2$—, —NR$^N$—;

$R_{11}$ is independently $R^N$, halo, —OH, —NH$_2$, —CN, —CF$_3$, or —OCF$_3$;

$R^N$ is independently hydrogen, an optionally substituted C1-C8 aliphatic group, an optionally substituted cycloaliphatic, an optionally substituted heterocycloaliphatic, an optionally substituted aryl, or an optionally substituted heteroaryl;

$R_1$ is an optionally substituted C1-C6 aliphatic, an optionally substituted $C_{1-6}$ alkoxy, an optionally substituted C3-C10 cycloaliphatic, —CN, halo, or hydroxy;

$R_4$ is selected from (a)

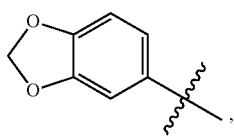

(b)

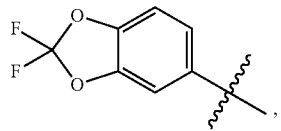

(c)

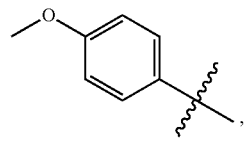

(d)

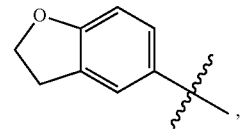

(e)

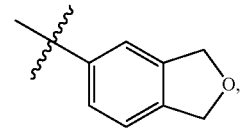

(f)

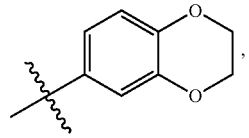

(g)

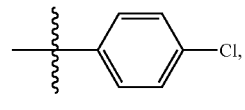

(h)

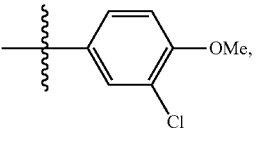

(i)

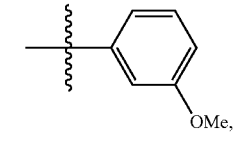

(j)

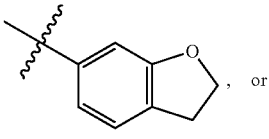

or (k)

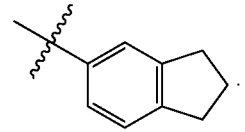

2. The compound according to claim 1, wherein said compound has formula VIA:

VIA
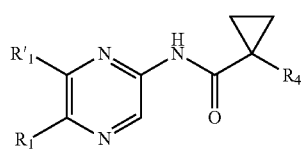
or a pharmaceutically acceptable salt thereof, wherein:
R'₁ is
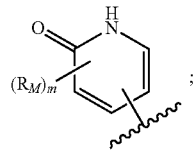
wherein
m is 0-3;
R₁ is C1-C6 aliphatic, halo, or —CN; and
R₄ is selected from;
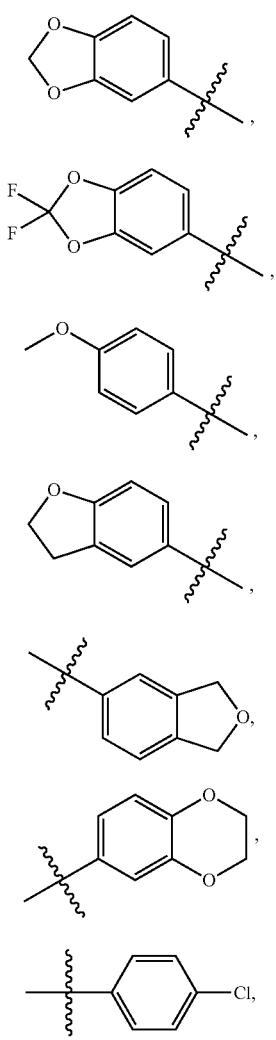
(a)
(b)
(c)
(d)
(e)
(f)
(g)
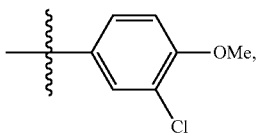
(h)
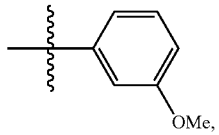
(i)
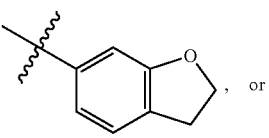
, or (j)
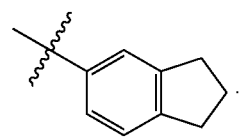
(k)
3. The compound according to claim 1, wherein said compound has formula VIB:
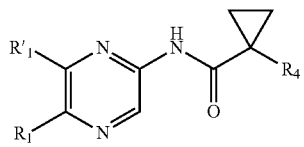
VIB
or a pharmaceutically acceptable salt thereof, wherein:
R'₁ is
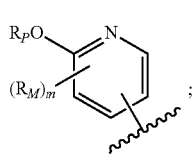
(ii)
wherein:
m is 0-3;
R₁ is C1-C6 aliphatic, halo, or —CN; and
R₄ is selected from:
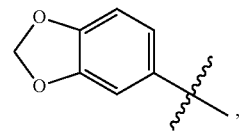
(a)
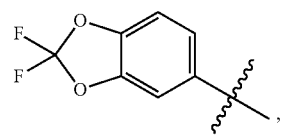
(b)

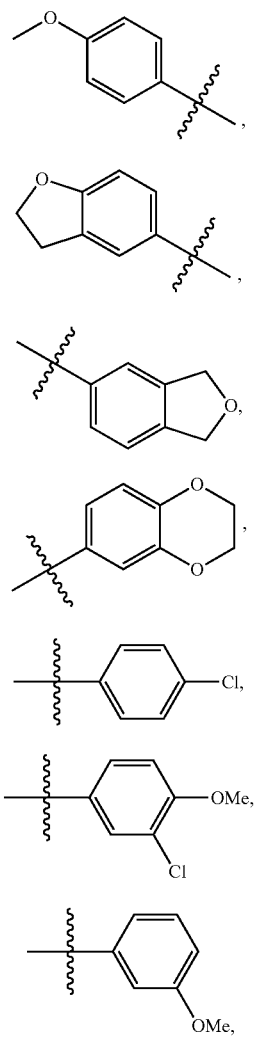

4. A pharmaceutical composition comprising:
   (i) a compound or a pharmaceutically acceptable salt thereof according to claim 1; and
   (ii) a pharmaceutically acceptable carrier.

5. A method of modulating CFTR activity comprising the step of contacting said CFTR with a compound or a pharmaceutically acceptable salt thereof according to claim 1.

6. A method of treating or lessening the severity of a disease in a patient, wherein said disease is cystic fibrosis, said method comprising the step of administering to said patient an effective amount of a compound or a pharmaceutically acceptable salt thereof according to claim 1.

7. A kit for use in measuring the activity of CFTR or a fragment thereof in a biological sample in vitro or in vivo, comprising:
   (i) a composition comprising a compound or a pharmaceutically acceptable salt thereof according to claim 1; and
   (ii) instructions for:
      a) contacting the composition with the biological sample; and
      b) measuring activity of said CFTR or a fragment thereof.

* * * * *